(12) United States Patent
Cyr et al.

(10) Patent No.: US 9,829,429 B2
(45) Date of Patent: *Nov. 28, 2017

(54) DETERMINING A POLARIZATION-RELATED CHARACTERISTIC OF AN OPTICAL LINK

(71) Applicant: EXFO Inc., Quebec (CA)

(72) Inventors: Normand Cyr, Quebec (CA); Hongxin Chen, Chino Hills, CA (US); Gregory Walter Schinn, Quebec (CA)

(73) Assignee: EXFO INC, Quebec (CA)

( * ) Notice: Subject to any disclaimer, the term of this patent is extended or adjusted under 35 U.S.C. 154(b) by 820 days.

This patent is subject to a terminal disclaimer.

(21) Appl. No.: 13/767,851

(22) Filed: Feb. 14, 2013

(65) Prior Publication Data

US 2014/0071436 A1 Mar. 13, 2014
US 2016/0161397 A9 Jun. 9, 2016

Related U.S. Application Data

(63) Continuation-in-part of application No. 12/568,554, filed on Sep. 28, 2009, now abandoned, which is a
(Continued)

(51) Int. Cl.
G01N 21/21 (2006.01)
G01M 11/00 (2006.01)
G06F 17/18 (2006.01)

(52) U.S. Cl.
CPC ......... *G01N 21/21* (2013.01); *G01M 11/3163* (2013.01); *G01M 11/3181* (2013.01);
(Continued)

(58) Field of Classification Search
CPC ............ G01M 11/31; G01M 11/3109; G01M 11/3118; G01M 11/3127; G01M 11/3136;
(Continued)

(56) References Cited

U.S. PATENT DOCUMENTS 4,750,833 A 6/1988 Jones
5,966,207 A 10/1999 Haskins et al.
(Continued)

FOREIGN PATENT DOCUMENTS

WO 2005041449 5/2005
WO 2005080936 9/2005
(Continued)

OTHER PUBLICATIONS

Jiang et al., "PMD Monitoring in Traffic-Carrying Optical Systems and its Statistical Analysis", Sep. 1, 2008, vol. 16, No. 18, Optics Express.
(Continued)

*Primary Examiner* — Gordon J Stock, Jr.
(74) *Attorney, Agent, or Firm* — Norton Rose Fulbright Canada LLP; Alexandre Daoust

(57) ABSTRACT

A polarization-related characteristic of an optical path is determined from a predetermined function of the meansquare of a plurality of differences between polarizationanalyzed optical power parameters corresponding to pairs of wavelengths mutually spaced about a midpoint wavelength by a small optical frequency difference. At least some of the said differences correspond to wavelength pairs measured under conditions where at least one of midpoint wavelength, input state of polarization (I-SOP) or analyzed state of polarization (A-SOP) of a pair is different.

40 Claims, 46 Drawing Sheets

Related U.S. Application Data continuation-in-part of application No. 11/992,797, filed as application No. PCT/CA2006/001610 on Sep. 29, 2006, now Pat. No. 7,920,253, said application No. 12/568,554 is a continuation-in-part of application No. PCT/CA2008/000577, filed on Mar. 28, 2008.

(60) Provisional application No. 60/721,532, filed on Sep. 29, 2005, provisional application No. 60/907,313, filed on Mar. 28, 2007.

(52) U.S. Cl.
CPC ........ *G01M 11/335* (2013.01); *G01M 11/336* (2013.01); *G06F 17/18* (2013.01)

(58) Field of Classification Search
CPC ......... G01M 11/3145; G01M 11/3154; G01M 11/3163; G01M 11/3172; G01M 11/3181; G01M 11/319; G01M 11/33; G01M 11/331–11/338; G01N 21/21; G06F 17/18
See application file for complete search history.

(56) References Cited

U.S. PATENT DOCUMENTS

| | | | |
|---|---|---|---|
| 6,204,924 B1 | 3/2001 | Cyr | |
| 6,229,599 B1 | 5/2001 | Galtarossa | |
| 6,614,513 B2 | 9/2003 | Hoyer | |
| 6,697,150 B1 | 2/2004 | Galtarossa et al. | |
| 6,724,469 B2 | 4/2004 | Leblanc | |
| 6,850,318 B1 | 2/2005 | Ito et al. | |
| 6,946,646 B2 | 9/2005 | Chen et al. | |
| 7,116,419 B1 | 10/2006 | Weiner et al. | |
| 7,126,678 B2 | 10/2006 | Fayolle et al. | |
| 7,133,615 B2 | 11/2006 | Ogusu | |
| 7,164,469 B1 | 1/2007 | Chen et al. | |
| 7,170,913 B2 | 1/2007 | Araujo et al. | |
| 7,174,107 B2 | 2/2007 | Boroditsky et al. | |
| 7,180,582 B2 | 2/2007 | Yano et al. | |
| 7,190,442 B1 | 3/2007 | Chen et al. | |
| 7,203,428 B2 | 4/2007 | Waarts et al. | |
| 7,212,281 B2 | 5/2007 | Tanigawa et al. | |
| 7,227,645 B2 | 6/2007 | Cyr | |
| 7,256,876 B1 | 8/2007 | Boroditsky et al. | |
| 7,373,027 B2 | 5/2008 | Wuilpart | |
| 7,414,711 B1 | 8/2008 | Boroditsky et al. | |
| 7,463,346 B2 | 12/2008 | Goto et al. | |
| 7,711,266 B1 | 5/2010 | Harris | |
| 7,773,207 B1 | 8/2010 | Boroditsky et al. | |
| 7,873,273 B2 | 1/2011 | Koyamada | |
| 7,920,253 B2 * | 4/2011 | Cyr et al. | 356/73.1 |
| 2003/0133652 A1 | 7/2003 | Andrekson et al. | |
| 2004/0046955 A1 | 3/2004 | Fayolle et al. | |
| 2005/0201751 A1 | 9/2005 | Yao | |
| 2008/0100828 A1 * | 5/2008 | Cyr et al. | 356/73.1 |
| 2009/0244522 A1 | 10/2009 | Cyr et al. | |
| 2010/0266275 A1 | 10/2010 | Xia et al. | |
| 2011/0032605 A1 | 2/2011 | Kliner et al. | |

FOREIGN PATENT DOCUMENTS

| | | | |
|---|---|---|---|
| WO | WO 2007036051 A1 * | 4/2007 | |
| WO | 2008116314 | 10/2008 | |
| WO | WO 2008116314 A1 * | 10/2008 | |

OTHER PUBLICATIONS

Jiang et al., "PMD Monitoring in Traffic-Carrying Optical Systems", ECOC 2008, Sep. 21-25, 2008, Brussels, Belgium.

Yu et al., Technical Publication: Optics Communications "Multiwave Length Pulse Generation in Semiconductor-Fiber Ring Laser Using a Sampled Fiber Grating", vol. 200, Issue No. 1-6 Dec. 2001.

Xu et al., Technical Publication: IEEE Photonics Technology Letters "Tunable Dual-Wavelength-Switching Fiber Grating Laser", vol. 10, Issue No. 3 Mar. 1998.

Chen et al., "Single-Frequency Operation of a Widely Tunable SOA-Based Ring Laser" Optical Fiber Comm. & Optoelectronics Exposition & Conference 2006, Oct. 2006.

Galtarossa et al., "Reflectrometric Measurements of Polarization Properties in Optical-Fiber Links", Journal of Optical Fiber Communications Reports, vol. 1, Issue No. 2, pp. 150-179, Oct. 2004.

Rogers, "Distributed Measurement of Strain Using Optical-Fibre Backscatter Polarimetry", Society for Experimental Mechanics (SEM)—STRAIN, vol. 36, Issue No. 4, pp. 133-142, Nov. 2000.

Wuilpart et al., "Fully-Distributed Polarization Properties of an Optical Fiber Using the Backscattering Technique" Proceedings of SPIE—Applications of Photonic Technology—ICAPT 2000, vol. 4087, 2000, pp. 396-404.

Ellison et al., "Using Polarimetric Optical Time-Domain Reflectrometry to Estimate Linear Birefringence Suppression in Spun Fibre" IEEE Proceedings—Optoelectronics, vol. 146, Issue No. 3, pp. 137-141, Jun. 1999.

Bebbington et al., "Fully Polarimetric Optical Time-Domain Reflectometer With 1-m Spacial Resolution", Optical Fibre Communication Conference—OFC 1997, pp. 185-186, Feb. 21, 1997.

Ozeki et al., "Birefringence Distribution Along Fiber Length", Optical Fiber Communications Conference—OFC 1996, pp. 295-297, Mar. 1, 1996.

Ellison et al., "Automatic Matrix-Based Analysis Method for Extraction of Optical Fiber Parameters from Polarimetric Optical Time Domain Reflectometry Data", Journal of Lightwave Technology, vol. 18, Issue No. 9, pp. 1226-1232, Sep. 2000.

Galtarossa et al., "Spatially Resolved PMD Measurements", Journal of Lightwave Technology, vol. 22, Issue No. 4, pp. 1103-1115, Apr. 2004.

Williams et al., "Narrowband Measurement of Polarization-Mode Dispersion Using the Modulation Phase Shift Technique", Symposium on Optical Fiber Measurements (SOFM 1998), Sep. 15-17, 1998, Boulder, CO, NIST Special Publication 930, pp. 23-26.

Noe et al., "Polarization Mode Dispersion Detected by Arrival Time Measurement of Polarization-Scrambled Light", Journal of Lightwave Technology, vol. 20 (2), 2002, pp. 229-235.

Wang et al., "PMD Tolerance Testing of a Commercial Communication System Using a Spectral Polarimeter", Journal of Lightwave Technology, vol. 24 (11), 2006, pp. 4120-4126.

Wielandy et al., "Optical Performance Monitoring Using Nonlinear Detection", Journal of Lightwave Technology, vol. 22 (3), 2004, pp. 784-793.

N. Kikuchi' "Analysis of Signal Degree of Polarization Degradation Used as Control Signal for Optical Polarization Mode Dispersion Compensation", Journal of Lightwave Technology, vol. 19 (4), 2001, pp. 480-486.

Poole et al., "Polarization-Mode Dispersion Measurements Based on Transmission Spectra Through a Polarizer", IEEE/OSA TJ Lightwave Technology, vol. 12 (6), 1994, pp. 917-929.

Cyr, Normand, "Polarization-Mode Dispersion Measurement, Generalization of the Interferometric Method to Any Coupling Regime", IEEE/OSA J. Lightwave Technolgy, vol. 22 (3), 2004, pp. 794-805.

Corsi et al., "Continuous-Wave Backreflection Measurement of Polarizastion Mode Dispersion Characterization", IEEE Photonics Technology Letters, vol. 11, No. 4, Apr. 1999, pp. 451-453.

Galtarossa et al., "Single-End Polarizastion Mode Dispersion Measurement Using Backreflected Spectra Through a Linear Polarizer", IEEE/OSA J. Lightwave Technology, vol. 17, No. 10, Oct. 1998, pp. 1835-1842.

Sunnerud et al., "Polarization-Mode Dispersion Measurements along Installed Optical Fibers Using Gated Backscattered Light and a Polarimeter", IEEE/OSA J. Lightwave Technology, vol. 18, No. 7, Jul. 2000, pp. 897-904.

(56) References Cited

OTHER PUBLICATIONS

Sunnerud et al., "Measurement of Polarization Mode Dispersion Accumulation Along Installed Optical Fibers", IEEE Photonics Technology Letters, vol. 11, No. 7, Jul. 1999, pp. 860-862.

Dong et al., "Single-End Spectral Resolved Measurement of Polarization Mode Dispersion in Optical Fibers", Paper JThA20, Optical Fiber Communications Conference, Mar. 25-29, 2007, Anaheim, CA, USA.

Huttner, B., "Distributed PMD Measurement with a Polarization-OTDR in Optical Fibers", Journal of Lightwave Technology, vol. 17, pp. 1843-1948, Mar. 1999.

Corsi et al., "Beat Length Characterization Based on Backscattering Analysis in Randomly Perturbed Single-Mode Fibers", Journal of Lightwave Technology, vol. 17, Issue No. 7, Jul. 1999.

Galtarossa et al., "Measurement of Local Beat Length and Differential Group Delay in Installed Single-Mode Fibers", Journal of Lightwave Technology, vol. 18, No. 10, Oct. 2000 (N.B. only total PMD end-to-end is measured for comparison, not cumulative PMD vs z).

Galtarossa et al., "Measurement of Beat Length and Perturbation Length in Long Single-Mode Fibers", Optics Letters, vol. 25, No. 6, Mar. 15, 2000.

Gonazlea-Herraez et al., "Single-End Measurement of PMD Using the Interferometric Method", Institute de Aplicada, CSIC. Serranco 144 28006 Madrid, Spain.

Jaworski et al., "Accurate PMD Measurements Using OSA and Polarization Scrambling", ICTON 2007, pp. 51-54.

Galtarossa et al. "POTDR Techniques for Measurement of Fiber Birefringence Properties" OFC 2002, Session WA4, pp. 174-175.

Ozeki et al. "PMD Distribution Measurement by an OTDR with Polarimetry Considering Depolarization of Backscattered Waves", Journal of Ligntwave Technology, vol. 24 No. 11, Nov. 2006, pp. 3882-3888.

Shatalin et al. "Location of High PMD Sections of Installed System Fiber", Journal of Lightwave Technoloby, vol. 24, No. 11, Nov. 2006.

Bhandari et al. "Dynamic Reconfiguration for Optical Network". Proceedings of ICCCN 2005. Oct. 17-19, 2005.

Jiang et al. "PMD Monitoring in Traffic-carrying Optical Systems". Proceedings of ECOC 2008, Sep. 21-25, 2008. Brussels, Belgium., vol. 3, pp. 209-210.

Jiang et al. "PMD monitoring in traffic-carrying optical systems and its statistical analysis", Sep. 1, 2008, vol. 16, No. 18, Optics Express, pp. 14057-14063.

Lecoeuche et al., "Non-Intrusive In-Service PMD Measurements: A Novel Approach Based on Coherent Detection", ECOC Technical Digest, 2011, Optical Society of America, Th. 12, pp. 1-3.

\* cited by examiner

DETERMINING A POLARIZATION-RELATED CHARACTERISTIC OF AN OPTICAL LINK

CROSS-REFERENCE TO RELATED DOCUMENTS

This application is a Continuation-in-Part of U.S. patent application Ser. No. 12/568,554 filed Sep. 28, 2009, which is a Continuation-in-Part of: (1) U.S. patent application Ser. No. 11/992,797 filed Mar. 28, 2008 now granted as U.S. Pat. No. 7,920,253, which is a national stage entry of international patent application no. PCT/CA2006/001610 filed Sep. 29, 2006 claiming priority from U.S. provisional application No. 60/721,532 filed Sep. 29, 2005; and (2) international patent application no. PCT/CA2008/000577 filed Mar. 28, 2008 claiming priority from U.S. provisional application No. 60/907,313 filed Mar. 28, 2007. The entire contents of each of U.S. patent application Ser. No. 12/568,554, U.S. provisional application No. 60/721,532 and U.S. patent application Ser. No. 11/992,797 are incorporated herein by reference and the reader is directed to them for further reference.

TECHNICAL FIELD

This invention relates to a method and system for measuring polarization-related characteristics of optical paths, which may lead to impairments of a data-carrying signal propagating therealong. The optical path normally comprises mostly optical waveguide, such as an optical fiber link in a telecommunications network Preferred embodiments of the inventive concept are especially applicable to the measurement of differential group delay (DGD) of an optical path at a particular wavelength, or root-mean-square or mean DGD over a specified wavelength range. When the specified wavelength range is sufficiently wide, the root-mean-square or mean DGD measurement closely approximates the polarization mode dispersion (PMD) behavior of the optical path.

Other preferred embodiments are especially applicable to the monitoring of temporal pulse spreading of data-carrying optical signals induced by DGD-related polarization characteristics of the optical path along which the signals are propagating.

DEFINITIONS

Within this specification, certain terms are accorded the following meanings:

"Optical frequency" ($\upsilon$) and "wavelength" ($\lambda$) are used interchangeably, the two being related by $\lambda=c/\upsilon$, where c represents the speed of light in vacuum. Note that wavelength, as used hereinbelow, corresponds to that which would be measured in a vacuum.

"Fiber-Under-Test" (FUT) designates a guided optical propagation medium for which one wishes to measure at least one polarization-related characteristic. The FUT comprises primarily optical fiber for which the guiding properties are "single mode" at the optical frequencies of interest, but it may also include intervening optical elements such as optical amplifiers, optical switches and routers, etc. FUT is a special case of "optical link", since the latter does not necessarily imply that measurements of polarization-related characteristics will be taken thereof. Note that FUT does not necessarily correspond to a link connecting network nodes, but may be a portion of such a link for which access may be gained via "tap" or monitor ports for "in-service" measurements, or by temporarily breaking into the fiber path for "dark fiber" measurements.

"Lightpath" refers to a particular restricted spectral region of an optical link within which a particular data-carrying signal normally propagates (often termed optical "channel"), whether or not said spectral width is delimited by intervening optical filtering.

"Dark channel" refers to an optical channel within which no optical signals are propagating.

"DWDM" refers to Dense Wavelength-Division Multiplexing, whereby multiple SUTs, each corresponding to a distinct central wavelength, may be propagated along the same optical fiber link, such the central wavelengths of respective adjacent SUTs may be mutually spaced by optical-frequency differences typically of 100 GHz or less.

"Signal-Under-Test" (SUT) designates a normally data-carrying optical signal traversing an optical link, such as may be employed in an active telecom optical network. In this specification, "live" signal and "data-carrying" signal will be used interchangeably with SUT.

"State of Polarization" (SOP) defines the polarization properties of a light beam (i.e. the relative amplitude and phases of the electric field) within a particular short time interval and at a particular location.

"Differential Group Delay" (DGD) is a parameter quantifying, for a given optical frequency $\upsilon$ and within a particular short time interval, the maximum difference in optical propagation time along a guided propagation medium (primarily a single-mode optical fiber), for all possible SOPs launched into the propagation medium.

"Input Principal States of Polarization" (Input-PSPs) are, for a given optical frequency and at a particular time, the two SOPs of the light launched into the guided propagation medium corresponding, respectively, to the slowest and fastest propagation times in the medium.

"Output Principal States of Polarization" (Output-PSPs) are the two SOPs of light exiting the propagation medium corresponding to, respectively, the two Input-PSPs.

"Analyzer" refers to an element that permits detection of only that fraction of the incident light corresponding to an SOP aligned with its low-loss ("maximum-transmission") axis. This element may be highly polarization-dependent (e.g. a linear polarizer, or polarization beam splitter PBS), having mutually-orthogonal low-loss and high-loss axes. Alternatively, it may comprise other means, such as optical combining means to combine polarized highly-coherent local oscillator light (e.g. from a tunable laser) with the light under test to interfere at subsequent heterodyne-detection means, the degree of detected heterodyne signal depending upon the relative alignment of the local oscillator SOP with the SOP of the light under test.

"Analyzer SOP" ("A-SOP") refers to the SOP of light corresponding to maximum subsequent detection as it enters a combination of a polarization-controller and an analyzer. Although A-SOP varies as the polarization controller is varied, in some variants it may be fixed (e.g. to act as a quarter-wave plate), as is the case for a polarimeter having three analyzers, the (fixed) A-SOPs of the analyzers being normally mutually orthogonal.

"Polarimetric head" refers to the optical portion of a polarimeter, comprising at least three analyzers having mutually linearly-independent A-SOPs and associated optical elements (e.g. optical fiber, beam splitters, attenuators, lenses, etc.), and means to propagate the resulting analyzed light to optical detectors external thereto.

"Input SOP" ("I-SOP") refers to the state of polarization of light as it is launched into the FUT.

"Polarization Mode Dispersion" (PMD) is the polarization-related physical phenomenon giving rise to polarization-dependent temporal spreading of an optical pulse. Although in theory it is defined as an average of the DGD($\upsilon$) values over all possible optical frequencies, in practice it is normally estimated from an average of DGD($\upsilon$) over a significantly wide prescribed spectral range encompassing wavelengths of interest (e.g., the telecom C or C+L bands of minimal-loss transmission). In telecom optical fiber, moderate to high PMD may cause DGD($\upsilon$) to vary significantly over the prescribed spectral range. PMD is usually defined as the root-mean-square (rms) average of DGD($\upsilon$) over the prescribed spectral range ("rms PMD", or simply "PMD"), but, alternatively, may be defined as the arithmetic mean of DGD($\upsilon$) over this same spectral range ("mean PMD").

"Overall PMD" is the PMD measured over the full length L of an FUT (whether or not that fiber spans the full distance between two nodes in the network).

"Cumulative PMD" is the value of the PMD from the input end of the FUT up to a distance z along the FUT, where z≤L.

"Partial DGD" ($DGD_P$) is a parameter quantifying the degree to which the DGD of the guided propagation medium (e.g. optical fiber), for a given optical frequency $\upsilon$ and within a particular short time interval, will induce temporal pulse spreading of an SUT launched therein with a particular input SOP. This parameter is thus a polarization-dependent characteristic of the optical lightpath, manifest by its effect upon the SUT. For a given optical frequency and at a particular time, the DGD will have a value less than or equal to the corresponding DGD value—hence the terminology "partial DGD".

"Degree of polarization" (DOP) of a light beam is defined as the relative difference between the maximum and minimum power of a light beam that traverses an adjustable polarization controller and analyzer combination disposed in the physical light path. In other words, if, upon suitable adjustment of the polarization controller, the light power in the beam may be extinguished by 90% from its maximum transmission value by the analyzer, the DOP=90%.

"In-service link" refers to an optical link, comprising primarily optical fiber, within which at least one data-carrying signal (i.e. which is not light from a test source) "test" signal) normally propagates.

"OTDR" is an abbreviation for Optical Time Domain Reflectometer, a test instrument that launches optical pulses into an optical fiber and detects the resulting backreflected light to provide distance-resolved information characterizing a FUT.

"Monitoring" and "measurement" are used interchangeably, unless otherwise clearly specified. Although "monitoring" generally implies a collection of measurements taken over a long period of time from particular fixed locations in a network, and "measurement" generally refers to sporadic or ad hoc acquisitions, often with portable apparatus in the context of maintenance or troubleshooting, the underlying method and apparatus as described herein are identical.

MOTIVATION AND BACKGROUND ART

Polarization mode dispersion (PMD) is a polarization-related physical phenomenon that often limits the bandwidth-distance product of a fiber-optic-based telecom transmission link. In other words, PMD may be the primary impairment limiting the reach (i.e. maximum propagation distance) of high bit-/symbol-rate signals, and PMD may limit the bandwidth that may be carried in a single optical channel along a "long-haul" (i.e. long-distance) optical link.

Thus, it is desirable to be able to characterize one or more PMD-related parameters of an optical link, or of lightpaths thereof or of which they form a part.

Embodiments of aspects of the present invention enable characterization of different PMD-related parameters, and are particularly well suited to particular monitoring or measurement needs associated with optical networks. To facilitate detailed discussion and provide context for these embodiments, exemplary applications now will be presented.

1) Manifestation of PMD as a Function of Wavelength: DGD and "Partial DGD"

New optical networks will increasingly be based on a "mesh" topology or variants thereof, comprising multiple nodes connected by a corresponding multiplicity of fiber links. Such mesh networks may also employ Reconfigurable Optical Add-Drop Multiplexers (ROADMs) at the nodes to individually route any particular signal wavelength along a lightpath made up of different combinations of fiber links than the paths traversed by some of the other signal wavelengths. Signals at different wavelengths may carry payload at different bandwidths (e.g. 40 Gb/s instead of 10 Gb/s). The particular choice of route in the mesh may be determined by high-level control plane software, based on criteria such as:

(i) avoiding blocking or interference from other lightpaths having the same wavelength along certain node-to-node links in the network;
(ii) restoring a network after a cable cut along one or more such links; and
(iii) capacity of a particular lightpath to propagate the particular signal bandwidth without introducing an unacceptable level of impairments, e.g. arising from PMD.

To this end, it may be advantageous to verify, using light from a test source, the differential group delay (DGD) at the wavelength of the particular lightpath shortly beforehand in order to ensure that the lightpath is suitable, i.e. there would not be excessive PMD-related impairment of the re-routed high-bandwidth data-carrying signal. Furthermore, the test source itself should not unduly perturb the network, e.g. affect the automatic gain control of the optical amplifiers, etc., or otherwise affect network operations.

The extent to which the PMD phenomenon induces temporal spreading of the symbols constituting a particular data-carrying signal (i.e. digital time slots, or "unit intervals") at a given time is termed "partial DGD" ($DGD_P$). $DGD_P$ is dependent upon both the wavelength and the SOP of the signal being launched into the optical fiber, in contrast to DGD, whose value is independent of the launched SOP. For a given optical frequency, the "worst-case" partial DGD corresponds to the DGD at that same optical frequency, which obtains when the magnitudes of the projection of the SOP of the signal onto each of the two (orthogonal) principal states of polarization (PSPs) at the input to the fiber are equal. In general, however, the signal SOP at the fiber input is not well controlled (and often may change unpredictably over time), and consequently the level of signal $DGD_P$ at a particular wavelength is less than the corresponding DGD at that same wavelength.

Measurement of partial DGD may prove advantageous in optical network troubleshooting, where an operator may need to determine whether sudden observed "bursts" in bit error rate (BER) may be PMD-related, rather than having been caused by other phenomena such as optical amplifier instabilities, self-phase modulation, intermittent connections, etc. As described by Boroditsky et at (US patent publication number 2005/0232640 A1), a correlation of the observed BER bursts with a sudden increase in $DGD_P$, as monitored in real- or near-real time would indicate that PMD is indeed the likely cause of the problem. Furthermore, by carrying out such a $DGD_P$ measurement at points along the signal lightpath through the network (e.g. not necessarily limited to a particular optical link between two nodes of a mesh network), one may be able to approximately isolate the section primarily responsible for the PMD impairment.

2) PMD Determination of an in-Service Optical Link

If a telecom operator wishes to upgrade one or more channels of an existing in-service DWDM link by increasing the signal bandwidth (i.e. bitrate, including possibly a concomitant increase of the symbol rate), he may need to first verify whether the PMD of the existing optical link is sufficiently low to support transmission at this higher bandwidth. If measurements of the link PMD had been taken at some earlier date (e.g. during installation of the fiber plant), the documentation of these measurements may have been lost or misplaced, for instance following acquisition of existing fiber plant purchased from a third party. Furthermore, PMD values taken several years earlier may no longer be indicative of current PMD behavior, due to fiber ageing, etc.

Measurement methods and apparatus suitable for field characterization of fiber plant during initial installation, such as widely-used fixed-analyzer (or "wavelength scanning") [1] and interferometric [2,3] methods, generally require a polarized broadband light source to launch test light, encompassing the spectral region of interest, into one end of the FUT and suitable receiver instrumentation at the opposite end. Obviously, the launch of a continuous spectrum of broadband light from a test source would likely disrupt network operations and, hence, would be incompatible with the concurrent transmission of active data-carrying signals in the same FUT. It would thus be desirable to be able to characterize PMD of an in-service optical link without disrupting the data-carrying signals.

In-service PMD may be determined by two approaches known in the art:

(i) DGD measurements in "dark channels" using test source(s): Polarized light from a test sources (e.g. broadband light, light from a tunable laser source) is launched into one end of the FUT, preferably at a multiplicity of wavelengths corresponding to respective "dark-channel" lightpaths, the wavelengths being distributed over a wide spectral region. At each wavelength, the test light is preferably launched with a multiplicity of substantially different SOPs. The resulting light is detected at the opposite end of the FUT—hence, this approach is classified as being "two-ended". In this way, the $DGD(\upsilon)$ may be determined for each lightpath wavelength. As will be described in detail hereinbelow, this approach advantageously offers good accuracy;

(ii) $DGD_P$ measurements using "live" signal(s): In place of "test sources", at least one, and preferably a multiplicity of widely-spaced data-carrying signals of the in-service network are used, the launched SOPs of which generally do not vary substantially with time. In this way, the $DGD_P(\upsilon)$ or $DGD_P(\upsilon,t)$ may be measured for each lightpath wavelength. As will be discussed hereinbelow, advantages are that test equipment need be placed only at one location (i.e. no test source is required) and that the measurement is completely "non-intrusive", since light may be detected via existing tap couplers along the link. (Although a dedicated test source is not required in this approach, since the live data-carrying signals serve as "test sources", it is convenient also to classify this approach as being "two-ended", in opposition to "single-ended" OTDR-based to be described hereinbelow.)

3) Single-Ended Measurement of Overall PMD of an Inactive Optical Link

Prior art approaches for measurement of overall (i.e. "end-to-end") PMD in an (unlit) optical link usually involve launching polarized light from a test source into one end of the FUT, detecting and analyzing the light exiting the FUT, and deducing the PMD therefrom using suitable analysis. However, there are significant additional operational costs involved with placing a dedicated source at one end and the measurement equipment at the other, in addition to the difficulties often associated with providing regular communication between the equipment placed at the opposing ends.

There is therefore a need for a single-ended measurement approach necessitating minimal intervention at the opposite end of the FUT, and which furthermore would be capable of measurement over the often 80 km or longer spans between optical amplifiers or ROADMs, etc.

4) Measurement of Cumulative PMD Along an Inactive Optical Link

As explained in commonly-owned U.S. Pat. No. 6,724,469 (Leblanc), in optical communication systems, an unacceptable overall polarization mode dispersion (PMD) level for a particular long optical fiber may be caused by one or more short sections of the optical fiber link. Where, for example, a network service provider wishes to increase the bit rate carried by an installed optical fiber link, say up to 40 Gb/s, it is important to be able to obtain a distributed measurement of PMD, i.e., obtain the PMD information against distance along the fiber, and locate the singularly bad fiber section(s) so that it/they can be replaced—rather than replace the whole cable.

Accordingly, Leblanc discloses a method of measuring distributed PMD which uses a polarization OTDR, to identify high or low PMD fiber sections, but does not provide a truly quantitative PMD value for the FUT. Consequently, because of its inherently "qualitative" nature, Leblanc's technique is not entirely suitable for development as a commercial single-ended overall PMD testing instrument that may measure the total PMD value for the entire of fiber link.

It is known to employ a so-called polarization-sensitive optical time domain reflectometer (POTDR; also commonly referred to as a "Polarization optical time domain reflectometer") to try to locate such "bad" sections. Basically, a POTDR is an OTDR that is sensitive to the state of polarization (SOP) of the backreflected light. Whereas conventional OTDRs measure only the power of backreflected light to determine variation of attenuation along the length of an optical path, e.g., an installed optical fiber, POTDRs utilize the fact that the backreflected light also exhibits polarization dependency in order to monitor polarization dependent characteristics of the transmission path. Thus, the simplest POTDR comprises an OTDR having a polarizer between its output and the fiber-under-test (FUT) and an analyzer in the return path, between its photodetector and the FUT. (It should be appreciated that, although a typical optical transmission path will comprise mostly optical fiber, there will often be other components, such as couplers, connectors, etc., in the path. For convenience of description, however, such other components will be ignored, it being understood, however, that the term "FUT" used herein will embrace both an optical fiber and the overall transmission path to be characterized, according to context.)

A detailed review of the relevant prior art is provided in United States patent publication number US2010/0073667 A1 supra.

In order that the cumulative PMD may be characterized along fiber lengths commonly used in installed systems, typically spanning the 60-80 km distances between optical amplifiers, ROADMs, etc. in optical networks, the POTDR should have a dynamic range sufficient to characterize at least half the end-to-end fiber length. The other half may then be characterized by repeating the measurement process from the other end of the link, and the data from each end may be "stitched" together to provide a full cumulative PMD profile along the link.

(In this specification, the term "cumulative PMD" is used to distinguish from the aforementioned "overall" PMD that is traditionally measured from end-to-end. Because PMD is not a localized quantity, PMD(z) is an integral from 0 to z, bearing resemblance to a cumulative probability rather than the probability distribution. When distance z is equal to the overall length of the FUT, of course, the cumulative PMD is equal to the overall PMD.)

SUMMARY OF THE INVENTION

The present invention seeks to eliminate, or at least mitigate, the disadvantages of the prior art discussed above, or at least provide an alternative.

According to one aspect of the present invention there is provided a method of measuring a polarization-related characteristic of an optical path (18) wherein light comprising polarized light is propagated, the method comprising the steps of using:

polarization-controller-and-analyzer means (14,20A; 14A,14B,20; 14A,14B,20A; 14,20; 14,20C; 14A,45) connected to the optical path at or adjacent either the proximal end thereof or a distal end thereof to control at least one of state of polarization (I-SOP) of light launched in the optical path and state of polarization (A-SOP) used to analyze light leaving the optical path, detecting means (22; 22A,22B; 22D) to detect the analyzed light and provide corresponding detection signals, and processing means (40) to process the detection signals to derive said polarization-related characteristic, wherein said light leaving the optical path is analyzed to provide transmitted coherent optical power at each wavelength of light in each of at least two groups of wavelengths, and wherein the lowermost ($\lambda_L$) and uppermost ($\lambda_U$) said wavelengths in each said group of wavelengths are separated by a first small optical frequency difference;

and wherein each of the said at least two groups comprises a wavelength pair, said pair in each group defining a midpoint wavelength therebetween, and being mutually spaced by a second small optical-frequency difference, the second small optical-frequency difference being equal to or less than the first optical-frequency difference, said second small optical-frequency difference ($\delta v$) being the same for corresponding wavelength pairs in different groups, and wherein the I-SOP and A-SOP are substantially constant for each coherent optical power at each said wavelength in each said group, and wherein at least one of the midpoint wavelength, I-SOP and A-SOP is different between the respective said groups, the processing step including the steps of:

(i) computing at least one difference between a pair of measured power parameters each corresponding to a respective one of the wavelengths in said wavelength pair for each of the said at least two groups, each said measured power parameter being proportional to transmitted coherent optical power of the said analyzed and subsequently detected light, thereby defining for said at least two groups a set of at least two measured power parameter differences;

(ii) computing a mean-square value of said set of at least two measured power parameter differences; and (iii) calculating the polarization-related optical path characteristic as a predetermined function of said mean-square value, said predetermined function being dependent upon the said second small optical-frequency difference between the wavelengths corresponding to the said each of at least said two pairs of wavelengths.

According to a second aspect of the invention, there is provided measurement instrumentation for measuring a polarization-related characteristic of an optical path (18) wherein light comprising polarized light is propagated, the measurement instrumentation comprising:

polarization-controller-and-analyzer means (14,20A; 14A,14B,20; 14A,14B,20A; 14,20; 14,20C; 14A,45) for connection to the optical path at or adjacent either the proximal end thereof or a distal end thereof and operable to control at least one of a state of polarization (I-SOP) of light launched in the optical path and a state of polarization (A-SOP) used to analyze light leaving the optical path, detecting means (22; 22A,22B; 22D) for detecting the analyzed light corresponding to at least one analyzer SOP (A-SOP) and providing corresponding detection signals, and processing means (40) for processing the detection signals to derive said polarization-related characteristic, wherein said light leaving the optical path is analyzed to provide transmitted coherent optical power at each wavelength of light in each of at least two groups of wavelengths, and wherein the lowermost ($\lambda_L$) and uppermost ($\lambda_U$) said wavelengths in each said group of wavelengths are separated by a first small optical frequency difference;

and wherein each of the said at least two groups comprises a wavelength pair, said pair in each group defining a midpoint wavelength therebetween, and being mutually spaced by a second small optical-frequency difference, the second small optical-frequency difference being equal to or less than the first small optical-frequency difference, and defining a midpoint wavelength therebetween, said second small optical-frequency difference ($\delta v$) being the same for corresponding wavelength pairs in different groups, and wherein the I-SOP and A-SOP are substantially constant for each said wavelength in each said group, and wherein at least one of the midpoint wavelength, I-SOP and A-SOP is different between the respective said groups, the measurement instrumentation being operable to:

i) compute at least one difference between a pair of measured power parameters each corresponding to either or an average of the measured optical power parameters at wavelengths corresponding to respective ones of a wavelength pair centered about said midpoint wavelength, said wavelength pair comprised within each of the said at least two groups, each said measured power parameter being proportional to transmitted coherent optical power of the said analyzed and subsequently detected light, thereby defining for said at least two groups a set of at least two measured power parameter differences;

ii) compute a mean-square value of said set of at least two measured power parameter differences; and iii) calculate the polarization-related optical path characteristic as a predetermined function of said mean-square value, said predetermined function being dependent upon the said second small optical-frequency difference between the wavelengths corresponding to the said each of at least said two pairs of wavelengths.

According to a third aspect of the invention, there is provided a method of measuring a polarization-related characteristic of an optical path wherein light comprising polarized light is propagated, the method comprising:

polarization analyzing light having propagated in the optical path according to at least two different analyzer states of polarization (A-SOP);

for each said at least two different analyzer states of polarization:

detecting transmitted coherent optical power of the analyzed light at each wavelength of light in a group of wavelengths, wherein said group comprises at least one wavelength pair, said pair defining a midpoint wavelength therebetween and being mutually spaced by a small optical-frequency difference, and computing a difference between a pair of measured power parameters each corresponding to a respective one of the wavelengths in said wavelength pair, each said measured power parameter being proportional to transmitted coherent optical power of the said analyzed and subsequently detected light, thereby defining a set of corresponding at least two measured power parameter differences;

computing a mean-square value of said set of measured power parameter differences; and calculating the polarization-related optical path characteristic as a predetermined function of said mean-square value.

Preferred embodiments and implementations of the foregoing aspects of the invention are set out in the dependent claims appended hereto.

The foregoing and other objects, features, and advantages of the present invention will become more apparent from the following detailed description, in conjunction with the accompanying drawing, of preferred implementations of embodiments of the invention which are described by way of example only.

BRIEF DESCRIPTION OF THE DRAWINGS

Two-Ended "Test-Source-Based" PMD Measurement (FIG. 1 Through 1L)

Two-Ended Partial-DGD Measurement and Determination of PMD Therefrom (FIGS. 2H Through 2K, and 11 Through 13)

(For ease of understanding, the letter suffixes of FIGS. 2H to 2K have been chosen to indicate similarities in the basic hardware between these Figures and their counterparts, FIGS. 1H to 1K, for the two-ended "test-source-based" implementations.)

Figure 2H:
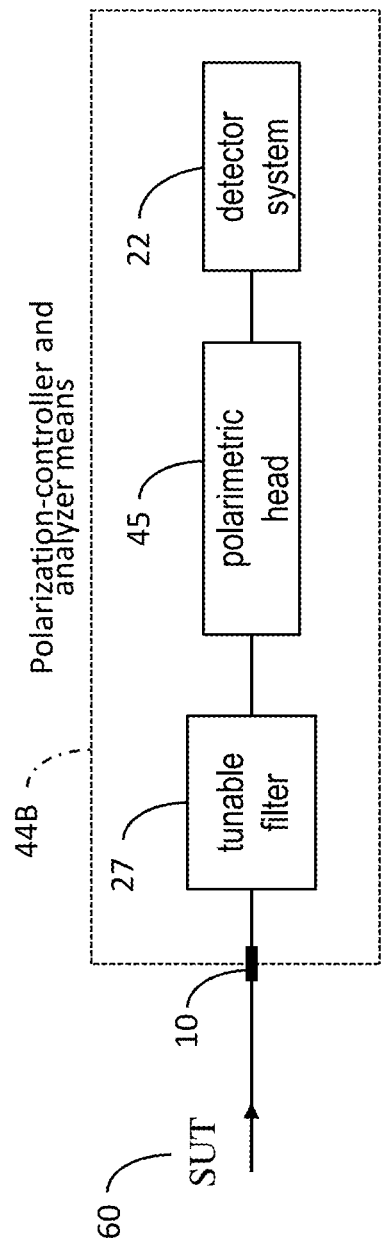

FIG. 2H is a simplified schematic illustration of measurement instrumentation suitable for measurement of partial-DGD, employing narrow-band tunable filtering (i.e. having a spectral passband less than the spacing of the closely-spaced optical frequencies to be measured), and employing a polarimetric head as a polarization analyzer.

Figure 1:
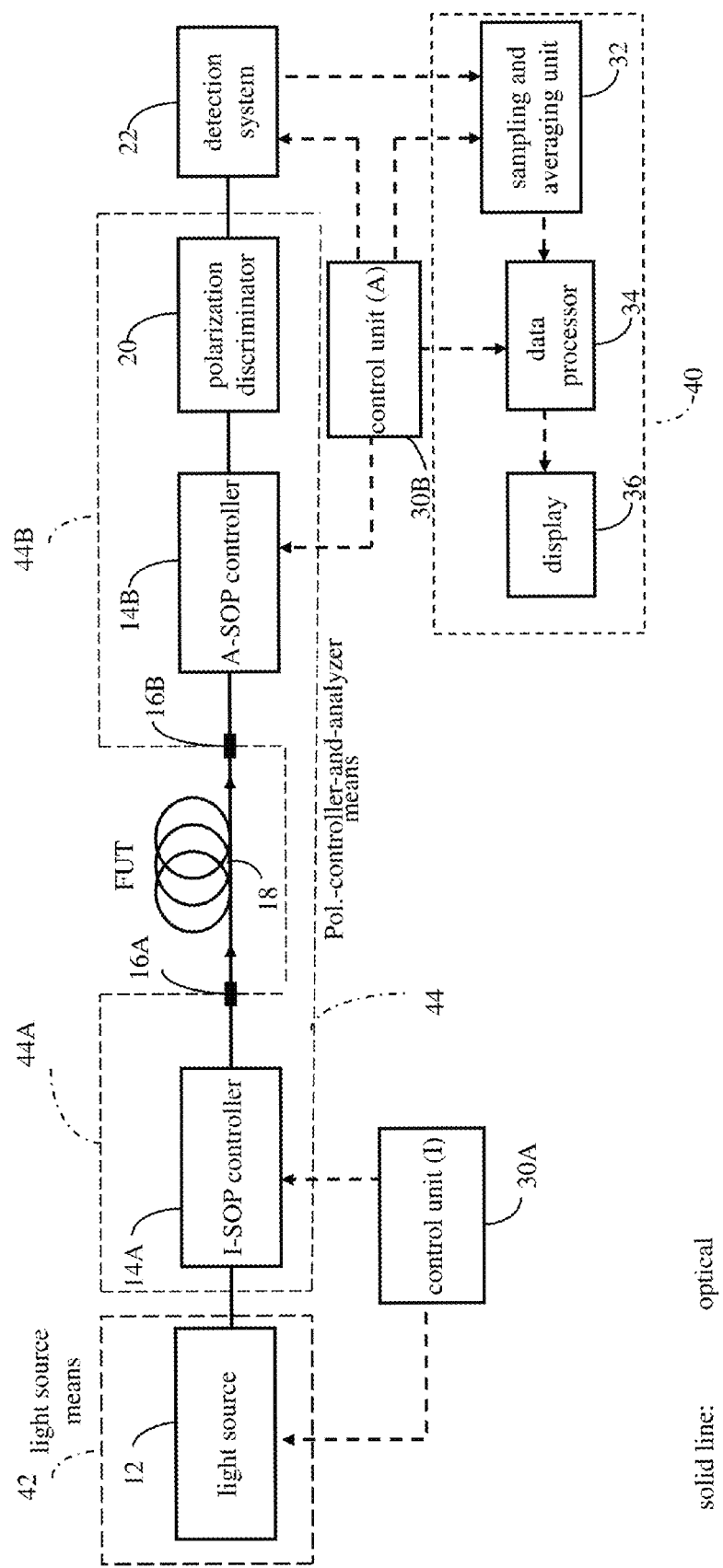
FIG. 1 is a simplified generalized schematic illustration measurement instrumentation having two portions connected to opposite ends, respectively, of an optical path, specifically a fiber-under-test (FUT), for performing two-ended measurements on the optical path to determine DGD at one or more wavelengths and/or mean DGD and/or rms DGD.
Figure 2I:
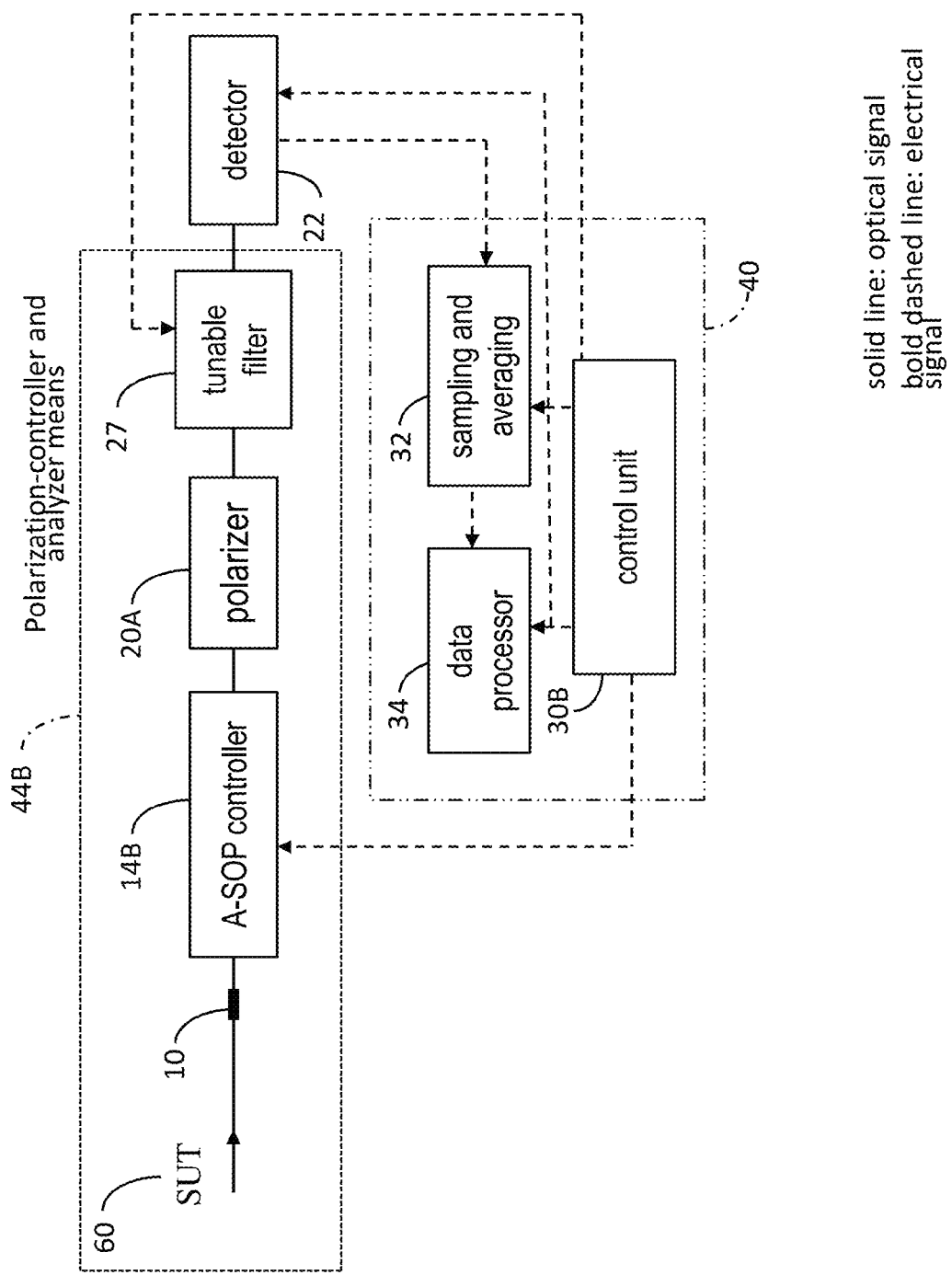
Figure 2J:
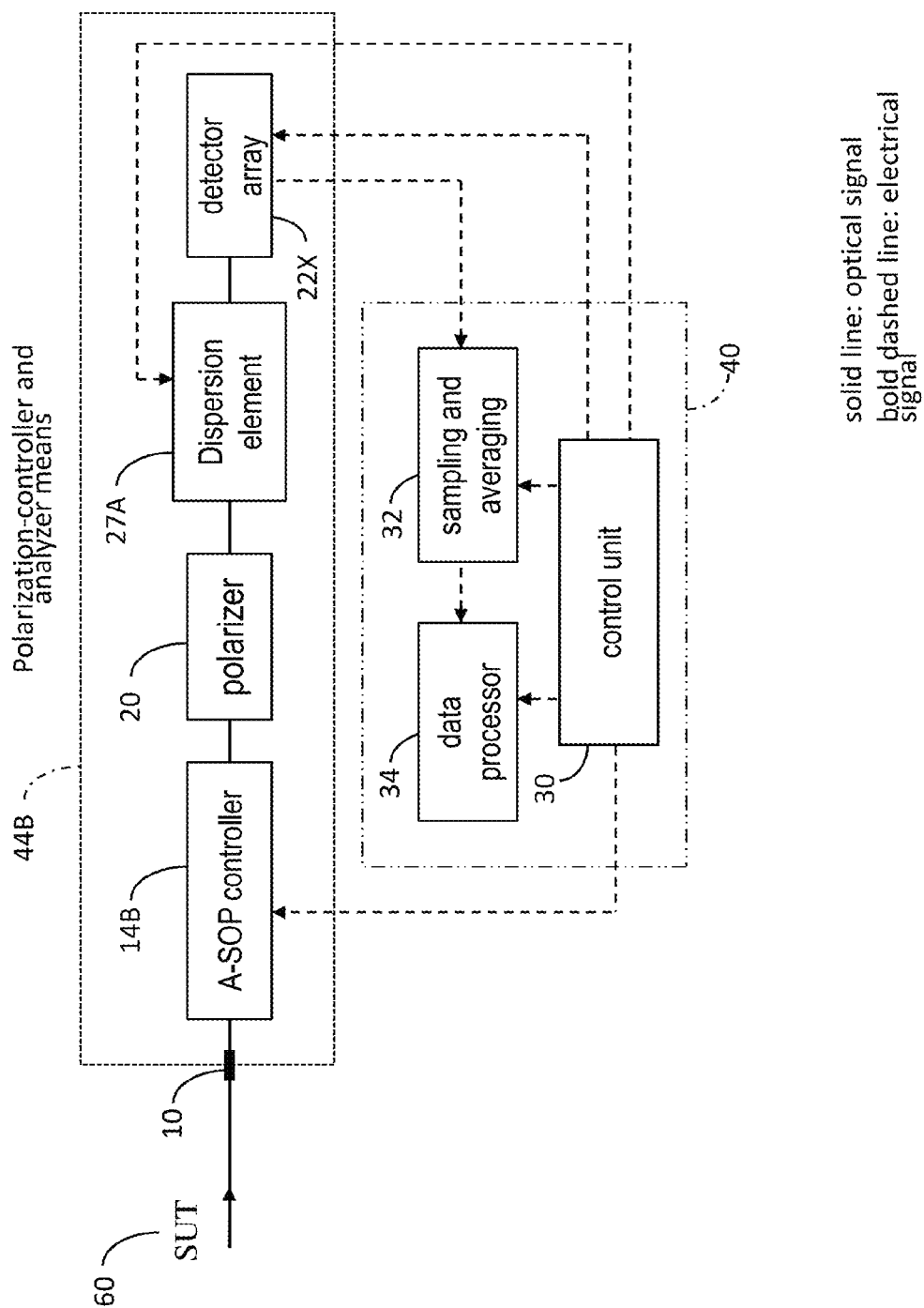
Figure 2K:
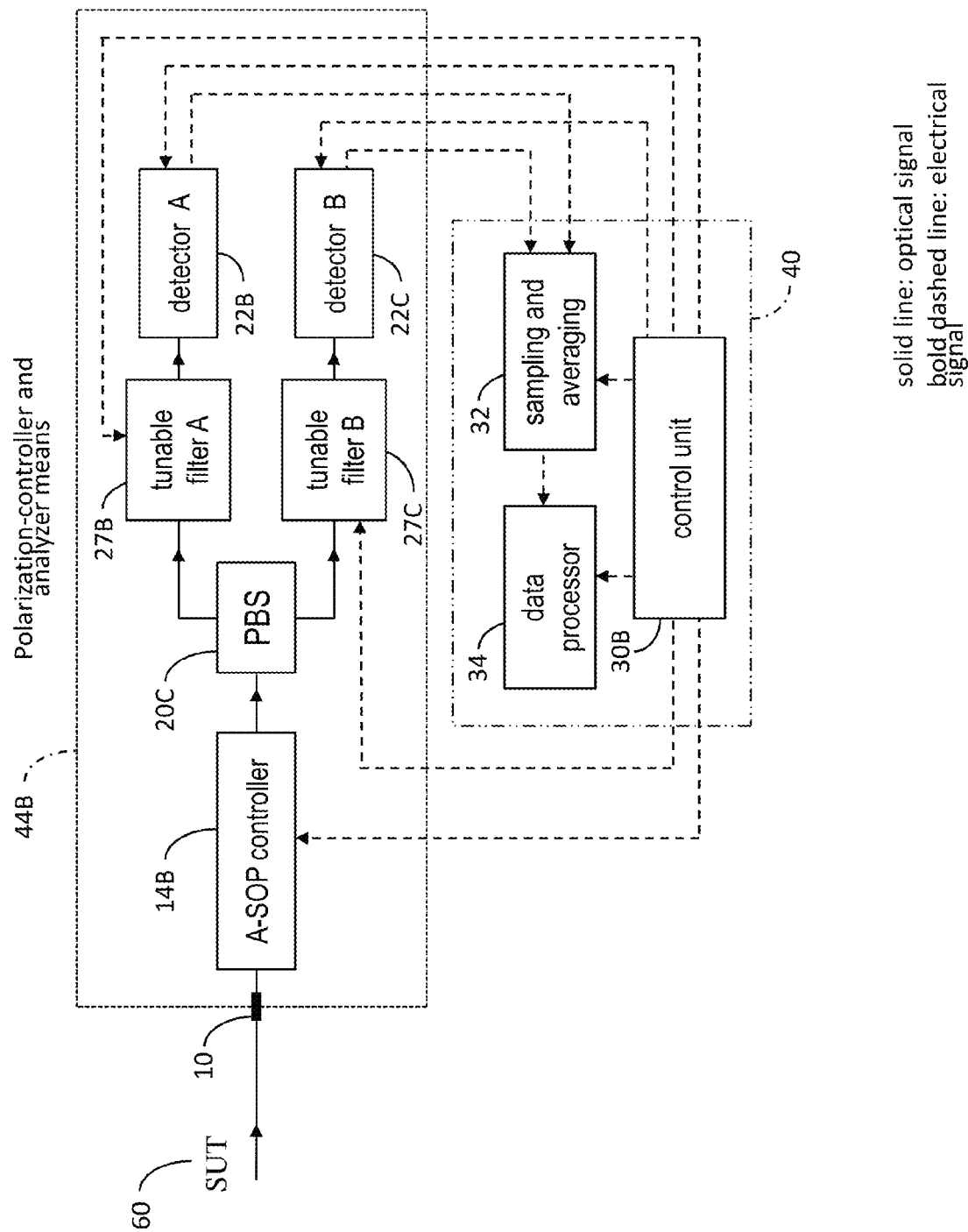
Figure 2M:
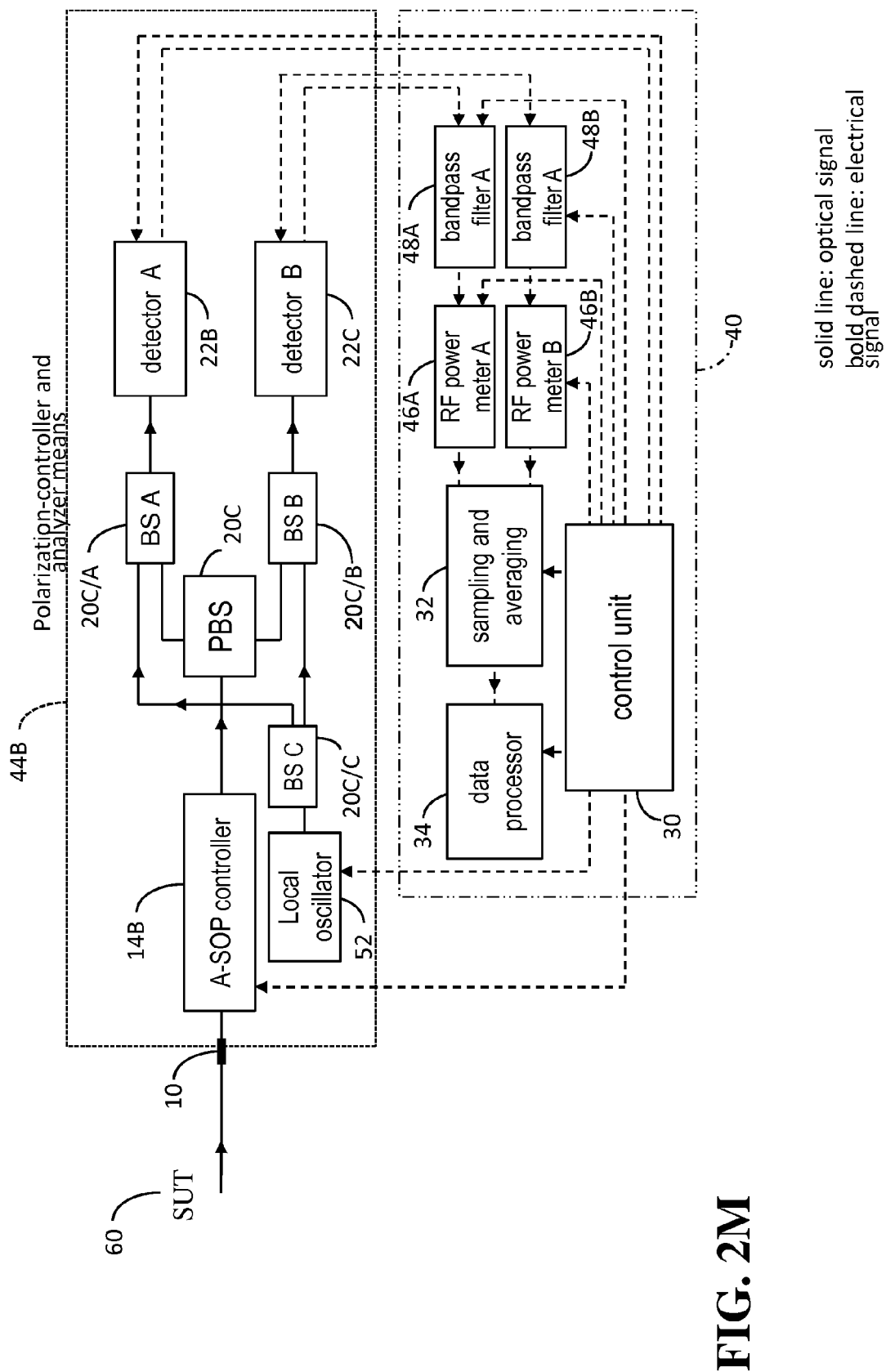
Figure 2N:
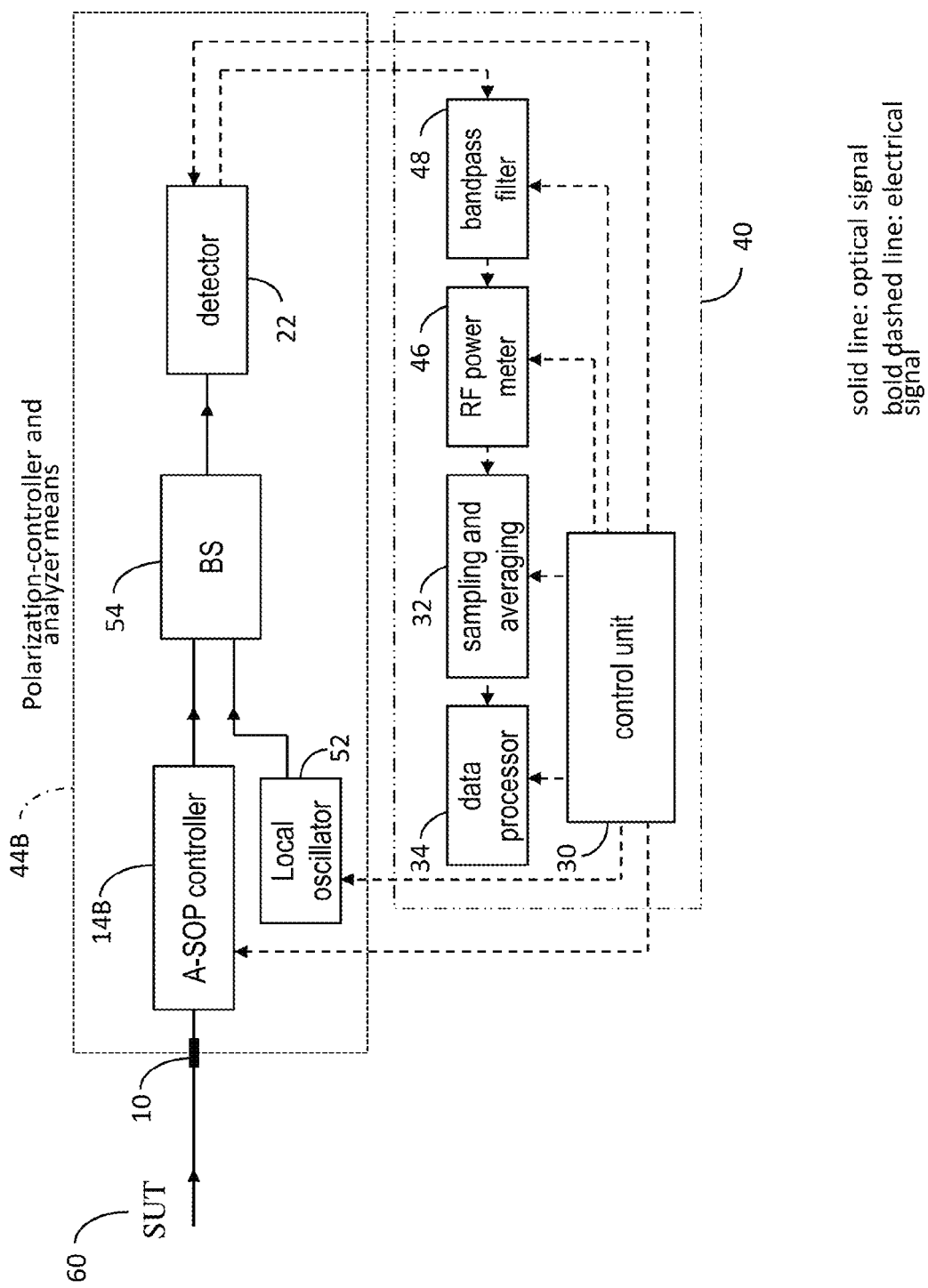
Figure 11:
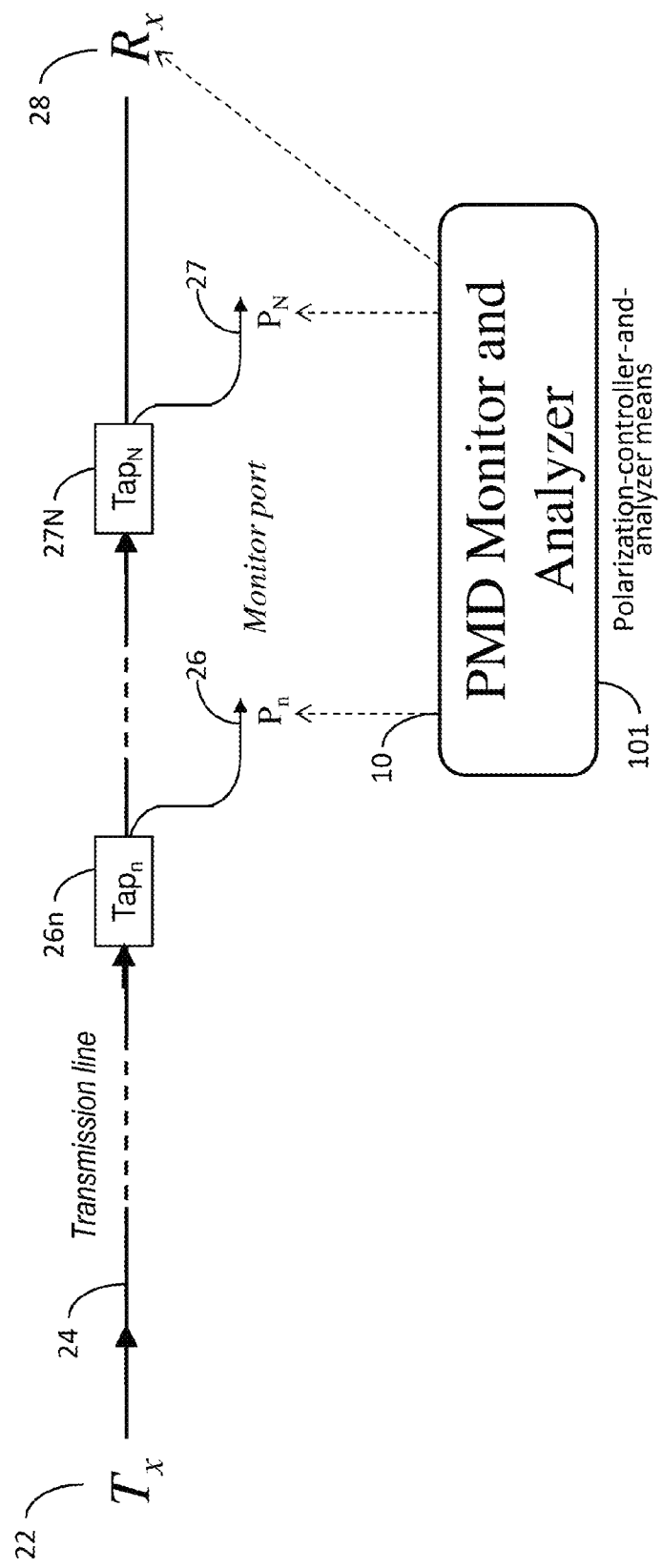
Figure 12A:
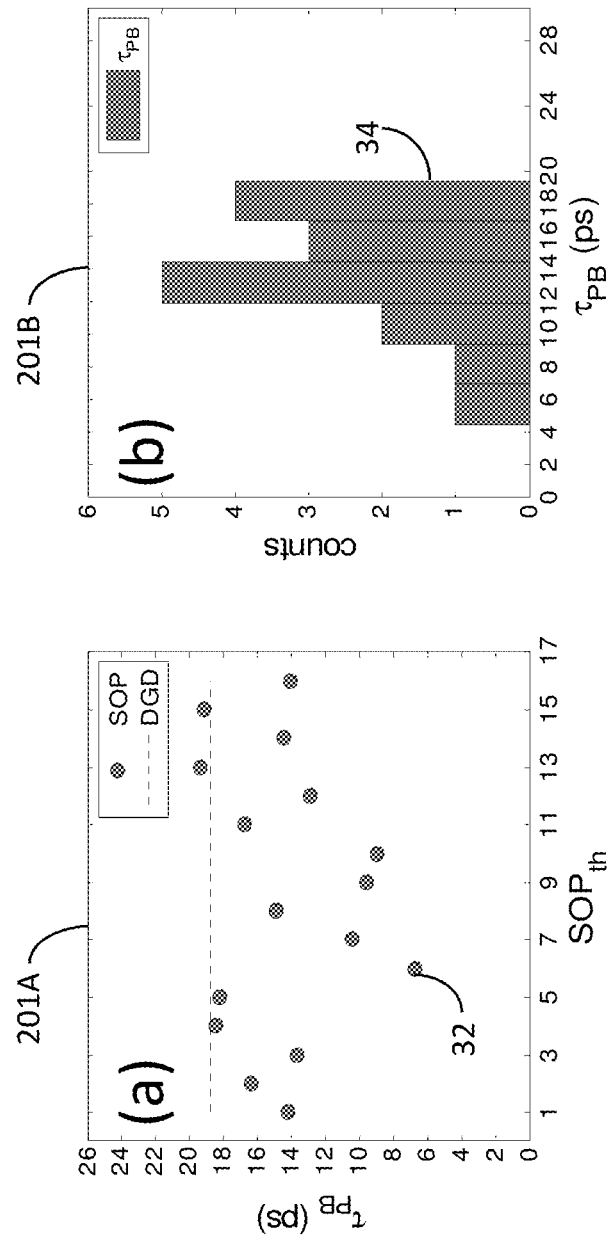
Figure 12B:
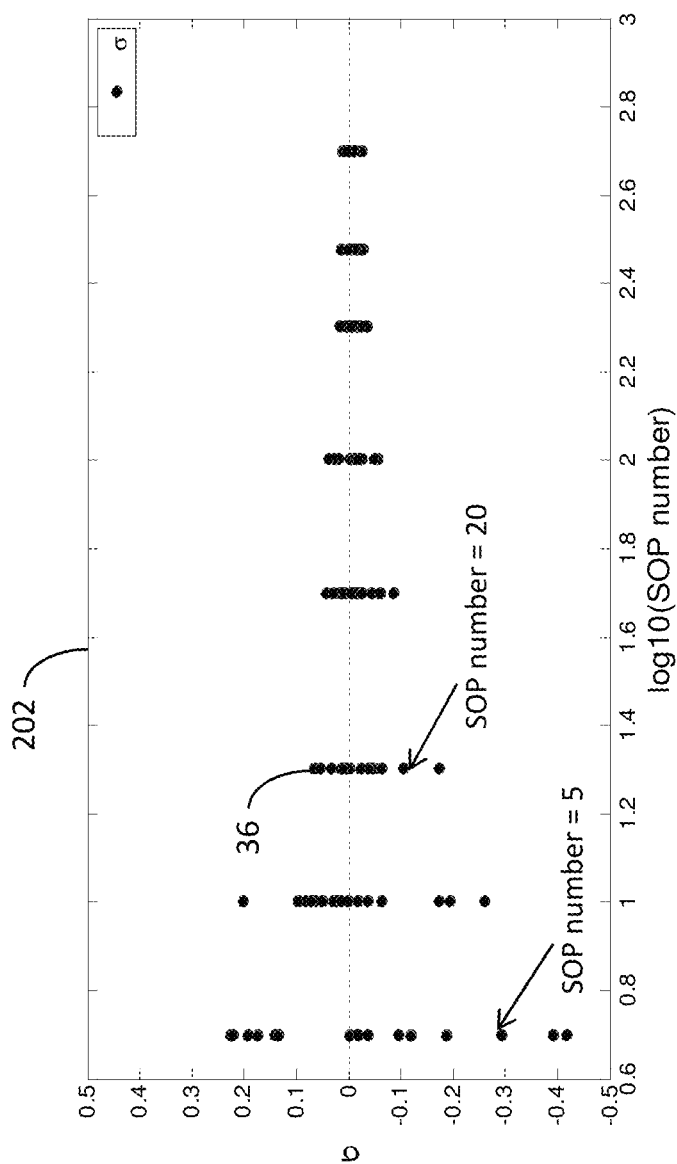
Figure 13:
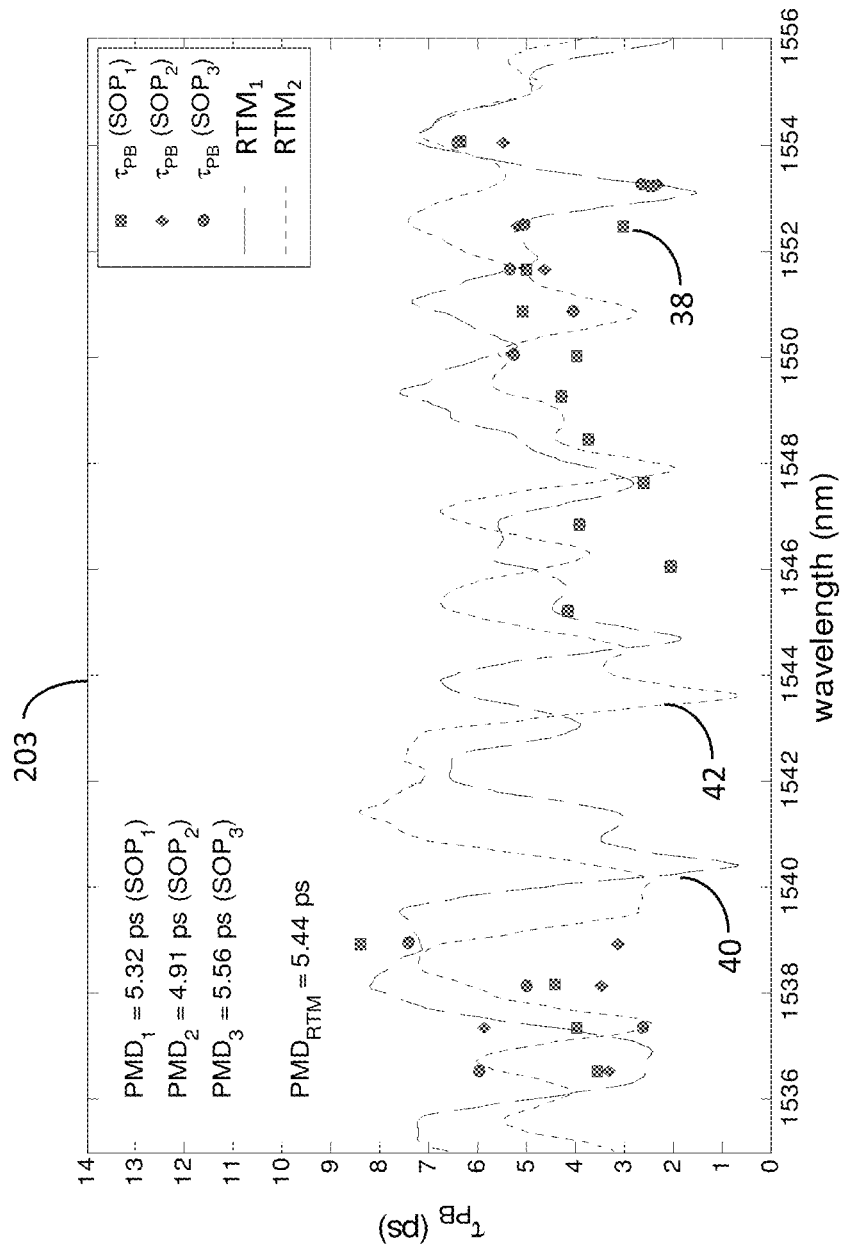

FIG. 2I is a schematic diagram measurement instrumentation suitable for measurement of partial-DGD, which employs narrow-band tunable filtering, and a polarization controller and polarizer (serving as an analyzer) combination to actively vary the A-SOP. Note that only one detector is used, and hence normalization requires averaging over many approximately uniformly-distributed random A-SOP values; or the generation of a fixed grid of A-SOPs uniformly distributed on the Poincaré Sphere;

FIG. 2J is a simplified schematic illustration similar to FIG. 2I but where a dispersion element (e.g. bulk-optic diffraction grating) and detector array replace the tunable filter and detector;

FIG. 2K is a simplified schematic illustration of elements of partial-DGD measurement instrumentation comprising a polarization beam splitter (PBS) and an A-SOP controller, two tunable filters A and B, and two detectors A and B to measure analyzed light in a polarization-diverse manner. In one embodiment, the A-SOP controller generates random A-SOPs. In a variant, the A-SOP controller generates at least two and preferably three known A-SOPs, preferably mutually orthogonal (90 degrees) on the Poincaré Sphere;

FIG. 2M is a simplified schematic illustration of a high-resolution optical spectrum analyzer based on polarization-diverse heterodyne detection. A narrow-linewidth tunable laser serves as a Local oscillator (LO) and is tuned so that a portion of its light beats with orthogonally-polarized portions of the SUT light at respective detectors, and the relative optical power of the analyzed SUT light at two chosen filtered RF frequencies can be determined. The A-SOP controller, shown disposed along the optical path of the SUT before the PBS, could equivalently be placed along the optical path of the LO light;

FIG. 2N is a simplified schematic illustration similar to FIG. 2M but of measurement instrumentation comprising one detector. The A-SOP controller, shown disposed along the optical path of the SUT before the beamsplitter BS, could equivalently be placed along the optical path of the LO light;

FIG. 11 shows how PMD determination may be carried out using measurement instruments suitable for partial-DGD measurement of a plurality of SUTs at any (non-filtered) monitoring point along a link. For the case of a filtered monitoring port (e.g. an optical DeMux port), DGDP of the respective SUT may be measured/monitored;

FIG. 12A illustrates several measured $DGD_P$ for different fiber-launched input SOPs corresponding to a SUT having a fixed DGD value of 18.5 ps, obtained using prototype instrumentation corresponding to the design shown in FIG. 2K;

FIG. 12B plots $DGD_P$ measurement uncertainty ($\sigma$) vs the number of A-SOPs associated with the particular measurement, for a test setup having a fixed DGD value of 18.5 ps using a prototype instrument based on the embodiment of FIG. 2K;

FIG. 13 shows an example of PMD values corresponding to three different measurements (i.e. 5.32 ps, 4.91 ps, and 5.56 ps, respectively) of a particular fiber link comprising a PMD emulator derived from $DGD_P$ measurements of sixteen different 50-GHz-spaced live ITU channels, using a prototype instrument based upon the design of FIG. 1. The "expected" PMD value of 5.44 ps was determined by averaging two separate results as measured by a Reference Test Method (RTM) between 1530 nm and 1610 nm.

Figure 3:
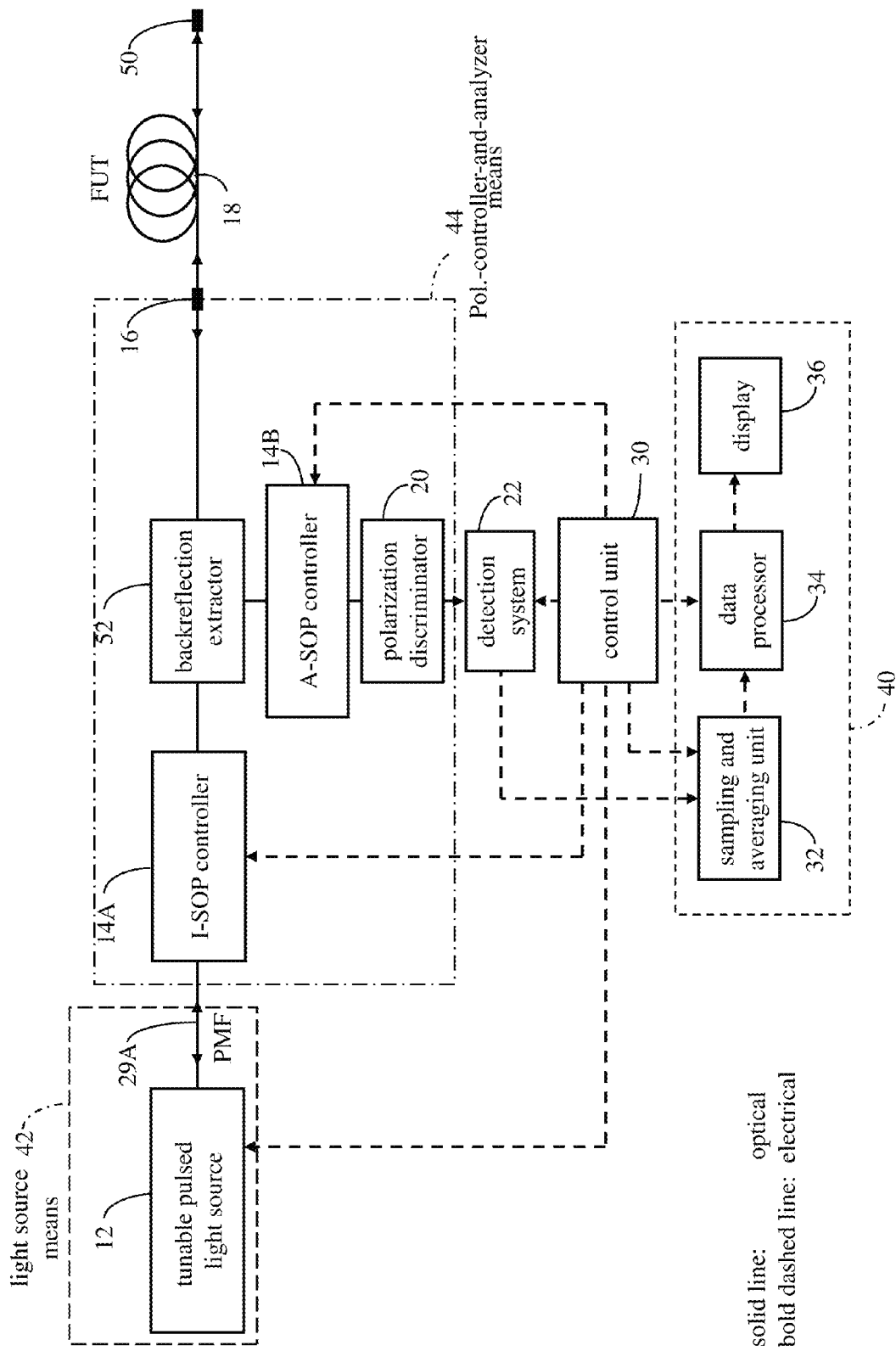
Figure 3B:
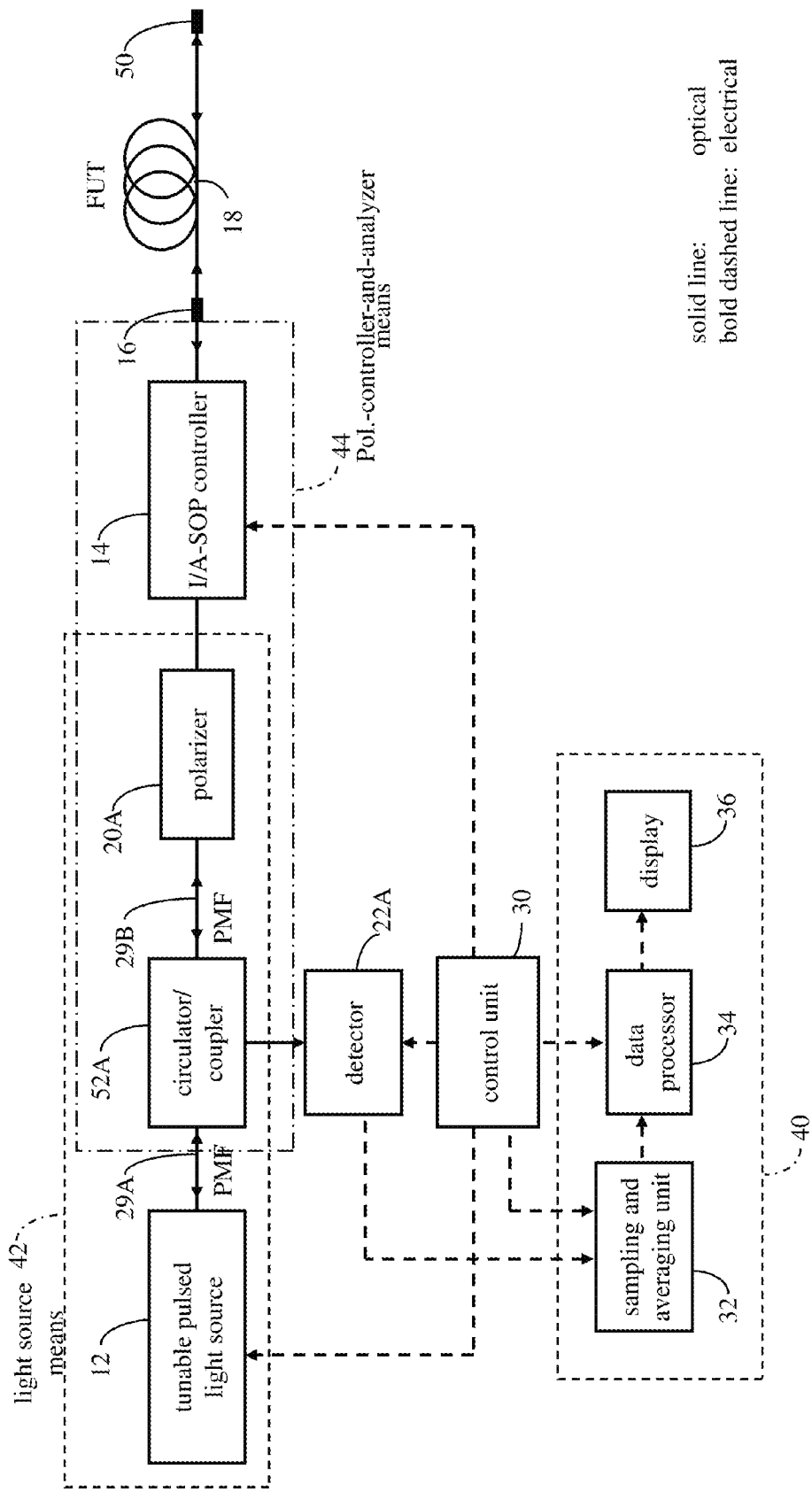
Figure 3C:
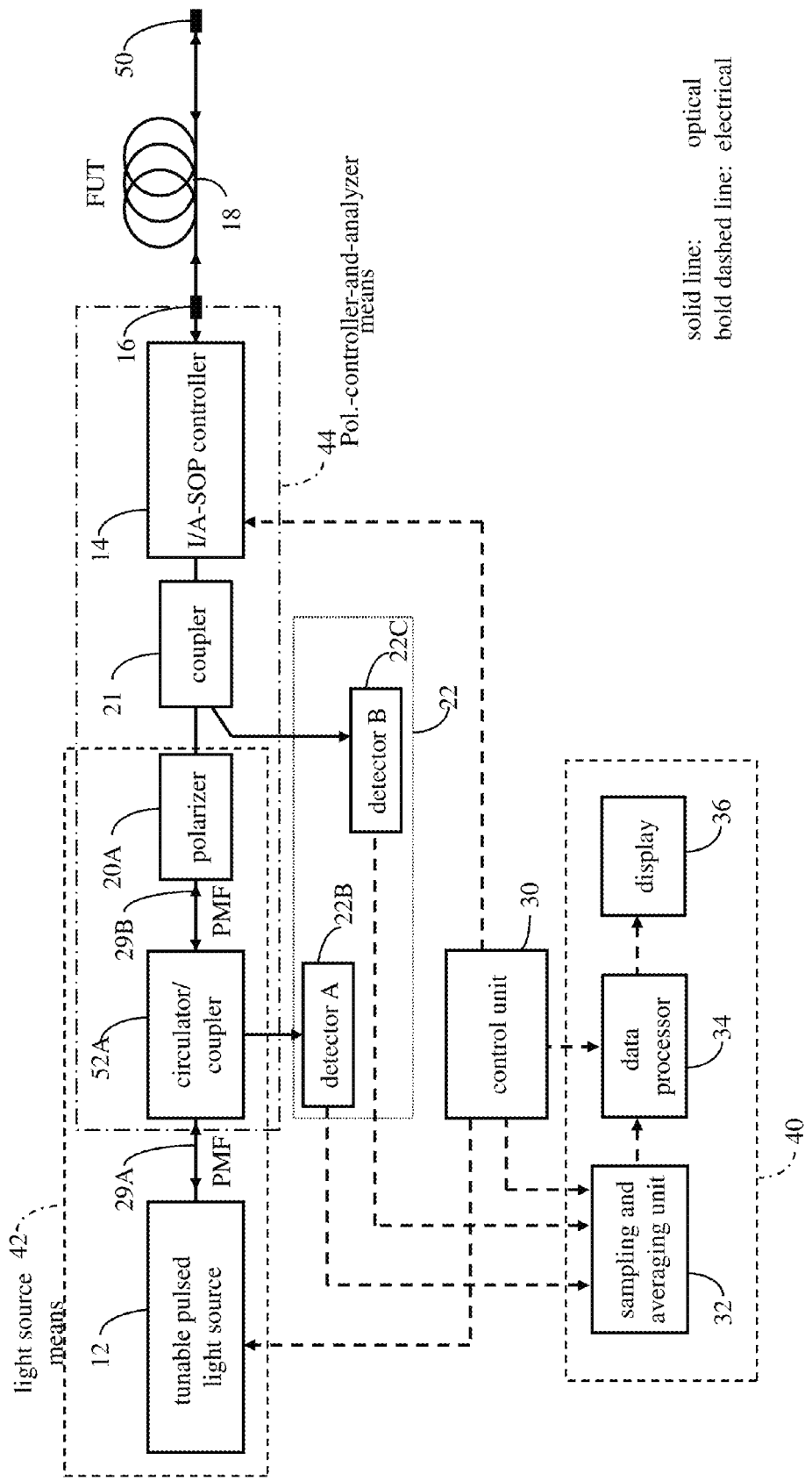
Figure 3D:
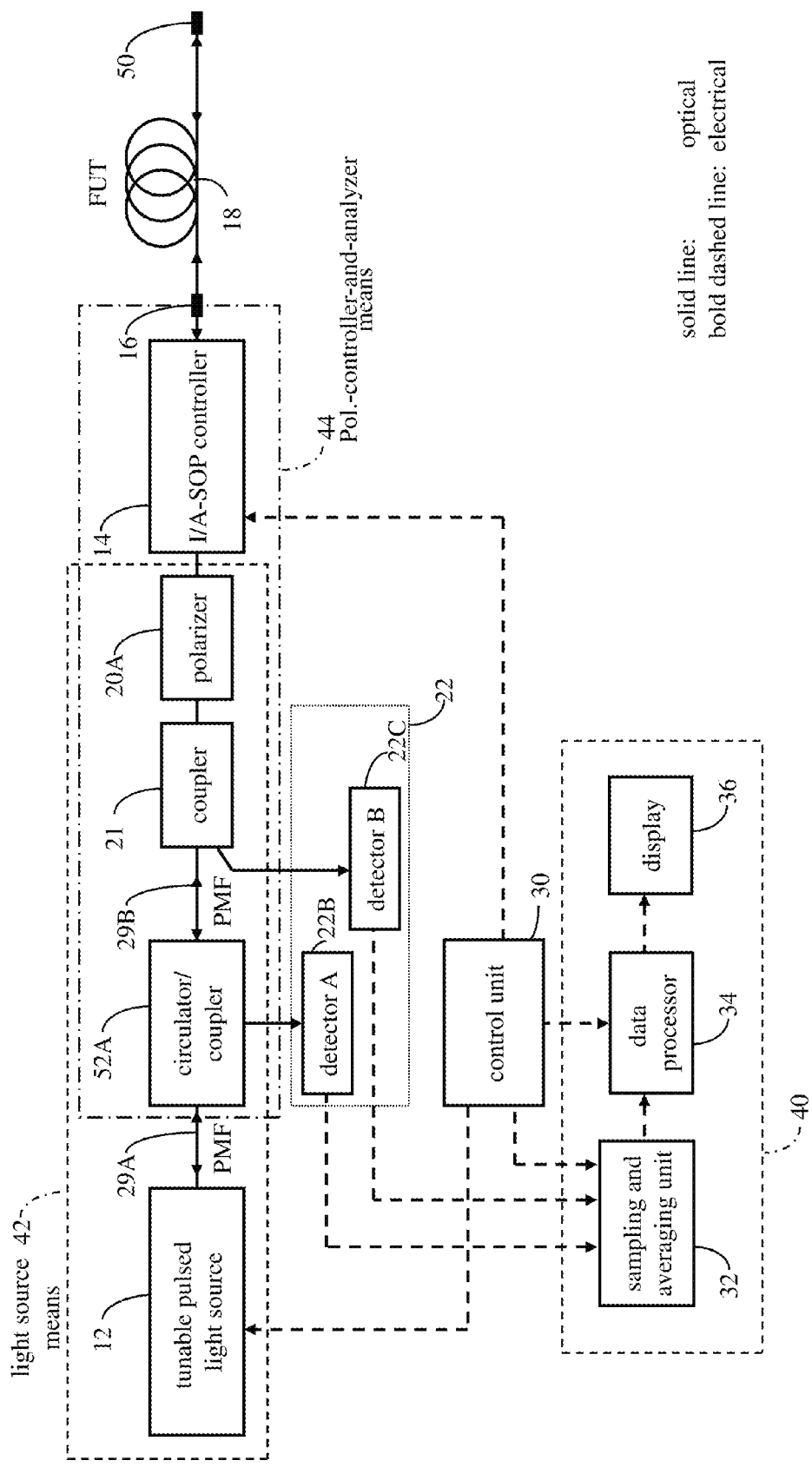
Figure 3E:
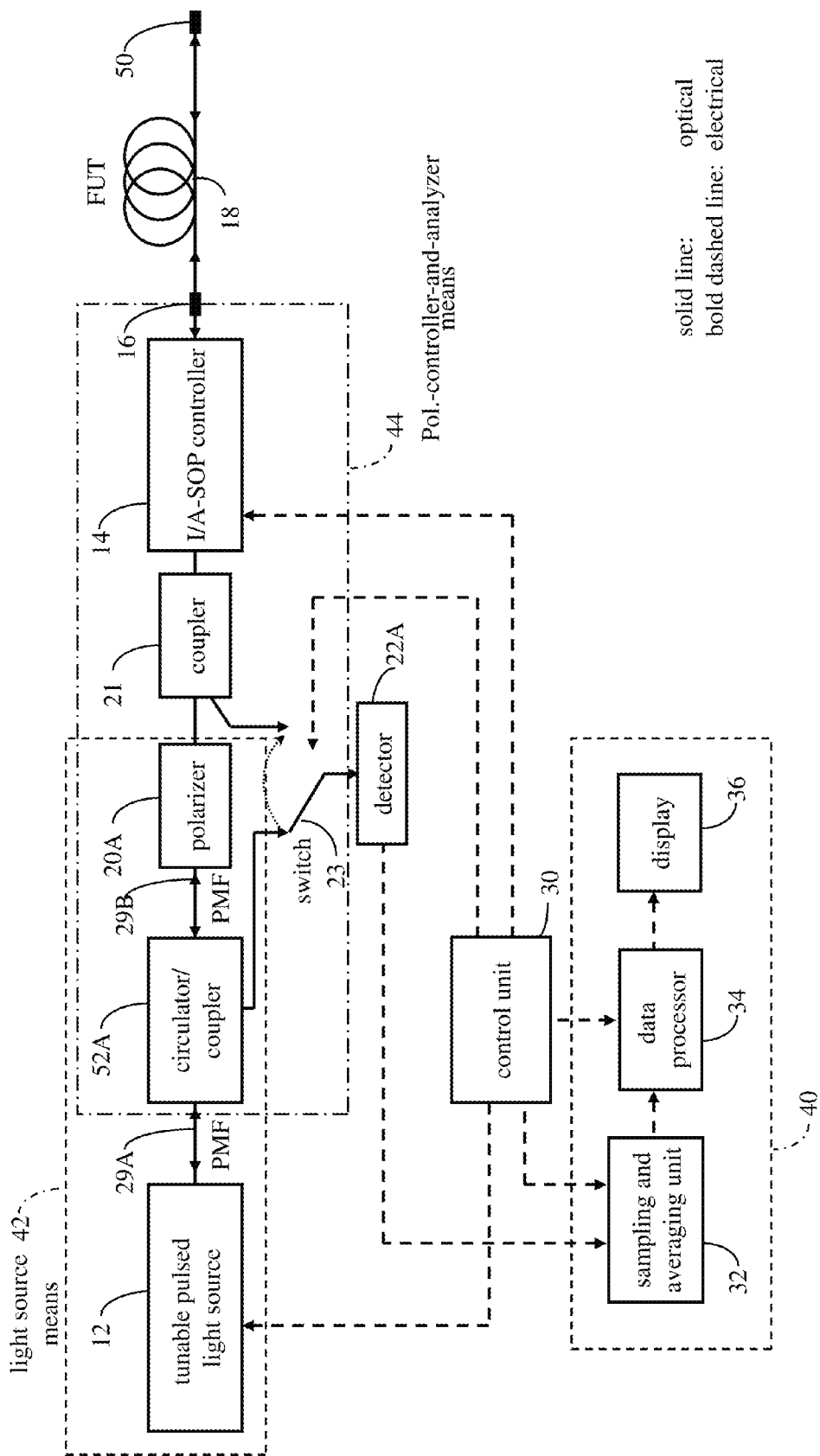
Figure 3F:
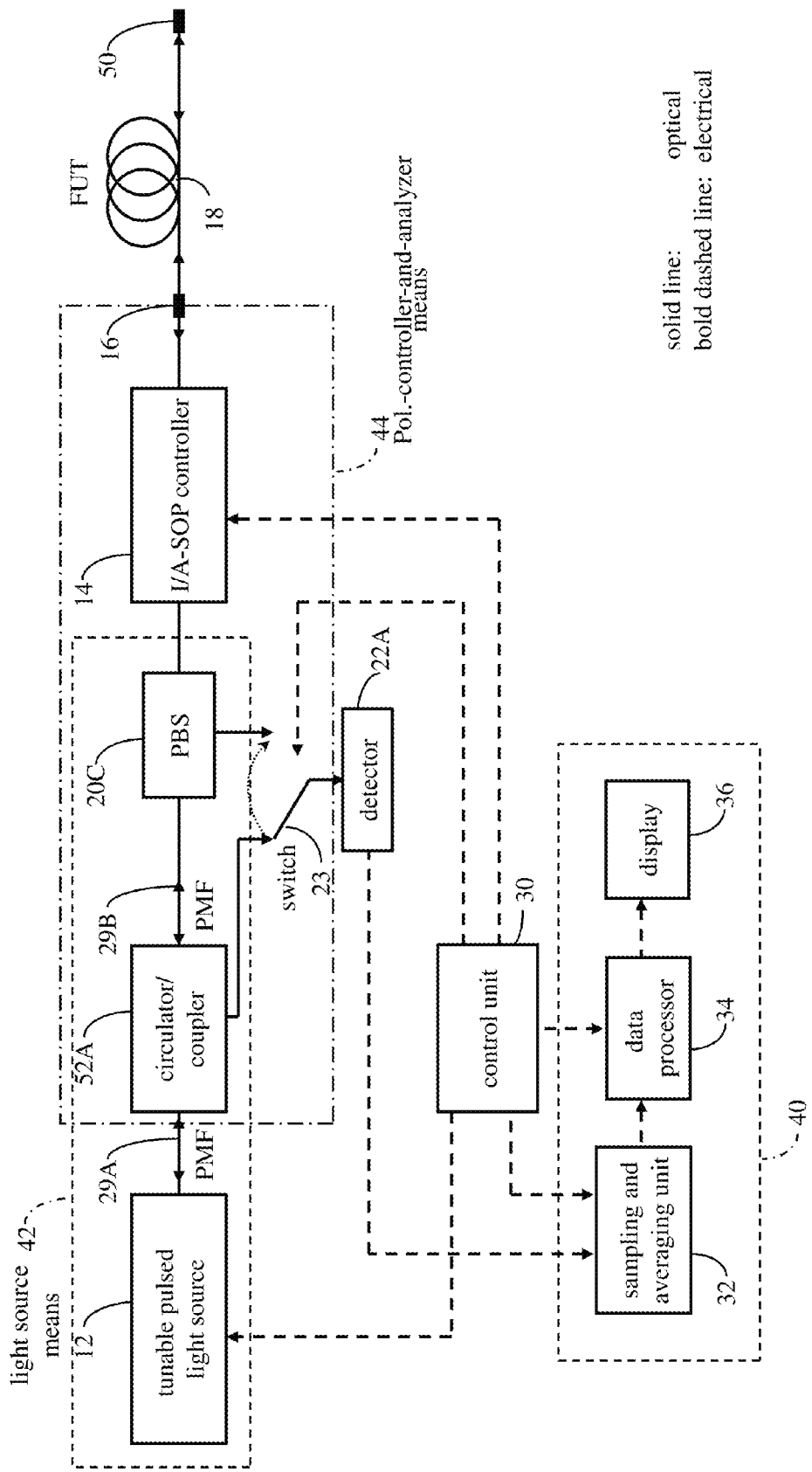
Figure 3G:
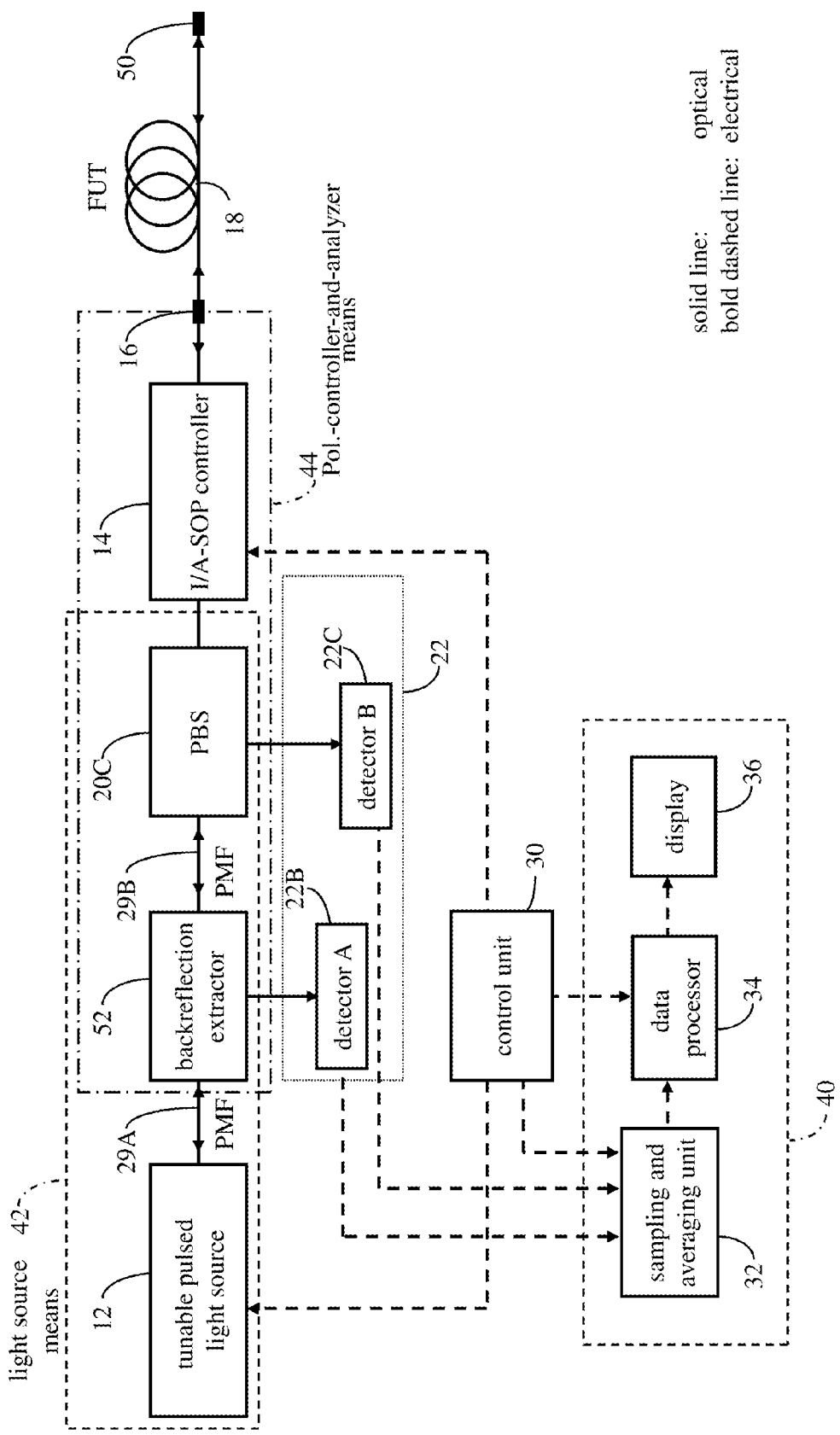

Single-Ended Overall PMD Measurement (FIGS. 3-3G)

FIG. 3 corresponds to FIG. 1 but is a simplified schematic diagram of measurement instrumentation for single-ended measurement of overall PMD;

FIGS. 3B to 3G correspond to FIGS. 1B to 1G, respectively, and illustrate corresponding single-ended measurement instrumentation in which both portions of the measurement instrumentation are at the same, proximal end of the FUT.

Single-Ended Cumulative PMD Measurement

Figure 1B:
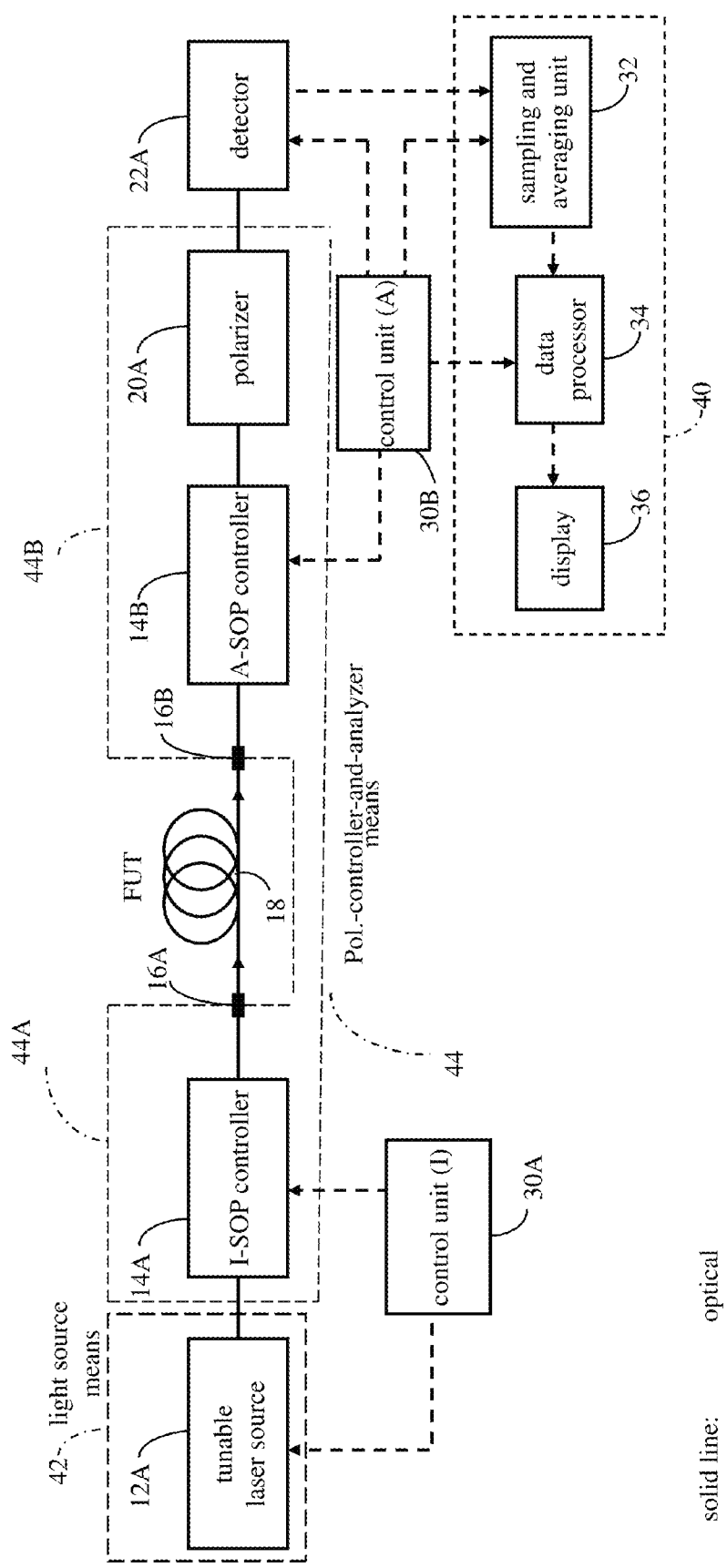
FIG. 1B is a simplified schematic diagram similar to FIG. 1 but of measurement instrumentation using a tunable laser light source, one input-SOP controller (scrambler), one analyzer SOP (A-SOP) controller (scrambler), a polarizer/analyzer and where only the analyzed light is detected, by means of one detector, and where normalization of the detected powers is carried out by means of an averaging procedure over a plurality of acquisitions.
Figure 1C:
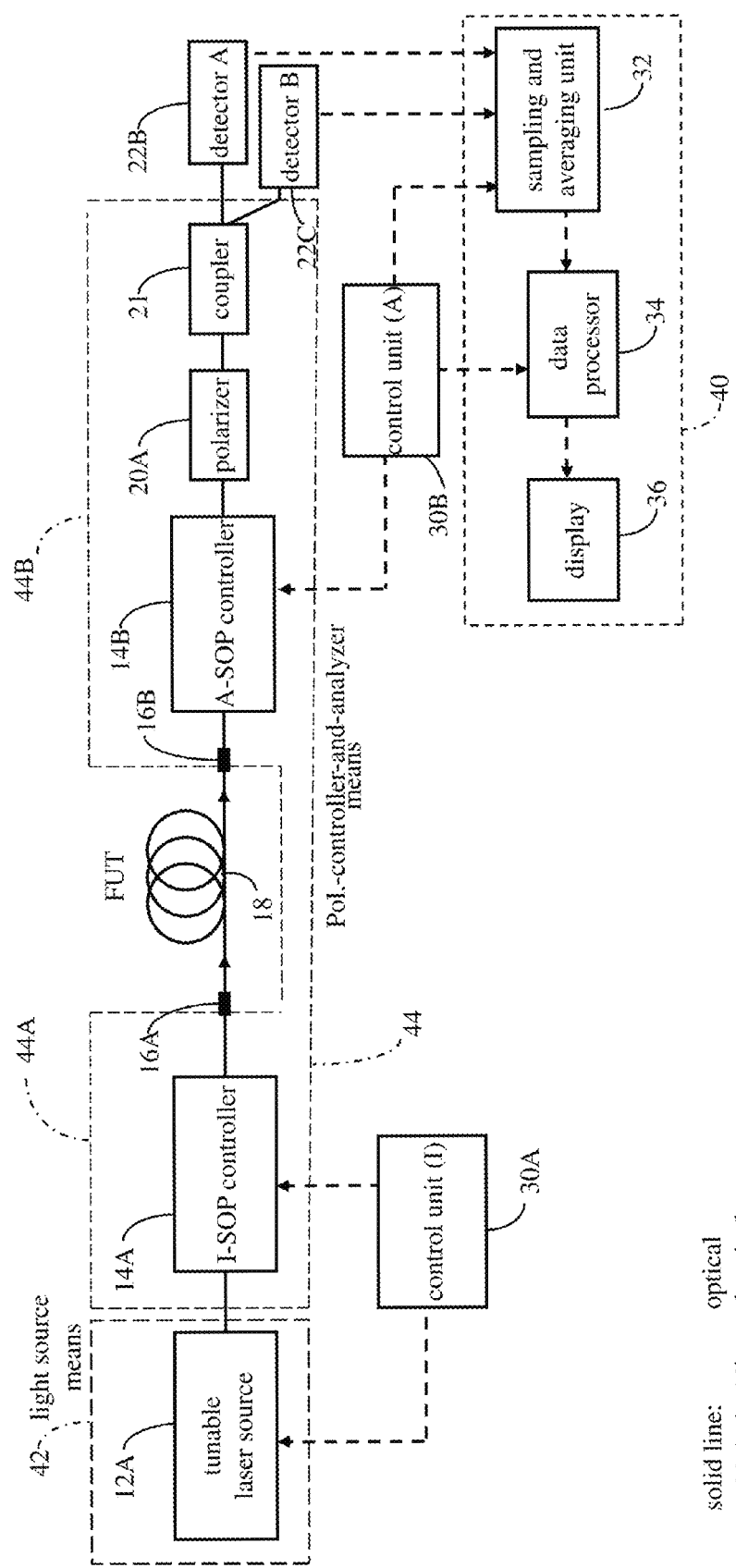
FIG. 1C is a simplified schematic diagram of measurement instrumentation similar to that illustrated in FIG. 1B, for which normalization of the detected analyzed powers is also carried out by means of an averaging procedure over a plurality of acquisitions, but where the analyzed light is split into two parts and respectively detected by two detectors connected to the coupler, in order to measure simultaneously two repeated powers, thereby reducing uncorrelated noise contributions to the measurement.
Figure 1D:
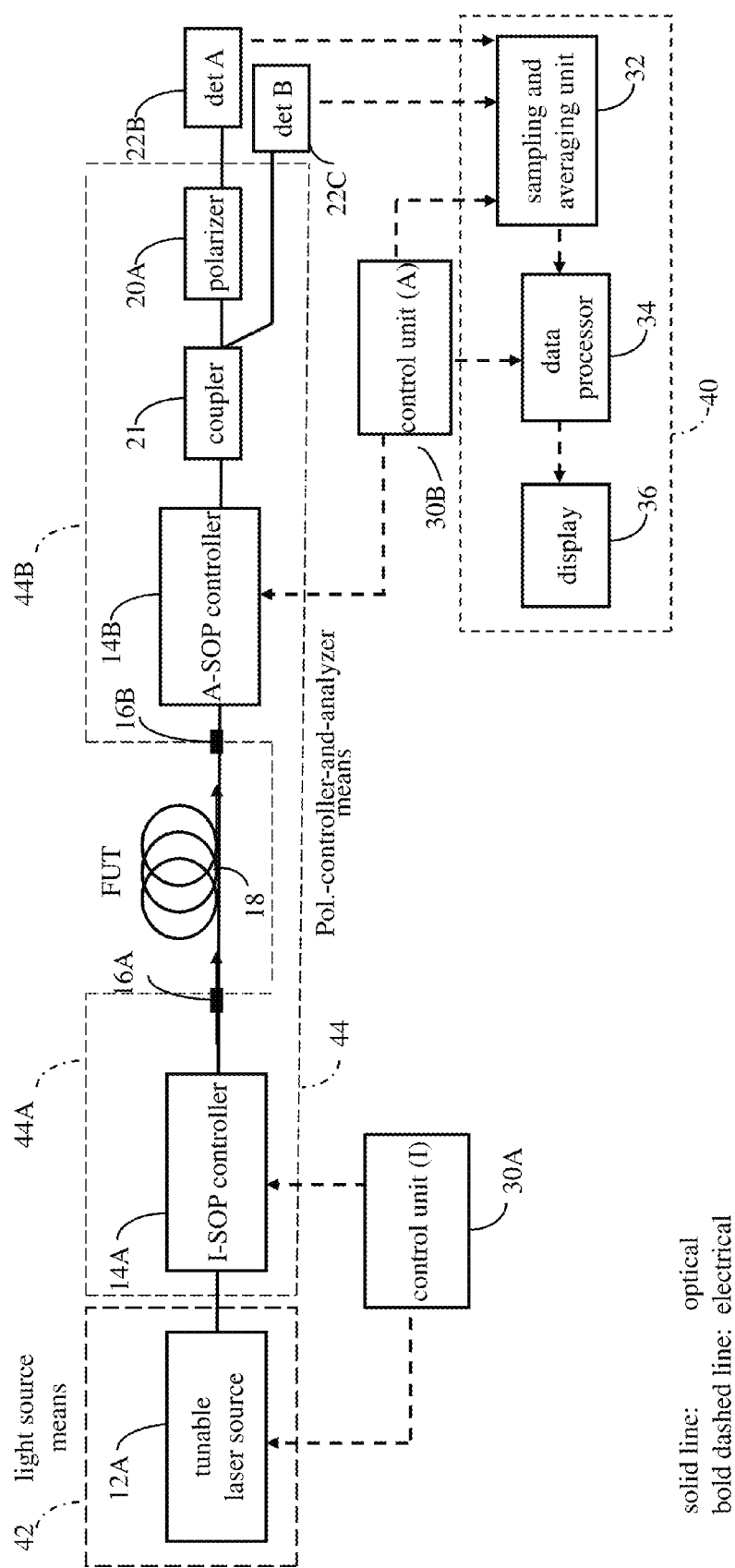
FIG. 1D is a simplified schematic diagram of measurement instrumentation similar to that shown in FIG. 1 but of measurement instrumentation using a tunable laser light source, one input-SOP controller (scrambler), one analyzer SOP (A-SOP) controller (scrambler), a coupler, a polarizer/analyzer and two detectors; one detector for measuring analyzed light after the polarizer and the other detector for measuring non-analyzed light, i.e. light that is proportional to a total output light power from FUT, said measured non-analyzed light being used to normalize the detected analyzed powers.
Figure 1E:
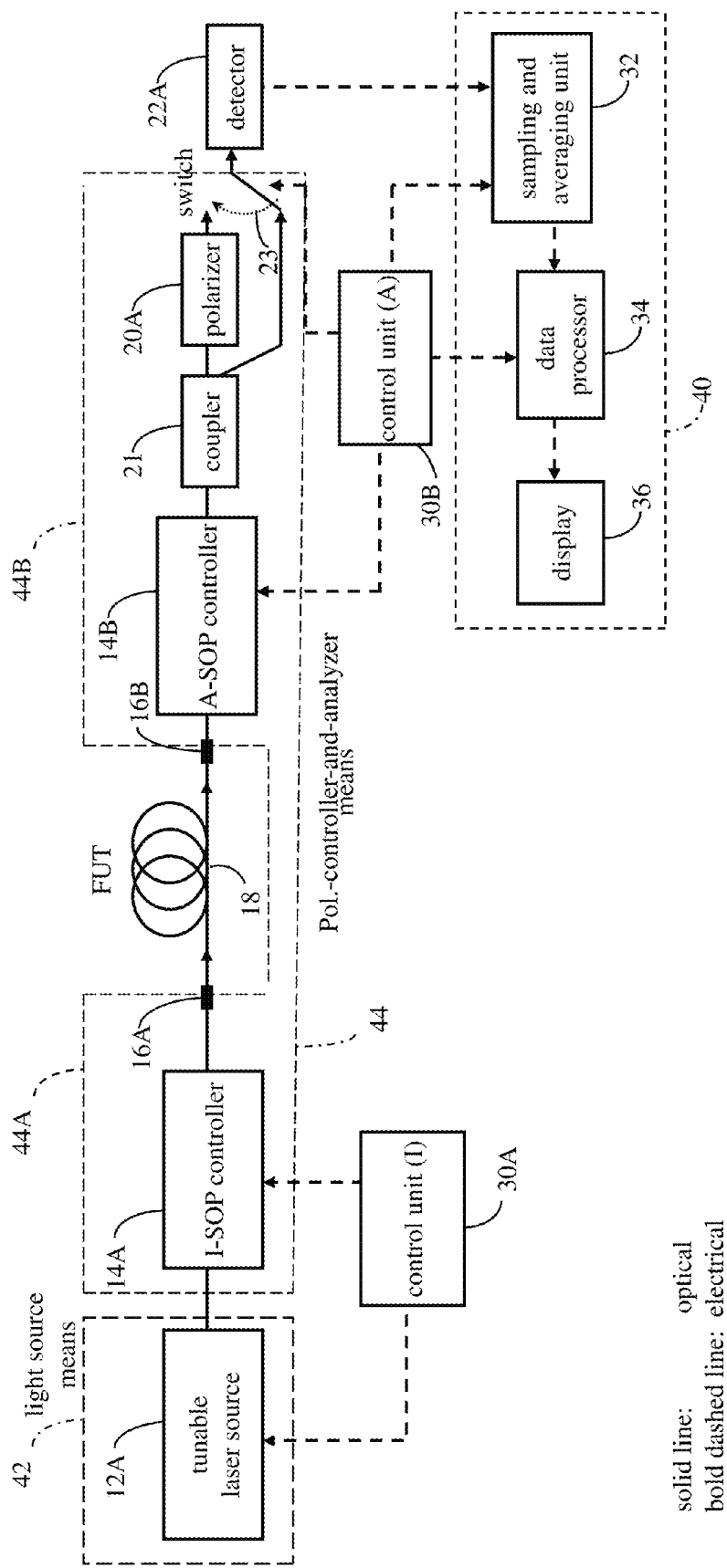
FIG. 1E is a simplified schematic diagram of measurement instrumentation similar to that shown in FIG. 1D but having a single detector and an optical switch for connecting the detector alternatively to measure analyzed light from the polarizer and non-analyzed light from the coupler proportional to a total output light power from the FUT, said measured non-analyzed light also being used to normalize the detected analyzed powers.
Figure 1F:
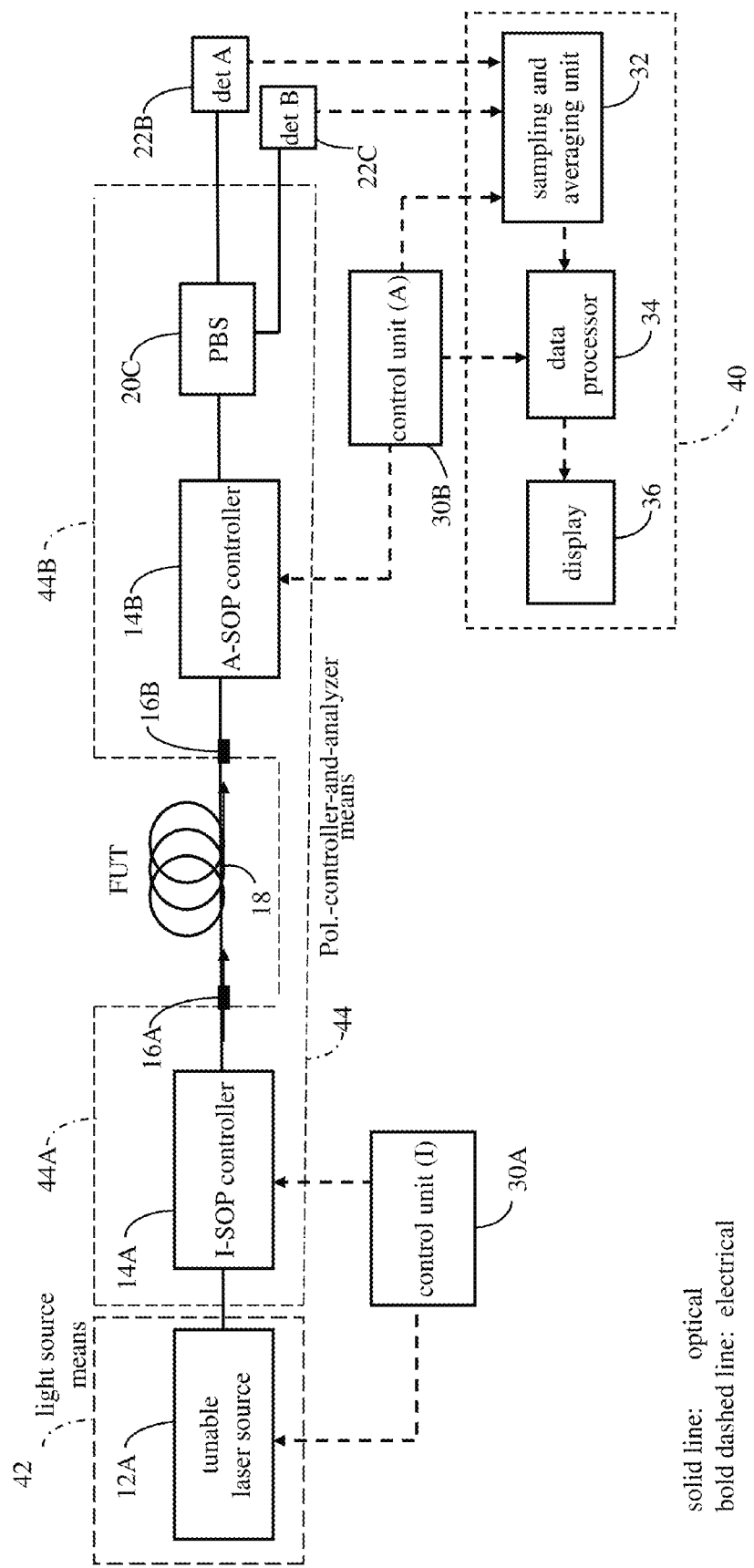
FIG. 1F is a simplified schematic diagram of measurement instrumentation using a tunable laser light source, one input-SOP controller (scrambler), one analyzer SOP (A-SOP) controller (scrambler), a polarization beam splitter (PBS), serving as a polarization analyzer, and two detectors connected to the two outputs thereof, each detector thereby detecting orthogonally-analyzed optical powers, and these orthogonally-analyzed powers being used to normalize the detected analyzed powers.
Figure 4:
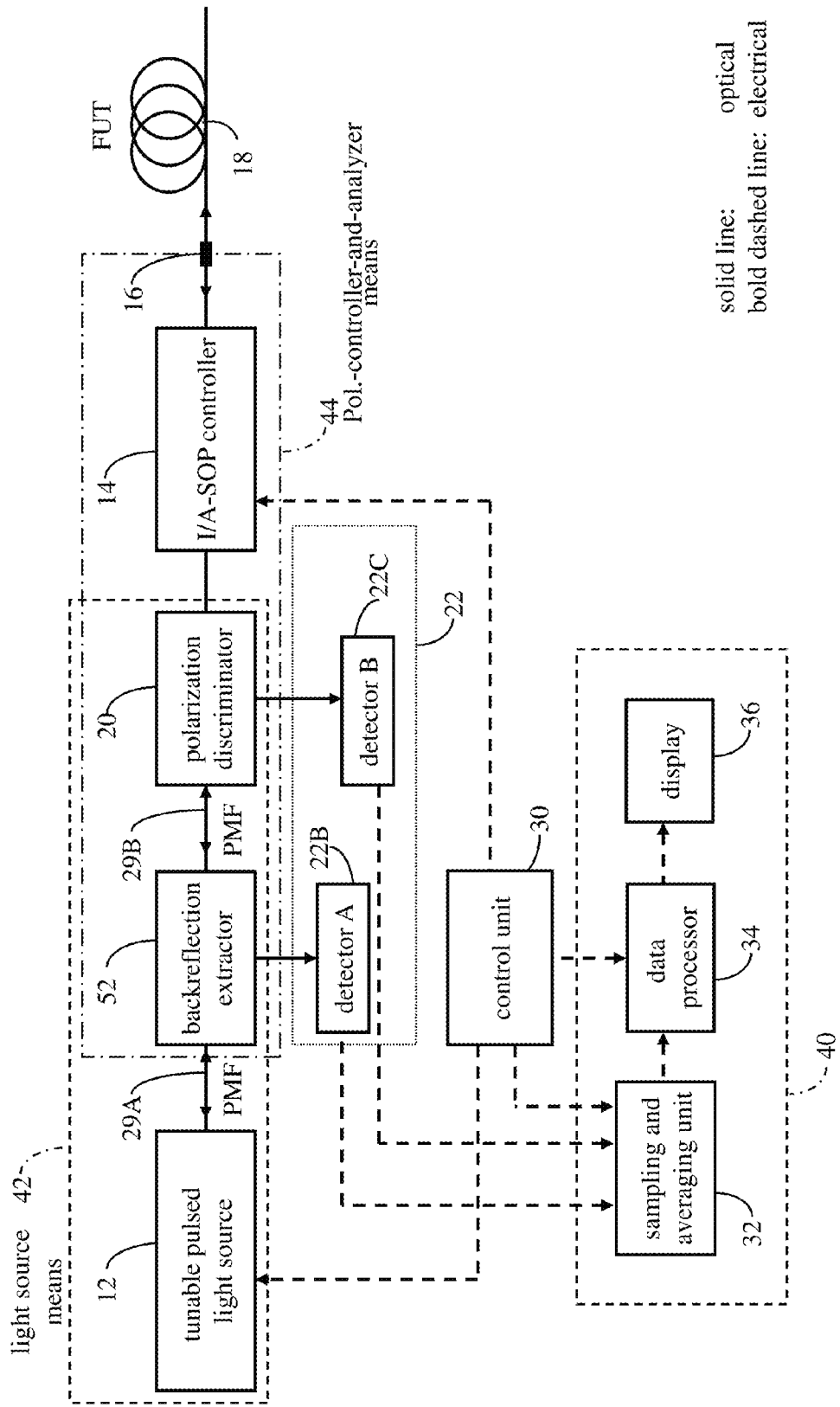
Figure 4A:
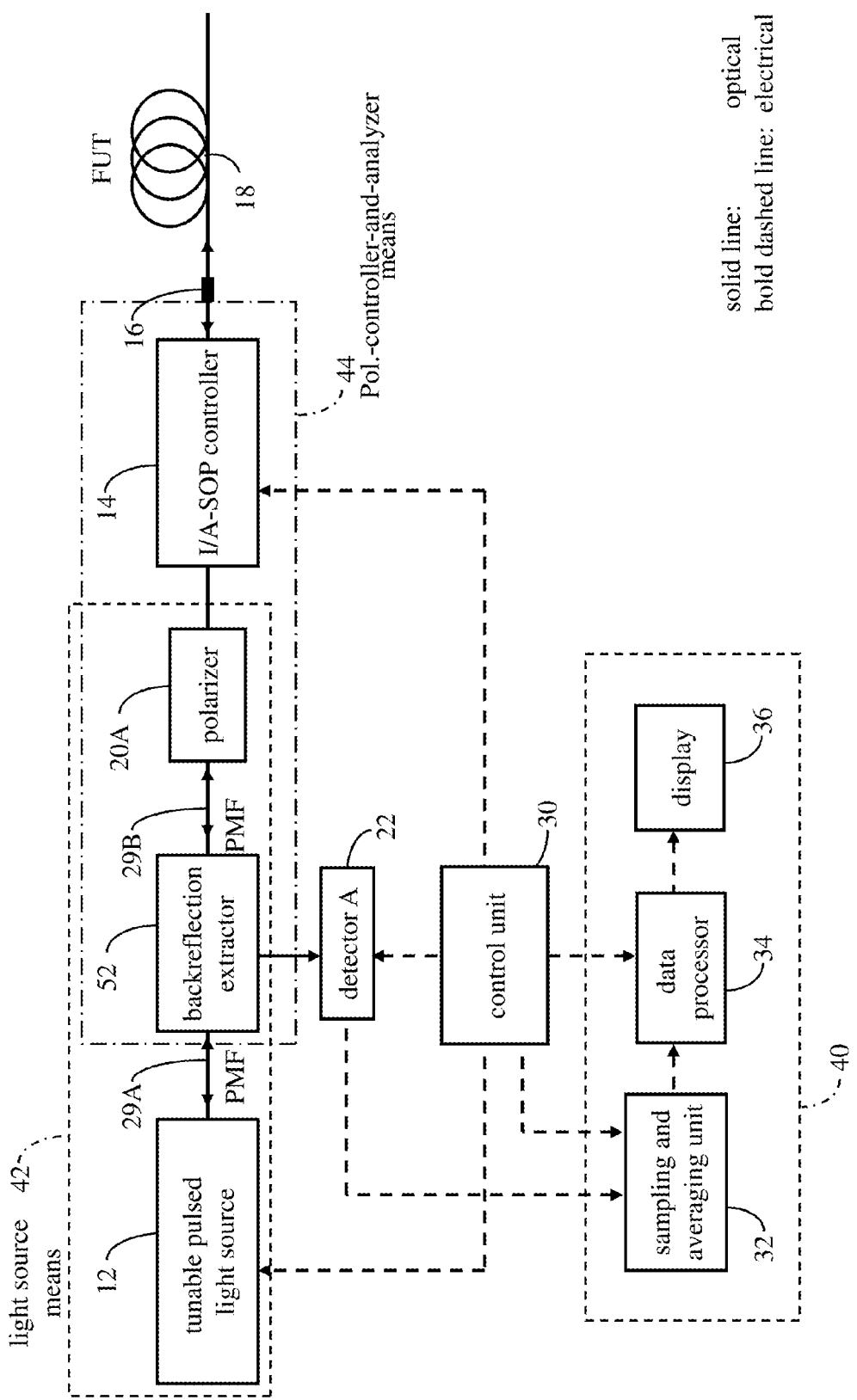
Figure 4B:
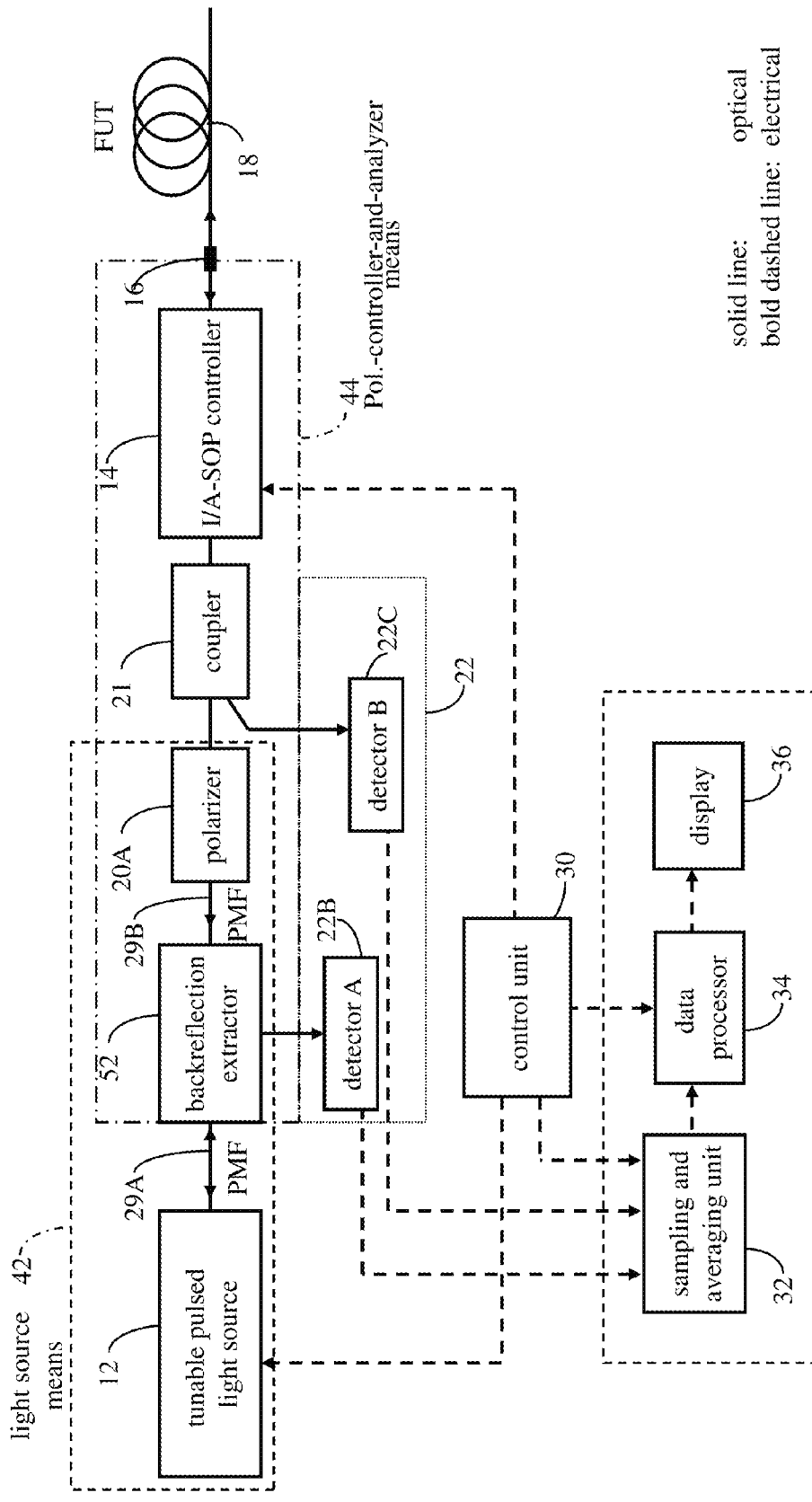
Figure 4C:
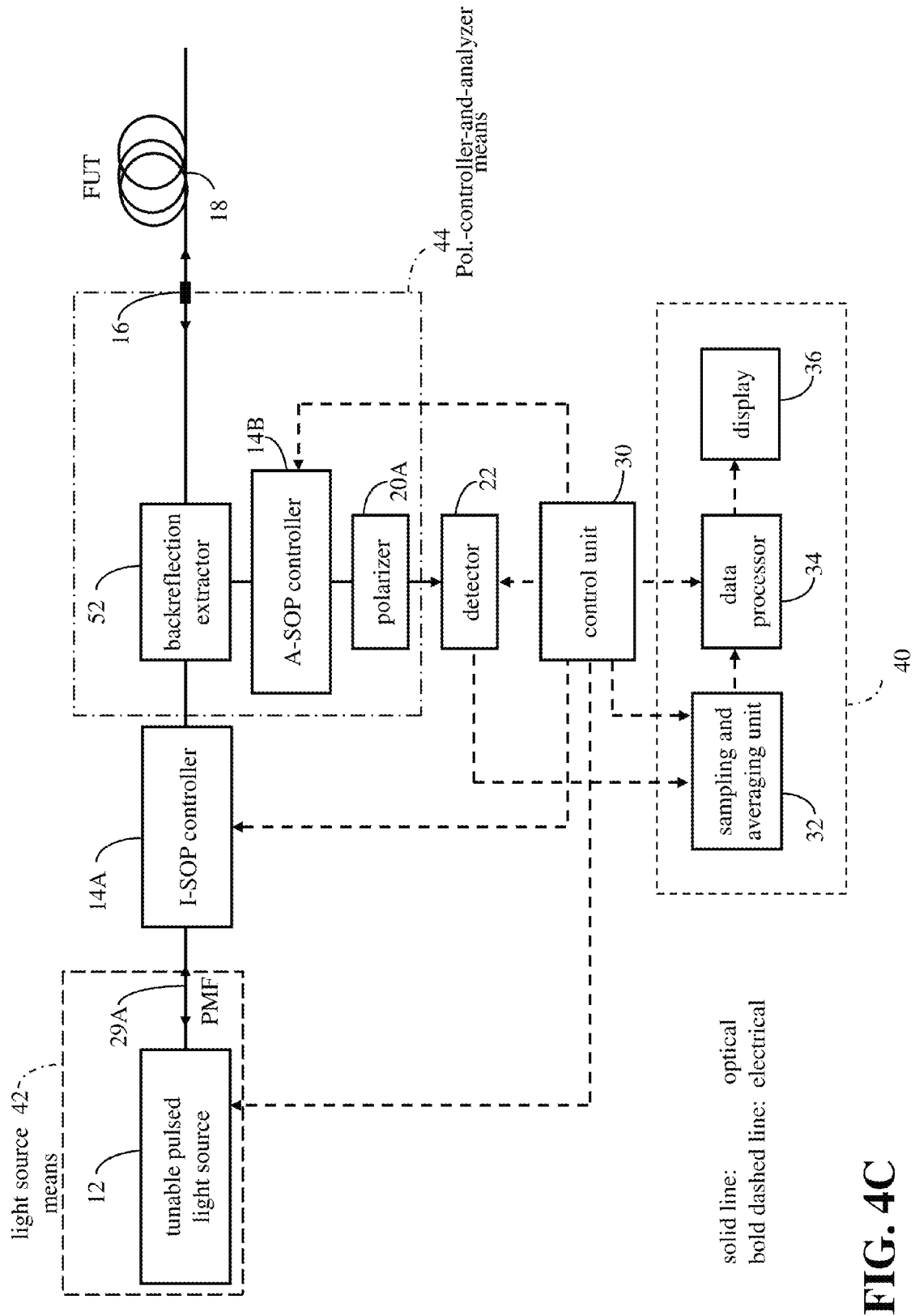
Figure 5A:
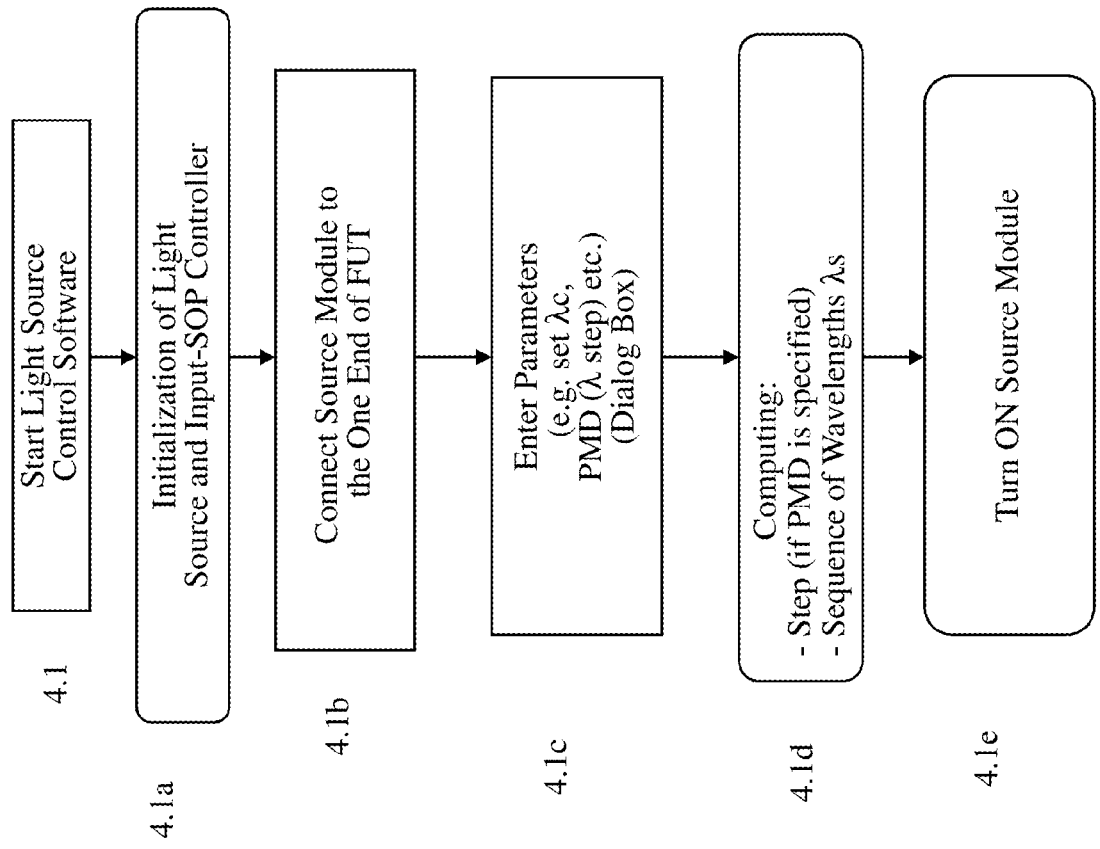
Figure 5B:
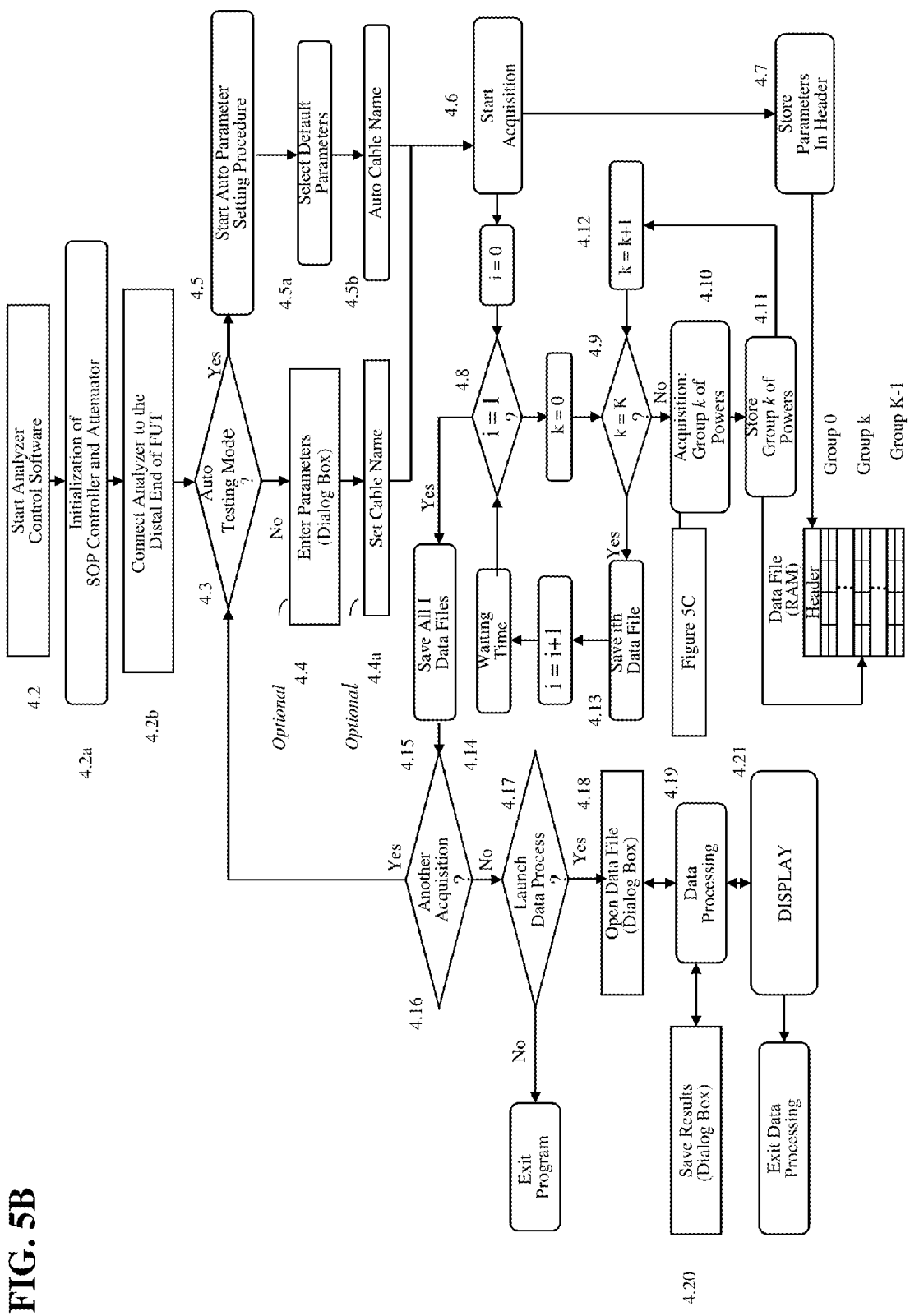
Figure 5C:
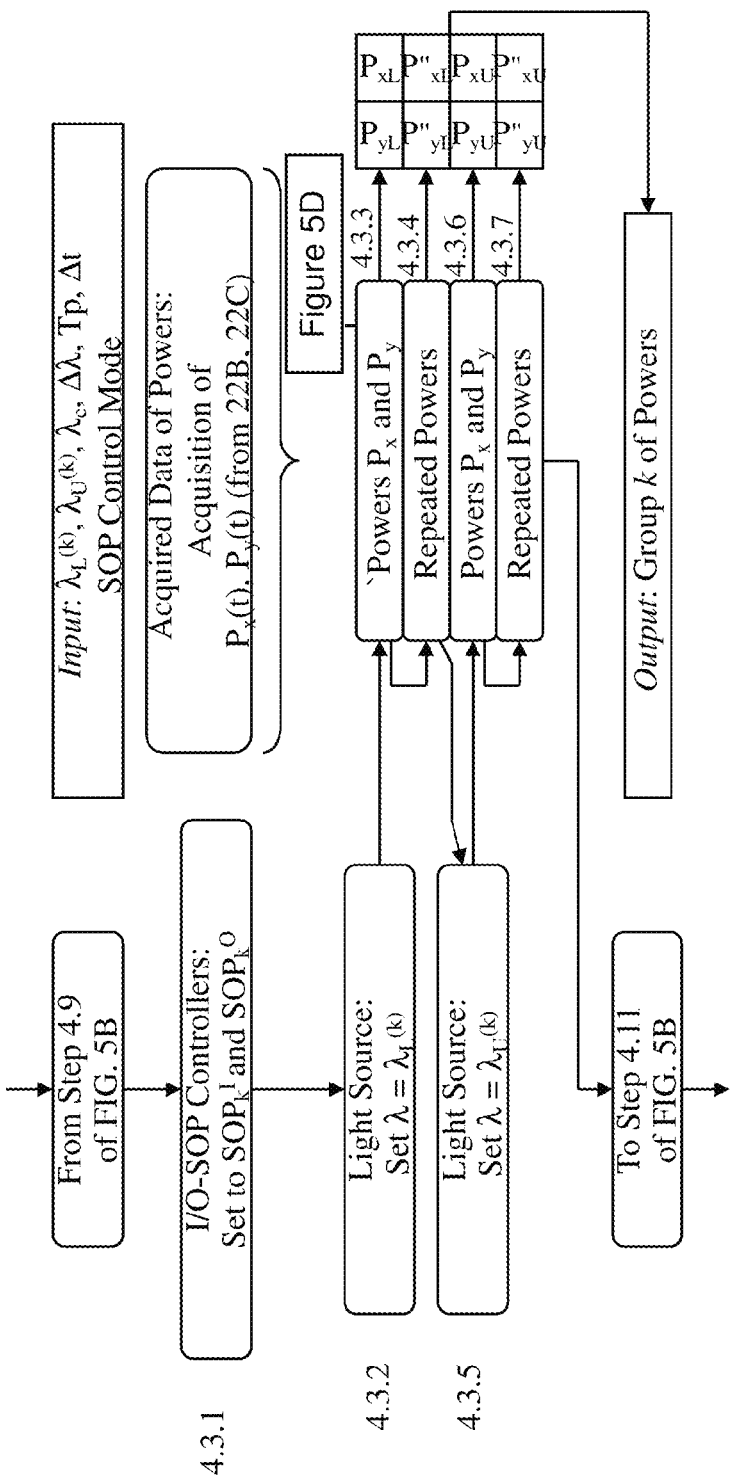
Figure 5D:
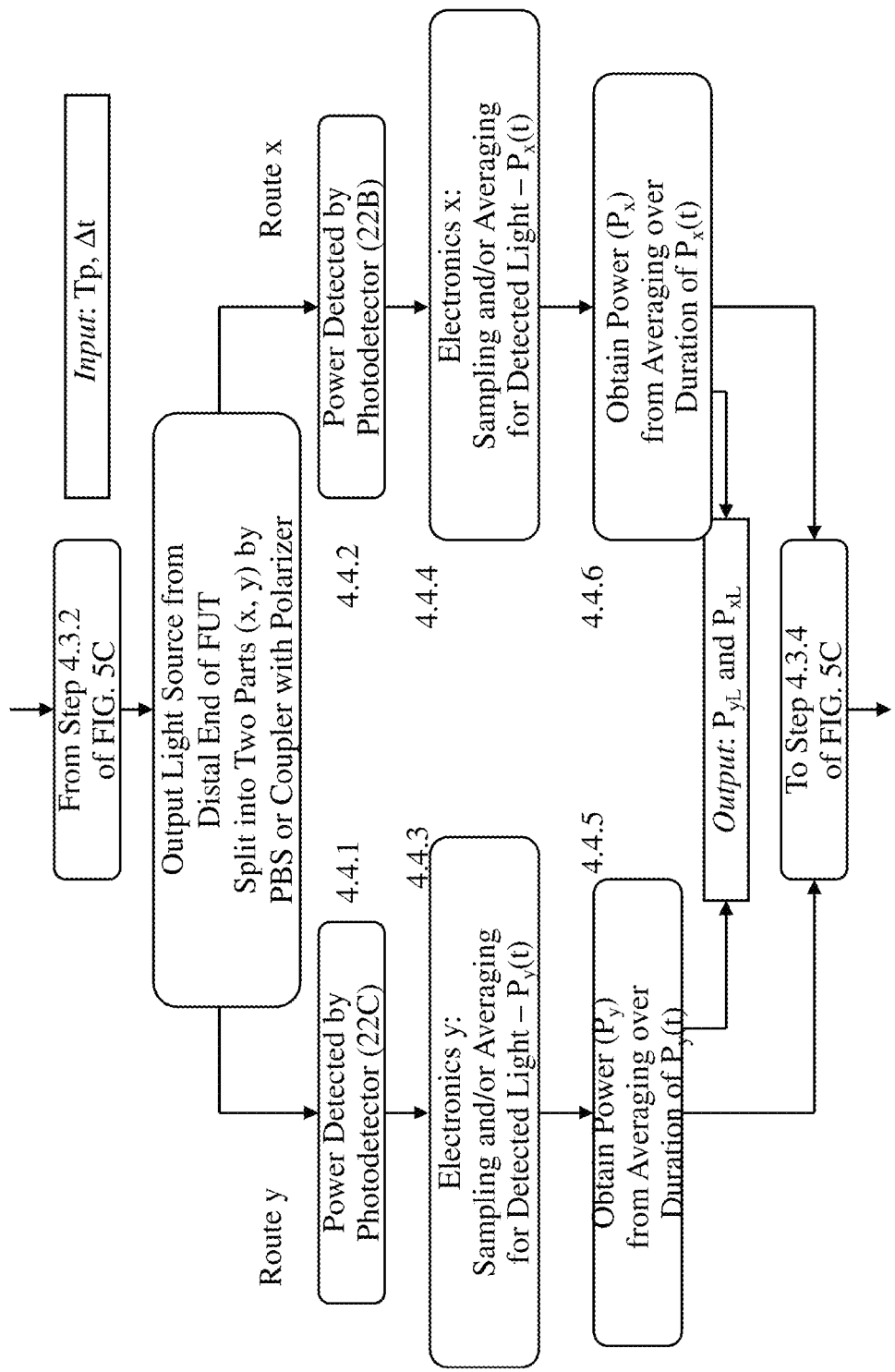
Figure 6A:
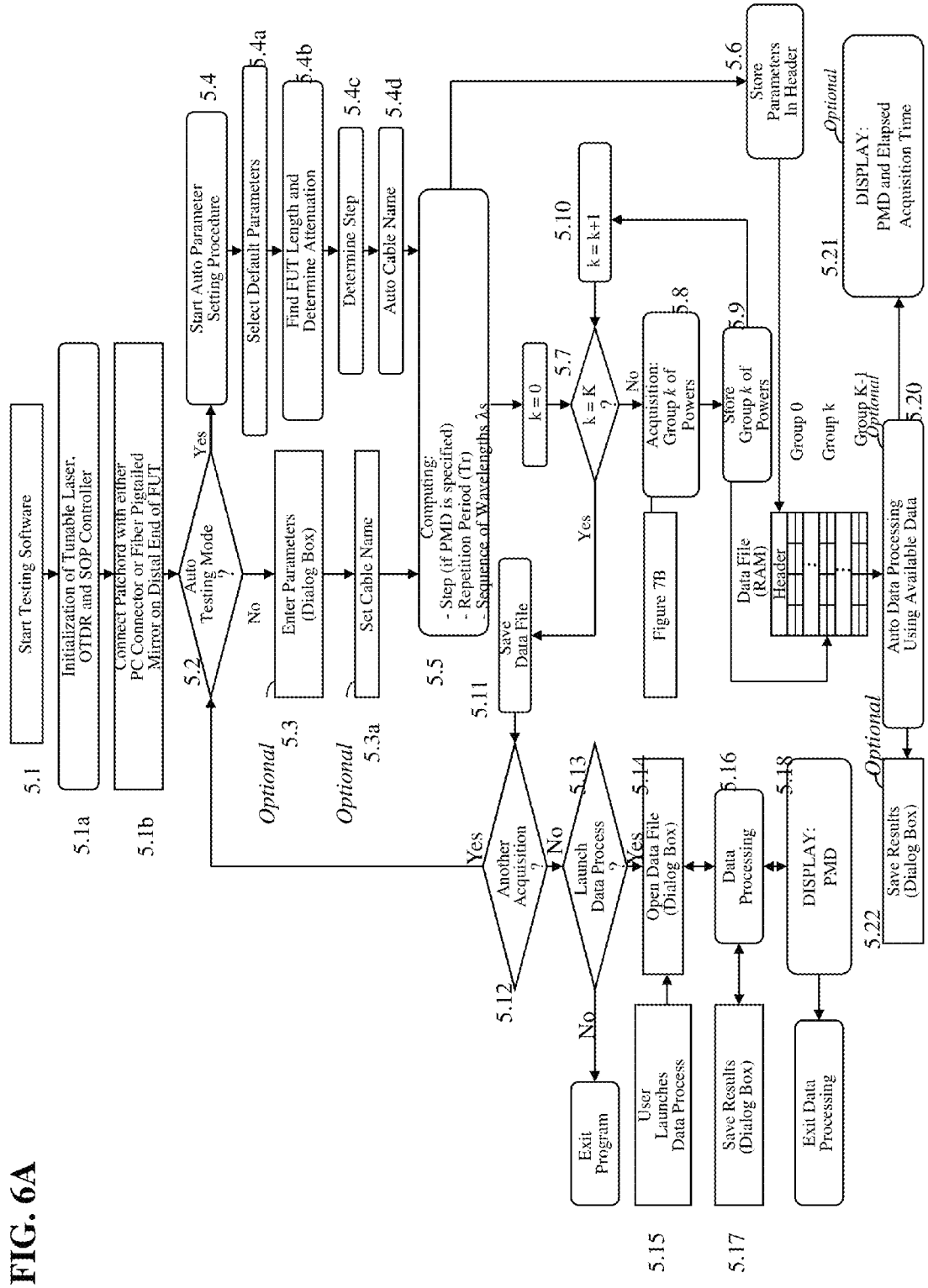
Figure 6B:
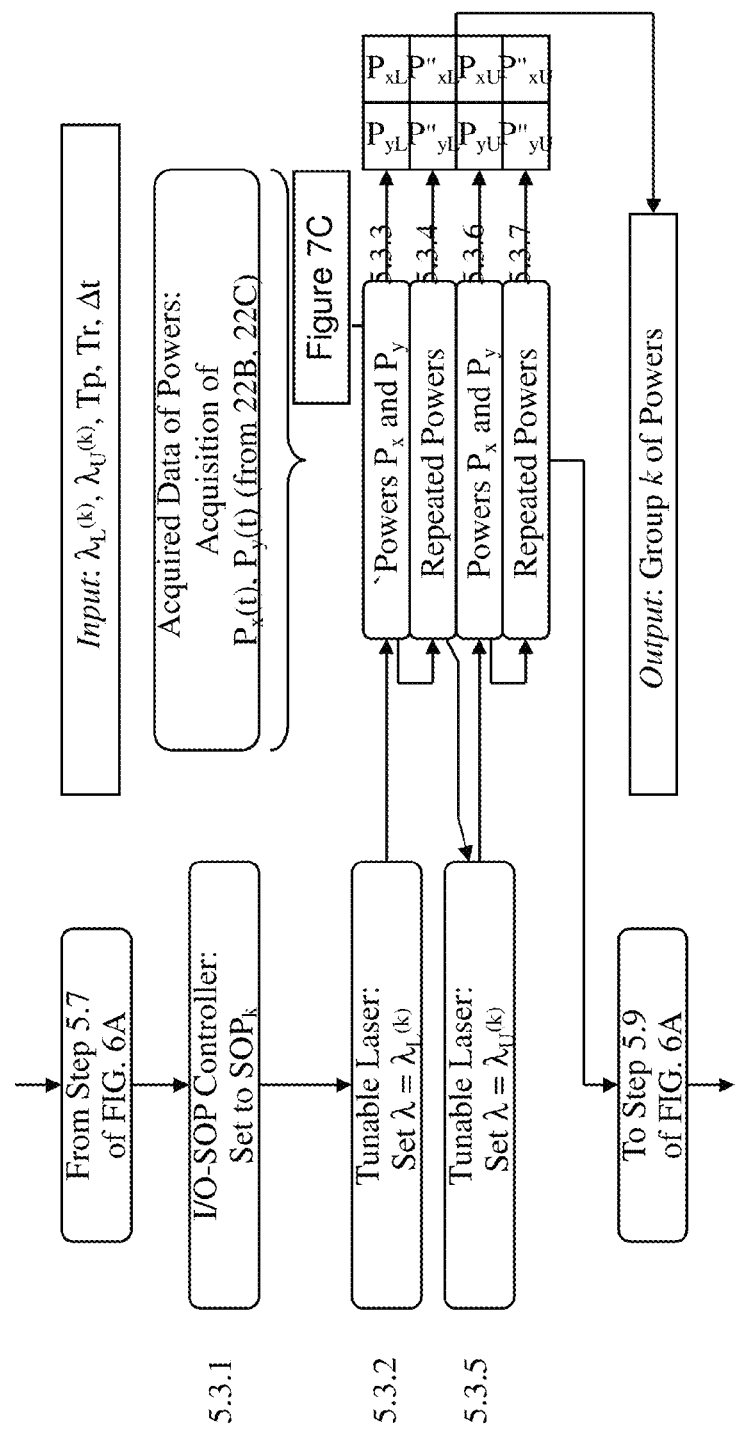
Figure 6C:
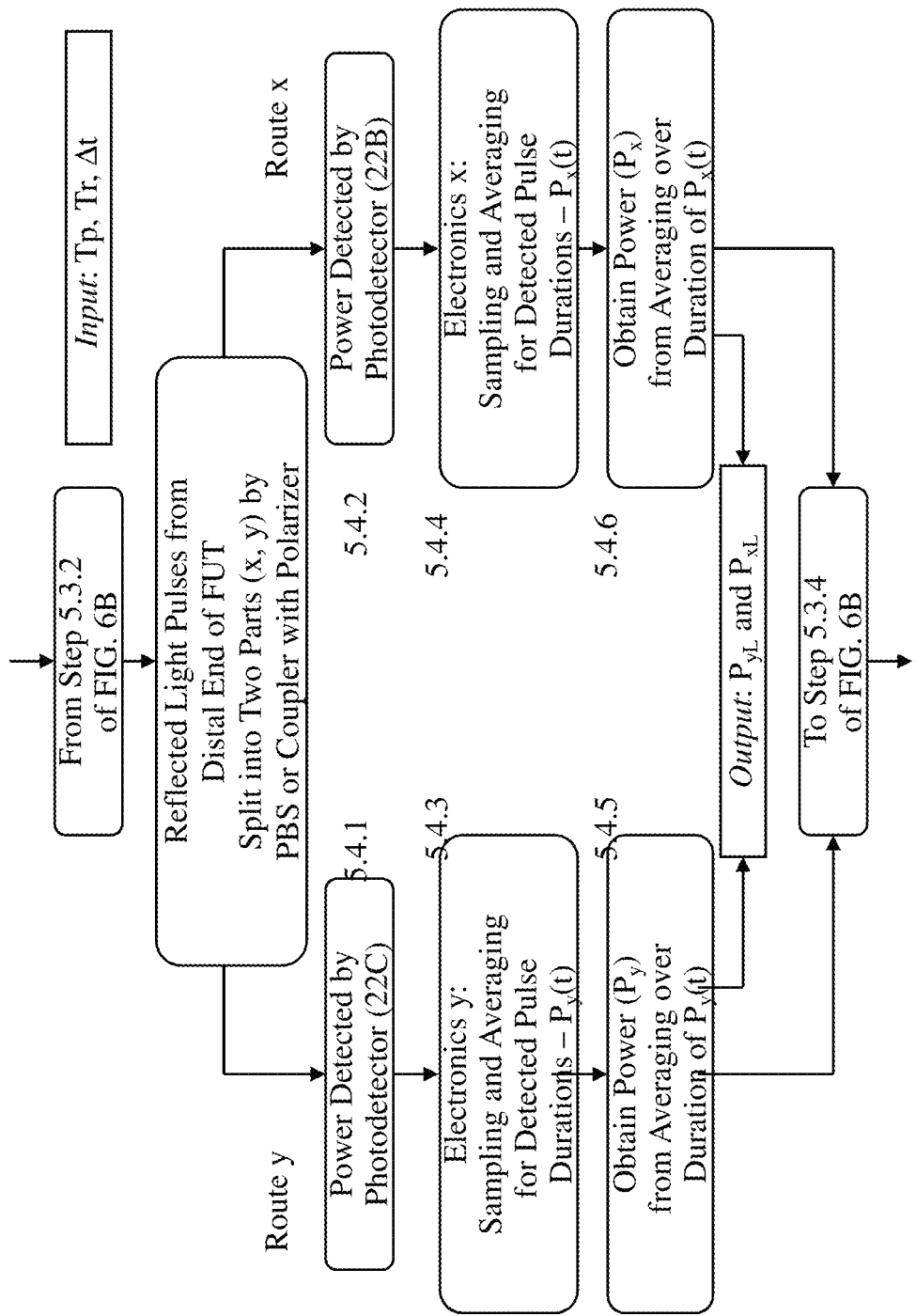
Figure 7A:
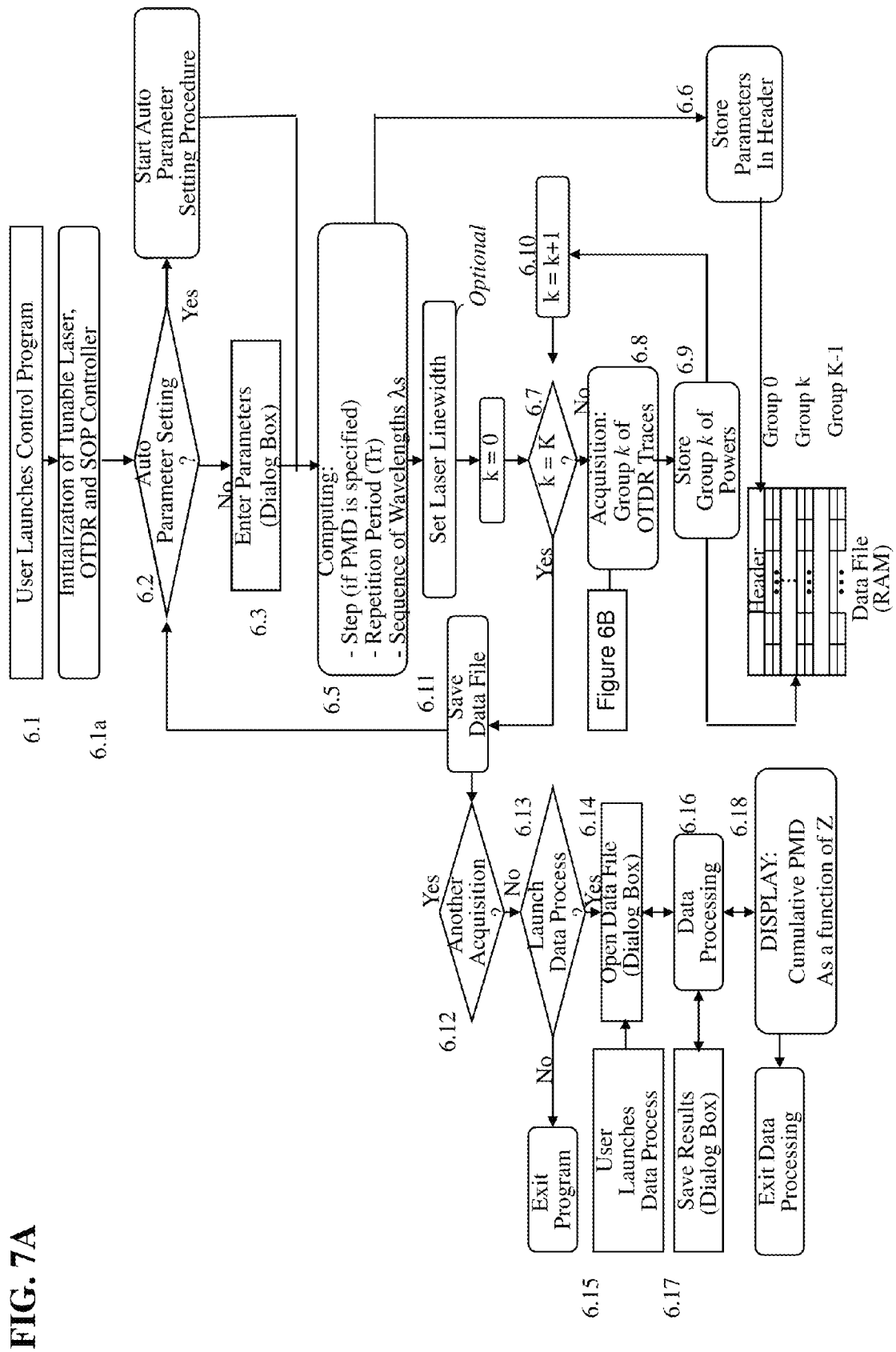
Figure 7B:
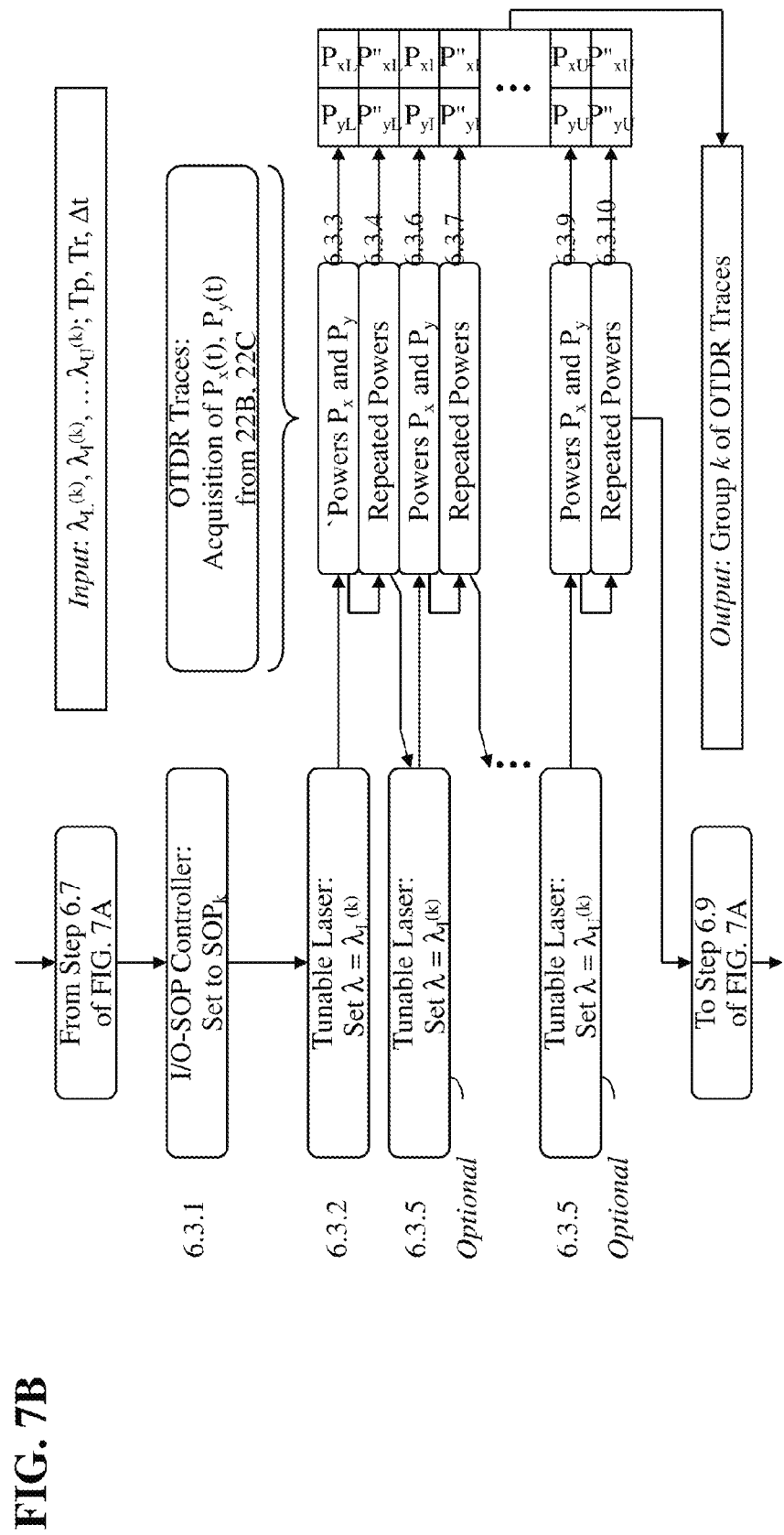
Figure 8A:
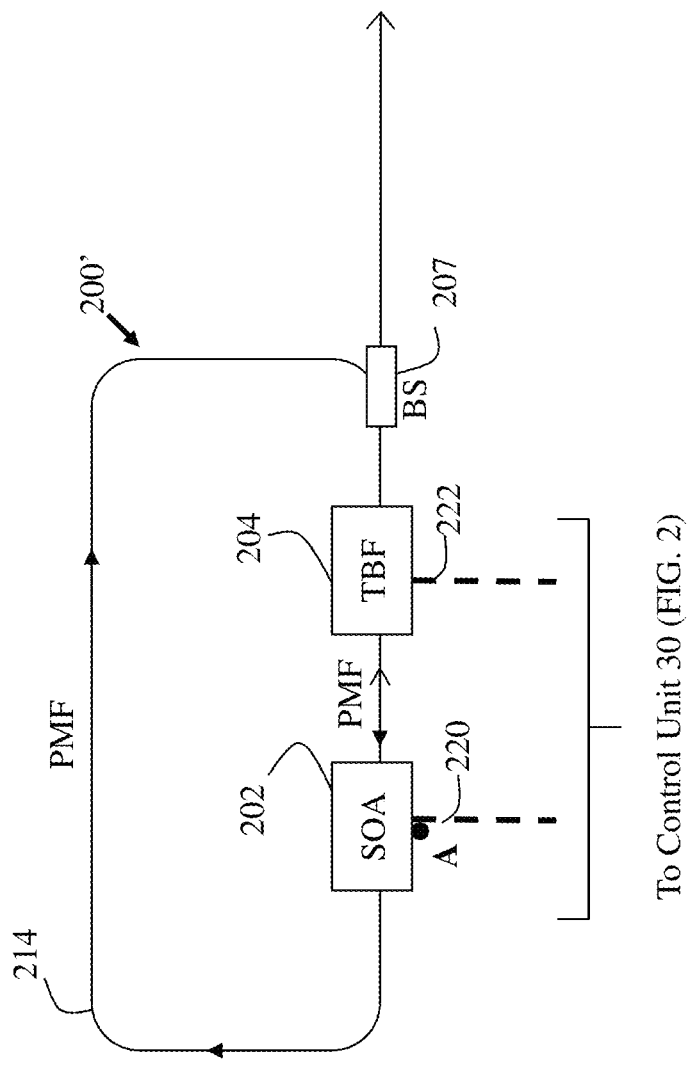
Figure 8B:
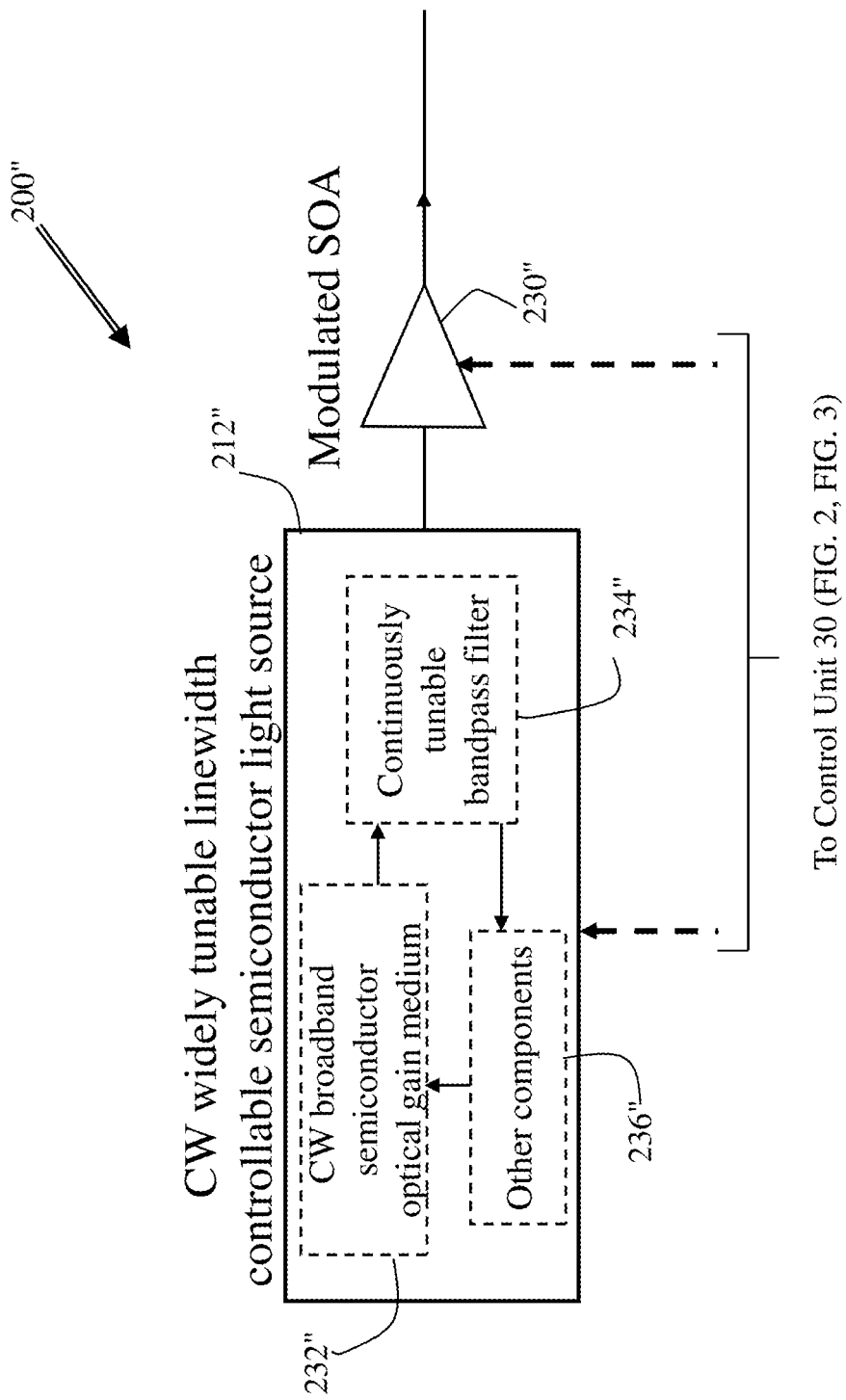
Figure 9:
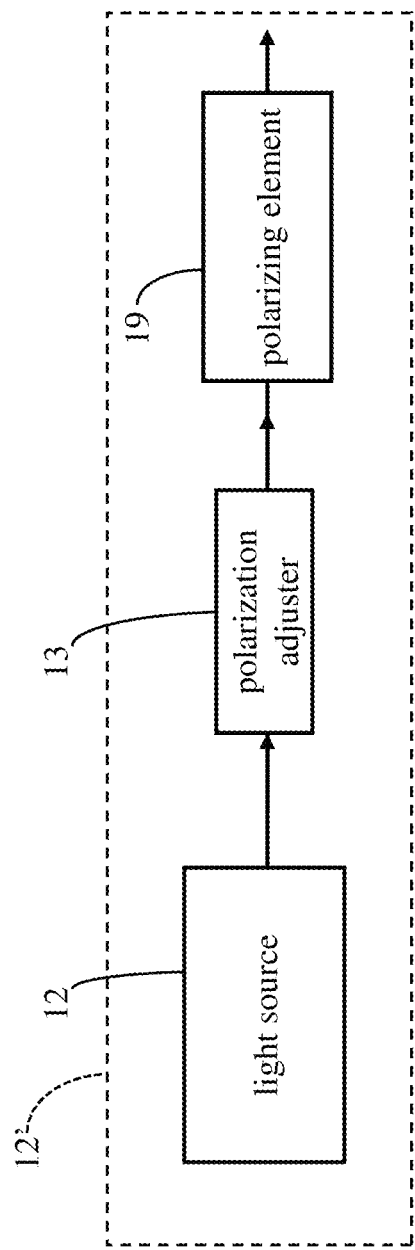
Figures 10A, 10B:
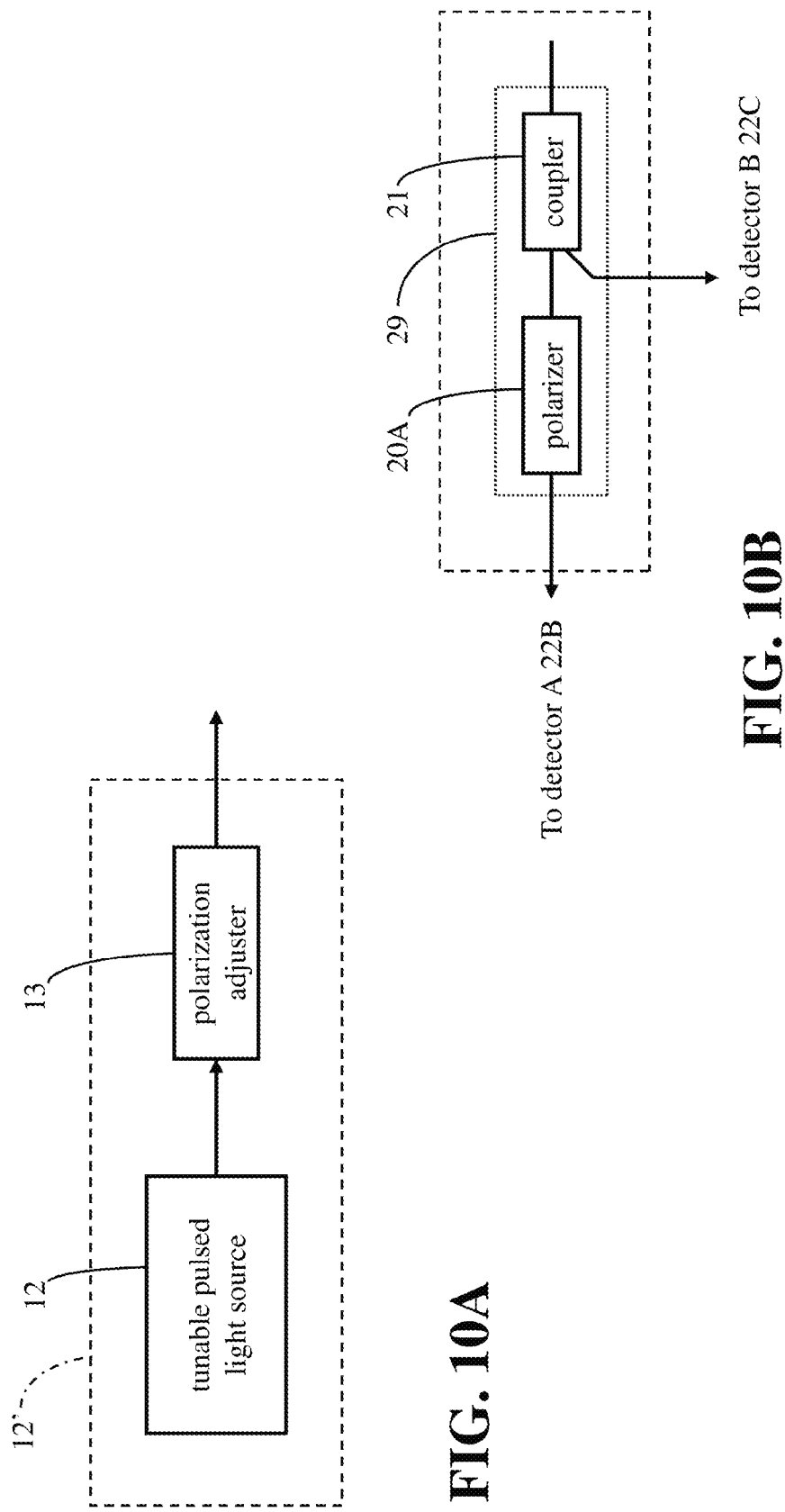

FIG. 4 is a simplified schematic diagram of a polarization-sensitive optical time domain reflectometer (POTDR) embodying an aspect of the present invention;

FIG. 4A is a simplified schematic diagram of another polarization-sensitive optical time domain reflectometer embodying an aspect of the present invention;

FIG. 4B is a simplified schematic diagram of yet another polarization-sensitive optical time domain reflectometer embodying an aspect of the present invention;

FIG. 4C is a simplified schematic diagram of still another polarization-sensitive optical time domain reflectometer embodying an aspect of the present invention;

FIG. 5A is a flowchart illustrating operation of the light source means and input I-SOP controller of the two-ended PMD measurement instrument of FIGS. 1D and 1F;

FIG. 5B is a flowchart illustrating operation of polarization controller-and-analyzer means of the two-ended PMD measurement instrumentation of 1D and 1F;

FIG. 5C is a flowchart illustrating details of the acquisition of a $k^{th}$ group of powers, as described in the flowchart of FIG. 5B;

FIG. 5D is a flowchart illustrating a power (data) acquisition step of the flowchart of FIG. 5C;

FIG. 6A illustrates sections of a flowchart illustrating operation of the single-ended PMD measurement of FIGS. 3D and 3F;

FIG. 6B is a flowchart illustrating a group of power (data) acquisition steps of the flowchart of FIG. 6A;

FIG. 6C is a flowchart illustrating a power (data) acquisition step of the flowchart of FIG. 6B;

FIG. 7A is a flowchart illustrating operation of the POTDR of FIG. 4;

FIG. 7B is a flowchart illustrating a trace acquisition step of the flowchart of FIG. 7A;

FIG. 8A is a schematic diagram illustrating another alternative tunable pulsed light source that can be used for single-ended overall PMD measurement;

FIG. 8B illustrates schematically yet another alternative tunable pulsed light source that can be used for both single-ended overall PMD measurement and single-ended cumulative PMD measurement;

FIG. 9 is a simplified schematic diagram of light source means comprising a laser source that has been modified to ensure that the emitted light has a high degree of polarization (DOP);

FIG. 10A is a schematic diagram illustrating another alternative tunable pulsed light source that can be used for single-ended overall PMD measurement;

FIG. 10B illustrates schematically yet another alternative tunable pulsed light source that can be used for both single-ended overall PMD measurement and single-ended cumulative PMD measurement;

DESCRIPTION OF PREFERRED EMBODIMENTS

In the drawings, the same or similar components in the different figures have the same reference numeral, where appropriate with a prime or suffix letter indicating a difference.

1.1 Preferred Embodiments

The various embodiments of the present invention are predicated upon the same underlying theory. The following four preferred embodiments, including their respective implementations, will be described in more detail in this Section:

1) Two-ended determination of PMD and/or DGD($\upsilon$) using test light source;
2) "Two-ended" determination of PMD and/or $DGD_P(\upsilon)$ using one or more data-carrying signals (SUT) as the test light source(s);
3) Single-ended determination, using optical reflectometry, of the overall PMD of an optical link (FUT);
4) Single-ended determination, using optical reflectometry, of PMD(z), i.e. the cumulative value of the PMD at any point along a FUT.

The invention should not be construed as being limited to these preferred embodiments, nor to the afore-mentioned applications, but may be otherwise embodied and/or find application to the determination of other polarization-related characteristics of an optical link or, more generally, any single-mode optical fiber.

Each of the preferred embodiments of this invention described hereinafter comprises three main parts, namely (i) light source means (which, in the case of Embodiment (2), is not comprised within the test instrumentation), (ii) polarization-controller-and-analyzer means, (iii) detection means, and (iv) analog-and-digital processing means, together with one or more control units. In so-called two-ended cases, the light source means will be located at a proximal end of the FUT while a second portion of the polarization-controller-and-analyzer means, the detection means, and, conveniently, the analog-and-digital processing means will be located at the distal end of the FUT.

Although methods embodying this invention usually will employ the above-described four parts or sections, each preferred embodiment may comprise different possible implementations, according to the nature of the application, e.g. as described in Section 2 hereinabove.

It should be noted that the detection of analyzed power of light corresponding to two closely-spaced wavelengths (i.e. optical frequencies) is common to all embodiments of this invention. For convenience, a "midpoint wavelength" is defined "notionally" as the mean of these two closely-spaced wavelengths, $\lambda_U$, $\lambda_L$, where the "U" and "L" subscripts designate "uppermost" and "lowermost", respectively. As such, the midpoint wavelength is not explicitly needed anywhere in the computations (to be described hereinbelow), and neither detected wavelengths constituting a pair is equal the midpoint wavelength. Only the knowledge of the optical-frequency spacing (sometimes referred to as wavelength "step" hereinbelow) is needed. (When more than one wavelength pair is used per group, as will be further discussed hereinbelow, it is useful to introduce the concept of "center wavelength" as a wavelength "label" corresponding to the particular group.)

Preferred implementations of the three main embodiments for PMD measurement, including measurement methods and measurement instrumentation configurations for two-ended PMD measurement, single-ended overall PMD measurement and single-ended cumulative PMD measurement according to the invention, and modifications, alternatives and substitutions thereto, will now be described in Sub-sections 1.2-1.5, with reference to FIGS. 1 through 13.

1.2 Embodiment (1)

Two-Ended Test-Source-Based PMD and/or DGD Measurement

1.2.1 Description of Apparatus and Summary Description of Operating Mode

For Embodiment (1), there is also normally a "first portion" of polarization-controller-and-analyzer means disposed in the optical path between the light source means and the proximal end of the FUT. A first control unit at the proximal end of the FUT controls the light source means and the first portion of the polarization-controller-and-analyzer means and a second control unit at the distal end of the FUT controls the second portion of the polarization-controller-and analyzer means and the analog-and-digital signal processing means.

For two-ended "test-source-based" measurement of PMD and/or DGD in either unlit fiber or "dark channels" of an in-service optical link (Embodiment (1)), the light source means usually comprises an at least partially polarized light source, for example a tunable laser or a broadband source, and supplies light to an input SOP (I-SOP) controller for controlling the SOP of light from the light source means before injection ("launch") into the FUT. The polarization-controller and analyzer means may comprise, in addition to an analyzer SOP (A-SOP) controller, a polarizer and a detection means/system comprising one detector, or a PBS and two detectors, or a coupler and a polarizer with two detectors, and so on. Where the light source is broadband, the polarization-controller-and-analyzer means may also comprise a tunable filter for selecting the optical frequency. (Alternatively, but less advantageously, the light source could comprise such a tunable filter.) The analog-and-digital processing means may comprise a data acquisition unit, a sampling-and-averaging unit, wherein analog-to-digital conversion is carried out, and a data processor unit.

For this embodiment, the polarization-controller-and-analyzer means and the analog and digital processing means must be configured to measure two or more closely-spaced wavelengths. For example, where the light source means at the proximal end emits broadband polarized light, this could be effected using narrow-band optical filtering within the second portion of the polarization-controller-and-analyzer means, at the distal end. Alternatively, the source at the proximal end may be a laser that is able to set or modulate its optical frequency to produce two or more closely-spaced wavelengths at different times, in which case the polarization-controller-and-analyzer means does not necessarily comprise optical filtering.

In the following description for the two-ended PMD measurement, the term "modulated optical pulse" is used to refer to propagating light, which, over a defined time interval, is differentiated from at least some other pulses by one or more of a characteristic wavelength, characteristic average power, characteristic pulse duration, characteristic superposed amplitude or phase modulation at a frequency much greater than the reciprocal of the pulse duration, characteristic extinction ratio following its duration, characteristic duration of sampling of the said light in the acquisition process, or any other measurable distinguishing property.

In a first preferred implementation of Embodiment (1) illustrated in FIG. 1, measurement instrumentation for two-ended measurement of DGD/PMD comprises light source means 42 situated at or adjacent a proximal end of fiber-under-test (FUT) 18. A first portion 44A of a polarization-controller-and-analyzer means 44 is disposed between light source means 42 and the proximal end of FUT 18, and comprises an input SOP controller means 14A (conveniently referred to as an I-SOP controller or scrambler means), which controls the SOP of light from the light source 12 before injecting it into the FUT 18 via connector 16A. A second portion 44B of polarization-controller-and-analyzer means 44 is situated at or adjacent a distal end of the FUT 18 and connected thereto by a connector 16B.

A first (input) control unit 30A controls the wavelength of the light source 12 and the setting of the input I-SOP controller 14A, specifically to scramble the SOP of the light from light source 12 before it is injected into the FUT 18.

The second portion 44B of polarization-controller-and-analyzer means 44 comprises an output SOP controller (A-SOP) 14B (conveniently referred to as an A-SOP controller or scrambler means), followed by a polarization discriminator 20. The output of the polarization discriminator is supplied to detection means, specifically detection means/system 22. If the detection means 22 is not able to correctly measure high optical power levels, power controller means (not shown), for example an optical attenuator, may be interposed to attenuate the light extracted from the FUT 18 before it is applied to the detection means 22. The purpose of the optical attenuator is to ensure that the light level at the distal end is not so high as to potentially "saturate" or render non-linear the detection means 22. Such may be the case if, for instance, the measurement is carried out over a short optical fiber link, wherein the overall attenuation induced by the fiber is small. For long links, the optical attenuator will normally be set to induce minimum attenuation.

The analog-and-digital signal processing unit 40 comprises a sampling-and-averaging unit 32 and a data processor means 34, optionally with a display means 36 for displaying results. Components of the polarization-controller-and-analyzer means 44B and the analog-and-digital signal processing unit 40 are controlled by a second, output control unit (A) 30B which also controls the detection system 22.

Under the coordination of control unit 30B, the sampling-and-averaging unit 32, in known manner, uses an internal analog-to-digital converter to sample the corresponding electrical signals from the detectors 22B and 22C as a function of time (as shown, for example, in FIGS. 1C, 1D, 1F), and the sampled signal is time-averaged over a portion of its duration to provide a corresponding digital level. This portion is chosen so as to avoid transient effects and/or bandwidth limiting effects in the detected power, polarization, and/or wavelength arising from one or more of the light source means 12,—the polarization-controller-and-analyzer means (comprising the I-SOP controller 14A, the A-SOP controller 14B and, where applicable, polarization discriminator means 20), and/or any distortion in the (pulsed) signal arising from bandwidth limitations of the analog electronics.

The resulting averaged powers are used by data processor 34 to derive the DGD at a particular wavelength or PMD value over a prescribed wavelength range of the FUT 18, as will be described in more detail hereinafter according to the particular implementation of the embodiment.

Figure 1G:
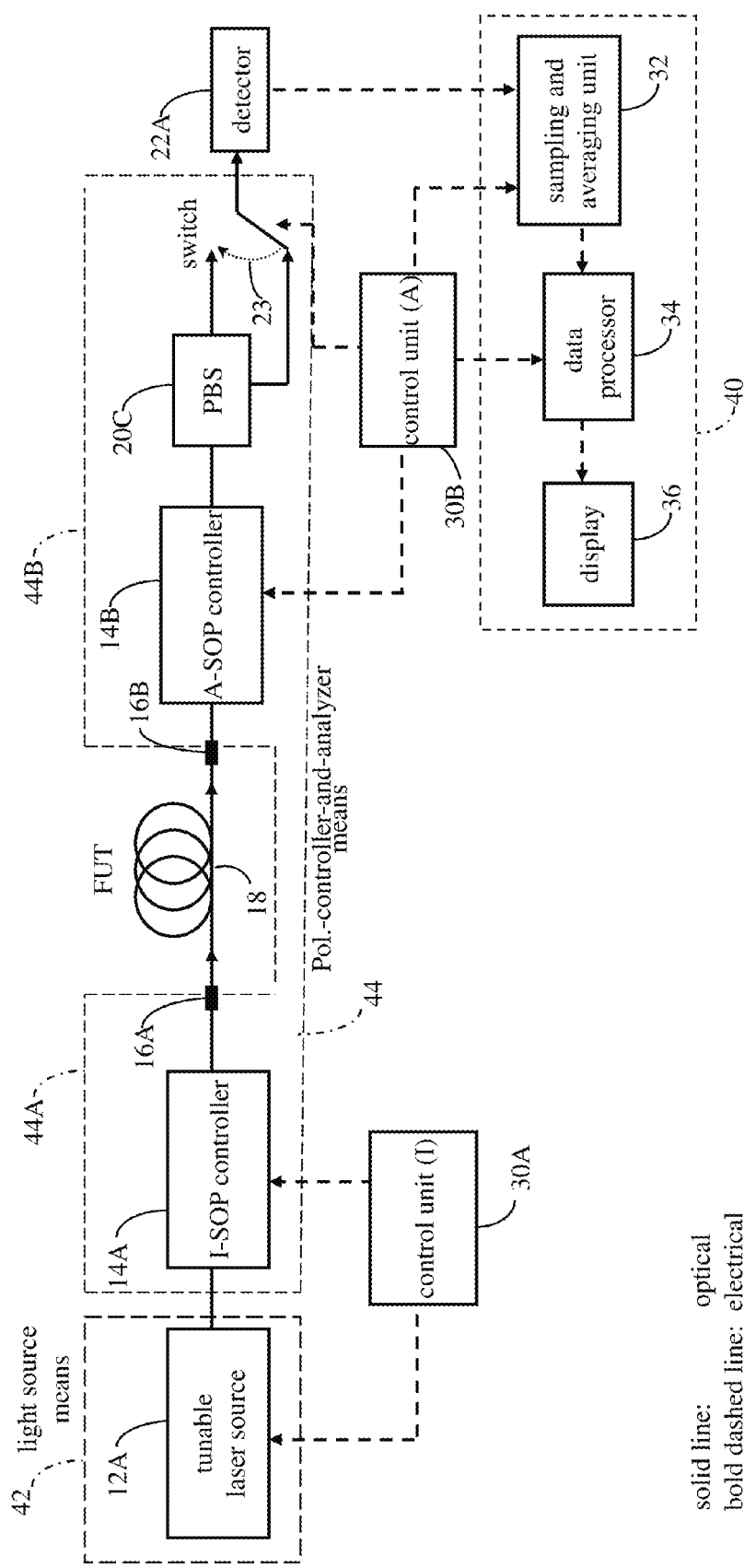
FIG. 1G is a simplified schematic diagram of measurement instrumentation similar to that shown in FIG. 1F but rather than employing two detectors each in continuous optical continuity with the respective outputs of the PBS, only one detector is used, and the orthogonally-analyzed light exiting each of the two output of the PBS is directed to the detector, successively, by means of an optical switch. The orthogonally-analyzed powers also being used to normalize the detected analyzed powers.
Figure 1H:
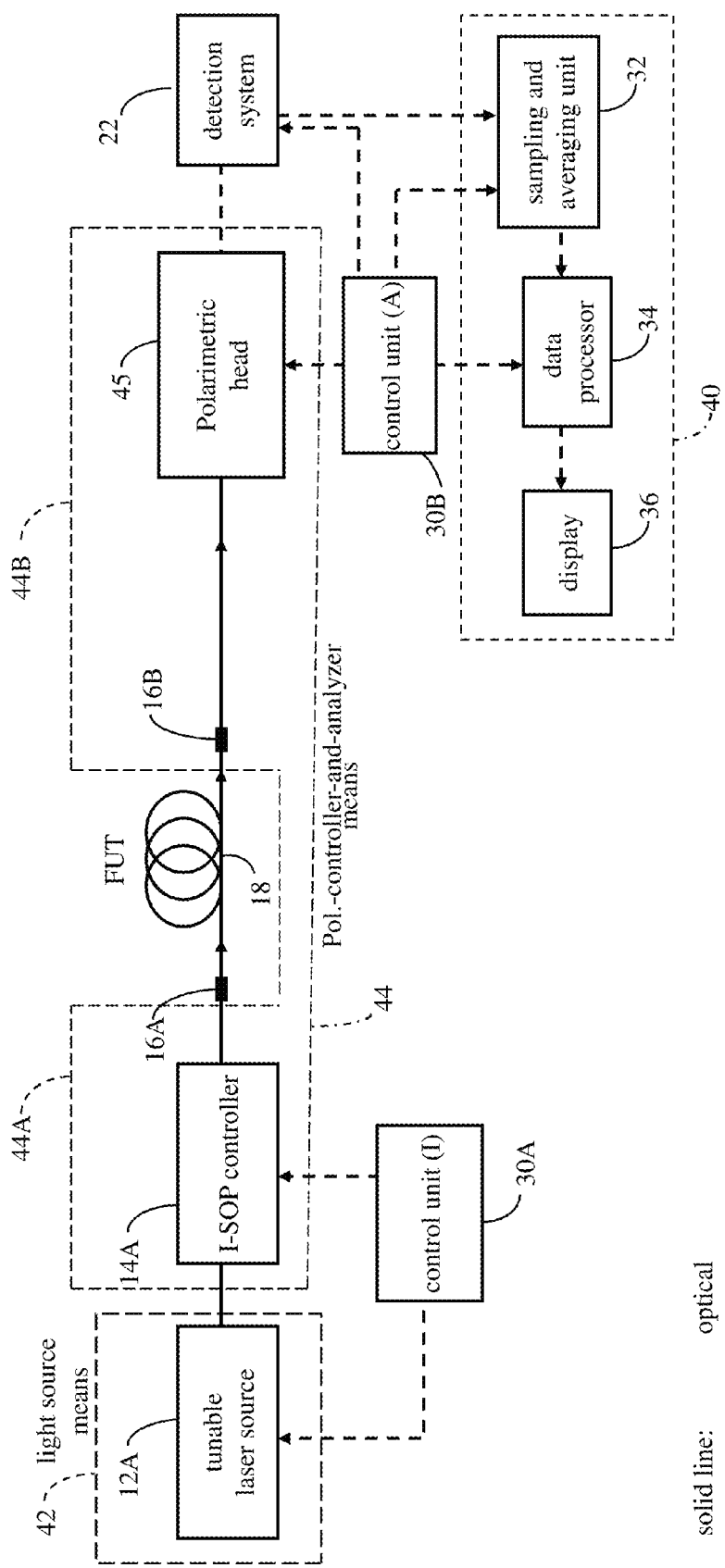
FIG. 1H is a simplified schematic diagram of measurement instrumentation similar to that shown in FIG. 1 but which has a polarimetric head for analyzing light from the FUT.

Various configurations of the two-ended measurement instrumentation of FIG. 1 that employ an A-SOP controller 14B are illustrated in FIGS. 1B to 1G and 1I to 1K, and a further implementation in which the second portion of the polarization-controller-and-analyzer means and detection system/means are replaced by a polarimetric head 45 is illustrated in FIG. 1H; these configurations will now be described briefly. The measurement instrumentation configurations depicted in FIGS. 1 to 1H have in common that they use a tunable laser source 12A whereas those depicted in FIGS. 1I to 1K use a broadband source 12B.

Thus, in each of the "two-ended" measurement instrumentation configurations illustrated in FIGS. 1B to 1H, the light source 12A comprises a tunable modulated laser source 12A whose output is coupled to either a polarization maintaining fiber (PMF) or singlemode fiber (SMF), as appropriate, for injecting modulated optical pulses into the fiber-under-test (FUT) 18 via the (input) state of polarization (I-SOP) controller means 14A and input connector 16A. The output light extracted from the FUT 18 via connector 16B and A-SOP controller 14B is analyzed by optical components comprising or equivalent to the polarization discriminator 20 of FIG. 1, and the analyzed light is measured during a time period during which light from the light source means 12A is detected, successively, at each of two different wavelengths, $\lambda_L^{(k)}$ and $\lambda_U^{(k)}$, that are closely-spaced relative to each other.

The main differences between the different configurations lie in the second portion 44B of the polarization-controller-and-analyzer means 44, and consequently in the manner in which normalization of the detected analyzed powers may be done. (Details of the normalization procedures will be provided hereinbelow.)

FIGS. 1B and 1C illustrate measurement instrumentation configurations for which, at a given A-SOP setting, only light power corresponding to one analysis condition is measured. Consequently, for both of these configurations, normalization of the analyzed light powers is carried out using an averaging procedure (over changes in at least one, and preferably at least two of A-SOP, I-SOP, and midpoint wavelength) described hereinbelow.

In FIG. 1B, in the polarization-controller-and-analyzer means 44 of the measurement instrumentation, the polarization discriminator comprises a linear polarizer 20A and the detection means comprises a single detector 22A. The measurement instrumentation illustrated in FIG. 1C is similar to that illustrated in FIG. 1B but differs in that a coupler 21 is disposed after the polarizer 20A, and two detectors 22B and 22C are connected to respective outputs of the coupler 21 to measure two repeated powers. Such repeated power measurements enable the contribution of uncorrelated noise to be suppressed in the processing steps, as will be described hereinbelow.

FIGS. 1D and 1E illustrate measurement instrument configurations for which, at a given A-SOP setting, both non-analyzed light power and light power corresponding to one analysis condition may be directly measured. Consequently, for both of these configurations, normalization of each of the detected analyzed powers may be carried out by normalization with respect to the corresponding non-analyzed light power, as described in more detail hereinbelow.

FIG. 1D shows measurement instrumentation similar to that shown in FIG. 1B but which differs in that it has two detectors 22B and 22C and a coupler 21 interposed between the A-SOP controller 14B and the polarization discriminator (polarizer) 20A. Detector 22B is connected to the coupler 21 via polarizer 20A and measures analyzed light received therefrom and detector 22C is connected directly to the coupler 21 and measures non-analyzed light that is proportional to a total power of the light extracted from the FUT 18. Thus, the SOP of the extracted light is transformed by the A-SOP controller or scrambler 14B, following which the light is split into two parts by coupler 21. The first detector 22B connected to one of the two outputs of the coupler 21 via the polarizer 20A detects one of the (analyzed) polarization components and the second detector 22C connected to the other output of the coupler 21 measures a power that is proportional to a total output light power from FUT. Preferably, the respective light portions are detected approximately simultaneously by detectors 22B and 22C, although they may be detected at slightly different times provided that any variation (e.g. instabilities) of the total output light power from the FUT occurs over a longer time scale than the difference in detection times.

The measurement instrumentation shown in FIG. 1E differs from that shown in FIG. 1D in that the former employs only one detector 22A, and the optical switch 23, controlled by control unit 30B, connects the input of detector 22A in alternating fashion to the output of the coupler 21 and the output of polarizer 20A to measure, respectively, the analyzed light and non-analyzed output light power from the FUT 18.

FIGS. 1F and 1G illustrate measurement instrument configurations for which light power is analyzed in a polarization-diverse manner, i.e. a PBS analyzes the light under orthogonal analysis conditions. Since the sum of the detected powers of these two orthogonally-analyzed parts is proportional to the total non-analyzed optical power (i.e. the Stokes parameter $S_0$), normalization of each of the detected analyzed powers may be readily carried out for both of these configurations, as described in more detail hereinbelow.

The measurement instrumentation shown in FIG. 1F employs two detectors 22B, 22C, each in optical continuity with a respective one of the two outputs of PBS 20C. The SOP of the light from the distal end of the FUT 18 is transformed by the A-SOP controller 14B, following which the light is decomposed by the PBS 20C into two components having orthogonal SOPs, typically linear SOPs at 0- and 90-degree relative orientations, and detected approximately simultaneously by detectors 22B, 22C. Of course, these detectors need to be suitably calibrated to take into account the relative detector efficiencies, wavelength dependence, etc., as will be described hereinafter. In FIG. 1G, an optical switch 23 and a single detector 22A are used instead. For this configuration, the control unit 30B causes the switch 23 to connect the detector 22A alternately to the respective output ports of the PBS 20C to measure the analyzed light from each port.

For both of the configurations of FIGS. 1E and 1G, an optical switch 23 is employed to successively select for detection by detector 22A light routed through one of two optical paths: in the case of FIG. 1E, either directly from coupler 21 or via polarizer 20A and in the case of FIG. 1G, from one or the other of the two outputs of PBS 20C. For both of these configurations, the light from the two different optical paths is detected at different times, the time interval preferably being kept as small as practicable. This enables use of only one detector (and associated electronics) while maintaining many of the advantages associated with the use of two detectors. Of course, the cost reduction associated with the use of only one detector likely would be largely counteracted by the increased cost of introducing the optical switch, and there would also be a measurement time penalty.

The measurement instrumentation illustrated in FIG. 1H is similar to that shown in FIG. 1B but differs in that the second portion 44B of the polarization-controller-and-analyzer means 44 comprises a polarimetric head 45 having its input connected to the FUT 18 via connector 16B and its output connected to detection system 22.

Figure 1I:
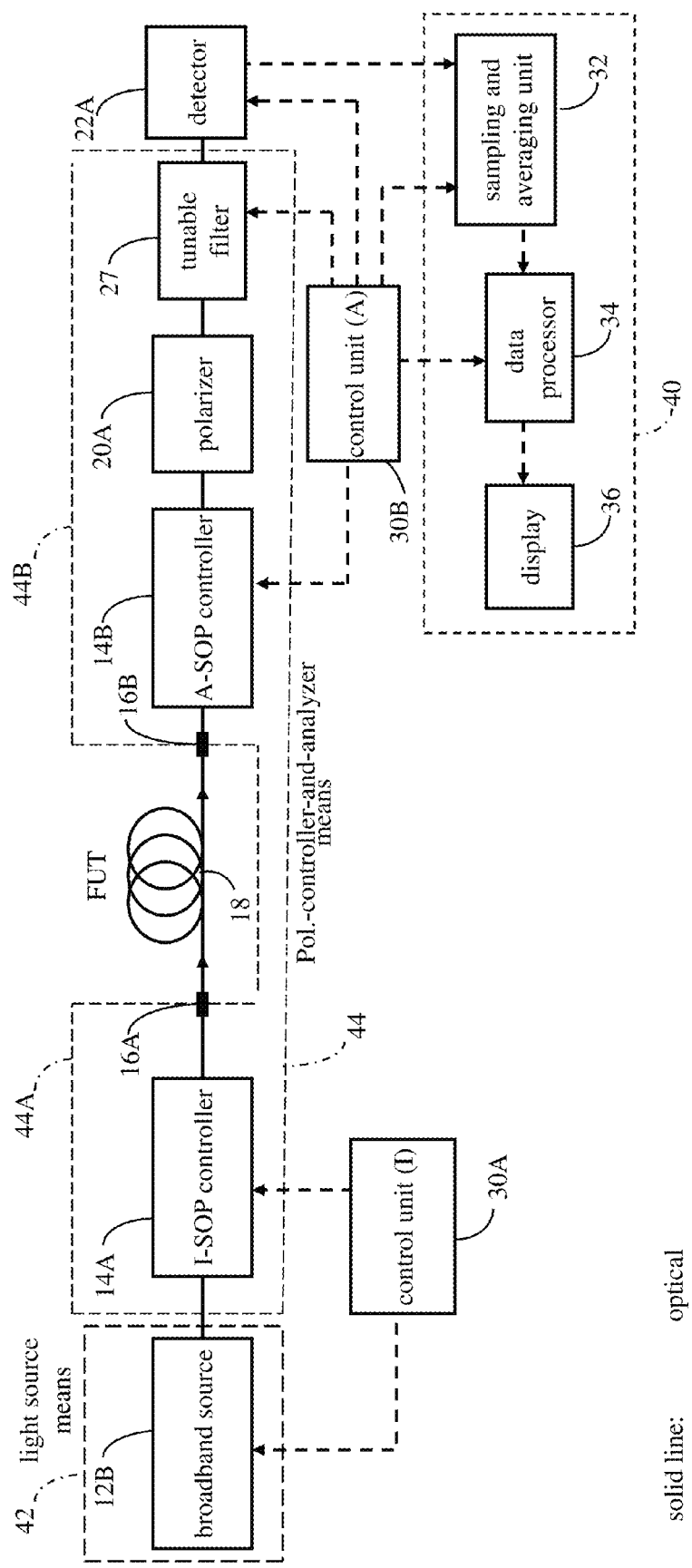
FIG. 1I is a simplified schematic diagram of broadband light source based two-ended PMD measurement instrumentation which is similar to that shown in FIG. 1B but uses a light source to provide spectrally wide light encompassing the desired wavelength range and a narrow-band tunable filter (between polarizer and a detector) to enable detection of only that fraction of light corresponding to a small spectral width centered about the passband wavelength of the narrow-band tunable filter.

Preferred implementations of the two-ended "test-source-based" embodiment will now be described with reference to FIGS. 1I, 1J and 1K, which use, instead of a tunable laser source 12A, a broadband source 12B that has a very wide spectrum, or a tunable broadband source that has a moderately wide spectrum whose center wavelength is tunable. The measurement instrumentation illustrated in FIG. 1I is similar to that described with reference to and as shown in FIG. 1B, but differs in that its light source means 42 comprises a polarized broadband light source 12B instead of a tunable laser source and its polarization-controller-and-analyzer means 44 differs from that shown in FIG. 1B because it comprises a narrow-band tunable filter 27 placed after the polarizer 20A in order to spectrally filter, and hence render coherent, the analyzed light before it is applied to the detector 22A. Tunable filter 27 is controlled by control unit 30B.

It should be appreciated that the tunable filter 27 could alternatively be placed anywhere in the optical path between the output of the FUT at connector 16B and the detector 22A, while remaining in close proximity to control unit 30B, and is not limited to being placed between the polarizer 20A and the detector 22B as shown in FIG. 1I. Indeed, more generally the tunable filter 27 could be placed anywhere between the broadband source 12B and the detector 22A. However, placing the tunable filter 27 in the light source means 42 at the proximal end of the FUT 18 may lead to control and synchronization difficulties, as communication between the tunable filter 27 at the proximal end and the control unit 30B at the distal end of the FUT may be difficult.

Figure 1J:
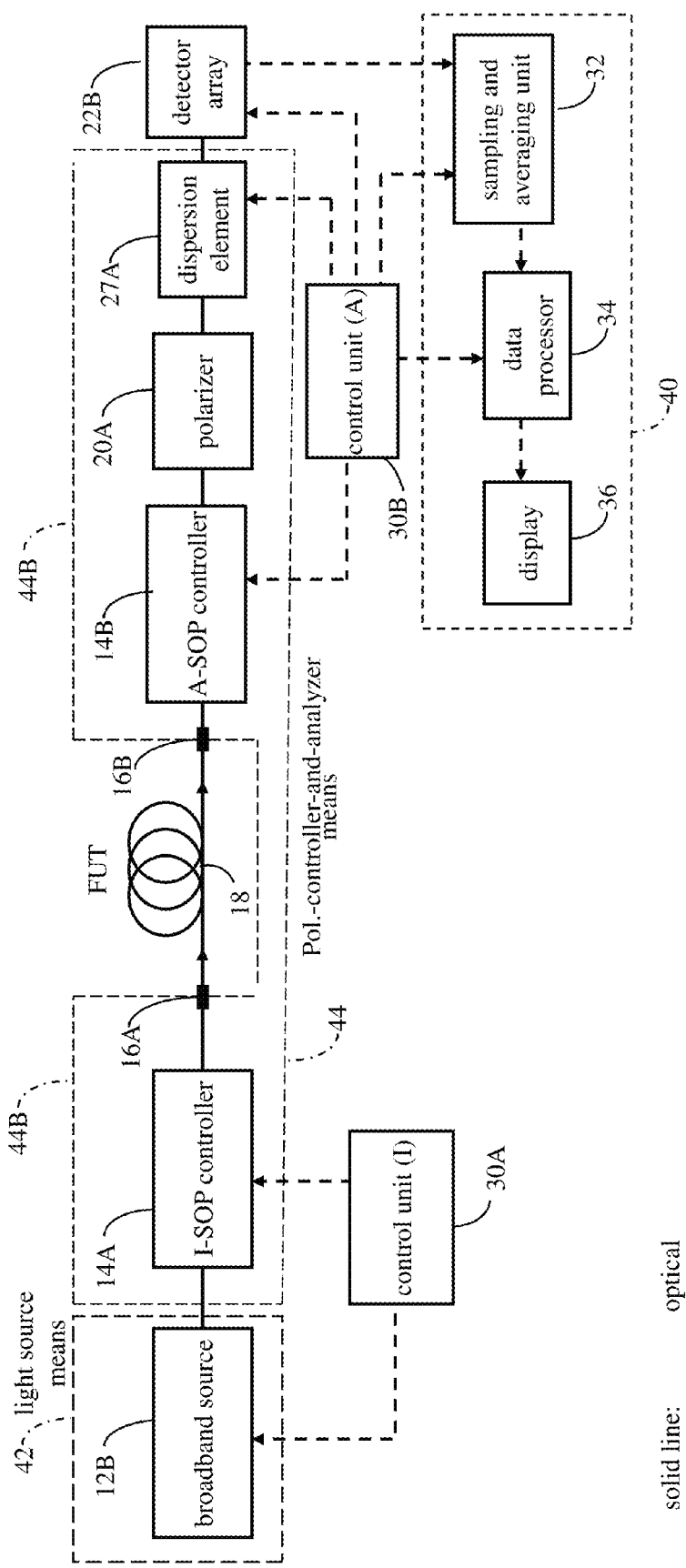
FIG. 1J is a simplified schematic diagram of broadband light source based two-ended PMD measurement instrumentation similar to that shown in FIG. 1I but employs a dispersion element (multi-channel filter) and multi-channel detector array means that measures analyzed light after the polarizer simultaneously or within a short time period.

The measurement instrumentation illustrated in FIG. 1J is similar to that shown in FIG. 1I but differs in that the tunable filter 27 is replaced by a spectrometer means or multi-channel filter means, specifically a dispersion element 27A, for example a grating-based wavelength separator, to separate the different wavelengths of light as a function of angle. The single detector 22A is replaced by detection means for detecting light powers at these wavelengths approximately simultaneously, for example, a multi-channel detector array 22B or similar means. Alternatively, such a detector array 22B may be replaced by several fiber pigtailed photodetectors that may be connected to a fiber array to detect light at different spatial positions, or simply to launch light at different spatial positions having different optical wavelengths into different photodetectors. Although there would be a higher cost associated with this design, it could measure DGD or PMD rapidly.

Figure 1K:
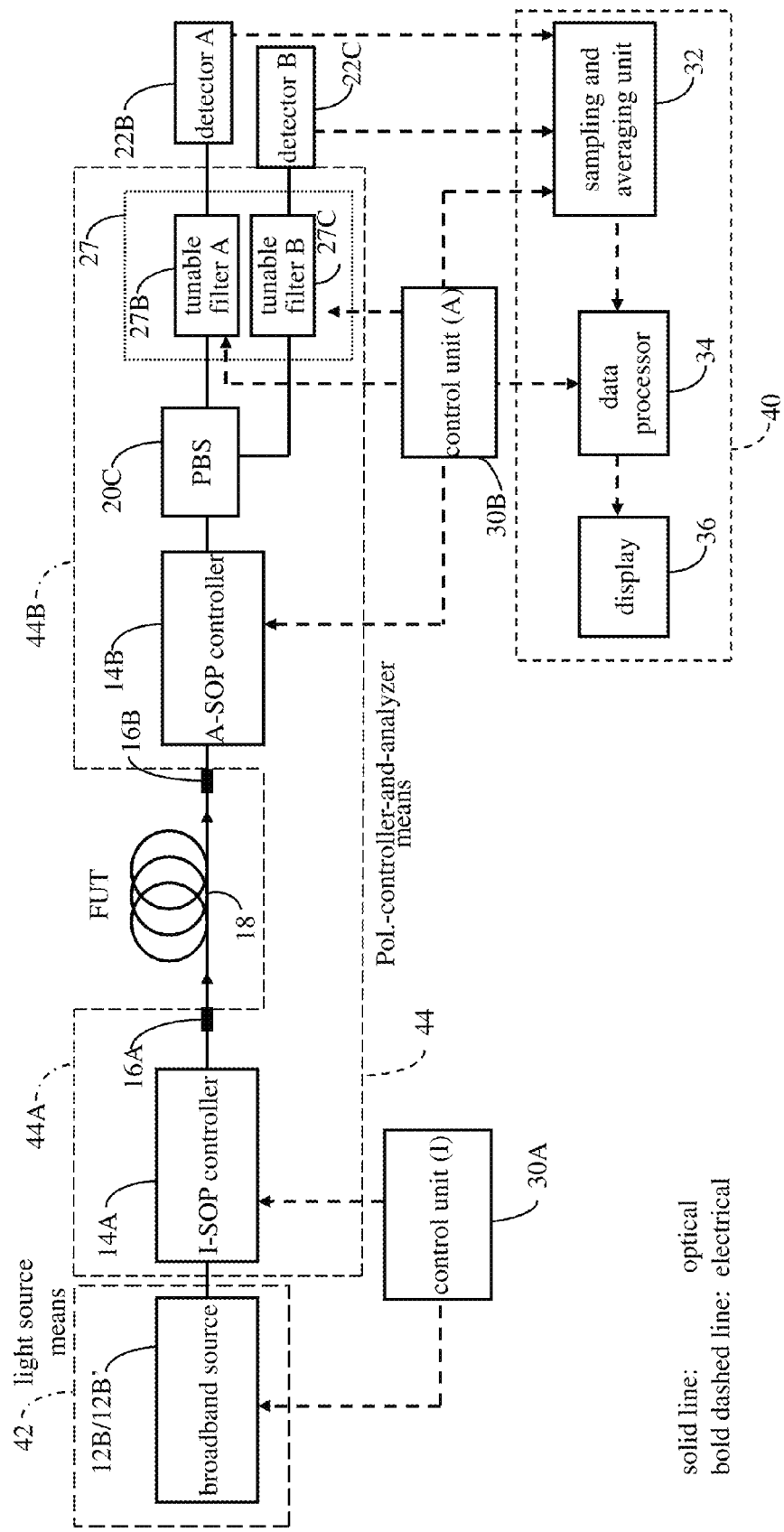
FIG. 1K is a simplified schematic diagram of broadband light source-based two-ended PMD measurement instrumentation which is similar to that shown in FIG. 1F but uses a light source to provide the spectrally wide light encompassing the desired wavelength range, a PBS in the polarization-controller-and-analyzer means, two synchronously-controlled narrow-band tunable filters between the PBS and the respective detectors, to enable polarization-diverse detection of light corresponding to a small spectral width centered about the passband wavelength of the narrow-band tunable filter.

In another implementation, shown in FIG. 1K, the measurement instrumentation is similar to that shown in FIG. 1I, but differs in that the tunable filter 27 of FIG. 1I is replaced by two synchronously-controlled narrow-band tunable filters 27B, 27C, conveniently as respective channels of a two-channel grating-based scanning monochromator 27, and the polarizer 20A of FIG. 1I is replaced by a PBS 20C. The two orthogonal analyzed outputs from the PBS 20C are conveyed (via optical fiber) to respective ones of the two channels of the scanning monochromator 27. Detectors 22B, 22C, detect light, substantially simultaneously, from respective ones of the two outputs of the two-channel scanning monochromator 27, resulting in "polarization-diverse" detection as a function of wavelength. (An example of an optical spectrum analyzer based on such a polarization-diverse two-channel scanning monochromator design is described in commonly-owned U.S. Pat. No. 6,636,306 (He et al.) The analog-and-digital signal processing unit 40 then can process this data to extract DGD and PMD information.

Once suitably calibrated to take into account the relative detector efficiencies, wavelength dependence, etc., as will be described hereinafter, the sum of the detected powers from detectors 22B and 22C, respectively, is proportional to the total incident (i.e. non-analyzed) power (often referred to as the Stokes parameter $S_0$) within the monochromator 27 optical bandwidth.

For implementations where the tunable filter 27 is employed, the tunable filter 27 is operated to allow the selection and subsequent detection of each of the wavelengths corresponding to the groups comprising the wavelength pair; the selected filtered light corresponding to the two or more wavelengths being subsequently detected by two or more detectors, respectively, e.g. detectors 22B and 22C. It should be noted that the tunable filter 27 can be a single channel filter that is operated in a "continuous sweep" mode, or may be operated under a "stepped wavelength" selection mode where a particular step may correspond to an optical frequency at which two detected analyzed powers are acquired (i.e. repeated powers, as will discussed in more detail hereinbelow). It should be also noted that the tunable filter 27 can be designed as a spectrometer, for example as shown in FIG. 1J, enabling powers at different wavelengths to be measured contemporaneously. Also note that different polarization components may be detected by different detectors, as shown in FIG. 1K, or the same detector but at different times by using appropriate polarization controlling means.

Preferably, in the "two-ended test-source-based" implementations of the measurement instrument shown in FIGS. 1 to 1K, there is little or no "upstream" communication between the control unit 30B at the distal end of the FUT 18 and the control unit 30A at the proximal end. For the implementations shown in FIGS. 1 to 1H, the control unit 30B comprises software or firmware that allows it to determine, from information encoded onto the optical signal by the optical light source means 42, conveniently under the control of control unit 30A, whether a particular detected modulated optical pulse extracted from the FUT 18 corresponds to an uppermost, lowermost, or, where applicable, intermediate closely-spaced wavelength. If a "widely broadband" source means is employed in the implementations shown in FIGS. 1I to 1K, there is advantageously no need for the control unit 30B to receive wavelength information from the light source means 42, as all wavelength selection is performed at the same end of the FUT as the control unit 30B. If a tunable "moderately broadband" light source means 42 is employed in the implementations depicted in FIGS. 1I to 1K, suitable for measuring the DGD of a particular DWDM channel, there is a need to initially tune ("set") the light source means 42 to encompass all or most of the passband of the desired DWDM channel, an operation that may necessitate communication between operators at the two corresponding sites.

The preferred implementations described hereinbefore are common to principal aspects of this invention. Further details of the preferred implementations, including details of their operation, corresponding to each of these principal aspects/implementations will be described in more detail in Sections 2 and 3 hereinbelow.

1.2.2 Measurement of DGD at a Particular Wavelength

In a narrow DWDM channel, it is frequently not practical to measure the DGD at more than one wavelength ($\lambda_{mid}$) within the channel (or at least not more than a very limited number of wavelengths), since the optical-frequency spacing of the closely-spaced wavelengths may be a significant fraction of the useable optical passband of the DWDM channel and, consequently, measurement at another midpoint wavelength may cause one of the two closely-spaced wavelengths to experience excessive attenuation, polarization-dependent loss, and other deleterious effects that may render the measurement unreliable or impractical. (As will be described in more detail hereinafter, the choice of a very small optical-frequency spacing may not be compatible with the measurement of a small DGD value.)

It may be useful to perform this DGD measurement as a function of optical frequency at at least two optical frequencies ("midpoint wavelengths"), within an "optical channel" bandwidth, as such a measurement enables an estimation of at least one component of the second-order PMD, i.e. the component proportional to $d(DGD(\upsilon))/d\upsilon$. As known in the prior art (see, for instance, Foschini et al, Journal of Lightwave Technology, vol. 17(9), pp 1560-1565 (1999), in particular Eq. 8) for a strongly mode-coupled FUT, such as is the case with almost all long telecom single-mode fibers, this measurement of this second-order PMD component provides an independent (i.e. uncorrelated) additional estimate of DGD. In other words, although the DGD so-obtained at the particular wavelength is not the real ("first-order") DGD, if this measurement is repeated for a plurality of DWDM channels, for instance, these additional "second-order-PMD" DGD estimates can be used to improve the overall uncertainty of the PMD value determined via an rms (or arithmetic mean) of all the DGD estimates, whether derived directly, or indirectly via the second-order PMD. It should also be noted that the measurement of DGD at a particular wavelength is not limited to "in-channel" applications such as testing optical links through DWDM channels.

Note that, for DGD measurement in a "dedicated" DWDM channel, i.e., a measurement that is always to be undertaken at approximately the same particular wavelength, it is not necessary that the light source means 12 or 12B be widely tunable or very broadband, but only that it be either:

a "moderately" tunable coherent light source capable of emitting coherent light at each of two different closely-spaced wavelengths centered about the aforesaid "particular wavelength", for the case where there is no narrowband optical filtering in the analyzing-and-detection means;

a "moderately" broadband source capable of emitting at least partially polarized light having a spectral width encompassing at least the "closely-spaced wavelengths" separation, and preferably all or most of the bandpass of the "dedicated" DWDM channel-under-test, for the case where the analyzing and detection means comprises narrow-band optical filtering.

Thus, depending upon the particular measurement implementation, the light source means 42 may comprise one of a tunable coherent source (e.g., a laser), a "widely" broadband source (for instance, having a spectral width encompassing all desired DWDM channels to be measured, for instance), or a "hybrid" thereof, for instance, a tunable "moderately" broadband source. In this latter case, the source should be at least sufficiently broadband to encompass all or most of the DWDM channel passband, thereby clarifying the meaning of "moderately", and this broadband "spectral slice" may be tuned or "set" to be centered upon any one of a number of other DWDM channel wavelengths, for instance in the telecommunications C and/or L bands. More details concerning the tunable light source, widely broadband light source, or tunable moderately broadband source means are provided in a later sub-section.

In field installations, DGD can vary with time and/or environmental conditions, on time scales that may range from minutes to weeks, or in some cases even years. For many measurement applications, the speed ("update rate") of the measurement is not critical. Consequently, it is advantageous for cost reasons to use inexpensive polarization scramblers for the Input-SOP (I-SOP) controller 14A and for the Analyzer-SOP (A-SOP) controller 14B of the polarization-controller-and-analyzer means 44. An example of a low-cost SOP scrambler that may be suitable for both of the I-SOP and A-SOP controllers 14A and 14B is described in co-owned U.S. Pat. No. 8,373,852 (Ruchet et al), the contents of which are incorporated herein by reference.

The actual SOP of light exiting the input I-SOP controller 14A is, in general, unknown, but undergoes "continuous" transformation, i.e. is varied slightly between groups of closely-spaced wavelengths, such that over a sufficiently long time, normally corresponding to the minimum time for a reliable DGD measurement, the SOPs will cover the Poincaré sphere approximately uniformly.

The analyzer A-SOP controller 14B, located at the distal end of the FUT 18, may also cause the SOP of the light exiting the FUT 18 to be varied slowly in a similar manner to the input I-SOP controller 14A, although in general the respective rates of variation would not be the same and the SOPs exiting either the I-SOP controller 14A or the A-SOP controller 14B would be uncorrelated. Alternatively, the analyzer A-SOP controller 14B may vary the SOP in a discrete and random fashion, since there are normally no synchronization difficulties with the co-located control unit 30B.

More specifically, for a particular measurement sequence k, the control unit 30B causes the light signal, analyzed by the intervening polarization discriminator, such as a polarization beam splitter (PBS) or polarizer, to be measured during a portion of time during which light from the light source means 42 is detected, successively, at each of two different wavelengths, $\lambda_L^{(k)}$ and $\lambda_U^{(k)}$, that are closely-spaced relative to each other, during which portion of time the SOPs exiting the I-SOP controller 14A and A-SOP controller 14B, respectively, are approximately constant and form a k-th SOP couple (I-SOP$_k$, A-SOP$_k$). (Preferably, the aforementioned portion is less than 50% of the "physical" pulse length, for reasons that will be explained further below.) The midpoint wavelength of the pair of modulated light pulses is defined as the average of the actual optical frequencies of the modulated light pulses, which to a very high degree of approximation can be expressed in terms of wavelength as $\lambda_{mid}^{(k)} = (\lambda_L^{(k)} + \lambda_U^{(k)})/2$. (The labels L and U refer, for convenience and ease of understanding, to "lowermost" and "uppermost" with respect to the midpoint wavelength $\lambda_{mid}^{(k)}$ and more accurately the midpoint wavelength is expressed as $$\lambda_{mid}^{(k)} = \frac{2\lambda_L^{(k)} \cdot \lambda_U^{(k)}}{\lambda_L^{(k)} + \lambda_U^{(k)}}.)$$

The measured analyzed light signal is converted to an electrical signal by the sampling and averaging means 32 and subsequently digitized before application to the data processor 34 for subsequent processing thereby.

During the transition from one closely-spaced wavelength to the other, the light from the light source means 12A is briefly extinguished, say for about 40 μs, a period that is much shorter than the typical reaction period of DWDM channel equalizers found in many optical networks. The precise period of this extinction serves to encode, for use by the control unit 30B, information indicating whether the subsequent pulse corresponds to an uppermost or lowermost wavelength.

The measurement sequence described above is repeated for K different groups, each group corresponding to a slightly different I-SOP and A-SOP. In practice, if the SOP is "scanned" (i.e. transformed) in a continuous fashion, the aforesaid "sufficiently long time" typically would correspond to K values greater than 1000 to obtain fully satisfactory results.

The time period corresponding to light emission at each of the closely-spaced wavelengths is not particularly critical, but clearly a longer duration will lead to a longer overall measurement time for this method. A good compromise between measurement time and limitations on the light-source wavelength switching speeds has been found to be a period of about 1 ms.

If the expected DGD to be measured is not roughly known, it is possible that the optical-frequency difference of the closely-spaced wavelength pairs will be too large to permit accurate measurement of high DGD values, or, conversely, too small to permit measurement of low DGD values. In such a case, it may be desirable to perform a preliminary rough DGD estimation using this method using only a limited number of K values. (It should be noted that, with the continuous SOP scanning approach, K necessarily must still be relatively large, e.g. 〉500, for a rough measurement, whereas if the alternative "macroscopic-step SOP selection" approach is used, as described hereinafter, K may be a much smaller value, e.g. approximately 10.) Then, depending on the result, the spacing of the closely-spaced wavelengths may be adjusted, while maintaining the midpoint wavelength at the same value. However, as mentioned above, in a narrow DWDM channel, which may, for instance, only have a useable passband width of approximately 35 GHz, it is not always possible to increase the wavelength spacing.

An alternative approach for "adapting" the optical frequency difference between the closely-spaced wavelengths is to use more than two closely-spaced wavelengths in each group, the wavelength spacing between pairs of wavelengths being unequal. If, as described above, the preliminary DGD estimation indicates that the wavelength spacing should be different, one need only slightly shift the midpoint wavelength corresponding to the "optimal" closely-spaced wavelength pair to the midpoint wavelength corresponding to the initial closely-spaced wavelength pair.

Advantageously, in order to estimate, and partially compensate for, the contribution of noise in the measurements, "repeated measurements" are taken for each group at the same two closely-spaced wavelengths, these repeated measurements being in principle substantially perfectly correlated to the "original" measurements, in the absence of noise (i.e. identical if taken under the same polarization analysis conditions, or perfectly complementary if taken under orthogonal polarization conditions, e.g. via the two outputs of a polarization beam splitter). In practice, such noise may arise from any combination of ASE noise (from intervening optical amplifiers in the fiber link), polarization noise (caused by swaying aerial cables, for instance), light source power fluctuations, uncorrelated electronic noise, etc. The method by which this technique is used to improve the measurement sensitivity will be described in more detail hereinafter.

It should be noted, however, that it is actually convenient not to transmit distinct "physical" repeated pulses in the preferred implementation, but rather to perform the functional equivalent in the acquisition process by sampling the "physical pulse" (corresponding to the period during which the laser emits at a particular wavelength) during a different portion of time than the portion during which the "initial" measurement was taken. Consequently, in a preferred implementation, each "physical pulse" comprises two "optical modulated pulses".

The computational method by which the data thus acquired can be converted into a reliable DGD measurement, including in the presence of significant ASE noise, will be described in more detail hereinafter.

1.2.3 RMS or Mean DGD Measurement Using Repeated DGD(λ) Measurements

By repeatedly applying the above-described method of measuring DGD at a particular wavelength of the invention over a prescribed wavelength range, it is possible to estimate the polarization mode dispersion (PMD) of a fiber link (according to either or both of the "rms" or "mean" PMD definitions) from the DGD as a function of wavelength. Preferably, the wavelengths should be approximately uniformly distributed across a prescribed wavelength range.

For reasons of overall measurement time, it is advantageous to replace the continuous SOP scanning described in the Summary of Invention hereinbefore with "macroscopic-step SOP selection", i.e. where I-SOP controller 14A and A-SOP controller 14B set the different input and analyzer SOPs in a pseudo-random manner, such that the points whereby such SOPs conventionally are represented on the Poincaré sphere are uniformly-distributed over the surface of said sphere, whether the distribution is random or a uniform grid of points. An example of a suitable commercially-available controller for such an application is the General Photonics Model PolaMight™ (multifunction polarization controller).

As mentioned in the context of the above-described measurement of DGD at a particular wavelength, it is frequently the case that the optical frequency difference of the closely-spaced wavelength pairs is, for instance, too large to permit accurate measurement of high DGD values, or too small to permit measurement of low DGD values. In such a case, it may be desirable to perform a preliminary rough DGD estimation using this method but with a limited number of K values (e.g. 10), and then, depending on the result, change the spacing of the closely-spaced wavelengths. Note that, in this case, where the rms or mean DGD is calculated over a prescribed wavelength range, it is usually not necessary to maintain exactly the same midpoint wavelength for this measurement with a different optical-frequency difference. The final DGD averaging over the wavelengths can take into account this slightly different wavelength.

A preferred method of carrying out this approach with various implementations of the light source means 42 will now be described, which is applicable to the measurement instrumentation configurations already described with reference to FIGS. 1, 1B to 1K. (For simplicity of the foregoing description, we assume that the "repeated pulse" method, described in the measurement of DGD at a particular wavelength above, is not applied. The "intermediate wavelength" method described here can be readily generalized to include the "repeated pulse" method.)

First, the light source means 42 injects into the FUT 18, for each group comprising a wavelength pair of optical pulses, a third additional optical pulse having a wavelength ($\lambda_{1I}$) intermediate and unequally spaced with respect to the uppermost and lowermost wavelengths ($\lambda_{1U}, \lambda_{1L}$) respectively, of the group. The input SOP selected by I-SOP controller 14A and the analyzer-SOP determined by A-SOP controller 14B, respectively, are approximately constant for all three optical pulses. All three analyzed pulses are detected by the detection system or means 22, and are identified by their respective "extinction periods", as described in the measurement of DGD at a particular wavelength above. The three aforementioned optical pulses correspond to three different combinations of optical-frequency differences (in comparison with two different close-spaced wavelengths, which, of course, correspond to only one possible optical frequency difference), and hence only add about 50% to the overall measurement time. Using the computation method described in more detail hereinafter with reference to the flowchart shown in FIG. 7B noise-and/or sensitivity-optimized DGD measurements can be made at different approximately uniformly spaced (midpoint) wavelengths over the prescribed wavelength range.

It should be noted that, if a significantly uneven distribution of the same number of DGD(λ) were used, a PMD value could still be calculated by a straightforward modification of the method that would be obvious to someone of average skill in the art, but this PMD value would not be, in general, as reliable as a PMD value obtained with approximately uniformly distributed wavelengths.

For the case where the light source means 42 comprises a tunable laser 12A (as in FIGS. 1B to 1H and 10A), it is desirable that the choice of midpoint wavelengths defined by the closely-spaced wavelengths that are generated by the tunable laser source 12A (FIGS. 1(B-H)) or by tunable filter 27 (FIG. 1I) be predetermined for the prescribed wavelength range (e.g. C band, from 1530-1565 nm), in order to avoid having to use potentially complicated communication between the light source means 42 and the polarization-controller-and-analyzer means 44. In this way, there is no need for the numerical values of the injected wavelengths to be explicitly communicated, as these values can be inferred by the control unit 30B from simple coding information in the extinction times, as discussed earlier. It may, however, be desirable for an initial "ready" signal to be sent from the light source means 42 to begin the measurement sequence. Again, this signal could be encoded in the light injected into the FUT, via the extinction period or other simple pulse frequency modulation.

Once a set of DGD($\lambda$) values have been obtained as described above, it is straightforward to compute, using standard statistical definitions, either or both of the rms DGD and the mean DGD from the different values of DGD obtained within the prescribed wavelength range. Note that such a measurement is particularly useful, since most current commercial approaches do not permit the PMD to be directly measured using both rms and mean definitions.

1.2.4 RMS DGD Measurement (without Individual DGD($\lambda$) Measurements)

The underlying measurement approach can be applied for the direct measurement of the rms DGD (i.e. PMD according to the rms definition) across a prescribed wavelength range. If information concerning the DGD as a function of wavelength is not required, implementations of the "two-ended test-source-based" embodiment of the invention may provide for a much more rapid PMD measurement (for the same overall level of accuracy) than the method of RMS measurement using repeated DGD($\lambda$) measurements described above. In addition, since the polarization-controller- and analyzer means 44 does not need to "know" the actual value of the wavelength being transmitted (only whether the wavelength corresponds to the "uppermost", "lowermost" or one or more "intermediate" wavelengths), there is no need for the use of predetermined wavelengths or an explicit "start" signal for the measurement, thereby simplifying the measurement procedure.

The computational method by which the data thus acquired can be converted into a reliable DGD measurement, including in the presence of significant ASE noise, is much the same as in the above described measurement of DGD at a particular wavelength, except that individual measurements taken with each group of closely-spaced wavelengths are averaged over "center wavelengths" (see later for a definition of center wavelength) approximately uniformly distributed across the prescribed range, as well as over different I-SOPs and A-SOPs. In certain implementations, the choice of midpoint wavelengths may be quasi-random, or at least not sequential in ascending or descending wavelength. In other implementations, it may be preferable to perform the measurements sequentially in ascending or descending wavelengths. Computational details will be described hereinafter.

As with the above described rms or mean DGD measurement using repeated DGD($\lambda$) measurements, it is advantageous to inject more than two different closely-spaced wavelengths in each group of wavelengths, in order that the optimal optical-frequency spacing can be used in the computational process.

Before the measurement procedure for these implementations is described in more detail, and with a view to facilitating an understanding of such operation, the theoretical basis will be explained, it being noted that such theory is not to be limiting.

1.2.5 RMS DGD Measurement Using Rapid Wavelength Sweeping

An alternative approach to measure the rms and/or mean DGD over a prescribed wavelength range is to use a rapidly swept tunable laser (FIGS. 1B-1H) (or polarized broadband source/tunable narrowpass filter combination (FIG. 1I), or a polarized broadband source/polarization-diverse scanning monochromator combination (FIG. 1K)), where either or both of I-SOP and A-SOP vary little or not at all during the sweep. If the detection electronics are sufficiently rapid, this "spectral acquisition step" will provide a quasi-continuum of detected polarization-analyzed transmitted coherent optical power data as a function of optical frequency. In the subsequent data analysis, any desired closely-spaced wavelength step could be selected, and the average DGD determined from different wavelength pairs so selected in a similar fashion to that described earlier. Of course, if I-SOP and A-SOP vary during the sweep, this would further improve the accuracy of the measurement, provided that neither I-SOP nor A-SOP varies significantly between any two closely-spaced wavelengths in the sweep. Furthermore, repeating this procedure with multiple sweeps will of course further improve its accuracy.

This alternative approach also has the advantage that there is no need for encoding in the source (12A, 30A; 12B, 30A) to identify "upper, lower and intermediate" closely-spaced wavelengths, as described earlier. (Of course, for the swept tunable laser case, there may be a need to indicate the beginning of the sweep, but such an indication would be straightforward to implement.)

1.2.6 Various Modifications to the Two-Ended PMD Measurement Means

The invention encompasses various modifications to the two-ended PMD measurement instrumentation configurations shown in FIGS. 1-1K. Although these modifications may be applied separately, certain implementations of the invention may include several such modifications.

A person of ordinary skill in this art would be able, without undue experimentation, to adapt the procedure for calibrating the relative sensitivities of the two detectors 22B and 22C, as shown in FIG. 1G or 1K, including the losses induced by the intervening coupler, etc., described hereinbefore with reference to the two-ended PMD measurement of FIGS. 1G and 1K. That said, it should be appreciated that, in the implementation of FIG. 1D, calibration of the mean relative gain is not required; the measured total power is independent of SOP, and there is no need for an "absolute" calibration to directly measure absolute transmission values; they can be obtained to within an unknown constant factor. The subsequent normalization over the mean powers averaged over SOPs, as described hereinbefore, eliminates the unknown factor.

Where the detection means 22 comprises a single detector 22A (e.g., FIG. 1B) detecting only analyzed light, normalized powers (or transmissions) can be obtained by computing an average of all of the powers in first and second groups of powers, and dividing each of the powers by the said average power to obtain first and second groups of normalized powers, as described in detail hereinafter.

FIG. 1B illustrates PMD measurement instrumentation suitable for determining DGD or PMD using normalized powers obtained in this way. The PMD measurement illustrated in FIG. 1B is similar to that illustrated in FIG. 1D but with coupler 21 and detector 22C omitted. The data processor 34 will simply apply different normalization equations.

Where a polarimetric head 45 is used (see FIG. 1H), several (typically three) different polarization components of light exiting from FUT 18 can be measured, either simultaneously or at different times, dependent on the polarimetric-head design.

It should be noted that the single-ended measurement instrumentation of FIG. 3 could also be adapted to use a polarimetric head 45 in its polarization-controller-and-analyzer means 44, although this would likely be accompanied by a significant reduction in dynamic range.

In the polarized broadband light source based two-ended PMD measurement instrumentation shown in FIG. 1I, a tunable filter 27 is used to select light wavelength. This tunable filter can be located after polarizer 20A (FIG. 1I) or before polarizer 20A. It is normally preferable that the tunable filter be polarization-insensitive. Normally, the tunable filter will be operable to select different wavelengths at different times.

Although the tunable filter 27 in FIG. 1I need only exhibit low or modest polarization-dependent loss (PDL), it should be noted that, if the tunable filter 27 is highly polarization sensitive, e.g. polarization-dependent loss (PDL) $>$ 20 dB, it may combine the functions of polarizer 20A and (low or modest PDL) tunable filter 27 in FIG. 1I.

In any of the above-described implementations, the input I-SOP controller 14A and analyzer A-SOP controller 14B each operate in such a manner that, for a given SOP of the light received at its input (which can be any SOP on the Poincaré Sphere), the SOP of the light leaving its output (i.e. leaving either I-SOP 14A or A-SOP 14B) will be any other one of a number of substantially uniformly distributed SOPs on the Poincaré Sphere, whether the distribution is of random or deterministic nature. Typically, the number of input and output states of polarization is about 100-100,000, but it could be any practical number allowing for a reasonable coverage of the Poincaré Sphere. However, it may also be possible to use just one SOP for both the I-SOP and the A-SOP. It is noted that the distribution of the SOPs need not, and generally will not, be truly random; so "pseudo-random" might be a more appropriate term in the case where a random distribution is indeed used for convenience because it is easier and less expensive to implement than a uniform grid of SOPs (the latter being in any case very susceptible to movement of the FUT 18 during measurement).

The detection means 22, whether a single detector, a pair of detectors, a filter plus detector, or a detector array, and the sampling-and-averaging unit 32, may be as used in standard commercial power meters that are known to a person skilled in this art.

The control unit 30B may advantageously be a separate computer. However, it is noted that a single computer could perform the functions of the data processor 34 and the control unit 30B.

Various other modifications to the above-described implementations may be made within the scope of the present invention. For instance the tunable modulated light source 12 and components of respective parts 44A and 44B of the polarization-controller-and-analyzer means could be replaced by some other means of providing the different polarization states of the modulated light entering the FUT 18 and analyzing the resulting light leaving the distal end of FUT 18.

The polarimetric head 45 used in the measurement instrumentation shown in FIG. 1H, (typically comprising splitters with three or four analyzers) analyzes more than one polarization component of the signal or power approximately simultaneously, but other similar configurations are feasible. Alternatively, an I-SOP controller 14A may launch three or more pre-defined input SOPs of light, for example corresponding to a Mueller set, which is well known in the art. The polarimetric head 45 then may be used in place of an A-SOP controller at the distal part 44B of the polarization-controller-and-analyzer means and the detection means.

It should be noted that each group is not limited to one pair of modulated optical pulses or one pair of series of modulated optical pulses. Indeed, it may use three or more different closely-spaced wavelengths per group of powers, instead of the minimally-required two closely-spaced wavelengths $\lambda_L$ and $\lambda_U$.

However, it should also be noted that more than one pair of modulated optical pulses and more than one pair of light pulses usually may not be required for two-ended overall PMD measurement if one may know a rough PMD value of the FUT. Otherwise, such as discussed previously in Section 1.2.2 in the context of a "rough" auto pre-scan, more than one pair of modulated optical pulses or more than one pair of series of light pulse may be used for the acquisition.

It should also be noted that a single DGD at one given midpoint wavelength may be obtained by averaging over a large number of random I-SOP and A-SOP settings for a given constant midpoint wavelength having two closely-spaced wavelengths. Therefore, the DGD as a function of wavelength in a given wavelength range may also be obtained by measuring many individual DGDs at different midpoint wavelengths within the given wavelength range. The mean DGD and/or rms DGD may be then be computed therefrom by averaging over all or most of these individual DGD values at different wavelengths in the given wavelength range. Alternatively, the rms DGD may also be computed from a mean-squared difference that is obtained by averaging over wavelength and/or SOP, without ever explicitly measuring the DGD at a particular wavelength.

Although the above-described method of operation changes the midpoint wavelength for each SOP, this is not an essential feature of the present invention. While superior performance can be obtained by covering a large wavelength range in order to obtain the best possible average of DGD, as per the definition of PMD, a PMD measurement embodying the present invention will work with no bias and may provide acceptable measurements of PMD, with a constant center-wavelength or even both constant input and output SOPs and constant center-wavelength with one pre-defined wavelength step (or frequency difference).

1.3 Embodiment (2)

Partial-DGD Measurement Employing Data-Carrying Signals and PMD Estimation Derived Therefrom

1.3.1 Description of Hardware and Summary of Operating Procedure

FIG. 2K shows a preferred implementation of an apparatus suitable for measuring average partial DGD ($DGD_P$). The SUT 60 carries modulated data of any modulation format (e.g. OOK, DPSK, QPSK, etc.) for which the detected DOP is greater than zero, and, preferably, exceeds 50%, and will usually encompass a spectral extent roughly equivalent to its modulation symbol rate (i.e. typically between 10-50 GHz), spaced by typically either 50 or 100 GHz from its nearest neighbor in an adjacent ITU channel. SUT 60 is input into analyzer-and-detection means 101 (i.e. the PMD monitor-and-analyzer) disposed at or adjacent e.g. a monitor port tapped from an optical transmission line 24 or the distal end of an optical path 24. As shown in FIG. 2K, the analyzer-and-detection unit 101 normally comprises an A-SOP controller 12, a polarization beam splitter (PBS) 20C serving as a polarization discriminating means, tunable filter means comprising two tunable filters (27B,27C), and two photodetectors (22B, 22C). In the preferred implementation, the tunable filter means is usually disposed such that the tunable filters (27B,27C) have approximately the same passband width (which normally determine instrumental resolution bandwidth—RBW), central passband wavelength and passband shape. The A-SOP controller 12, tunable filters A and B (27B,27C), and two photo-detectors A and B (22B,22C), are controlled by control unit 30.

For most DWDM optical networks, a monitor port along the optical link may extract portions of all signals (SUTs) corresponding to the different spectrally-multiplexed ITU channels, but at the distal end of the optical link, after the optical demultiplexer (just before the Rx), there is usually only one extracted SUT corresponding to a single ITU channel.

Under the coordination of control unit 30, the sampling-and-averaging circuitry 32, in known manner, uses an internal analog-to-digital converter to sample the corresponding electrical signals from the detectors 22B and 22C as a function of time, and the sampled signal is time-averaged over a portion of its duration to provide a corresponding digital level. This portion is chosen so as to avoid transient effects that might arise during the measurement process, e.g. as the A-SOP is rapidly changed by the A-SOP controller 14B.

Variants of the instrument configuration of FIG. 2K are illustrated in FIGS. 2I, 2M and 2H and will now be described briefly.

The instrument illustrated in FIG. 2I is similar to that illustrated in FIG. 2K but differs in that the polarizer 20A is used instead of PBS 20C as a polarization-discrimination means (i.e. analyzer), and only one tunable filter 27 and one photodetector 22 are employed.

FIG. 2M illustrates an alternative apparatus, a heterodyne Optical Spectrum analyzer, which may be employed with methods of this invention. An optical local oscillator 52, conveniently a tunable laser, is disposed, via splitting and combining optics (20C, 20C/A, 20C/B, 20C/C) so that portions of its polarized output are combined with two orthogonal A-SOPs of the SUT at respective detectors 22B, 22C. Each detector (and associated pre-amplification stage—not shown) then provides an electrical signal of the rf baseband, whose spectrum effectively provides high-resolution spectral information. As described in J. Jiang et at (op.cit), it is convenient to electrically filter, via bandpass filters 48A,48B and rf power meters 46A, 46B), the polarization-diverse beat signal at pre-determined rf spacing Δv. It should be appreciated that this spacing is equivalent to the spacing of the "closely-spaced optical frequencies" described in preferred embodiments of methods of this invention.

In an alternate implementation shown in FIG. 2H a spectrally-resolved polarimeter, e.g. tunable filter (TF) 16, polarimetric head 45 and detection system 22 comprising detectors, may be used, where the polarimetric head 45 may be disposed either before or after TF 27. The polarimetric head 45 may be designed to constitute a space-division polarimeter (i.e. normally employing a separate detector for each portion of analyzed light) or a time-division polarimeter (i.e. normally employing an analyzer whose polarization axis varies very rapidly over orthogonal SOPs on the Poincare sphere). Advantageously, the embodiment of FIG. 2H, in conjunction with the method of this embodiment, may provide fast and accurate $DGD_P$ measurement that could be rendered operable to provide updated $DGD_P$ values on a time scale of a few ms or less.

If the rapidity of $DGD_P$ determination is most critical and cost of somewhat less importance, the polarization-diverse configuration of FIG. 2K or the single-detector configuration of FIG. 2I, may be operable to select the A-SOPs in a deterministic manner. For instance, A-SOP controller 14B may be a polarization state generator (e.g. PolaPal™ polarization state generator from General Photonics Corp.), which can rapidly and successively transform the SOP of the SUT signal 60 between a set of predefined analyzer SOPs, preferably but not limitatively corresponding to three orthogonal A-SOPs on the Poincare sphere) whilst the tunable filters 27B, 27C are scanned in wavelength. For such "deterministic" embodiments, it is preferable that the time interval corresponding to acquisition of a set of these rapidly switched analyzer states (A-SOP) be shorter than the time interval required for the tunable filters 27B and 27C to scan over an optical-frequency range equal to the passband of the filter (i.e. RBW).

In another variant of the configuration of FIG. 2K or FIG. 2I, the A-SOP controller 14B may be a two-state polarization switch, which for instance may rapidly transform the A-SOP between two A-SOPs which are orthogonal on the Poincare sphere (e.g. A-SOPs corresponding respectively to linear polarization at 0 and 45 degrees—not to be confused with "orthogonal" with respect to a linear polarizer, for instance). The use of only these two A-SOPs suffices if SUT depolarization, e.g. due to amplified spontaneous emission (ASE) and signal depolarization, etc., is known or negligible. Again, the time interval corresponding to the acquisition of the two rapidly switched analyzer states (A-SOP) is preferably shorter than the time interval required for the tunable filters (27B,27C; 27) to scan over an optical-frequency range approximately equal to the passband of the filter (i.e. RBW). Although the aforedescribed two A-SOPs may have any known mutual non-zero angle, it is preferable that they be orthogonal on the Poincaré Sphere, as this permits the third Stokes component to be extracted based on the first two measured Stokes components corresponding to orthogonal analyzer A-SOPs.

FIG. 11 shows an example of a practical application of such instrument for measuring $DGD_P$ of live signals (SUTs). However, this type of field measurement may also be employed to measure link PMD, provided that: a) a plurality of spectrally multiplexed signals (e.g. corresponding to a many DWDM channels) may be detected; b) the respective transmitters are co-located (e.g. in the same rack or within the same central office); c) the relative SOPs among this multiplicity of signals launched (input) into the fiber link are random (i.e. uncorrelated); and d) following propagation through the fiber link, the DOP of these signals (i.e. the corresponding SUTs) is greater than 0, and, preferably greater than 50%. As indicated in FIG. 11, such a PMD determination measurement can be carried out non-intrusively by simply extracting ("tapping") a small fraction of the power of the DWDM channels via a monitor port. Note that such a monitor port may be located at any location along the optical fiber link where there may be an available monitor port, e.g. 26 or 27, or, alternatively, after the optical DeMux filter on the Rx side 28 (if additional optical switching means—not shown—is provided to enable a portion of each de-multiplexed DWDM channel to be detected). The $DGD_P$-based PMD instrument 101 may be located in any convenient location, provided that there is an optical-fiber connection between the monitor port (26; 27) and the input 10 to the instrument 101. Advantageously, the method presented in this invention not only can measure overall PMD of a fiber link but, if acquisitions are taken at such monitor ports along the link, it also can be used to identify and quantify potential high-PMD sections within the link.

For a large number of randomly chosen SOP conditions of the (transmitter) signal as it is launched into the fiber, the "worst-case" $DGD_P$ of the SUT at a given wavelength is equal to the DGD of the optical link at that same wavelength (neglecting any second- or higher-order PMD effects). This behavior was experimentally confirmed, as illustrated in FIG. 12A 201A. Sixteen measured (average) DGD values were computed using hereinbelow-described equation (2.22a) for corresponding sixteen different launched input-SOPs, are shown in FIG. 12A 201A. The maximum $DGD_P$ value is very close to the 18.5-ps DGD value of a single high-birefringence fiber emulator (i.e. displaying "weak" mode coupling) at that same wavelength as independently measured with a "reference test method" (RTM—implemented in a model FPMD-5600, EXFO Inc.). Each $DGD_P$ value presented in FIG. 12A 201A is computed from acquisitions employing 1000 random A-SOPs. FIG. 12A 201B presents a histogram plot of the distribution of the $DGD_P$ values corresponding to FIG. 12A 201A.

FIG. 12B 202 provides an indication of the dependence of the DGD measurement uncertainty on the number of different A-SOP analyzer states used for each computed DGD value. For example, the measurement uncertainty ($\sigma$) obtained from sixteen different $DGD_P$ measurements, each having an A-SOP number of 20, is indicated in FIG. 12B 36. Note that the measurement uncertainty ($\sigma$) is defined here as a measured $DGD_P$ (always for sixteen measurements), each measurement corresponding to a particular number of A-SOPs divided by the "expected" DGDP value, where the "expected" value is assumed to be that obtained using an A-SOP number of 1000. These measurements were undertaken on a testbed employing the aforedescribed PMD emulator having a fixed DGD value of 18.5 ps, and with a commercially available polarization-diverse OSA instrument (i.e. FTB-5240BP, EXFO Inc., which incorporates a polarization controller/scrambler after its input), having the design configuration depicted in FIG. 2K.

FIG. 13 203 is an example of three separate PMD measurements, each corresponding to different launched-light SOPs into sixteen different 50-GHz-spaced ITU-channel lightpaths, on a test bed comprising an in-line (strong-mode-coupled) PMD emulator, the average DGD value of which had been previously measured by a reference test method (implemented in a model FPMD-5600, EXFO Inc.) to be 5.44 ps between 1530 nm and 1610 nm. For each of the three sets of launched SOPs, sixteen corresponding spectrally-averaged $DGD_P$ values are determined. For all three sets of measurements, the launched SOPs are the same for the six spectrally-averaged DGDP measurements between 1545 and 1550 nm, whereas the other ten spectrally-averaged $DGD_P$ measurements have different (randomly oriented) launched SOPs, and for each of the three sets, a respective PMD value was calculated (i.e. 5.32 ps, 4.91 ps and 5.56 ps, respectively). The average of these three PMD measurements yields a PMD estimate of 5.26 ps, which differs by only 3.2% in comparison with the RTM PMD value. (Although for each channel, "average" $DGD_P$ rather than $DGD_P(\nu)$ was used, it should be appreciated that $DGD_P(\nu)$ alternatively could have also employed, leading to little change in the statistical uncertainty of the PMD estimation.)

The preferred embodiments described hereinbefore are common to principal aspects of this invention. However, the details of the preferred embodiments, including details of their operation, corresponding to each of these principal aspects will be described in more detail in the next subsections.

1.3.2 Measurement of $DGD_P$ at a Particular Optical Frequency

For monitoring and measuring $DGD_P$ as a function of optical frequency (wavelength) in a narrow high bit-rate working data-carrying signal (SUT) bandwidth, i.e., a measurement that is always to be undertaken at approximately the same small particular wavelength range of a signal bandwidth, however, such acquisition can be for many SUTs in many channels, for example if a monitor port 26 or 27 is used. As described in the "Background Art" section hereinbefore, the $DGD_P$ is very sensitive to launch SOP and time-varying environmental conditions, and consequently the PMD-induced system penalty for the traffic signal also varies.

The A-SOP controller 14B may be operable to vary the SOP of the SUT 60 continuously and slowly, or alternatively and preferably, the A-SOP controller 14B may vary A-SOP in a discrete and random fashion, where the resulting A-SOPs are approximately uniformly distributed in the Poincare sphere. or alternatively, in order to achieve fast $DGD_P$ monitoring or measurement of a limited number (e.g. 3-6) of predetermined set of analysis states may be used, e.g. four A-SOPs corresponding to four equidistantly-spaced points on the Poincare sphere.

More specifically, for a particular measurement sequence k, the light signal analyzed by the intervening polarization discriminator, such as a polarization beam splitter (PBS) 20C or polarizer 20, to be measured during a portion of time during which light from the SUT 60 is detected, successively, at each of two closely-spaced optical wavelengths, $\lambda_L^{(k)}$ and $\lambda_U^{(k)}$, that are closely-spaced relative to each other, during which portion of time the SOPs exiting the A-SOP controller 14B is approximately constant. The midpoint wavelength of this closely-spaced pair is defined as the average of the actual optical frequencies of the SUT 60 lights, which to a very high degree of approximation can be expressed in terms of wavelength as $\lambda_{mid}^{(k)} = (\lambda_L^{(k)} + \lambda_U^{(k)})/2$. (The labels L and U refer, for convenience and ease of understanding, to "lowermost" and "uppermost" with respect to the midpoint wavelength $\lambda_{mid}^{(k)}$ and more accurately the midpoint wavelength is expressed as $$\lambda_{mid}^{(k)} = \frac{2\lambda_L^{(k)} \cdot \lambda_U^{(k)}}{\lambda_L^{(k)} + \lambda_U^{(k)}}.)$$

The measured analyzed light signal is converted to an electrical signal by the sampling-and-averaging means and subsequently digitized before application to the data processor for subsequent processing thereby.

The measurement sequence described above is repeated for K different groups, each group corresponding to a different A-SOP with the same or approximately the same SOP in the group. In practice, K should be greater than 20 to 1000 to obtain satisfactory results for random scrambling of the A-SOPs, or preferably a limited number of predetermined set of analysis states may be used.

If the expected $DGD_P$ to be measured is not roughly known, it is possible that the selected optical-frequency difference of the closely-spaced wavelength pairs for the computation is, for instance, corresponding to an optimized optical-frequency difference to permit accurate measurement of $DGD_P$ value from the SUT 60. However, as mentioned above, in a narrow DWDM channel, which may, for instance, only have a useable optical passband width of approximately 35 GHz, it is not always practical to select very different optical-frequency differences.

Advantageously, in order to estimate, and partially compensate for, the contribution of noise in the measurements, "repeated measurements" are acquired for each group at the same two closely-spaced wavelengths, these repeated measurements being in principle substantially perfectly correlated to the "original" measurements (i.e. identical if taken under the same polarization analysis conditions, or complementary if taken under orthogonal polarization conditions, e.g. via the two outputs of a polarization beam splitter). In practice, such noise may arise from any combination of ASE noise (from intervening optical amplifiers in the fiber link 24), cross-phase-modulation (XPM) induced signal depolarization, polarization noise (caused by swaying aerial cables, for instance), optical-source power fluctuations, uncorrelated electronic noise, etc. The procedure by which this technique is used to improve the measurement sensitivity and accuracy will be described in more detail hereinafter. It should be appreciated however that this "repeated-measurement" procedure is predicated upon the use of a "mean-square" average (rather than, e.g. a simple arithmetic mean) of the acquired ΔT values corresponding to the detected power difference between the closely-spaced wavelengths.

The computational method by which the data thus acquired can be converted into a reliable $DGD_P$ monitoring and measurement, including in the presence of significant ASE noise, nonlinear polarization scattering, etc, will be described in more detail hereinafter.

1.3.3 Measurement of Spectrally- and Non-Spectrally-Averaged $DGD_P$ Using $DGD_P(v)$ By repeatedly applying the above-described method of measuring $DGD_P$ at a particular wavelength over a prescribed wavelength range in a SUT 60 bandwidth, it is possible to accurately estimate the PMD-induced PMD power penalty of a SUT 60 related to the system performance of a network according to a either "mean" or "rms" $DGD_P$ value or signal spectrally-weighted "mean" or "rms" $DGD_P$ value over a SUT bandwidth from the said obtained $DGD_P$ as a function of wavelength.

Once a set of $DGD_P(\lambda)$ values have been obtained as described above and a light power spectrum $S(\lambda)$ of a SUT 60 has been extracted, it is straightforward to compute either means or rms $DGD_P$ or a spectrally-weighted average $DGD_P$ from the different values of $DGD_P(\lambda)$ obtained within the prescribed SUT 60 bandwidth wavelength range.

Moreover, it is also possible to estimate the PMD of the optical path (i.e. lightpath) in the DWDM network by either or both of the "rms" or the "mean" $DGD_P$ (without any weighting) from the said obtained $DGD_P$ as a function of wavelength, and preferably, the wavelengths should be approximately uniformly distributed across a wavelength range, which most preferably consists of many 'discontinuous' small wavelength regions from a number of different SUTs bandwidths located along the ITU channel grid (e.g. having spacings of either 50 or 100 GHz).

1.3.4 Measurement of $DGD_P$ Using Rapid Wavelength Sweeping

A preferred approach (see FIG. 2K) for measuring $DGD_P$ at each wavelength, especially an average (mean or rms) $DGD_P$ value or a signal spectral weighted average $DGD_P$ value over a prescribed wavelength range in a SUT bandwidth is to use a rapidly wavelength sweeping by a tunable narrow bandpass filter, e.g. from an OSA with a polarization controller 12 for the A-SOP setting, or other similar technique, e.g. a polarization-diverse scanning monochromator, where A-SOP from an output polarization controller 12 varies little or not at all during the sweep. If the detection electronics are sufficiently rapid, this "spectral acquisition step" will provide a quasi-continuum of detected polarization-analyzed transmitted coherent optical power data as a function of optical frequency. In the subsequent data analysis, any desired closely-spaced wavelength step could be selected. Of course, if A-SOP or the state of polarization of a SUT varies slightly during the sweep, provided that the A-SOP or signal light polarization does not vary significantly between any two closely-spaced wavelengths in the sweep, this would further affect the accuracy of the $DGD_P$ monitoring and measurement. However, such impacting can be reduced by an averaging over many A-SOPs. Furthermore, repeating this procedure with multiple sweeps with a approximately uniform A-SOP distribution will further improve its accuracy and also enable relatively rapid $DGD_P$ monitoring. For example, it may be envisaged that a $DGD_P$ value having an acceptable level of uncertainty be obtained with only 4-6 A-SOPs/scans of tunable filters 27B and 27C (e.g. by an OSA).

By applying the above-described method of measured $DGD_P$ at each wavelength of the invention over a SUT bandwidth with measured signal light power spectrum, it is possible to estimate the polarization mode dispersion (PMD) induced power penalty of a SUT 60 related to the system performance of a network according to either the "mean" or "rms" or signal spectral weighted "mean" or "rms" $DGD_P$ value from the obtained $DGD_P$ as a function of wavelength. It is also possible to estimate the PMD of the lightpath in the DWDM network by either or both of the "mean" or the "rms" $DGD_P$ (without any weighting) from the said obtained $DGD_P$ as a function of wavelength for a SUT (bandwidth) and preferably over a number of different SUT bandwidths.

1.3.5 Various Modifications to the $DGD_P$ Monitoring and Measurement Means

In any of the above-described implementations, the output SOP controller 12 operates in such a manner for A-SOP to have substantially uniformly distributed SOPs on the Poincare Sphere, whether the nature of the distribution is random or deterministic.

If the distribution is random, the number of analyzed states (A-SOP) should be sufficiently large to ensure reasonable coverage on the Poincaré sphere. It should be appreciated that the distribution of the SOPs need not be, and generally will not be, truly random; so "pseudo-random" might be a more appropriate term in the case where a random distribution is indeed used for convenience because it is easier and less expensive to implement than a uniform grid of SOPs.

If the distribution is deterministic, a smaller number of predetermined set of A-SOPs may be employed, which should be uniformly distributed on the Poincare sphere. The minimum number of A-SOPs which can be uniformly distributed, i.e. equidistantly spaced, on the Poincaré Sphere, is four. It should be appreciated that a (well-calibrated) polarimetric head, for which the A-SOPs normally are mutually-orthogonal (e.g. 0-degree linear, 45-degree linear, and left-circular), provides a deterministic distribution of six equidistantly spaced points on the Poincaré sphere, since, for each of the aforementioned mutually-orthogonal A-SOPs, the respective antipodal states are automatically determined.

The detection-system means, whether comprising a single detector, a pair of detectors, a filter plus detector, or a detector array, and the sampling-and-averaging circuitry unit, may be as used in standard commercial power meters that are known to a person skilled in this art.

The control unit may advantageously be a separate computer. However, it is noted that a single computer could perform the functions of the data processor and the control unit.

Where a polarimetric head 45 is used, several (typically three) different polarization components of light comprising SUT 60 can be measured, either simultaneously or at different times, dependent on the design of the polarimetric head 45.

The polarimetric head 45 used in the instrument shown in FIG. 2H (typically splitters with three or four analyzers and photodetectors in parallel), measures more than one polarization component of the signal or power approximately simultaneously, but other similar configurations are feasible. For instance, one may apply a polarization modulation to a variant of the implementation of FIG. 2K, where the polarization modulation period is much shorter than the time required for tunable filters to scan across a SUT bandwidth, and wherein the modulated polarization may switch between several predefined analysis states, e.g. three orthogonal A-SOPs.

It should also be noted that a single $DGD_P$ at one given midpoint wavelength may be obtained by averaging over a large number of randomly-selected output SOPs for a given constant midpoint wavelength having two closely-spaced wavelengths. Therefore, the $DGD_P$ as a function of wavelength in a given wavelength range may also be obtained by measuring many individual $DGD_P$s at different midpoint wavelengths within the given wavelength range of a signal bandwidth. The (non-spectral-weighted) mean $DGD_P$ and/or rms $DGD_P$ may be then be computed therefrom by averaging over all or most of these individual $DGD_P$ values at different wavelengths for several or many different live channels SUT 60. Alternatively, the rms or mean average value may also be computed from a mean-squared difference or mean difference that is obtained by averaging over SUT wavelengths and/or SOP, without ever explicitly measuring the $DGD_P$ at a particular wavelength.

1.4 Embodiment (3)

Single-Ended Overall PMD Measurement 1.4.1 Description of Hardware and Summary of Operating Mode For the "single-ended" embodiments (3) and (4), all of the active components of the measurement instrumentation are at the proximal end of the FUT, and hence the two control units may be combined into a single control unit. (In single-ended embodiments where the "overall PMD" is being measured, a highly-reflective element may be connected to the distal end of the FUT to improve the dynamic range of the measurement.)

As mentioned hereinbefore, if DGD/PMD is to be measured from one end of the FUT 18, both parts of the polarization-controller-and-analyzer means 44 and the processing means 40 can be co-located with the light source means 42 at the proximal end of the FUT 18, together with a single control unit 30 performing the control functions of the control units 30A and 30B in the two-ended embodiments. This co-location enables certain parts to be combined, their components being modified as appropriate. Single-ended measurement-instrumentation configurations will now be described with reference to FIGS. 3 to 3G, which correspond to FIGS. 1 to 1G for the two-ended measurement-instrumentation configurations.

Thus, FIG. 3 shows a tunable OTDR-based single-ended overall PMD measurement instrumentation similar to the two-ended measurement instrumentation of FIG. 1 but in which the light source means 42 and the polarization-controller-and-analyzer means 44 are co-located at the proximal end of the FUT 18 and share a backreflection extractor 52 which connects the input I-SOP controller 14A and the analyzer A-SOP controller 14B to the FUT 18 via connector 16. The backreflection extractor 52 is bidirectional in that it conveys the light from the I-SOP controller 14A to the FUT 18 and conveys the backreflected light from the FUT 18 to the A-SOP controller 14B. As was the case in FIG. 1, the tunable pulsed light source 12 is connected to I-SOP controller 14A by PMF 29A.

A fiber patchcord with either a PC (FC/PC or FC/UPC) connector or a fiber pigtailed mirror 50 is connected to the distal end of FUT 18 to provide a localized reflector at the distal end of the FUT 18. In fact, any type of reflector may be used if it can reflect the light from the end of FUT 18 back into the measuring instrumentation.

The other change, as compared with FIG. 1, is that the measurement instrumentation shown in FIG. 3 has a single control unit 30 which controls the tunable pulsed light source 12, the I-SOP controller 14A and A-SOP controller 14B, the sampling-and-averaging unit 32 and the data processor 34. Otherwise, the components of the measurement instrumentation shown in FIG. 3 are similar or identical to those of the measurement instrumentation shown in FIG. 1 and operate in a similar manner. The signal processing, however, must be adapted so as to allow for the fact that the extracted light comprises light from the light source 12 that travelled the FUT 18 for at least part of its length and then was backreflected and travelled the same path back to the backreflection extractor 52.

It should be noted that the term "tunable OTDR" mentioned hereinbefore in the context of this single-ended overall PMD measurement instrumentation is not limited to a fully functional, commercial-type OTDR, but rather refers to an apparatus that can provide optical pulses for injection into a fiber, and subsequently detect and perform time-gated averaging only on those pulses corresponding to reflections corresponding to a particular time delay (i.e. distance corresponding to the end of the fiber). Nonetheless, the use of an OTDR permits the FUT end to be identified and the FUT length measured, thereby enabling the time-gated window to be correctly selected.

It should be noted that the various modifications and alternatives described with reference to the two-ended measurement instrumentation of FIGS. 1 to 1H could, for the most part, be applied to the single-ended measurement instrument shown in FIG. 3. Such modified configurations of the single-ended measuring instrument will now be described briefly with reference to FIGS. 3B to 3G.

In the measurement instrumentation shown in FIG. 3B, the light source means 42 and the polarization-controller-and-analyzer means 44 share a polarization discriminator (polarizer) 20A and a backreflection extractor comprising either a circulator or coupler 52A. Like the polarizer 20A and circulator/coupler 52A, the VA-SOP controller 14 is used bidirectionally in the sense that it conveys input light towards the FUT 18 via the connector 16 and backreflected light returning from the FUT 18 in the opposite direction. The I/A-SOP controller 14 hence combines the functions of the separate I-SOP controller 14A and A-SOP controller 14B depicted in FIG. 3, but where the scrambling is now necessarily highly correlated for light traversing it in either direction. The circulator/coupler 52A is connected to the light source means 42, specifically tunable pulsed light source 12, by PMF 29A and to the input of the polarization discriminator (polarizer) 20A by a second PMF 29B. The circulator/coupler 52A conveys the backreflected light to a detection system/means which, in FIG. 3B, is shown as a single detector 22A. The output of the polarization discriminator (polarizer) 20A is connected to the input of the bidirectional I/A-SOP controller 14 by regular fiber. Other components are the same as in FIG. 3.

The measurement instrumentation shown in FIG. 3C is similar to that shown in FIG. 3B in that the light source means 42 comprises tunable pulsed light source 12, and shares a backreflection extractor 52A and polarizer 20A with bidirectional VA-SOP controller 14 of the polarization-controller-and-analyzer means 44. The backreflection extractor is shown as a circulator/coupler 52A. However, the measurement instrumentation of FIG. 3C differs from that of FIG. 3B because the polarization-and-analyzer means 44 comprises a coupler 21 connected between the backreflector extractor polarizer 20A and the VA-SOP controller 14, this coupler extracting a portion of non-analyzed light. In addition, the detection means comprises two detectors 22B and 22C, the former connected to the output of the circulator/coupler 52A and the latter connected to an output of the coupler 21. Respective outputs of the detectors 22A and 22B are connected to the sampling-and-averaging unit 32.

As before, the input light from the light source means 42 is injected into FUT 18 via a fiber connector 16 and backreflected light reflected from any localized reflection (such as Fresnel reflection) from the distal end 50 of FUT 18 returns back to the polarization-controller-and-analyzer means 44 and enters the VA-SOP controller 14 in the reverse direction, following which the light returns back to the coupler 21 which passes one portion via the polarizer 20A to detector 22B via the circulator/coupler 52A and a second portion directly to detector 22C.

In the measurement instrumentation shown in FIG. 3C, the backreflected light reflected from any localized reflection from the distal end 50 of FUT 18 returns back to the I/A-SOP controller 14 in the reverse direction, following which the light returns back through the polarizer 20A and then is divided two parts by coupler 21. The detectors 22B and 22C are connected to two outputs of coupler 21 to produce two repeated measured powers; detector 22B being connected by way of circulator/coupler 52A.

It should be noted that simultaneously detecting the backreflected light with two detectors 22B and 22C may not be always necessary. It may also be detected at slightly different time.

In use, in the measurement instrumentation shown in FIG. 3E, the input light from light source means 42 is launched into FUT 18 via fiber connector 16 and backreflected light caused by any localized reflection (such as Fresnel reflection from the distal end 50 of FUT 18) returns back to polarization-controller-and-analyzer means 44 via fiber connector 16, entering the I/A-SOP controller 14 in the reverse direction. Its I/A-SOP is transformed by the I/A-SOP controller (or scrambler) 14, following which the light is decomposed by the polarization discriminator, specifically a PBS 20C, into two components having orthogonal SOPs, typically linear SOPs at 0- and 90-degree relative orientations. Detector 22C is connected to one of the two outputs of the PBS 20C to receive one of these orthogonal components and the backreflection extractor 52 (e.g. circulator/coupler) is connected to the other output (with respect to backreflected light from the FUT 18). Detector 22B is in turn connected to that output port of the backreflection extractor 52 that transmits light from the PBS 20C, so as to receive the other orthogonal component. Once suitably calibrated to take into account the relative detector efficiencies, wavelength dependence, circulator loss, etc., as will be described hereinafter, the sum of the detected powers from detectors 22B and 22C is proportional to the total backreflected power ($S_0$). The backreflected light may be detected approximately simultaneously by detectors 22B and 22C.

Also note that one detector with one optical switch 23 may also be used. In this case, two detectors 22B and 22C may be replaced by one detector 22A plus one optical switch 23 (FIGS. 3E and 3F). The optical switch 23 is used to route the backreflected light from different optical paths, either from circulator (or coupler) 52A or the PBS 20C (FIG. 3G) or the coupler 21 (FIG. 3E), into the same detector and thereby the backreflected light from different optical paths may be detected at different times.

The control unit 30 not only controls the tunable laser light source 12, but also controls the sampling and averaging unit/circuitry 32, in known manner, specifically to use an internal analog-to-digital converter to sample the corresponding electrical signals from the detector 22 as a function of time to obtain the corresponding electrical response signals. The electrical response signals then may be sampled and averaged to provide the mean response pulse for a particular series of light pulses, and the backreflected light power for that series obtained by averaging said mean response pulse over a substantial portion of its duration to provide a backreflected light power. This procedure is repeated resulting in a plurality of backreflected light powers. The said duration represents a time window for averaging (or time gating) and may depend upon the pre-filtering of the sampling-and-averaging electronics. The resulting averaged powers are used by data processor 34 to derive the DGD or PMD value, i.e., the differential group delay (DGD) or polarization mode dispersion (PMD) of the FUT 18 from its distal end or any other connectors. It will be appreciated that the usual conversions will be applied to convert time delay to distance according to refractive index to obtain the length of fiber.

In addition to controlling the sampling-and-averaging circuit 32, the control unit 30 controls the wavelength of the tunable pulsed laser source 12 and the I/A-SOP selected by PA-SOP controller 14. More specifically, for each setting k of the VA-SOP controller 14, the control unit 30 causes the light backreflected power to be measured for at least one pair of wavelengths $\lambda_L^{(k)}$ and $\lambda_U^{(k)}$, respectively, that are closely-spaced relative to each other. The midpoint wavelength of the pair of series of light pulses is defined as the average of the actual wavelengths of the series of light pulses, i.e., $\lambda_k = (\lambda_L^{(k)} + \lambda_U^{(k)})/2$. (The labels L and U refer, for convenience and ease of understanding, to "lower" and "upper" with respect to the midpoint wavelength $\lambda_k$). It should be appreciated that, where the group comprises one or more than one pair of series of light pulses, the midpoint wavelength as defined above in fact differs for each pair in the group.

The one, or more than one, pair of wavelengths in one group may also be used to measure the powers of the backreflections from the localized reflection at the distal end of FUT and then to extract PMD values for the FUT 18. However, it may not be necessary to use more than one pair of wavelengths for the single-ended PMD measurement unless for auto pre-scan acquisition (see more detailed discussion about auto pre-scan below). An optimal pair of wavelengths may satisfy the relationship $PMD_{FUT} \sim \alpha_L (\pi \delta \nu)^{-1}$, where $\nu_L^{(k)} - \nu_U^{(k)} = \delta \nu$, and $\nu_L^{(k)}$ and $\nu_U^{(k)}$ correspond to the pair of wavelengths $\lambda_L^{(k)}$ and $\lambda_U^{(k)}$ under $\nu = c/\lambda$ where c is light speed in vacuum.

It must also be appreciated that the center wavelength is only a conceptual definition, defined only for the purpose of facilitating description when a group comprises more than two wavelengths. In the limit where a group comprises only two wavelengths, it is of course equivalent to the "midpoint wavelength" defined hereinbefore. Center wavelength is not needed anywhere in the computations, and there is no need for accurately "centering" the group on some target center wavelength since the latter is defined as the midpoint wavelength, and there is no need to set the laser wavelength at the center wavelength. Only the knowledge of the step(s) is needed, i.e., the difference between any pair that is used in the computations of cumulative PMD, irrespective of the center wavelength.

The VA-SOP controller 14 sets the different I-SOPs and A-SOPs in a pseudo-random manner, such that the points conventionally representing SOPs on the Poincaré sphere are uniformly-distributed over the surface of said sphere, whether the distribution is random or a uniform grid of points.

Before the tunable-OTDR-based single-ended overall PMD measurement procedure is described in more detail in Section 3.4, and with a view to facilitating an understanding of such operation, the theoretical basis will be explained in Section 2, it being noted that such theory is not to be limiting.

1.5 Various Modifications to the Single-Ended PMD Measurement Means

Implementations of the "single-ended overall-PMD" measurement embodiment encompass various modifications to the measurement instrument shown in FIG. 3.

If the optical path between the output of tunable pulsed light source means 12 and the input of the polarization discriminator 20 (e.g. PBS in FIG. 3F) is polarization-maintaining, the backreflection extractor of FIG. 3F would conveniently comprise either a polarization-maintaining circulator or a polarization-maintaining coupler (e.g., a 50/50 coupler). The circulator is preferred, however, because it gives about 3 dB more dynamic range than a 50/50 coupler.

It is also envisaged that the polarization discriminator 20 could be a polarizer or polarizer and coupler, as shown in FIGS. 3B and 3C. In that case, the detector 22C would be connected to the coupler 21 to receive backreflected light that is not polarization-dependent.

If the optical path between the output of the tunable pulsed laser source 12 and the input of the polarization discriminator, e.g. polarizer 20A and polarization beam splitter (PBS) 20C, is not polarization maintaining, the backreflection extractor, i.e., coupler or circulator 52A, need not be polarization-maintaining.

A patchcord with either a FC/PC (or FC/UPC) connector or a fiber-pigtailed mirror may be connected at the distal end of FUT to create a localized reflection for measuring an overall PMD from the FUT.

The light pulse length (or, equivalently duration) from the tunable OTDR is usually preferably chosen to be long, for example from 1 to over 20 µs, but a short pulse length may also be applied.

Instead of PBS 20C in FIG. 3F, the polarization discriminator 20 may comprise a polarizer 20A and coupler 21 combination (FIG. 3D), at the expense of approximately 3-dB dynamic range for the case of a 50/50 coupler. The second detector 22C (FIG. 3D) is connected to one of the arms of the coupler 21 so as to detect a fraction of the (non-analyzed) backreflected light for processing to deduce the total backreflected power of the pulses.

A person of ordinary skill in this art would be able, without undue experimentation, to adapt the procedure described hereinbefore for calibrating the relative sensitivities of the two detectors A and B (22B and 22C), including the losses induced by the intervening circulator or coupler, etc., for use with the single-ended overall PMD measurement instrument of FIG. 3G. It should be appreciated that, in the embodiment of FIG. 3C, calibration of the mean relative gain is not required; the measured total power is independent of SOP, and there is no need for an "absolute" calibration to directly measure absolute transmission values; they can be obtained to within an unknown constant factor. The subsequent normalization over the mean traces averaged over SOPs, as described hereinbefore, eliminates the unknown factor.

It is envisaged that, where the detection means 22 comprises a single detector 22A (FIG. 3B), normalized powers can be obtained by computing an average of all of the powers in first and second groups of powers, and dividing each of the powers by the said average power to obtain first and second groups of normalized powers, as described in detail hereinafter.

FIG. 3B illustrates a single-ended PMD measurement suitable for obtaining the PMD using normalized powers obtained in this way, which is similar to that illustrated in FIG. 3D but with coupler 21 and detector B 22C omitted. The data processor 34 will simply use the different set of normalization equations.

In any of the above-described embodiments, the operation of the I/A-SOP controller 14 is such that, for a given SOP of the light (which can be any SOP on the Poincaré Sphere) received at its input, the SOP of the light leaving its output will be any one of a number of substantially uniformly distributed SOPs on a Poincaré Sphere, whether the distribution is of random or deterministic nature. Typically, the number of output states of polarization is about 100-500, but it could be any practical number. However, it is possible to use one I/A-SOP controller (rather than two SOP controllers for the two-ended PMD measurement as shown in FIG. 1). It is noted that the distribution of the SOPs need not, and generally will not, be truly random; so "pseudo-random" might be a more appropriate term in the case where a random distribution is indeed used for convenience because it is easier and less expensive to implement than a uniform grid of SOPs.

The detector means 22, whether a single detector or a pair of detectors, and the sampling-and-averaging unit 32, may be the same or similar to those employed in standard commercial OTDRs that are known to a person skilled in this art.

Where the polarization discriminator 20 comprises a polarizer 20A and coupler 21 combination rather than a PBS 20C, there will be a penalty of approximately 3-dB dynamic range (for the case of a 50/50 coupler). Hence, a circulator is generally preferred, although in many cases such reduced power may not be critical for the measurement.

The control unit 30 may advantageously be a separate computer. However, it is noted that a single computer could perform the functions of the data processor 34 and the control unit 30.

1.6 Embodiment (4)

Single-Ended Cumulative PMD Measurement

The polarization-sensitive optical time domain reflectometer (POTDR) illustrated in FIG. 4 comprises tunable pulsed light source means 12, bidirectional polarization controller means 14 (conveniently referred to as an VA-SOP controller means), sampling-and-averaging unit 32 and data processor means 34, all controlled by a control unit 30, and detection means 22 comprising first and second detectors A and B, 22B and 22C, respectively. The tunable pulsed light source means 12 is coupled to a polarization maintaining fiber (PMF) 29A for producing light pulses for launching into a fiber-under-test (FUT) 18 from connector 16 via the I/A-SOP controller means 14, which, as explained later, also receives corresponding backreflected light from the FUT 18 via connector 16.

The light source means 42 and polarization-controller-and-analyzer means 44 comprise a backreflected light extractor, specifically a polarization-maintaining circulator 52 in FIG. 4, a polarization discriminator (PD) means 20, specifically a polarization beam splitter (PBS) in FIG. 4, and an input and analyzer-SOP controller (or scrambler) I/A-SOP 14. The circulator 52 is coupled to the input of PBS 20 by a second PMF 29B so that the optical path from the tunable laser source 12 to the PBS 20 is polarization-maintaining Preferably, single-mode fiber is used to optically couple the PBS 20 to the I/A-SOP controller (or scrambler) 14.

Backreflected light caused by Rayleigh scattering and, in some cases, discrete (Fresnel) reflections, from the FUT 18 enters the I/A-SOP controller 14 in the reverse direction. Its SOP is transformed by the I/A-SOP controller 14, following which the light is decomposed by the PBS 20 into two components having orthogonal SOPs, typically linear SOPs at 0- and 90-degree relative orientations. The first detector 22C is connected to one of the two outputs of the PBS 20 to receive one of these orthogonal components and the circulator 52 is connected to the other output (with respect to backreflected light from the FUT 18). The second detector 22B is in turn connected to that output port of the circulator 52 that transmits light from the PBS 20, so as to receive the other orthogonal component. Once suitably calibrated to take into account the relative detector efficiencies, wavelength dependence, circulator loss, etc., as will be described hereinafter, the sum of the detected powers from detectors 22B and 22C is proportional to the total backreflected power ($S_0$).

Under the control of control unit 30, which also controls the tunable laser source 12, the sampling-and-averaging unit 32, in known manner, uses an internal analog-to-digital converter to sample the corresponding electrical signals from the detectors 22B and 22C as a function of time to obtain the corresponding electrical impulse response signals, then averages the impulse-response signals corresponding to a particular series of light pulses to produce an OTDR trace for that series. The resulting OTDR traces are used by a data processor 34 to derive the cumulative PMD curve PMD(z), i.e., the polarization mode dispersion (PMD) as a function of the distance z along the FUT 18 from its proximal end, that is the end which is coupled to the polarization-controller-and-analyzer means 44. It will be appreciated that the usual conversions will be applied to convert time delay to distance according to refractive index.

In addition to controlling the sampling and averaging circuit 32, the control unit 30 controls the wavelength of the tunable pulsed laser source 12 and the I-SOP and A-SOP couple selected by I/A-SOP controller 14. More specifically, for each setting k of the VA-SOP controller 14, the control unit 30 causes the backreflected power to be measured at at least one pair of wavelengths $\lambda_L^{(k)}$ and $\lambda_U^{(k)}$, respectively, that are closely-spaced relative to each other. The midpoint wavelength of the pair of series of light pulses is defined as the average of the actual wavelengths of the series of light pulses, i.e., $\lambda_k = \lambda_L^{(k)} + \lambda_U^{(k)}/2$. (The labels L and U refer, for convenience and ease of understanding, to "lower" and "upper" with respect to the midpoint wavelength $\lambda_k$).

It should be appreciated that, where the group comprises more than one pair of series of light pulses, the center wavelength as defined above in fact differs for each pair in the group. It must also be appreciated that the center wavelength is only a conceptual definition, and was defined only for the purpose of facilitating description of the basic one pair implementation. It is not needed anywhere in the computations, and there is no need for accurately "centering" the pair on some target center wavelength since the latter is defined as the mean of the actual pair. Nor is the laser wavelength set at the center wavelength. Only the knowledge of the step is needed, i.e., the difference between any pair that is used in the computations of cumulative PMD, irrespective of the center wavelength, even if it were to be random and unknown.

The I/A-SOP controller 14 sets the different (I-SOP, A-SOP) couples in a pseudo-random manner, such that the points conventionally representing SOPs corresponding to each member of the couple are uniformly distributed over the surface of the Poincaré sphere, whether the distribution is random or a uniform grid of points. Before the operation of the POTDR is described in more detail, and with a view to facilitating an understanding of such operation, the theoretical basis will be explained, it being noted that such theory is not to be limiting.

Various Modifications to the Single-Ended Cumulative PMD Measurement Means

The invention encompasses various modifications to the embodiment shown in FIG. 4.

If the optical path between the output of tunable pulsed light source means 12 and the input of the polarization discriminator 20 is polarization-maintaining, the polarization-maintaining circulator 18 in FIG. 4 could be replaced by a polarization-maintaining coupler (e.g., a 50/50 coupler). The circulator is preferred, however, because it gives about 3 dB more dynamic range than a 50/50 coupler.

If the optical path between the output of the tunable pulsed laser source 12 and the input of the polarization discriminator 20 is not polarization maintaining, the back-reflection extractor, i.e., coupler or circulator 52 need not be polarization-maintaining.

Instead of a PBS for the polarization discriminator 20, the polarization discriminator 20 may comprise a polarizer 20A and coupler 21 combination, as shown in FIG. 4B, at the expense of approximately 3-dB of dynamic range for the case of a 50/50 coupler. The detector 22C is connected to one of the arms of the coupler 21 so as to detect a fraction of the backreflected light for processing to deduce the total backreflected power of the pulses.

In the POTDR of FIG. 4, an analogous procedure to that described above with respect to the embodiment of FIG. 4 could then be carried out, although not required as stated above, to calibrate the relative sensitivities of the two detectors 22B and 22C, including the losses induced by the intervening circulator or coupler, etc.

A person of ordinary skill in this art would be able, without undue experimentation, to adapt the calibration procedure described hereinbefore with reference to the POTDR of FIG. 4 for use with the embodiment of FIG. 4. It should be appreciated that, in the embodiment of FIG. 4B, calibration of the mean relative gain is not required; the measured total power is independent of SOP, and there is no need for an "absolute" calibration to directly measure absolute transmission values; they can be obtained to within an unknown constant factor. The subsequent normalization over the mean traces averaged over SOPs, as described hereinbefore, eliminates the unknown factor.

It is envisaged that the detection means 22 might comprise a single detector and normalized OTDR traces be obtained by computing an average of all of the OTDR traces in first and second groups of OTDR traces, and dividing each of the OTDR traces by the said average OTDR trace, point by point, to obtain first and second groups of normalized OTDR traces, as described in detail hereinbefore.

FIG. 4A illustrates a POTDR suitable for obtaining the PMD using normalized OTDR traces obtained in this way. The POTDR illustrated in FIG. 4A is similar to that illustrated in FIG. 4B but with coupler 21 and detector B 22C omitted. The data processor 34 will simply use the different normalization equations given in the Method of Operation provided hereinbefore.

In any of the above-described embodiments, the operation of the I/A-SOP controller 14 is such that, for a given SOP of the light (which can be any SOP on the Poincaré Sphere) received at one end, the SOP of the light leaving the other end will be any one of a number of substantially uniformly distributed SOPs on the Poincaré Sphere, whether the distribution is of random or deterministic nature. The number of I-SOPs and A-SOPs is preferably greater than 10, in each case, and typically is about 100-200 for high quality results; but it could be any practical number. It is noted that the distribution of each of the I-SOPs and A-SOPs need not, and generally will not, be truly random; so "pseudo-random" might be a more appropriate term in the case where a random distribution is indeed used for convenience because it is easier and less expensive to implement than a uniform grid of I-SOPs and A-SOPs.

Although it is preferred to simultaneously measure the two orthogonal polarization components simultaneously with respective two detectors, it is envisaged that the two detectors in the embodiments of FIGS. 4 and 4B could be replaced by one detector plus one optical switch. The optical switch is used to route the two orthogonal polarization components (FIG. 4) or to route the one output from polarizer and another output directly from coupler (FIG. 4B) of the backreflected light to the same detector, for example alternately, so that two orthogonal polarization components or one output from polarizer and another output directly from coupler of the backreflected light can be detected sequentially by the same detector.

A normalized OTDR trace for that series of light pulses would be obtained by dividing at least one of the OTDR traces corresponding to the two detected different polarization components for that series by the sum of the OTDR traces corresponding to the two detected different polarization components for that series. This alternative may be used regardless of whether the polarization-controller-and-analyzer means comprises a PBS or a coupler. Any modification to the normalization and processing is expected to be minor and within the common general knowledge of a person skilled in this art.

Alternatively, such an arrangement of one detector plus one optical switch could be used to detect one polarization component and the total optical power sequentially by the same detector. As before, the optical switch would route one polarization component and the total reference optical power to the same detector, and the normalized OTDR trace corresponding to that particular series of light pulses would be obtained by dividing the OTDR trace for that series by the OTDR trace for that series corresponding to total power. It should be noted that the use of one detector with one optical switch instead of two detectors disadvantageously at least doubles the total acquisition time in comparison with embodiments using two detectors, It is also envisaged that a rotating polarization discriminator (PD), whether it is a polarizer or a PBS, may be used to sequentially acquire two orthogonal components for example via rotating the polarization discriminator by 90° to switch from detecting Px to detecting Py, or from detecting Py to detecting Px. The detector means 22, whether a single detector or a pair of detectors, and the sampling and averaging circuitry unit 232, may be the same or similar to those employed in standard commercial OTDRs that are known to a person skilled in this art.

The control unit 30 may advantageously be a separate computer. However, it is noted that a single computer could perform the functions of the data processor 34 and the control unit 30.

It may also be envisaged that certain parts of the signal processing may be performed remotely, either approximately in "real time" or during post-processing, for instance using "cloud computing".

Various other modifications to the above-described implementations of the embodiment may be made within the scope of the present invention.

For instance, the tunable pulsed laser source 12 and I/A-SOP controller 14 could be replaced by some other means of providing the different polarization states of the pulses entering the FUT 18 and analyzing the resulting backreflected signal caused by Rayleigh scattering and/or discrete reflections leaving the FUT 18.

Thus, a polarimetric head may be used (splitters with three or more analyzers and photodetectors in parallel), which measures more than one polarization component of the backreflected signal simultaneously, or some other configuration, so that the power that reaches the photodetectors is dependent on the SOP of the backreflected light.

It should be noted that each group is not limited to one pair of series of light pulses. Indeed, it may be advantageous to use three or more different closely-spaced wavelengths per group of traces obtained with a common SOP, instead of the minimally-required two closely-spaced wavelengths $\lambda_L$ and $\lambda_U$ (each group then comprises $2 \cdot N_\lambda$. OTDR traces instead of four, two sets of $2 \cdot N_\lambda$ traces in the case of the two-photodetector embodiments, where $N_\lambda$ is the number of wavelengths in a group of series of light pulses). For example, in the case where three closely-spaced wavelengths are used, one can choose the series of light pulses at the lowermost and intermediate wavelengths as one pair, and the series of light pulses at the intermediate and uppermost wavelengths as a second pair, such that the wavelength step between the light pulses in one pair is greater than the wavelength step between the light pulses in the other pair, perhaps a few times larger.

Since there are three combinations of wavelength steps corresponding to three wavelengths (i.e., $N_\lambda(N_\lambda-1)/2$), one can simultaneously obtain the data corresponding to two significantly different wavelength steps within a measurement time that is only 1.5 times greater than the time required to perform a one-step measurement. Thus, proceeding with three wavelengths (or more) per group proves highly advantageous because the cumulative PMD value can increase significantly along the length of the FUT 16 (from zero to the overall PMD of the FUT), and hence the use of two, three, or more different steps allows one to maintain a satisfactory relative precision (e.g. in %) at all positions along the fiber. It will be appreciated that one could also select the light series at the lowermost and uppermost wavelengths as a third pair, with a wavelength step greater than both of the others. The use of only one step gives a particular absolute uncertainty, as for example ±0.1 ps, which represents a small percentage uncertainty at a distance where the PMD has grown to a value of 10 ps, but is not good in percentage at short distances where the PMD is, for example, only 0.2 ps. To obtain a smaller uncertainty for smaller PMD values, a larger step must be selected. Hence the obvious advantage of implementing such an alternate embodiment where more than two wavelengths per group are used. It changes nothing to the setup, nor to the principle of the invention as described above, but saves time in the overall measurement process.

Although the above-described embodiment changes the center wavelength for each SOP, this is not an essential feature of the present invention. While superior performance can be obtained by covering a large wavelength range in order to obtain the best possible average of DGD, as per the definition of PMD, a POTDR embodying the present invention will work with no bias and may provide acceptable measurements of PMD(z), with a constant center-wavelength.

1.7 Various Modifications Common to Preferred Embodiments

For the three preferred embodiments comprising a test light source (i.e. Embodiments (1), (3), and (4)), if the degree of polarization (DOP) of the light source 12;12A;12B is not high, the DOP may be increased by inserting a polarizing element 19 (e.g. polarizer, polarization beam splitter, etc.) into the optical path downstream from the light source 12 (not shown)). However, if standard single-mode fiber (e.g. SMF-28 fiber marketed by Corning Inc.) rather than polarization maintaining fiber (PMF) is used to optically connect the light source 12 and the polarizing element 19 (which for the OTDR-based "single-ended" embodiments may be functionally replaced by polarizer/polarizing splitter 20, 20A, 20C), it may be necessary to add an additional polarization adjuster 13 (generally a "factory-set" polarization controller), as shown in FIG. 10A, in order to approximately maximize the power transmitted through the polarizing element 19; 20, 20A, 20C.

Preferred implementations of the OTDR-based "single-ended" embodiments couple the output of the light source into PMF. The alignment of PMF 29A and 29B is fixed in the factory in such a manner that substantially all of the optical power from the tunable pulsed laser source 12 is maintained in one of the two axes of the fiber 29A and 29B (conventionally, the "slow" axis). Since the backreflection extractor 52 (e.g. circulator) is polarization-maintaining, this alignment is maintained until the distal end of PMF 29B, at its point of attachment to PBS 20. During attachment of each end of the PMFs 29A and 29B to the component concerned, the azimuthal orientation of the PMF 29A/B is adjusted to ensure maximum transmission of the optical pulses towards the FUT 18.

2. Underlying Theory

2.1 SOP Scrambling Analysis (SOP) for PMD Measurement

Although the applicant does not wish to be constrained by theory, the following discussion of the underlying theory is provided so as to facilitate understanding of the various embodiments of the invention.

The computation of the DGD or rms DGD (i.e. PMD) is based on a method designated "State of polarization Scrambling Analysis" (SSA), which forms the basis of the present invention. The specific theory applied to the various aspects of this invention is closely related to the theory described in international patent application No. PCT/CA2006/001610 and the above-identified U.S. Continuation-in-Part application Ser. No. 11/727,759, the entire contents of each of which are incorporated herein by reference.

PMD is usually quantified as the statistical RMS value of differential group delay $DGD(\lambda)$, estimated by averaging over a wide wavelength range, or over a period of time, ideally both, so that the largest possible number of random occurrences of DGD are observed to obtain its RMS value. (As mentioned hereinbefore, the definition of PMD as the arithmetic mean of $DGD(\lambda)$ over a wide wavelength range is an alternative, though it is less widely employed. A skilled practitioner would readily be able to adapt the equations for PMD given hereinbelow from "RMS" to "mean".)

In this section, we describe the theory underlying the SSA method upon which the invention is predicated. As mentioned hereinabove, the SSA method is applicable to the characterization of PMD-related polarization characteristics of and arising from an optical link (FUT).

It should be appreciated that measurement or monitoring of partial-DGD employs a special case of SSA where the input SOP is necessarily not actively scrambled as part of the measurement process.

It should further be appreciated that, in all embodiments, the term "scrambling" in the designation does not preclude the use of predetermined SOP analysis conditions (e.g. via a polarimetric head), nor, where applicable, the launching of a set of predetermined "input" SOPs into the optical link. Such variants and implementations are discussed within this application.

The methods of operation, data processing and computational methods for preferred embodiments of applications will be described in detail in Section 3 hereinbelow.

To facilitate the description of SSA theory, it will first be described with reference to the schematic measurement set-up depicted in FIG. 1, associated with the two-ended "test-source-based" approach of preferred Embodiment (1) described in Section 5. It will become clear in context how the theory applied to Embodiment (1) can be readily modified for the other preferred embodiments.

In this specification, "analyzing" of the light refers to apportioning the optical power that can be decomposed to align with the transmission axis of a polarization analyzer for which the maximum optical power may subsequently be detected. An example of polarization-analyzer means is a combination of a polarization controller and linear polarizer. The SOP of the light incident upon the polarization-analyzer means that is maximally transmitted therethrough is defined as the "analyzer-SOP", or simply "A-SOP". As the polarization controller is adjusted (usually in a random fashion), this A-SOP value varies accordingly, and this transmitted power is detected.

All the embodiments described herein are predicated upon polarized light, emitted by a light source, having a spectral width greater than a small optical-frequency difference $\Delta \upsilon$ between two closely-spaced optical frequencies, $\nu_U$ and $\nu_L$, being launched into the FUT with a particular, usually unknown, SOP (denoted "input-SOP", or "I-SOP"). It is convenient to define a "notional" midpoint optical frequency, $\nu_{mid}$ ($=(\nu_U+\nu_L)/2$). According to the particular preferred embodiment, this light may be emitted by (i) (Embodiment 1) a test light source, emitting either polarized coherent light (e.g. from a laser) or polarized broadband light, the light source and the "receiving instrumentation" being located at opposing ends of the FUT;

(ii) (Embodiment 2) one or more permanently-installed network transmitters (Tx), which each are modulated to normally carry network traffic, this modulation necessarily imparting a spectral width to the light that is approximately equal to the symbol rate. The "receiving" instrumentation is located at the other end of the optical link. For convenience, the light from each such Tx of interest that has traversed the optical link is termed signal-under-test (SUT);

(iii) (Embodiments 3 and 4) a test light source, emitting polarized coherent pulsed light, the light source ("OTDR source") and the "receiving" portions of the instrumentation being co-located.

Embodiments (1), (3) and (4) all preferably determine the respective polarization-related polarization characteristics from data corresponding to different I-SOP conditions, these different I-SOP normally being generated by, for example, a polarization controller. On the other hand, by virtue of the Tx sources being part of an active network, there is normally no actively-induced variation of I-SOP associated with Embodiment (2). (Any variations of I-SOP associated with this latter embodiment tend to be slow effects due to environmental changes, etc.).

All the preferred embodiments described hereinabove involve analyzing and detecting the analyzed power of each member of the pair of the closely-spaced optical frequencies, centered about midpoint frequency, $\nu_{mid}$, that has traversed the FUT, where the analyzing conditions are the same for each member of the pair. In implementations of the preferred embodiments (1), (3), and (4) that do not comprise a polarimetric head, this analyzing and detecting process is repeated for a large number K of I-SOP and A-SOP conditions, i.e., comprising a large number of "SOP couples" (I-SOP$_k$, A-SOP$_k$) each referring to both the input-SOP and the analyzer-SOP of the received light. For Embodiment (2), there is no variation of I-SOP induced by the measurement procedure itself, and hence the analyzing and detection process is repeated for a large number K of A-SOP conditions.

In implementations of the preferred embodiments employing a polarimetric head, which typically analyzes for subsequent detection optical power corresponding to three mutually-orthogonal A-SOP conditions of the light, the number of A-SOP conditions, $K_{ASOP}=3$ suffices. (Of course, additional measurements may be acquired for better averaging, etc., but theoretically only $K_{ASOP}=3$ is required.)

The A-SOP, and if applicable I-SOP, values may be chosen in a random manner, such that the points conventionally representing SOPs on the Poincaré Sphere are approximately uniformly-distributed over it, whether the distribution is random or a substantially uniform grid of points.

2.2 Theory Specific to Embodiments (1), (3), and (4) Involving Actively-Induced I-SOP Variation 2.2.1 Determination of DGD and PMD A key element of SSA theory is that, on average over a sufficiently large, uniformly distributed number K of said "SOP couples", the mean-square difference between normalized powers observed at $\nu_U$ and $\nu_L$ is related to the DGD at its midpoint optical frequency $\nu_{mid}$ ($=(\nu_U+\nu_L)/2$) by a simple relationship. This relationship is valid in all cases for any type of practical FUT regardless of its degree of randomness or its polarization-coupling ratio, including even the extreme case of a PMF fiber, i.e., $$DGD(\nu) = \frac{1}{\pi \delta \nu} \arcsin\left(\alpha_{ds} \sqrt{\langle \Delta T^2(\nu) \rangle_{SOP}}\right) \quad (2.1)$$

where $\langle \ \rangle_{SOP}$ represents the average over the K SOP couples, $\delta\nu(=|\nu_U-\nu_L|)$ is the "step", and $\alpha_{ds}$ is a theoretical constant that is dependent on the implementation of the embodiment, as will be described further below. $\Delta T(\nu)$ is a difference between the analyzed normalized powers (i.e. transmission values) observed at closely-spaced optical frequencies $\nu_U$ and $\nu_L$, respectively, and its mean-square difference is, $$\langle \Delta T(\nu)^2 \rangle_{SOP} = \langle (T_U - T_L)^2 \rangle_{SOP} = \frac{1}{K}\sum_k \left(T_U^{(k)} - T_L^{(k)}\right)^2 \quad (2.2)$$

where the index k corresponds to a particular SOP couple.

For implementations for which there is no direct detection of the non-analyzed power, e.g. for the polarizer-based one-detector implementations illustrated in FIGS. 1B, 3A, 3B 4A, and 4C, the normalized powers are $$T_L^{(k)} = u_o \frac{P_L^{(k)}}{\langle P_L \rangle_{SOP}} \qquad T_U^{(k)} = u_o \frac{P_U^{(k)}}{\langle P_U \rangle_{SOP}} \qquad (2.3a)$$

where the reference mean-value $u_o$ is a theoretical constant that is dependent on measurement set-up configuration, i.e. either two-ended (e.g. FIG. 1B) or single-ended (e.g. FIGS. 3B and 4A) measurement configuration, and the average power is defined, $$\langle P_L \rangle_{SOP} = \frac{1}{K} \sum_k P_L^{(k)} \cdot \langle P_U \rangle_{SOP} = \frac{1}{K} \sum_k P_U^{(k)} \qquad (2.3b)$$

Furthermore, for a prescribed wavelength range, if one carries out the averages indicated in equations (2.2) and (2.3) over both many randomly-selected SOP couples and midpoint optical frequencies, both of which are changed from one group comprising two closely-spaced wavelengths to the next, the rms DGD (i.e. PMD) over the prescribed wavelength range is obtained:

$$PMD = \frac{1}{\pi\delta v}\arcsin\left(\alpha_{ds}\sqrt{\langle \Delta T^2(v) \rangle_{SOP;v}}\right) \qquad (2.4)$$

where $\langle\ \rangle_{SOP;v}$ is averaged over both SOP and optical frequency across a prescribed wavelength range.

In the limit of a sufficiently small optical-frequency difference ("step") between the closely-spaced optical frequencies, equations (6.1) and (6.4) tend to the following simpler differential formulae:

$$DGD(v) = \frac{\alpha_{ds}}{\pi\delta v} \cdot \sqrt{\langle \Delta T^2(v) \rangle_{SOP}} \qquad (2.1a)$$

$$PMD = \frac{\alpha_{ds}}{\pi\delta v} \cdot \sqrt{\langle \Delta T^2(v) \rangle_{SOP;v}} \qquad (2.4a)$$

(Of course, any other alternative mathematical function that provides a numerical result that falls within an acceptable difference from the said following differential formula for realistic values of DGD and PMD could be used instead, but such a formula would not be based on firm theoretical underpinnings. This would be true for any of the other analogous formulas presented elsewhere in this specification.)

The relationship in equation (2.1) holds for DGD·δν⟨ ½ for two-ended measurement configurations and DGD·δν ⟨ 0.3 for single-ended measurement configurations, these relationships thus defining the meaning of "closely-spaced wavelengths".

The normalized power will in fact be obtained differently in each embodiment, i.e., by suitable programming of the data processor 34. This explanation of the theory is provided for the basic single-photodetector embodiment of FIGS. 1B, 3B and 3A, where normalization over the average power is necessary, assuming total power is stable when the (I-SOP, A-SOP) couple is changed, or as a function of time. Note that the normalization procedure for the two-ended measurement configuration (FIG. 1B) and single-ended (FIGS. 3B and 4A) are very similar, but reference mean-values ($u_o$) (see equations (2.6) and (2.12)) are different. Also note, for the single-ended cumulative PMD measurement, a normalized power trace (T(z)) as function of distance z is computed. A detailed description of this normalization procedure is provided hereinafter.

2.2.2 Two-Ended PMD Measurement

The basic theory of the SSA method described above can be applied to two-ended PMD measurement, where the test link may or may not include an intervening optical amplifier. When optical amplifiers are used in the test link, the amplified spontaneous emission (ASE) from the amplifier will be mixed with the launched polarized coherent light from the light source means and, consequently, both ASE and launched light are measured by photodetector 22A (FIG. 1B).

Below we describe how to apply the basic SSA theory to two-ended PMD measurement for both the cases where ASE is absent and where ASE is present, without or with optical amplifiers, for the test link, by accessing two ends of FUT.

2.2.2.1 Two-Ended Measurement: DGD Measurement without Amplifiers in the Test Link If a tunable laser serves as a light source means, one can select its optical frequency by either tuning in a stepwise fashion, or frequency sweeping, or frequency modulation, or similar means. Alternatively, if a polarized broadband light source is used, then a tunable filter may be used to select the optical frequency. In both cases, an input polarization controller is placed at a proximal end of FUT and a polarization-controller-and-analyzer means, for example an output polarization controller, polarizer (or PBS) and a photodetector or power meter (combined with tunable filter if polarized broadband light source is used instead of tunable laser source) is located at the opposing end of FUT for measuring the power from fibers at two closely spaced optical frequencies, $v_U$ and $v_L$, around a given midpoint frequency, $v_{mid}$, for a large number K of input/output state of polarizations, i.e., comprising a large number of "SOP couples" (I-SOP$_k$, A-SOP$_k$) each referring to both the input-SOP and the analyzer-SOP of the analyzed light. Both the I-SOP and the A-SOP values are preferably chosen in a pseudo-random manner, such that the points conventionally representing SOPs on the Poincare sphere are substantially uniformly-distributed over the surface of said sphere, whether the distribution is random or approximately a uniform grid of points. By averaging over a sufficiently large, uniformly distributed number K of said SOP couples, the DGD at its midpoint frequency $v_{mid}$ is given by equation (6.1). Equation (2.1) is valid for DGD·δν⟨ ½ for two-ended measurement configurations, thus clarifying the meaning of "closely-spaced optical frequencies".

This DGD value may be alternatively designated as the "forward" DGD, a superfluous adjective if only two-ended measurements are of concern, but a useful distinction in the context of the "single-ended" embodiments to be described hereinbelow.

If the scrambling is carried out in such a way that either or both of the I-SOP and A-SOP is/are significantly different than its/their respective predecessor(s) or successor(s), i.e. when they are randomly or quasi-randomly selected on the Poincare sphere, K should be greater than 10, typically about 100 to 200 for good quality results.

On the other hand, if the scrambling is carried out in a slow, continuous fashion, as described in more detail hereinafter, such that at least one of I-SOP and A-SOP is only slightly different than its respective predecessor or successor, then K should be greater than 500, typically about 10,000, to ensure that the measurement involves an average over a substantially uniform Poincaré Sphere distribution, thereby reducing the measurement uncertainty.

As already mentioned, the PMD is defined in the context of this description as the root-mean-square (rms) value of DGD averaged over wavelength. The rms DGD (i.e. PMD) over the prescribed wavelength range may now be computed by equation (2.4). (It should be noted that a long time-averaged DGD measurement at a given wavelength, for which the FUT is subject to generally slow environmental perturbation, usually yields rms DGD rather than mean DGD).

For Embodiment (1) ("two-ended test-source-based DGD and/or PMD measurement") employing SOP scrambling at both ends, the theoretical constant $\alpha_{ds}$ used in equations (2.1), (2.1a), (2.4) and (2.4a) is:

$$\alpha_{ds} = \sqrt{\frac{9}{2}} \tag{2.5}$$

This value presupposes that changes in the I-SOP polarization controller and A-SOP polarization controller are not correlated, as would normally be the case. The relationship in Equations (2.1) and (2.4) holds for DGD·$\delta v$ < 0.5, thus clarifying the meaning of "closely-spaced optical frequencies".

For this two-ended configuration, the reference mean-value $u_o$ used for normalization in equations (2.3a) is $$u_0 = \frac{1}{2} \tag{2.6}$$

2.2.2.2 Two-Ended Measurement: DGD Measurement with Amplifiers in the Test Link

In many field applications, optical amplifiers (typically erbium-doped optical amplifiers) constitute part of the link. Hence, the FUT 18 may comprise at least one, and possibly several, optical amplifiers at various spacings (e.g. 60 km) within the FUT 18. When an optical amplifier is present, a power meter located at distal end of FUT 18 will likely also detect (substantially unpolarized) amplified spontaneous emission (ASE) light in addition to the signal emitted by the optical generator means. The presence of ASE in the detected signal can be taken into account by "scaling down" the mean-square differences $(\Delta T(v)^2)_{SOP}$ by a factor that can be computed independently from the same raw data. This factor, $\sigma_r^2(v)$, is a relative variance of the normalized powers defined as, $$\sigma_r^2(v) = \left(\frac{1}{\sigma_{20}}\right)^2 [\langle T(v)T''(v)\rangle_{SOP} - \langle T(v)\rangle_{SOP}^2] \tag{2.7}$$

where the reference variance is $\sigma_{20}^2 = 1/12$. The notation $\langle T(v)T''(v)\rangle_{SOP}$ and $\langle T(v)\rangle_{SOP}^2$ refer to averages over both normalized powers at $v_U$ and $v_L$ and T(v) and T''(v) are the normalized powers from repeated measurements in one group at one given optical frequency.

It should be noted that, if the noise power contribution may be neglected, then T(v) and T''(v) may be the same normalized power, i.e. corresponding to only one measurement in one group at one given optical frequency, and hence T(v) T''(v)=T²(v).

Then the (forward) DGD at a given midpoint wavelength is obtained by dividing the mean-square differences by the relative variance in equation (2.7) as, $$DGD(v) = \frac{1}{\pi\delta v}\arcsin\left(\alpha_{ds}\sqrt{\frac{\langle\Delta T^2(v)\rangle_{SOP}}{\sigma_r^2(v)}}\right) \tag{2.8}$$

And, moreover, the (forward) rms PMD for a prescribed wavelength range can be expressed by, $$PMD = \frac{1}{\pi\delta v}\arcsin\left(\alpha_{ds}\sqrt{\frac{\langle\Delta T^2(v)\rangle_{SOP,v}}{\sigma_r^2(v)}}\right) \tag{2.9}$$

where the average over SOP in equation (2.8) is now replaced by the average over both SOP and optical frequency (wavelength), and $\alpha_{ds}$ is given by equation (2.5). The relative variance of the normalized powers now is expressed as, $$\sigma_r^2 = \left(\frac{1}{\sigma_0}\right)^2 [\langle T(v)T''(v)\rangle_{SOP,v} - \langle T(v)\rangle_{SOP,v}^2] \tag{2.7a}$$

It should be noted that, if the normalized powers T(v) are averaged over a sufficient large number of randomly scrambled SOPs, then $$\langle T(v)\rangle_{SOP}^2 = \frac{1}{4}.$$

In the limit of a sufficiently small optical-frequency step, equations (2.8) and (2.9) respectively tend to the following differential formulae:

$$DGD(v) = \frac{\alpha_{ds}}{\pi\delta v}\cdot\sqrt{\frac{\langle\Delta T^2(v)\rangle_{SOP}}{\sigma_r^2(v)}} \tag{2.8a}$$

$$PMD = \frac{\alpha_{ds}}{\pi\delta v}\cdot\sqrt{\frac{\langle\Delta T^2(v)\rangle_{SOP,v}}{\sigma_r^2(v)}} \tag{2.9a}$$

If launched power corresponding to each of the two closely-spaced optical frequencies constituting a wavelength pair are equal and if the FUT (including possible intervening filters) introduces negligible differential spectral attenuation to members of the pair, then these measured "closely-spaced" powers can directly be applied to equations (2.8) and (2.9), i.e. there is no need to normalize the measured powers (although, in that case $\langle T(v)\rangle_{SOP}^2$ may not equal ¼). This obtains since the normalization procedure described above (see Eq. 6.3) yields a "constant factor" that is multiplied on measured powers in order to obtain normalized power (between 0 and 1), this factor being multiplied with both the mean-square difference and relative variance. The mean-square difference and relative variance appear in the numerator and denominator of equations (2.8) and (2.9), respectively, and hence mutually cancel when calculating DGD or PMD therefrom. In other words, equations (2.8) and (2.9) only require the use of relative powers that are proportional to normalized powers.

It should be appreciated that equations (2.8) and (2.9) are applicable with or without the presence of amplifier noise on the link under test.

Alternatively, an estimate of the PMD (i.e. rms or mean DGD value over an optical frequency range) can be obtained by first determining DGD(ν) (using either equation (2.1) or (2.10a)) at each of a plurality of midpoint wavelengths, and then performing an rms (or mean) average of these value. It is preferable that these midpoints wavelengths be approximately uniformly spread across this optical-frequency range, and that the range be significantly greater than the optical-frequency spacing at which the DGD values are correlated.

2.2.3 Single-Ended PMD Measurement

Single-ended PMD measurement is a very important measurement technique for field applications. The above-described basic SSA theory can also be applied to single-ended PMD measurement. Single-ended measurement of PMD-related characteristics described herein comprises two embodiments: Embodiment (3) measures the overall PMD of a FUT by analyzing backreflected light from the distal end of FUT, and Embodiment (4) enables determination of cumulative PMD as a function of distance along the FUT. As implied by the adjective "single-ended", both embodiments involve measurement instrumentation located at only one end of the FUT.

2.2.3.1 Single-Ended Measurement: Overall PMD

Single-ended PMD measurement using backreflected light from the distal end of the FUT may be used when there are no optical amplifiers along the fibers. Below we describe the basic SSA theory as applied to single-ended overall PMD determination via measurement instrumentation adjacent only one end of FUT.

If a mirror (such as a fiber-pigtailed mirror) is connected at the distal end of the FUT, and if one could neglect Rayleigh backscattering and any spurious discrete reflections (e.g. from any connectors or splices) along the FUT, the tunable OTDR could be replaced by a tunable CW laser (no pulses) and a power meter for measuring the power reflected from the mirror at the distal end of the FUT at two closely spaced optical frequencies, $\nu_U$ and $\nu_L$, around a given midpoint frequency, $\nu_{mid}$, for a large number K of (I-SOP, A-SOP) couples, i.e., one such setting referring to both the input-SOP and the analyzer-SOP of the backreflected light. The SSA theory provides a relationship for the roundtrip-DGD(ν) expressed in terms of the mean-square differences of normalized powers (i.e. transmission) observed at closely-spaced optical-frequencies $\nu_U$ and $\nu_L$, each pair corresponding to one of a multiplicity of (I-SOP, A-SOP) couples. This relationship, analogous to Equation (2.1), is valid in all cases for any type of practical FUT regardless of its degree of randomness or its polarization coupling ratio, including the extreme case of a PMF fiber, as, $$DGD_{RoundTrip}(\nu) = \frac{1}{\pi \delta \nu} \arcsin\left(\alpha_{ds} \sqrt{\langle \Delta T^2(\nu) \rangle_{SOP}}\right) \quad (2.10)$$

$\langle \ \rangle_{SOP}$ represents the average over the K (I-SOP, A-SOP) couples, $\delta\nu=(\nu_U-\nu_L)$ is the "step", $\Delta T$ is the difference between the normalized powers observed at $\nu_U$ and $\nu_L$, respectively. The relationship holds for $DGD_{RoundTrip} \cdot \delta\nu$ $\langle$ ½, thus clarifying the meaning of "closely-spaced optical frequencies".

If changes in the I-SOP polarization controller and A-SOP polarization controller are correlated (as would be the case in preferred implementations for which a common "I/A-SOP" polarization controller is employed), then $$\alpha_{ds} = \sqrt{\frac{15}{4}} \quad (2.11a)$$

If, however, the I-SOP and A-SOP polarization controllers are not correlated (e.g. see FIG. 3, then $$\alpha_{ds} = \sqrt{\frac{9}{2}} \quad (2.11b)$$

The relationship in equation (2.10) holds for DGD·δν$\langle$ 0.3 for single-ended measurement configurations, thereby defining the meaning of "closely-spaced optical frequencies".

The reference mean-value $u_o$ used in Equation (2.3a) for single-ended measurement configurations, the reference mean-value $u_o$ is $$u_0 = \frac{2}{3} \quad (2.12)$$

The roundtrip DGD(ν) derived by equation (2.10) is not simply twice the forward DGD(ν). The roundtrip $DGD_{RMS}$ (i.e. PMD) extracted from an rms average of DGD(ν) values over a wavelength range is also not simply twice double the forward $DGD_{RMS}$. For the latter case, however, when averaged over wavelength, or time, the PMD value (i.e. rms DGD) is related to the roundtrip-PMD (i.e. rms $DGD_{RoundTrip}$) through a simple factor, the roundtrip factor $\alpha_{rt} = \sqrt{3/8}$, i.e., $DGD_{RMS} = \alpha_{rt} \cdot DGD_{RoundTripRMS}$ or $PMD = \alpha_{rt} \cdot PMD_{RoundTrip}$, where PMD is defined as the root-mean-square (RMS) value of DGD.

For the alternative definition of PMD, i.e., the mean value of DGD, then $\alpha_{rt} = 2/\pi$.

Typically, in order to reliably measure overall PMD, a tunable OTDR is used. The tunable OTDR launches relatively long pulses into the FUT, the at least one photodetector in the OTDR then detecting the backreflected power of the localized reflection at the distal end of FUT.

The roundtrip DGD of the FUT section comprised between the output of the instrument and the selected reflection is obtained as previously from equation (12), where the power observed for a given (I-SOP, A-SOP) couple is now obtained as, for example, the power of the pulse backreflected from the selected reflection averaged over a predetermined portion of the pulse duration.

It should be noted that the above defined backreflected power may be obtained by averaging each response pulse over a substantial portion of its duration, therefore it is preferable to apply a long OTDR pulse (e.g. 1 to 20 µs) for this single-ended PMD measurement technique.

Furthermore, in preferred embodiments of the invention for which overall total PMD is to be measured, the averages indicated in equation (2.10) are preferably carried out over both I-SOP, A-SOP and midpoint-wavelengths, all three of which are changed from one group comprising two closely-spaced wavelengths to the next, thus obtaining the roundtrip PMD instead of only one particular DGD at one particular wavelength. A roundtrip rms DGD (i.e. roundtrip PMD) over the prescribed wavelength range is expressed as:

$$PMD_{RoundTrip} = \frac{1}{\pi\delta v}\arcsin\left(\alpha_{ds}\sqrt{\langle\Delta T^2(v)\rangle_{SOP;v}}\right) \quad (2.13)$$

Moreover, the forward PMD value (simply denoted as "PMD", and unless otherwise stated, assumed to be defined based on the RMS definition) is related to the round-trip PMD by the same "round trip factor", i.e. $\alpha_{rt}=\sqrt{3/8}$, yielding:

$$PMD = \alpha_{rt} \cdot PMD_{RoundTrip} \quad (2.14)$$

In the limit of a sufficiently small optical-frequency difference ("step") between the closely-spaced wavelengths, equations (6.10) and (6.13) tend to the following simpler differential formulae:

$$DGD_{RoundTrip}(v) = \frac{\alpha_{ds}}{\pi\delta v} \cdot \sqrt{\langle\Delta T^2(v)\rangle_{SOP}} \quad (2.10a)$$

$$PMD_{RoundTrip} = \frac{\alpha_{ds}}{\pi\delta v} \cdot \sqrt{\langle\Delta T^2(v)\rangle_{SOP;v}} \quad (2.13a)$$

A measurement of PMD based on equation (2.13) or (2.13a) offers the advantage of a relatively short acquisition time, since there is no need to perform intermediate determination of the $DGD_{RoundTrip}(v)$ according to equations (2.10) or (2.10a). Nevertheless, rms $DGD_{RoundTrip}$ or mean $DGD_{RoundTrip}$ may be obtained from individually measured $DGD_{RoundTrip}(v)$ for many different midpoint optical frequencies u by root-mean-square or mean $DGD_{RoundTrip}(v)$ from equation (2.10) or (2.10a) over a prescribed optical frequency range, e.g. rms $DGD_{RoundTrip} = \sqrt{\langle DGD_{RoundTrip}^2(v)\rangle_v}$ and mean $DGD_{RoundTrip} = \langle DGD_{RoundTrip}(v)\rangle_v$. Forward rms DGD and mean DGD are then obtained by simply multiplying a roundtrip factor of $\sqrt{3/8}$ and $2/\pi$ on rms $DGD_{RoundTrip}$ and mean $DGD_{RoundTrip}$, respectively.

It should be noted that the pulse length used for the single-ended overall PMD measurement should be less than fiber (FUT) length, preferably significantly less (to avoid excessive Rayleigh scattering noise, for instance), e.g. 1 µs corresponds to a fiber length of approximately 100 meters. It is also preferred to average the detected backreflected light power over several or many optical pulses, e.g. from 10 to 1000 pulses.

Also, it should be emphasized preferred PMD measurement from the single-ended overall PMD measurement should use several or many different midpoint wavelengths, e.g. 20 to 2000, in order to improve the fundamental PMD measurement accuracy.

2.2.3.2 Single-Ended Measurement: Cumulative PMD

Equations (2.10) and (2.13) applicable for overall PMD determination also apply to single-ended cumulative PMD measurement, for which the cumulative PMD is determined as a function of distance z by analyzing the Rayleigh backscattering light for each location (z) along FUT length. In order to resolve fiber beat length it is necessary to employ a short light pulse, for example from a tunable OTDR. However, the use of an unduly short light pulse would limit the measurable FUT length and an excessively long pulse might not be able to resolve the beat length of fiber.

Indeed, if a very short light pulse is used, OTDR "traces", or backreflected power as a function of distance z, are the same as if the above single-ended overall PMD measurement were repeated an infinite number of times, with the end reflector shifted by a distance increment dz between measurements. Providing that the pulses are very short, and also ignoring the fact that the "coherence noise" always adds to an OTDR trace, the same result as in equation (2.10) is obtained, except that it is obtained as a function of distance z in one step. The different $\Delta T(v,z)$ values obtained with different (I-SOP, A-SOP) couples are now differences between whole OTDR traces as a function of z, instead of just one number, and give $DGD_{RoundTrip}(v,z)$. Note $T(v,z)$ is a normalized trace as a function of fiber length z.

It is generally impractical to employ very short pulses in the field, however, since attaining a useful dynamic range would require an exceedingly long measurement time. Also, reduction of the high level of coherence noise resulting from the use of short pulses may require an unacceptably large equivalent laser linewidth, which results in a small maximum measurable PMD. The present invention takes account of the finding that, with spectrally-broad pulses, the mean-square differences $\langle\Delta T(v,z)^2\rangle_{SOP}$ are simply "scaled down" by a factor that can be computed independently from the same raw data. This factor, $\sigma_r^2(z,v)$, is the relative variance of the traces, a function of z depending on local characteristics of the fiber, defined as, $$\sigma_r^2(z, v) = \left(\frac{1}{\sigma_{10}}\right)^2 [\langle T(z, v)T''(z, v)\rangle_{SOP} - \langle T(z, v)\rangle_{SOP}^2] \quad (2.15)$$

where the reference variance is $\sigma_{10}^2 = 4/45$, and T" represents a repeated measurement. The roundtrip DGD at a given midpoint wavelength then is obtained by dividing the mean-square differences in equation (12) by the relative variance in equation (14), i.e.

$$DGD_{RoundTrip}(z, v) = \frac{1}{\pi\delta v}\arcsin\left(\alpha_{ds}\sqrt{\frac{\langle\Delta T^2(z, v)\rangle_{SOP}}{\sigma_r^2(z, v)}}\right) \quad (2.16)$$

Furthermore, in preferred implementations of the invention, the averages indicated in equations (2.15) and (2.16) are preferably carried out over both (I-SOP, A-SOP) couples and center wavelengths, both of which are changed from one group comprising two closely-spaced wavelengths to the next, thus obtaining the roundtrip PMD instead of only one particular DGD at one particular wavelength.

$$PMD_{RoundTrip}(z) = \frac{1}{\pi\delta v}\arcsin\left(\alpha_{ds}\sqrt{\frac{\langle\Delta T^2(z,v)\rangle_{SOP;v}}{\sigma_r^2(z)}}\right) \quad (2.17)$$

Since the typical user would prefer that the more practically useful "forward" PMD value be displayed rather than the roundtrip value, the round-trip result is multiplied by the above-specified roundtrip factor, $\alpha_{rt}=\sqrt{3/8}$. Thus, the forward PMD is $$PMD(z)=\alpha_{rt}\cdot PMD_{RoundTrip}(Z) \quad (2.18)$$

where the average over (I-SOP, A-SOP) couples in equation (2.14) is replaced by the average over both (I-SOP, A-SOP) couples and wavelength, i.e.

$$\sigma_r^2(z) = \left(\frac{1}{\sigma_{10}}\right)^2 [\langle T(z,v)T''(z,v)\rangle_{SOP;v} - \langle T(z,v)\rangle_{SOP;v}^2] \quad (2.15a)$$

Alternatively, the roundtrip rms DGD (i.e. roundtrip PMD according to the rms definition) can also be obtained by performing a root-mean-square average on the plurality of calculated roundtrip DGD values that correspond to a respective plurality of midpoint wavelength, as $$rms\ DGD_{RoundTrip}(z)=\sqrt{\langle\overline{DGD_{RoundTrip}^2(z,v)}\rangle_v}, \quad (2.19)$$

where T" represents a repeated measurement. Of course, by performing this "intermediate" calculation of DGD at each optical frequency, the overall time required to determine the PMD would be longer than directly applying Equation (2.17).

Forward rms DGD(z) is then obtained by simply multiplying rms $DGD_{RoundTrip}$ by the roundtrip factor $\alpha_{rt}=\sqrt{3/8}$.

Analogous calculations may be carried out to determine the forward mean DGD(z), employing the roundtrip factor $\alpha_{rt}=2/\pi$. However, for such calculations the additional noise reduction achieved using repeated measurements T" may not be rigorously correct, since relative variances (rather than arithmetic means) are used in equations (2.15) and (2.15a).

In the limit of a sufficiently small optical-frequency difference ("step") between the closely-spaced wavelengths, equations (2.16) and (2.17) tend to the following simpler differential formulae:

$$DGD_{RoundTrip}(z,v) = \frac{\alpha_{ds}}{\pi\delta v}\cdot\sqrt{\frac{\langle\Delta T^2(v)\rangle_{SOP}}{\sigma_r^2(z,v)}} \quad (2.16a)$$

$$PMD_{RoundTrip}(z) = \frac{\alpha_{ds}}{\pi\lambda v}\cdot\sqrt{\frac{\langle\Delta T^2(z,v)\rangle_{SOP;v}}{\sigma_r^2(z)}} \quad (2.17a)$$

As yet another possible, although less desirable alternative, it is envisaged that the averages over (I-SOP, A-SOP) couples and wavelengths in the above equations (2.8), (2.11), (2.13) and (2.16) could be replaced by averages over a large range of optical frequencies only, for which the (I-SOP, A-SOP) couple is kept constant. However, in this "constant-SOP" case, the method loses its applicability to all FUT types, i.e., if only the midpoint wavelength is scanned without scrambling of the (I-SOP, A-SOP) couples being applied, these relationships are no longer universally valid, and may be significantly less reliable and/or accurate—even if still roughly valid. Generally, if no scrambling is performed, the methods are only valid if the FUT is "ideal" or "nearly ideal", i.e., it exhibits excellent random coupling and has an infinite or "near-infinite" polarization coupling ratio, and if one chooses a large value of the PMD·Δv product (typically >10), where Δv is the width of the optical frequency range. As a consequence, in practice, small PMD values cannot be measured within a reasonable degree of uncertainty. In addition, one frequently wishes to perform measurement on older installed fibers, which are generally much less "ideal" than fibers produced since about 2001.

It should also be noted that any of the equations for computed DGD or PMD described herein, including those including a factor for relative variance, may be applied to both normalized power (including normalized OTDR trace) and relative power (including relative OTDR trace). It should also be appreciated that relative power or relative OTDR trace is proportional to normalized power or normalized OTDR trace, respectively.

It should be noted that a pulse length used for the single-ended cumulative PMD measurement should be not very significantly greater than the fiber beat length, e.g. preferably less than ten times the beat length.

As well, each measured OTDR trace should comprise an average over several or many optical pulses, e.g. from 10 to 10,000 pulses.

Also note that preferred PMD measurement from the single-ended cumulative PMD measurement should use several or many different midpoint wavelengths, e.g. 10 to 1000, as a greater number of such midpoint wavelengths will lead to a better fundamental PMD measurement accuracy.

2.3 Details of Theory Specific to Embodiment (2): Partial-DGD Measurement and Determination of DGD Therefrom 2.3.1 Pulse Spreading of Traffic Signal as a Manifestation of Optical-Link PMD The effect of PMD in an optical link is to induce temporal pulse spreading on a data-carrying signal (SUT) propagating therethrough. As discussed in Section 1.3 hereinabove, the extent of this pulse spreading is given by the partial-DGD" (denoted herein equivalently as $DGD_P$, or, for convenience, $\tau_{PB}$) is strongly dependent upon both the wavelength of the SUT and the SOP of the SUT as it enters the optical link. The input SOP may vary in an unpredictable manner over relatively short times (typically seconds to minutes) if patchcords or cabling at or near the network transmitter are moved or otherwise perturbed. Measurement of PMD-induced partial DGD is particularly important for optical communication systems because it is associated with PMD-induced system penalty, generally termed "PMD penalty" [1].

The partial-DGD, $\tau_{PB}(v,\phi)$, of a signal-under-test (SUT) at an optical frequency, v, may be expressed as:

$$\tau_{PB}(v,\phi)=\tau(v)\cdot\sin\phi \quad (2.20)$$

where $\tau(v)$ is the differential group delay (DGD) of a lightpath at an optical frequency, v. $\phi$ is the angle between two Stokes vectors defining, respectively, a PSP axis (e.g. slow axis) of the lightpath and the SOP of the SUT at either the input (as launched into the optical fiber link) or at the output of the fiber link (just before the analyzer), this angle being optical-frequency dependent and between 0 to 180 degrees.

The partial-DGD, $\tau_{PB}(\nu, \phi)$, of the SUT 60, defined in equation (2.20), corresponds to the magnitude of a perpendicular component of the polarization dispersion vector (PDV) with respect to the SOP of the SUT, the magnitude of the PDV being equal to the DGD ($\tau(\nu)$), of the optical fiber. Thus, the partial-DGD, $\tau_{PB}(\nu, \phi)$, of SUT 60 may vary from zero (no broadening) to the DGD($\nu$) value (maximum broadening), dependent upon the launched input-SOP with respect to the "slow" Input-PSP axis of the optical path and also vary in time as the DGD or PSP axis of the optical fiber may vary in time.

Performing rms averaging of equation (2.20) over all possible $\phi$ yields:

$$\sqrt{\langle \tau_{PB}^2(\nu, \varphi) \rangle_\varphi} = \sqrt{\frac{2}{3}} \cdot \tau(\nu) \qquad (2.21)$$

Equation (2.21) relates the rms DGD and DGD of the lightpath at the optical frequency of the SUT.

Moreover, if DGD values of a large of number of data-carrying signals (SUTs) are measured, where all the SUTs are generated by transmitters at or adjacent the proximal end of the optical link under test and where the respective wavelengths of the SUTs are spread across a substantial wavelength region (e.g. more than half of the telecom C-band extending from 1530-1565 nm), it is possible to estimate the PMD of all or part of the optical link (e.g. see equations (2.28)a).

The method described herein to monitor and/or measure $DGD_P$ of a SUT and, in a further aspect of the invention, to estimate the PMD of the optical link, is not predicated upon knowledge of the DGD of the lightpath (i.e. the DGD of the optical link at the particular wavelength of the optical channel corresponding to the lightpath, e.g. particular DWDM channel) nor upon the angle $\phi$ between the two Stokes vectors corresponding to the aforementioned lightpath PSP axis and the SOP of the input light.

We also point out here that it may be difficult or impractical to measure DGD according to the definition of equation (2.20), since both DGD and $\phi$ need to be known.

Note that, in order to simplify the notation in the subsequent description, $\tau_{PB}(\nu,\phi)$ will be expressed as $\tau_{PB}(\nu)$ since $\phi$ does not need to be known or determined for measuring the DGD in implementations of this embodiment, even though $\tau_{PB}$ is, in general, dependent on the angle $\phi$.

2.3.2 Random Output SOP Scrambling Analysis for DGD Monitoring of Traffic Signals The conceptual measurement process underlying determination of partial-DGD is very similar to that presented in Sec. 2.2 hereinabove, except that there is no "test-induced" variation of I-SOP, the state of polarization of the SUT as it enters the optical link (FUT). In other words, only A-SOP is varied—no explicit averaging is performed over I-SOP as part of the basic method to determine $DGD_P$ at any particular moment. The A-SOP values should be chosen in a random or predefined manner, such that the points conventionally representing SOPs on the Poincaré sphere are approximately uniformly-distributed over its surface, whether the distribution is random or comprises a uniform grid of points. Hence, SSA theory provides that, on average over a sufficiently large number, K, of such A-SOP values, a statistical moment, specifically the variance (second moment) of the differences between normalized powers observed at each of two closely-spaced optical frequencies, $\nu_U$ and $\nu_L$, is related to the DGD at its midpoint optical frequency $\nu_{mid}$ ($=(\nu_U+\nu_L)/2$) by a simple relationship. This relationship is valid for all practical lightpaths regardless of their degree of randomness or polarization coupling ratio, including the extreme case of weakly-coupled optical fiber, e.g. PMF fiber, in the optical path, i.e., $$DGD_P(\nu) = \frac{1}{\pi\delta\nu}\arcsin\left(\alpha_{ds}\sqrt{\langle \Delta T^2(\nu) \rangle_{SOP}}\right) \qquad (2.22)$$

where the theoretical constant $\alpha_{ds}=\sqrt{3}$, $\langle \ \rangle_{SOP}$ represents averaging over K A-SOP values (I-SOP is not varied as part of the measurement procedure), and $\delta\nu(=|\nu_U-\nu_L|)$ is the small optical-frequency difference ("step").

$\Delta T(\nu)$ is a difference between the analyzed normalized powers (i.e. transmissions) observed at optical frequencies $\nu_U$ and $\nu_L$, respectively, and its second moment or mean-square difference is, $$\langle \Delta T^2(\nu) \rangle_{SOP} = \langle (T_U - T_L)^2 \rangle_{SOP} = \frac{1}{K}\sum_k \left(T_U^{(k)} - T_L^{(k)}\right)^2 \qquad (2.23)$$

where the index k corresponds to a particular A-SOP, and where, for polarization-sensitive one-detector implementations shown in FIGS. 2I and 2N, the normalized powers are, $$T_L^{(k)} = u_o \frac{P_L^{(k)}}{\langle P_L \rangle_{SOP}} \quad T_U^{(k)} = u_o \frac{P_U^{(k)}}{\langle P_U \rangle_{SOP}} \qquad (.24a)$$

Here, the reference mean-value $u_o=\frac{1}{2}$ is a theoretical constant, and the average power is defined as, $$\langle P_L \rangle_{SOP} = \frac{1}{K}\sum_k P_L^{(k)} \cdot \langle P_U \rangle_{SOP} = \frac{1}{K}\sum_k P_U^{(k)} \qquad (2.24b)$$

As depicted schematically in FIG. 11 measurements may be undertaken at or adjacent the corresponding network receiver 28 (e.g. via a monitor port), or at monitor port 26 or 27 (tapped from the link) at an intermediate location along between the Tx 22 and Rx 28. For convenience, the following description assumes that an OSA having polarization-diverse detection means is employed.

Furthermore, in preferred implementations of the embodiment, for a prescribed optical-frequency range within the SUT bandwidth, e.g. defined as that lying between optical frequencies for which the (filtered) signal is 1 to 20 dB below its peak value, the computed $DGD_P$ in equation (2.22) may be convoluted with the SUT spectral profile to yield the PMD-induced $DGD_P$ parameter, expressed as:

$$\overline{\tau}_{PB_{SUT}} = \frac{\int_\nu S(\nu)\tau_{PB}(\nu)d\nu}{\int_\nu S(\nu)d\nu} \qquad (2.25)$$

where $S(\nu)$ is the optical-frequency-dependent signal power determined from an average over at least one but preferably a large of number of measured optical powers at each optical frequency under conditions of negligible ASE, e.g. OSNR⟩ 20 dB as:

$$S(v) = \langle P(v) \rangle_{SOP} \qquad (2.26)$$

The convolution procedure of equation (2.25) is necessary in order to obtain reliable $DGD_P(v)$ values across a substantial portion of the SUT spectral profile.

However, if $S(v)$ is sufficiently "flat" over the optical-frequency range encompassed by any pair of two closely-spaced frequencies across some specified restricted portion of the signal spectrum, then $S(v)$ may be considered constant in equation (2.25), and consequently the mean $DGD_P$ value over a specified optical-frequency range of the SUT bandwidth simplifies to:

$$\bar{\tau}_{PB_{SUT}} = \langle \tau_{PB}(v) \rangle_v \qquad (2.25a)$$

or alternatively a rms $DGD_P$ value:

$$\bar{\tau}_{PB_{SUT}} = \sqrt{\langle \tau_{PB}^2(v) \rangle_v} \qquad (2.25b)$$

where $\langle \ \rangle_v$ indicates an average over a specified optical-frequency range, e.g. of a SUT bandwidth between ~3 dB to ~−20 dB.

The signal power of a SUT 60 about each (midpoint) optical frequency is extracted from average of the power difference $\Delta P(v)$ for a large number of A-SOPs, so as to remove ASE power arising from, e.g., in-line optical amplifiers:

$$S(v) = \langle |\Delta P(v)| \rangle_{SOP} \qquad (2.26a)$$

or $$S(v) = \sqrt{\langle \Delta P^2(v) \rangle_{SOP}} \qquad (2.26b)$$

It should be appreciated that the calculated spectral power, $S(v)$, in equations (2.26) and (2.26a) may be multiplied by any factor that must be kept constant for any optical frequency within a frequency range of interest and preferably power value $P(v)$ used in equations (6.26) is an averaged value of $P(v+\frac{1}{2}\delta v)$ and $P(v-\frac{1}{2}\delta v)$, i.e. $P(v)$ being measured power at each midpoint optical frequency.

Based on above computed average $DGD_P$ value over a specified wavelength range, e.g. of a SUT bandwidth, in equations (2.25), (2.25a), or (2.25b), the degree to which the PMD of the lightpath may impair the SUT may be expressed as the PMD penalty, $\eta$ (usually expressed in dB), where:

$$\eta = A \cdot \left( \frac{\bar{\tau}_{PB_{SUT}}}{2B} \right)^2 \qquad (2.27)$$

where B is the bit period (or symbol period, if the SUT comprises a multibit/symbol modulation format), and A is a dimensionless parameter dependent on modulation format, pulse shape, network characteristics (e.g. optical noise, optical filter, etc.), and receiver characteristics (e.g. electric filter, noise, etc.), etc.

It should be appreciated that the above equation (2.27) is not the only possible one and it may be expressed as other formula, for example, as a PMD penalty, $\eta(\phi)$, including higher-order terms:

$$\eta = A_1 \cdot \left( \frac{\bar{\tau}_{PB_{SUT}}}{2B} \right)^2 + A_2 \cdot \left( \frac{\bar{\tau}_{PB_{SUT}}}{2B} \right)^4 \qquad (2.27a)$$

B is the bit (symbol) period, and $A_1$ and $A_2$ represent predetermined parameters, for example, that may be extracted from prior knowledge, or gleaned from experiments or simulations.

For measurement of link PMD for an in-service network, one may perform an rms average over computed $DGD_P$ for each of a plurality of SUTs, each corresponding to a network transmitter (Tx) having respective central wavelengths that are distributed across a significant spectral region (e.g. the telecom C, or C+L bands):

$$PMD = \sqrt{\frac{3}{2} \langle \tau_{PB}^2(v) \rangle_v} \qquad (2.28a)$$

where $\langle \ \rangle_v$ indicates an average over each of the SUTs. Improved accuracy may be obtained by evaluating $DGD_P$ across each of the SUT bandwidths as a function of optical frequency, for instance employing the convolution procedure of equation (2.25). It should be appreciated that such link PMD estimation is predicated upon all of the SUTs used in the measurement corresponding to co-located Tx at the opposite end of the FUT. In addition, it is preferable that the number of SUTs used in equation (2.28) be as large as practical, in order that there be an increased statistical probability that a wide variety of different input SOPs may be launched into the FUT, thereby improving the PMD estimate.

Alternatively, equation (2.28a) can be expressed as:

$$PMD = \frac{1}{\pi \delta v} \arcsin\left( \sqrt{\frac{9}{2} \langle \Delta T^2(v) \rangle_{SOP,v}} \right) \qquad (2.28b)$$

where the subscripted bracket $\langle \ \rangle_{SOP,v}$ indicates an average over both the A-SOP and midpoint optical frequencies.

In the limit of a sufficiently small optical-frequency difference ("step"), equations (2.22) and (2.28b) tend to the following simpler differential formula:

$$\tau_{PB}(v) = \frac{1}{\pi \delta v} \sqrt{3 \langle \Delta T^2(v) \rangle_{SOP}} \qquad (2.22a)$$

$$PMD = \frac{1}{\pi \delta v} \sqrt{\frac{9}{2} \langle \Delta T^2(v) \rangle_{SOP,v}} \qquad (2.28c)$$

Of course, any other alternative mathematical function that provides a numerical result that falls within an acceptable difference from the said following differential formula for realistic values of $DGD_P$ and PMD could be used instead. This would be true for any of the other analogous formulas presented elsewhere in this specification.

It should be noted that the relationships in equation (2.22) or (2.28b) hold for $\tau_{PB} \cdot \delta v < 0.20$ or $PMD \cdot \delta v < 0.15$.

The normalized power will in fact be obtained differently in each implementation (FIGS. 2H, 2I, 2K), i.e., by suitable programming of the data processor. First, a theoretical explanation of the normalization procedure is provided for the basic single-photodetector implementation of FIGS. 2I and 2J, where normalization over the average power (i.e. equation (2.24b)) is necessary, assuming total power is stable when the A-SOP is changed, or as a function of time. Note that the normalization procedure for the measurement configuration of FIGS. 2H and 2K is different. A detailed description of this normalization procedure is provided hereinafter.

It should be noted that equation (2.22) yields a $DGD_P$ value for a SUT at a given midpoint wavelength, defined as the average wavelength of the particular closely-spaced optical frequencies. Equation (2.25) provides a signal spectral-weighted average of $DGD_P$ value for a prescribed SUT bandwidth used for estimating a PMD-induced power penalty. Equation (2.28b) yields an estimated PMD value for a prescribed wavelength range from a large number of SUTs (e.g. $>$10-40). The PMD definition employed here is based on the root-mean-square (rms) value of DGD averaged over optical frequency.

2.3.3 $DGD_P$ Monitoring of Traffic Signal Including ASE and Nonlinear Depolarization The foregoing method for $DGD_P$ monitoring and optical-link PMD measurement presupposes negligible depolarization, that may arise from e.g. ASE of optical amplifiers, nonlinear depolarization, etc. However, in many field applications, optical amplifiers (typically erbium-doped optical amplifiers (EDFAs), Raman amplifiers) have been inserted into the optical fiber link. That is, the optical link 24 may comprise at least one, and possibly several, optical amplifiers at various spacings (e.g. ~50 km), and several or many data-carrying signals (e.g. 20-60 in C-band) and long optical fiber segments. When an optical amplifier and a multiplicity of traffic signals are present with a long optical path, a power meter located at tap monitor port 26 or 27 (see FIG. 11) or at distal end of a lightpath (e.g. at a receiver (Rx) side 28) will likely also detect (substantially unpolarized) amplified spontaneous emission (ASE) light. As well, there may be partial depolarization introduced by nonlinear effects, e.g. inter-channel cross-phase modulation (XPM), in addition to any residual depolarization on the light arising directly from the Tx 22. The presence of these depolarization effects in the detected signal can be taken into account by "scaling down" the mean-square differences $\langle \Delta T(v,\phi)^2 \rangle_{SOP}$ by a factor that can be computed independently from the same raw data. This factor, $\sigma_r^2(v)$, is a relative variance of the normalized powers defined as, $$\sigma_r^2(v) = 12[\langle T(v)T''(v) \rangle_{SOP} - \langle T(v) \rangle_{SOP}^2] \qquad (2.29)$$

The expressions $\langle T(v)T''(v) \rangle_{SOP}$ and $\langle T(v) \rangle_{SOP}^2$ refer to averages over both normalized powers at $v_U$ and $v_L$, and $T(v)$ and $T''(v)$ are the normalized powers from repeated measurements in one group at one given optical frequency. Then an (optical-frequency-dependent) $DGD_P$ at a given midpoint wavelength is obtained by dividing the mean-square differences by the relative variance in equation (2.28b) as, $$\tau_{PB}(v) = \frac{1}{\pi\delta v}\arcsin\left(\sqrt{3\frac{\langle \Delta T^2(v) \rangle_{SOP}}{\sigma_r^2(v)}}\right) \qquad (2.30)$$

It should be noted that, if the noise power contribution may be neglected, then $T(v)$ and $T''(v)$ may be the same normalized power, i.e. corresponding to only one measurement in one group at one given optical frequency, and hence $T(v) T''(v) = T^2(v)$.

It further should be noted that, if the normalized powers $T(v)$ are averaged over a sufficient large number of randomly scrambled SOPs, then $\langle T(v) \rangle_{SOP}^2 = 1/4$.

It should be appreciated that Eq. (2.30) may be replaced by Eq. (2.22) if depolarization effects are negligible or small.

Use of Eq. (2.22) for calculating $DGD_P$ of a significantly depolarized SUT (e.g. DOP~30%, due to a large fraction of co-propagating ASE and/or signal depolarization from XPM) would likely lead to a significant error, but may suffice for a very rough $DGD_P$ estimation.

Therefore, in order to obtain the PMD-induced $DGD_P$ parameter to estimate a PMD penalty, the spectral-power-weighted average over computed $DGD_P$ in equation (2.30) may be calculated using equations (2.25) and (2.26).

Preferably such signal power at each wavelength is extracted from an average over at least one power difference, $\Delta P(v)$, from at least two analyzed optical powers at each wavelength of light for a large number of A-SOPs to remove the ASE contribution, and thereby the signal light power at each wavelength of a SUT 60 can be expressed as:

$$S(v) = \langle |\Delta P(v)| \rangle_{SOP} \qquad (2.26a)$$

or $$S(v) = \sqrt{\langle \Delta P^2(v) \rangle_{SOP}} \qquad (2.26b)$$

where $\langle \ \rangle_{SOP}$ represents an average over the A-SOPs and $\Delta P(v)$ is a power difference value between two measured powers from either (i) two power measurements corresponding to two A-SOPs for the implementations of FIG. 2K using two photodetectors $PD_x$ 22B and $PD_y$ 22C with a PBS 20C or FIG. 2I using a single tunable filter (TF) 27 and single photodetector (PD) 22 with linear polarizer 20A where the only available powers are obtained here from the photodetector 22; or (ii) from two simultaneously measured powers using photodetectors $PD_x$ 22B and $PD_y$ 22C for same A-SOP for the implementation of FIG. 2K employing a PBS 20C and two tunable filters $TF_x$ 27B and $TF_y$ 27C, Alternatively, if S(v) is set equal to any constant value for above equations (2.25), a mean $DGD_P$ value over a specified wavelength range of a SUT bandwidth is obtained as:

$$\bar{\tau}_{PB_{SUT}} = \langle \tau_{PB}(v) \rangle_v \qquad (2.25a)$$

or alternatively an rms $DGD_P$ value as:

$$\bar{\tau}_{PB_{SUT}} = \sqrt{\langle \tau_{PB}^2(v) \rangle_v} \qquad (2.25b)$$

where $\langle \ \rangle_v$ is to average over a specified wavelength range, e.g. of a SUT bandwidth.

Based on above computed average $DGD_P$ value over all or at least a portion of the SUT bandwidth, in equation (2.25), (2.25a) or (2.25b), the corresponding PMD-induced impairment on the SUT propagating through a lightpath (e.g. of a DWDM network) may be related to the PMD penalty, $\eta$, via equations (2.27) or (2.27a) presented above.

In a further implementation of Embodiment (2), measurement of $DGD_P$ values at for a plurality of different SUTs, preferably roughly uniformly spaced across a wide spectral region (e.g. telecom C band) may be used to estimate the link PMD:

$$PMD = \sqrt{\frac{3}{2}\langle \tau_{PB}^2(v) \rangle_v} \qquad (2.31)$$

or $$PMD = \frac{1}{\pi\delta v}\arcsin\left(\sqrt{\frac{9}{2}\left\langle\frac{\Delta T^2(v)}{\sigma_r^2(v)}\right\rangle_{SOP;v}}\right) \qquad (2.32)$$

where the average over A-SOP in equation (2.30) is now replaced by the average over both SOP (i.e. A-SOP) and optical frequency. Note that a relative variance of the normalized powers may also be further calculated via a simple average over optical frequency, but such an average is usually not reliable because the power density of the SUTs usually is usually not flat.

In the limit of a small step, equations (2.30) and (2.32) tend to respective simpler differential formulae:

$$\tau_{PB}(v) = \frac{1}{\pi \delta v} \sqrt{3 \frac{\langle \Delta T^2(v) \rangle_{SOP}}{\sigma_r^2(v)}} \quad (2.30a)$$

$$PMD = \frac{1}{\pi \delta v} \sqrt{\frac{9}{2} \left\langle \frac{\langle \Delta T^2(v) \rangle}{\sigma_r^2(v)} \right\rangle_{SOP,v}} \quad (2.32a)$$

It should be noted that, if two powers of "closely-spaced optical frequencies" are equal and there is negligible differential spectral attenuation from SUT 60 for these "closely-spaced wavelengths", the measured powers for "closely-spaced wavelengths" can directly be applied to equations (2.30) and (2.32), i.e. without need for normalization of the measured powers (note in this case, $\langle T(v) \rangle_{SOP}^2$ may not be equal ¼). This arises since, under this condition, the normalization procedure described above may only produce a "constant factor" that is multiplied on measured powers in order to obtain normalized power (between 0 and 1), but by using equations (2.30) and (2.32) to compute $DGD_P$ or PMD, this constant 'factor' is eventually cancelled because the same 'factor' is applied to both the mean-square difference and relative variance if they are both directly computed from measured powers. In other words, if equations (2.30) and (2.32) are used, only relative powers that are proportional to normalized powers are required to be obtained to calculate the $DGD_P$ or PMD.

It should be appreciated that equations (2.30) and (2.32) are applicable whether or not amplifier noise is present on the link under test.

However, it should be noted that the equations (2.28a) and (2.31) no longer represent simple rms or mean averaging of all $DGD_P$ (v) values but include a statistical theoretical constant $$\left( \text{i.e. } \sqrt{\frac{3}{2}} \right).$$

Also note a similar equation may be applied for mean averaging over all single $DGD_P(v)$ values with a different statistical theoretical constant. (However, it is not the same as a standard PMD definition, i.e. where PMD is calculated/defined by rms or mean DGD values at different frequencies.)

We point out here that the calculation of a PMD estimate for an optical link 24 via equations (2.28a) and (2.31) is based on the statistical relationship between the measured $DGD_P$ values and the PMD. Moreover, equation (2.28a) or (2.31), or similar algorithms, may also be applied to other PMD measurement methods known by those skilled in this art, for example, measured maximum (polarization) differential time delays at different optical frequencies by a phase shift method, measured SOP or arc lengths at different optical frequencies e.g. by a spectrally-resolving polarimetric head, etc.

3. DATA PROCESSING AND COMPUTATION

Measurement of a polarization-related characteristic of an optical path (FUT) according to aspects of the present invention, including two-ended PMD measurement, single-ended overall PMD measurement and single-ended cumulative PMD measurement, are all based upon the random input and output state-of-polarization scrambling analysis (SSA) approach described herein, but their detailed implementations are not the same. For example, the two-ended measurement requires that the light source means be placed at one end of FUT and analyzer-and-detection means at the other end of FUT. The nature of the light source may also be different, for example, two-ended PMD measurement may employ either a continuous wave (CW) or pulsed light source if it can select or modulate optical frequency of light to produce two or three closely spaced wavelengths for the measurement, but for the single-ended PMD measurement, it is necessary to use a pulsed light source (usually a tunable OTDR) to resolve the reflections from the distal end of FUT. There are also differences in operation between single-ended "overall PMD" measurements and single-ended cumulative PMD measurements, for instance with respect to pulse length, number of closely spaced wavelengths, acquired data and data processing.

Therefore, below we will describe the method of operation, data processing and computation in three different sections for Two-Ended PMD Measurement, "Two-ended" Partial-DGD Measurement, Single-ended Overall PMD Measurement and Single-ended Cumulative PMD Measurement.

3.1 Methods of Operation

3.1.1 Method of Operation Embodiment (1)

Two-Ended "Test-Source-Based" DGD and/or PMD Measurement

The method of operation for a measurement instrument of Embodiment (1) ("two-ended PMD measurement) for measurement of DGD and/or PMD, as shown generically in FIG. 1, will now be described in more detail with reference to the flowcharts shown in FIGS. 5A, 5B, 5C and 5D.

In steps 4.1 and 4.2, the user first installs the application and, if applicable, inserts the test modules in the platforms. Then the user starts testing software to cause the system to initialize the test modules, specifically initializing the wavelength of the polarized light source 12 (either tunable laser source 12A or broadband light source 12B), the Input SOP controller (I-SOP) 14A, the analyzing means 14B and 20 and the detection 22 and processing section 34. Then one end of the fiber under test (FUT) 18 is connected to source module before I-SOP 14A and the opposite end of FUT 18 is connected to analyzer-and-detection module, and patch cords with either a PC or an APC connector (such as FC/PC or FC/APC), or direct bulkhead connectors, are used to connect the test modules with the FUT. Most instrument parameters will usually be factory set according to customer requirements, but the user may manually select parameters for both the light source and analyzer by steps 4.1c and 4.3, respectively. Assuming that the user selects manual parameter setting, the program proceeds to the manual parameter setting steps 4.1c and 4.4 and prompts the user as follows:

(a) Set a center wavelength for the tunable laser source 12A or (in the case of a broadband source) tunable filter 27.

(b) Set a wavelength range [λmin, λmax] for the group center wavelengths that will be encompassed by the light source 12 providing that it corresponds to an accessible wavelength range of the FUT 18.

(c) If available (i.e. not fixed at factory), set the step or difference δv (or δλ) between the pairs closely-spaced optical frequencies $v_U$ and $v_L$ (or wavelengths). Alternately, the user may enter the anticipated PMD value for the FUT and leave the processor to compute and then select the optical-frequency step. As an example, the step can be conveniently set to $\delta v = \alpha_{\delta v} \cdot PMD^{-1}$ where $\alpha_{\delta v} \sim 0.15$ to 0.2 and, thus, δλ can be extracted from $\delta \lambda \approx (c/v_c^2) \cdot \delta v$ where $v_c = (v_U + v_L)/2$. (Note: there is an optimal step for a given PMD value, as large as possible so as to maximize signal-to-noise ratio, but small enough to satisfy the above condition, i.e., PMD·δv<0.15 to 0.2. It is also noted that closely-spaced optical frequencies may also be more than two and this may be especially interesting for testing and monitoring where DGD or PMD from FUT may be varied versus time.)

(d) Set the number K of center-wavelengths and/or states of polarization selected by the I-SOP scrambler 14A and A-SOP scrambler 14B, i.e., the number (K) of groups of data to be acquired. For example, K may be set to 1000 to 100,000. Or, optionally, for the continuously scanning input and output SOP mode, only the number K of center-wavelengths and then set a scanning time for both input SOP controller 14A and analyzer SOP controller 14B and 20. Or, optionally, if only one center-wavelengths is selected, set the number K of states of polarization selected by the I-SOP scrambler 14A and A-SOP scrambler 14B or a scanning time for the continuously scanning both I-SOP scrambler 14A and A-SOP scrambler 14B.

(e) Optionally, set the number of pulses to be averaged to obtain each individual power (for example 2 or 〉100) for a series of modulated optical pulses to be launched into the FUT. No setting is required if only one modulated optical pulse is to be launched into the FUT.

(f) Set an overall total acquisition time for each individual PMD measurement and number of PMD measurement, as well as the waiting time between two successive measurements.

(g) Select the modulated optical pulse duration Tp. Typically, a long pulse length is selected for the measurement because it leads to a high dynamic range, and a high signal-to-noise ratio although a short pulse may still be used. (Typically, the modulated optical pulse length is chosen to be between 100 μs and 1 s, although pulse lengths outside of this range are also feasible.

(h) Optionally, set an input power of the tunable light source means.

(i) Optionally, adjust the power entering the analyzer module from the FUT by means of an optical attenuator in the optical path, for example, at a location just after the input of the analyzer module. Normally, however, this would be automatically set by the instrument.

(j) Optionally, enter the cable or fiber name and/or other relevant information.

(k) Save all measurement parameters to a data file that will be retrieved for data processing by the data processor 34.

If, in decision step 4.3, the user selects automatic parameter setting, the program starts the auto parameter setting procedure in step 4.5 and carries out the following steps:

(a) Select pre-defined certain default measurement parameters, namely (1) The center wavelength range [λmin, λmax] that will be covered by the light source 12, or in the case of a broadband source, the tunable filter 27;

(2) Number K of SOPs and/or center wavelengths by the I-SOP scrambler 14A and A-SOP scrambler 14B (for example, 1000-10,000) for one PMD data acquisition, or, alternatively, a scanning time of both or either of I-SOP scrambler 14A and A-SOP scrambler 14B;

(3) Time for each individual acquisition (measurement), waiting time between any two individual acquisitions, and number of repeated acquisitions;

(4) Frequency pulse duration Tp (or length) for tunable coherent source; and (5) Launched light power and received power.

(b) The test module may also be designed to have a pre-scan acquisition using a reduced number of groups, such as K=50-100, to obtain estimations of optimal wavelength step frequency difference δv (or δλ) between the two closely-spaced optical frequencies $v_U$ and $v_L$ (or wavelengths $\lambda_U$ and $\lambda_L$). Pre-scan data acquisition is performed to find the appropriate step or difference δv (frequency) or δλ (wavelength) between the two closely-spaced optical frequencies $v_U$ and $v_L$ (or $\lambda_U$ and $\lambda_L$). For example, such data acquisition may be carried out by using, for each group, four different laser wavelengths to obtain a total combination of six different frequency or wavelength steps. In this case, good communications between the two ends of the FUT may be required.

(c) Auto mode may also be designed to automatically produce cable or fiber name and/or other relevant information;

Once the measurement parameters have been entered, whether manually or automatically, the program proceeds to step 4.6 and computes wavelength step δλ (or frequency difference δv) if the anticipated total PMD of the FUT has been specified or estimated via the aforementioned auto-setting procedure, and the appropriate sequence of wavelengths based on the parameter settings. It is preferred to use three or four (or even more) different laser wavelengths to produce three or six (or even more) different wavelength steps to cover a wide measurable PMD range.

Finally, all the measurement parameters, whether directly specified or computed as described above, are stored in the header of the data file or instrument (Step 4.7).

It should be noted that a linewidth of the tunable coherent source will usually be set, in the factory or by design, at a relatively small level (e.g. of 〈 1 to 2 GHz) in order to ensure the ability to measure a high PMD (e.g. 〉50 ps) from the FUT.

It should be noted that, conveniently, at each SOP and/or center wavelength, the frequency difference δv (or wavelength step δλ) between the two closely-spaced optical frequencies $v_U$ and $v_L$ (wavelengths $\lambda_U$ and $\lambda_L$) may remain the same or similar. Each SOP and/or wavelength may only be set in a short time period.

It should be re-emphasized, that in order to obtain a reliable PMD measurement of the FUT, it is preferable that the acquisition should be undertaken for several or many (I-SOP, A-SOP) couples and/or different center wavelengths.

FIG. 5C shows in more detail the data acquisition step 4.10 to acquire a kth group of powers. The pre-defined wavelength step of δλ can be used to compute a sequence of wavelengths λs as already discussed in step 4.6. The frequencies $v_L^{(k)}$ and $v_U^{(k)}$ are calculated to satisfy the relation $v_L^{(k)} - v_U^{(k)} = \delta v$ where $\delta v$ is the frequency difference (or when the wavelength difference $\delta \lambda$ is used, it satisfies $\lambda_U^{(k)} - \lambda_L^{(k)} = \delta \lambda$). The maximum measurable PMD, $PMD_{max}$ corresponding to a given step $\delta v$, can be estimated as $PMD_{max} \sim \alpha_{rt}(\pi \delta v)^{-1}$ and $\delta \lambda$ can be extracted from $\delta \lambda = (\lambda_0^2/c) \cdot \delta v$ where $\lambda_0 = (\lambda_{min} + \lambda_{min})/2$. The control unit 30 control (b) of the test module to obtain the kth group of powers as follows:

(1) Set $SOP_k$ by the I-SOP scrambler 14A and A-SOP scrambler 14B (step 4.3.1 of FIG. 5C) if macroscopic SOP step selection is used for either or both of the scramblers (14A,14B), or, if continuous SOP scanning is used for either or both of the scramblers (14A,14B), set a scan time for both or either of input and output SOP scramblers (14A,14B) where the I-SOP and A-SOP may be slowly continuously and randomly scanned to uniformly cover the Poincaré Sphere. It should be noted I-SOP and A-SOP (14A,14B) may be set via either stepwise SOP adjustment or continuous SOP scanning according to the control mode that is selected.

(2) Control the light source 12 or tunable filter 27 to set the lower wavelength to $\lambda_L^{(k)}$ (Step of 4.3.2 of FIG. 5C). Processing means 40 will acquire data of powers as $P_{xL}$ and $P_{yL}$ (step 4.3.3 of FIG. 5C). More details of this data acquisition are shown in FIG. 5D and be described below. The same data acquisition process is repeated to obtain duplicate or repeated powers of $P_{xL}"$ and $P_{yL}"$ (step 4.3.4 of FIG. 5C).

(3) Repeat the same data acquisition for the upper wavelength $\lambda_U^{(k)}$ (where the $\lambda_U^{(k)}$ is also set by the light source 12 or tunable filter 27 while keeping the approximately same input and output SOPs conditions for both I-SOP scrambler 14A and A-SOP scrambler 14B. The processing means 40 then acquires, in addition to the just previously-acquired data of powers $P_{xU}$ and $P_{yU}$, corresponding duplicates $P_{xU}"$ and $P_{yU}"$ (steps 4.3.5, 4.3.6 and 4.3.7 of FIG. 5C). Alternatively, the repeated data may be acquired over a short time period, and then split it as two data that present at different time.

FIG. 5D gives more detail of the data acquisition of step 4.3.3 shown in FIG. 5C for acquisition of $P_{yL}$ and $P_{xL}$ in the kth group of powers. The launched modulated optical pulses from the light source 12 are sent into FUT 18 and the output modulated optical pulses then exit the distal end of FUT 18. The exited modulated optical pulses are then sent into the test analyzer module of the test instrument to be split into two portions traversing respective "routes"—y and x—by either a PBS 20 or 20C or a coupler 21, for example a 3-dB coupler, with one of two output arms being connected with a linear polarizer 20A. The split light optical pulses entering into routes y and x are detected by two photodetectors, for example, two APDs such as 22B and 22C (or 20) (Steps of 4.4.1 and 4.4.2 of FIG. 5D). Alternatively, the exited modulated optical pulses incident into the test analyzer module are directly sent to a linear polarizer. The light pulses are either directly detected by one photodetector, for example, one APD such as 22A (FIG. 1B) or split into two routes—y and x—by a coupler 21, for example a 3-dB coupler, entering into routes y and x are detected by two photodetectors, for example, two APDs such as 22B and 22C (FIG. 1C). The "durations" of the response signals of modulated optical pulses from the distal end of FUT are sampled or sampled and averaged to obtain "response" pulse signals, such as $P_y(t)$ and $P_x(t)$ (Steps of 4.4.3 and 4.4.4 of FIG. 5D). The final sampled or sampled-and-averaged power of $P_{yL}$ or $P_{xL}$ are then obtained by averaging said previously acquired response pulse signals over a substantial portion of its duration about the center of the pulse of impulse response signals, $P_y(t)$ or $P_x(t)$, (Steps 4.4.5 and 4.4.6 of FIG. 5D). The portion of the pulse duration to be averaged usually depends on the electronic pre-filtering.

Once the kth group of powers has been acquired as described above, in Step 4.10 (see FIG. 5B), the data of group k is saved into the data file in Step 4.11. Step 4.12 then increments the group number register.

The data acquisition step 4.10 and group storing step 4.11 will be repeated for different center-wavelengths and/or I-SOPs and A-SOPs selected by the I-SOP scrambler 14A and A-SOP scrambler 14B in accordance with the manual parameter setting step of 4.4 or from auto parameter setting of step 4.5 or default parameter setting until K groups of powers have been acquired and stored in the data file.

Step 4.9 decides whether or not this individual acquisition is completed. If decision step 4.9 gives a positive result and, then in step 4.13 this ith data is saved. Otherwise, the acquisition will process the steps 4.10 and 4.11 again.

The step 4.8 decides whether or not a new individual acquisition is to be initiated. If the entire measurement acquisition is finished, the step 4.15 saves all individual data for the overall entire acquisition. If not, the processor resets k=0 to start a new individual acquisition for steps of 4-9, 4.10, 4.11 and 4.12. Step 4.16 determines whether or not to start another acquisition.

At this stage, the measurement parameters and all groups of powers have been saved in the proper files.

The decision step 4.17 may launch data processor, step 4.18 may load currently available acquired data from data file, step 4.19 may process them to estimate the DGD value at given center wavelength or mean DGD or rms DGD (i.e. PMD) value over a wavelength range for the FUT and step 4.21 may display it. Optionally step 20 may allow the user to save the processed result, such as DGD or mean DGD or RMS DGD values versus time.

Optional decision from step 4.16 then may give the user an opportunity to initiate another acquisition process for the same FUT. If the user decides to do so, the program returns to the parameter setting step 4.3. If not, decision step 4.17 gives the user the option of exiting acquisition, in which case the data stored in the data file will be retained for later processing, or to initiate processing of already acquired and stored data of powers.

If processing is initiated, step 4.18 allows the user to select the data file to be processed in a conventional "open file" dialog box and the data processor 34 accesses the previously saved acquisition data comprising detected powers and associated measurement parameters from the data file, and uses the data to compute DGD or mean DGD or RMS DGD of the FUT.

It should be noted that, by employing the method described hereinbelow, the above steps may be used to obtain one or more of DGD at a given midpoint wavelength, rms-DGD (i.e. PMD) and DGD as function of wavelength, the latter enabling rms DGD or mean DGD to be computed. Such computations may also be included in data processing step 4.19.

Note that, for the case of K=1, i.e. the detected light powers correspond to only one group, i.e. within which the I-SOP, A-SOP, center-wavelength are the same. Nevertheless, one may still be able to roughly evaluate the PMD, although this simple case may not be able to provide a sufficiently accurate and meaningful result, as there will likely be a very significant associated uncertainty.

3.1.2 Method of Operation: Single-Ended Overall PMD Measurement

The method of operation of the tunable OTDR based single-ended PMD measurement illustrated in FIGS. 3F and 3D will now be described with reference to the flowcharts shown in FIGS. 6A, 6B and 6C. In step 5.1, the user first installs the application and inserts the test module in the platform, then starts testing software to cause the system to initialize the test module, specifically initializing the tunable pulsed light source 12, the I/A-SOP controller 14 and the OTDR detection means 22, and the OTDR processing means 40. Then the fiber under test (FUT) 18 would be connected to test module (i.e. instrument) and a patch cord with either a PC connector (such as FC/PC or FC/UPC) or a fiber-pigtailed mirror 50 is connected to the distal end of the FUT. This would create a localized reflection at the end of FUT that is used for the PMD measurement.

Decision step 5.2 prompts the user to select either manual parameter setting or automatic parameter setting. Assuming that the user selects manual parameter setting, the program proceeds to the manual parameter setting step 5.3 and prompts the user as follows:

(a) Set a wavelength range [$\lambda$min, $\lambda$max] for the group center wavelengths that will be encompassed by the tunable pulsed laser source 12;

(b) Set the step or difference $\delta v$ (or $\delta\lambda$) between the pairs closely-spaced optical frequencies $v_U$ and $v_L$ (or wavelengths). Alternately, the user may enter the anticipated PMD value for the FUT and leave the processor 34 to select the wavelength step. As an example, the step can be conveniently set to $\delta v = \alpha_{\delta v} \cdot PMD^{-1}$ where $\alpha_{\delta v} \sim 0.1$ to 0.15 and, thus, $\delta\lambda$ can be extracted from $\delta\lambda \approx (c/v_c^2) \cdot \delta v$ where $v_c = (v_U + v_L)/2$. (Note: there is an optimal step for a given PMD value, as large as possible so as to maximize signal-to-noise ratio, but small enough to satisfy the above condition, i.e., PMD·$\delta v \langle 0.1$ to 0.15.);

(c) Set the number K of center-wavelengths and/or states of polarization selected by the VA-SOP controller 14, i.e., the number (K) of groups of data to be acquired. For example, K may be set to 200;

(d) Set the averaging time $\Delta t$ of each individual power (for example, $\Delta t$=0.05 or 0.10 second), or set the number of durations of pulses reflected from the distal end of the FUT to be averaged to obtain each individual power (for example 50 or 100). Note that once the averaging time $\Delta t$ and the number K of center-wavelengths and/or states of polarization have been set. a total acquisition time for PMD measurement may be established;

(e) Select the pulse duration Tp (e.g. 275, 1000, 2500, 5000, 10000, 20000 ns) or, equivalently, the pulse length for OTDR. In order for the pulse reflected from the selected reflection not to be superposed in time with some portion of a pulse reflected from another reflection, the pulse length, $L_p$, shall be selected such that $L_p \langle \Delta z$, where $\Delta z$ is the distance along the FUT between the selected reflection and the nearest of anyone or all other reflections. Typically, a long pulse length is selected for the single-ended PMD measurement because it has advantages of leading to high dynamic range, and/or a high signal to noise ratio, and/or a short averaging time (thereby a short overall acquisition time) although a short pulse may still be used;

(f) Set the FUT length, normally the full effective optical length of the FUT;

(g) Optionally, select a high dynamic range or a low dynamic range according to the optical-fiber length. Typically, in a normal operation the test module prompts the user to select a high dynamic range, but it may also allow the user to test a very short fiber by choosing a low dynamic range for acquisition. With the low dynamic range mode, the output peak power of the launched OTDR pulses is reduced, either by inserting an optical attenuator in the optical path, for example, at a location just before the output of the test module, or electrically, for example, by decreasing the bias current of the gain medium of the tunable pulsed laser;

(h) Optionally, enter the cable or fiber name and/or related relevant information;

(i) Save all measurement parameters to a data file that will be retrieved for data processing by the data processor 34.

If, in decision step 5.2, the user selects automatic parameter setting, the program starts the auto parameter setting procedure in step 5.4 and carries out the following steps:

(a) Select pre-defined certain default measurement parameters, namely (6) The center wavelength range [$\lambda$min, $\lambda$max] that will be covered by the tunable pulsed laser source 12;

(7) Number K of (I-SOP, A-SOP) couples and/or center wavelengths to be set by the I/A-SOP controller 14 (for example, 200) for a real single-ended PMD data acquisition;

(8) Averaging time $\Delta t$ (for example, $\Delta t$=0.05 or 0.1 second) or the number of duration of pulse reflected from the distal end of the FUT to be averaged (for example 50 or 100) for each individual power; and (9) Pulse duration Tp (or length) for OTDR.

It is noted that these default parameters set in (1), (3) and (4) will also be used for pre-scan acquisition.

(b) The test module will conduct a pre-scan acquisition using a reduced number of groups, such as K=50, to obtain estimations of the FUT length, of total loss from FUT and of optimal wavelength step frequency difference $\delta v$ (or $\delta\lambda$) between the two closely-spaced optical frequencies $v_U$ and $v_L$ (or wavelengths $\lambda_U$ and $\lambda_L$). The OTDR will launch a standard OTDR pulse (e. g, 1 or 10 µs) to detect the end of the fiber (or a user defined localized reflection) so that the FUT length can be obtained and the pulse repetition period (Tr) can also be deduced according to the round-trip time through the length of the fiber. From this OTDR acquisition, a loss of FUT may also be estimated, otherwise, a saturation situation on photodetectors may be observed if there is any. Then a decision can automatically be made on whether or not to reduce the output peak power for the OTDR light pulses. Pre-scan data acquisition is performed to find the appropriate step or difference $\delta v$ (frequency) or $\delta\lambda$ (wavelength) between the two closely-spaced optical frequencies $v_U$ and $v_L$ (or $\lambda_U$ and $\lambda_L$). For example, such data acquisition may be carried out by using, for each group, four different laser wavelengths to obtain a total combination of six different frequency or wavelength steps. The optimally appropriate wavelength step to be used in the actual single-ended PMD measurement data acquisition may be found by processing of these pre-scan acquisition data of powers. To save all automatically-selected measurement parameters to the header of the data file that will be retrieved for data processing by the data processor 34.

(c) Auto mode may also be designed to automatically produce cable or fiber name and/or any other relevant information.

Once the measurement parameters have been entered, whether manually or automatically, the program proceeds to step 5.5 and computes wavelength step $\delta\lambda$ (or frequency difference $\delta v$) if the anticipated total PMD of the FUT has been specified or estimated via the aforementioned auto-setting procedure, the repetition period $T_r$ according to the round-trip time through the length of the fiber, and the appropriate sequence of wavelengths λs based on the parameter settings.

Finally, all the measurement parameters, whether directly specified or computed as described above, are stored in the header of the data file (Step 5.6).

It should be noted that the linewidth of the tunable pulsed light source will usually be set, in the factory, to a relatively small value (e.g. ⟨ 4 GHz) in order to ensure the ability to measure a high PMD of the FUT.

With the group number register initialized to k=0, decision step 5.7 determines whether the total number of groups of powers have been acquired. If not, the program proceeds to step 5.8 to acquire the kth group of powers.

It should be noted that, conveniently, at each SOP and/or center wavelength, the frequency difference $\delta v$ (or wavelength step $\delta \lambda$) between the two closely-spaced optical frequencies $v_U$ and $v_L$ (wavelengths $\lambda_U$ and $\lambda_L$) may remain the same or similar. Each SOP and/or wavelength may only be set in a short time period.

It should be also noted, that it is preferable to acquire data for several or many SOP couples and different midpoint wavelengths, in order to determine the overall PMD.

FIG. 6B provides more detail of the data acquisition step 5.8 to acquire a kth group of powers. The pre-defined wavelength step of $\delta\lambda$ can be used to compute a sequence of wavelengths as already discussed in step 4.5. The frequencies $v_L^{(k)}$ and $v_U^{(k)}$ are calculated to satisfy $v_L^{(k)} - v_U^{(k)} = \delta v$ where $\delta v$ is the frequency difference (or when the wavelength difference $\delta\lambda$ is used, it satisfies $\lambda_U^{(k)} - \lambda_L^{(k)} = \delta\lambda$). The maximum measurable PMD, $PMD_{max}$, corresponding to a given step $\delta v$, can be estimated as $PMD_{max} \sim \alpha_{rt} (\pi \delta v)^{-1}$ and $\delta\lambda$ can be extracted from $\delta\lambda \approx (\lambda_0^2/c)\cdot\delta v$ where $\lambda_0 = (\lambda_{min} + \lambda_{max})/2$. The control unit 30 controls the test module to obtain the kth group of powers as follows:

Set $SOP_k$ using the VA-SOP controller (Step of 5.3.1 of FIG. 6B).

Control the tunable pulsed laser 12 to set the lower wavelength to $\lambda_L^{(k)}$ (Step of 5.3.2 of FIG. 6B). Detection and processing unit 36 will acquire data of powers as $P_{xL}$ and $P_{yL}$ (Step of 5.3.3 of FIG. 6B). More details of this data acquisition are shown in FIG. 6C, which will be described below. The same data acquisition process is repeated to obtain duplicate or repeated powers of $P_{xL}"$ and $P_{yL}"$ (Step of 5.3.4 of FIG. 6B).

Repeat the same data acquisition for the upper wavelength $\lambda_U^{(k)}$ (where the $\lambda_U^{(k)}$ is also set by the tunable pulsed laser 12) while keeping the same (I-SOP, A-SOP) couple. The processing means 40 then acquiring data of powers $P_{xU}$ and $P_{yU}$ and duplicates $P_{xU}"$ and $P_{yU}"$ (Steps of 5.3.5, 5.3.6 and 5.3.7 of FIG. 6B).

FIG. 6C gives more detail of the data acquisition of step 5.3.3 shown in FIG. 6B for acquiring of $P_{yL}$ and $P_{xL}$ in the kth group of powers. The launched light pulses from the OTDR are sent into FUT and some fraction of the pulsed light is reflected from the localized reflector, such as a PC connector of the patchcord or a fiber-pigtailed mirror connected at the end of FUT. The reflected light pulses are then returned into the test module or instrument to be split into portions respectively traversing two routes—y and x—by either a PBS or a coupler, for example a 3-dB coupler, with one of two output arms being connected with a linear polarizer. The split light pulses entering into routes y and x are detected by two photodetectors, for example, two APDs such as 22'B and 22'C (Steps of 5.4.1 and 5.4.2 of FIG. 6C). The "durations" of the response signals from the light pulses reflected by the distal end of FUT or at any other locations along fiber are sampled and averaged to obtain "averaged" mean response pulse signals, such as $P_y(t)$ and $P_x(t)$ (steps 5.4.3 and 5.4.4 of FIG. 6C). The final averaged powers of $P_{yL}$ or $P_{xL}$ are then obtained by averaging said previously sampled and averaged mean response pulse signals over a substantial portion of its duration about the center of the pulse of impulse response signals, Py(t) or Px(t) (steps 5.4.5 and 5.4.6 of FIG. 6C). The portion of the pulse duration to be averaged usually depends on the electronic pre-filtering.

Once the kth group of powers has been acquired as described above, in Step 5.9 (see FIG. 6A), the data of group k is saved into the data file. Step 5.10 then increments the group number register.

The data acquisition step 5.8 and group storing step 5.9 will be repeated for different center-wavelengths and/or (I-SOP, A-SOP) couples selected by the I/A-SOP controller 14 in accordance with the manual parameter setting step of 5.3 or from auto parameter setting of step 5.4 until K groups of powers have been acquired and stored in the data file.

At this stage, the measurement parameters and all groups of powers have been saved in the same data file associated with the header information of measurement parameters.

During the data acquisition the step 5.20 (optionally) may load any currently available acquired data from data file and process them to estimate the RMS DGD (i.e. PMD) value for the FUT 18 and step 5.21 may display it as well as elapsed time of the acquisition, length and loss of the FUT. Note the estimated PMD value may frequently be varied until the end of the data acquisition. Optionally step 5.22 may allow the user to save the processed result.

Also at this stage, decision step 5.7 gives a positive result and, in step 5.11, the program saves and closes the data file in step 5.11.

Optional decision from step 5.12 then may give the user an opportunity to initiate the acquisition of another K groups of powers for the same FUT. If the user decides to do so, the program returns to the parameter setting step 5.2. If not, decision step 5.13 gives the user the option of exiting acquisition, in which case the data stored in the data file will be retained for later processing, or to initiate processing of already acquired and stored data of powers.

If processing is initiated, step 5.14 allows the user to select the data file to be processed in a conventional "open file" dialog box, whereupon, in step 5.16, the data processor 34 accesses the pre-saved acquisition data of powers and associated measurement parameters from the data file, and uses the data to compute total rms-DGD (i.e., PMD) of the FUT. On the other hand, box 5.15, which is not a "step" as such, indicates that the user may launch the data processing software independently at any time to process any previously acquired data file. In step 5.17, the data processor 34 saves the result of computed PMD value and measurement parameters in a file and in step 5.18 displays or otherwise outputs the measured PMD value with possible other results such as length and loss of the FUT.

Note that, for the case of K=1, i.e. the powers of light backreflection may be obtained in a similar manner for only one group having both the same (I-SOP, A-SOP) couple and same center-wavelength, one may also be able to roughly evaluate the PMD although this simple case may not be able to provide a sufficiently accurate result, as there may be a significant uncertainty on the measured result.

The manner in which the data processing step 5.16 processes the stored data will be described in the sections below.

It should note the above step may obtain rms DGD (i.e. PMD), but it can also obtain DGD as function of optical frequency (wavelength) and then rms DGD or mean DGD may be computed using the method described hereinbelow that may also be included in data processing step 5.16.

3.1.3 Method of Operation: Single-Ended Cumulative PMD Measurement

The method of operation of the POTDR illustrated in FIG. 4 for measuring cumulative PMD as function of FUT length will now be described with reference to the flowchart shown in FIGS. 7A and 7B. In step 6.1, the user causes the system to initialize the POTDR, specifically initializing the tunable pulsed light source 12, the I/A-SOP controller 14 and the OTDR detection and processing section. Decision step 6.2 prompts the user to select either manual parameter setting or automatic parameter setting. Assuming that the user selects manual parameter setting, the program proceeds to the manual parameter setting step 6.3 and prompts the user as follows:

(a) Set the wavelength range [λmin, λmax] of the group center wavelengths that will be covered by the tunable pulsed laser source 12.

(b) Set the step or difference δν (or δλ) between the pairs of closely-spaced optical frequencies $v_U$ and $v_L$ (or wavelengths). Alternatively, the user may enter the anticipated total PMD value of the FUT and leave the processor to select the wavelength step. As an example, the step can be conveniently set to $\delta v = \alpha_{\delta v} \cdot PMD^{-1}$ where $\alpha_{\delta v} \sim 0.1$ to 0.15. It should be noted that the POTDR may be configured to allow the user to select a number M of steps larger than one; the control program will then select M steps based on the anticipated total PMD of the FUT, with appropriate ratios between the steps (note: there is an optimal step for a given PMD value, as large as possible so as to maximize signal-to-noise ratio, but small enough to satisfy the above condition, i.e., $PMD \cdot \delta v \langle 0.1$ to 0.15. But the apparatus here described must perform the challenging task of measuring simultaneously a large range of cumulative PMD values as a function of z, from PMD=0, at z=0, to PMD=Total PMD of the FUT, at z=FUT length. This is the reason why a few measurements with different steps in order to measure all different "sections" of the FUT with similar relative (e.g. in %) accuracy is desirable, or alternatively as mentioned hereinabove, use more than two closely-spaced wavelengths per group, a number $N_\lambda$ of wavelengths per group leading to a theoretical number of $M = N_\lambda \cdot (N_\lambda - 1)/2$ pairs with different steps in each scan, so as to save time).

(c) Set the number (K) of center-wavelengths and/or (I-SOP, A-SOP) couples selected by the I/A-SOP controller 14, i.e., the number (K) of groups of traces to be acquired.

(d) Set the averaging time Δt of each individual trace (for example, Δt=1 or 2 seconds), or set the number electrical impulse response signals to be averaged to obtain each individual trace (for example 1250 or 2500).

(e) Set the pulse duration (e.g. Tp=10, 30, 50, 100, 200, 300, 500 ns).

(f) Specify the FUT length, normally the full effective optical length of the FUT.

If, in decision step 6.2, the user selects automatic parameter setting, the program proceeds to step 6.4 and carries out the following steps:

Select certain default measurement parameters, namely (1) center wavelength range [λmin, λmax] that will be covered by the tunable pulsed laser source 12, typically the whole wavelength range that the actual tunable laser can access;

(2) number K of (I-SOP, A-SOP) couples and/or center wavelengths to be set by the I/A-SOP controller 14, for example, 100 or 200, for final POTDR data acquisition;

(3) averaging time Δt (for example, Δt=1 or 2 seconds) or number of electrical impulse response signals to be averaged (for example 1250 or 2500) for each individual OTDR trace;

(4) pulse duration (e.g., Tp=10, 30, 50, 100, 200, 300, 500 ns); and (5) linewidth of tunable pulsed laser (optional).

It is noted that these default parameters set in (1), (3), (4) and (5) will also be used for pre-scan acquisition.

The POTDR conducts a pre-scan using a reduced number of groups, such as K=20, to obtain rough estimates of the FUT length and the optimal wavelength step δλ (or frequency difference δν) between the two closely-spaced optical frequencies $v_U$ and $v_L$ (or $\lambda_U$ and $\lambda_L$). Thus, the OTDR will launch a standard OTDR pulse (e.g. 1 μs) to detect the end of the fiber so that the FUT length can be obtained and the pulse repetition period deduced according to the round-trip time through the length of the fiber. Acquisition of OTDR traces then will be performed to find the best suited step or difference δν (or δλ) between the two closely-spaced optical frequencies $v_U$ and $v_L$ (or $\lambda_U$ and $\lambda_L$) via a fast estimate of the overall PMD of the FUT. For example, such acquisition may be carried out by using, for each group, four different laser wavelengths ($N_\lambda = 4$) to obtain a total combination of six different wavelength steps (M=6). The best suited wavelength step to be used in the actual POTDR data acquisition may be found by processing of these pre-scan data.

Once the measurement parameters have been entered, whether manually or automatically, the program proceeds to step 6.5 and computes wavelength step δλ (or frequency difference δν) if the anticipated total PMD of the FUT has been specified or estimated via the aforementioned auto-setting procedure, the repetition period $T_r$ according to the round-trip time through the length of the fiber, and the appropriate sequence of wavelengths based on the parameter settings.

Finally, all the measurement parameters, whether directly specified or computed as described above, are stored in the header of the data file (Step 6.6).

FIG. 7A shows an optional step (following step 6.5) for setting the laser linewidth, if allowed by the laser light source 12, according to the previously-entered parameters. For example, a small (large) linewidth may be chosen to measure large (small) total PMD. In the case where the total PMD is not specified and no auto-setting procedure has been carried out, the specified wavelength step (δλ) may be used to estimate the total PMD and then the laser linewidth may also be selected accordingly.

With the group number register initialized to k=0, decision step 6.7 determines whether the total number of groups of traces have been acquired; if not, the program proceeds to step 6.8 to acquire the group k of OTDR traces.

FIG. 7B shows in more detail the trace acquisition step 6.8 to acquire a kth group of OTDR traces. As described previously, there is at least one pre-defined frequency difference δν (i.e. wavelength step δλ) between the two closely-spaced optical frequencies $v_U$ and $v_L$ (i.e. wavelengths), and hence the number of total selected laser wavelengths must be at least two. If a plurality of different wavelength steps δλ are used, then these wavelength steps may be selected to optimally measure different ranges of PMD values. For example, one may choose to have two wavelength steps, $\delta\lambda_1$ and $\delta\lambda_2$, which requires $N_\lambda=3$ different wavelengths per group. Furthermore, a judicious choice of the ratio of said two steps may be, for example, $\delta\lambda_1/\delta\lambda_2=5$. The maximum measurable PMD, $PMD_{max}$ corresponding to a given step $\delta v$ can be estimated as $PMD_{max} \sim \alpha_{rt}(\pi\delta v)^{-1}$, and $\delta\lambda$ can be extracted from $\delta\lambda=(\lambda_0^2/c)\cdot\delta v$, where $\lambda_0=(\lambda_{min}+\lambda_{max})/2$. The control unit 30 controls the POTDR to obtain the kth group of traces as follows:

Set couple (I-SOP$_k$, A-SOP$_k$) by means of the I/A-SOP controller 14 (step 6.8.1 of FIG. 7B).

Control the tunable pulsed laser 12 to set wavelength to $\lambda_L^{(k)}$ (step 6.8.2 of FIG. 7B) and then launch OTDR light pulses. Detection and processing unit 36 acquires OTDR traces Px$_L$ and Py$_L$ (step 6.8.3 of FIG. 7B). The same data acquisition process is repeated to obtain duplicate or repeated traces Px$_L$" and Py$_L$" (step 6.8.4 of FIG. 7B).

Repeat the same data acquisition for the upper wavelength $\lambda_U^{(k)}$ while keeping the same (I-SOP$_k$, A-SOP$_k$) couple. The detection and processing unit 36 then acquires OTDR traces Px$_U$, Py$_U$ and duplicates Px$_U$", Py$_U$" (steps 6.8.9 and 6.8.10 of FIG. 7B).

Where the group comprises more than one pair of series of light pulses, to set the wavelength to at least one additional wavelength $\lambda_I^{(k)}$ intermediate the lower and upper wavelengths (step 6.8.5 of FIG. 7B). The processing means 40 acquires OTDR traces Px$_I$ and Py$_I$ (step 6.8.6 of FIG. 7B). The same data acquisition procedure is repeated to obtain the repeated traces Px$_I$" and Py$_I$" (step 6.8.7 of FIG. 7B).

Once the kth group of OTDR traces have been acquired as described above, in step 6.9 (see FIG. 7A) the group is saved into the data file. Step 6.10 then increments the group number register.

The data acquisition step 6.8 and group storing step 6.9 will be repeated for different center-wavelengths and/or (I-SOP$_k$, A-SOP$_k$) selected by the I/A-SOP controller 14 in accordance with the parameter setting step 6.2 or 6.3 until K groups of traces have been acquired and stored in the data file.

At this stage, the measurement parameters and all groups of OTDR traces will have been saved in the same data file.

Also at this stage, decision step 6.7 gives a positive result and, in step 6.11, the program closes the data file. Optional decision step 6.12 then gives the user an opportunity to initiate the acquisition of another K groups of traces for the same FUT. If the user decides to do so, the program returns to the parameter setting step 6.2. If not, decision step 6.13 gives the user the option of exiting, in which case the data stored in the data file will be retained for later processing, or initiating processing of already acquired and stored data.

If processing is initiated, step 6.14 allows the user to select the data file to be processed in a conventional "open file" dialog box, whereupon, in step 6.16, the data processor 32 accesses the pre-saved acquisition data and associated measurement parameters from the data file, and uses the data to compute cumulative PMD as a function of distance (z) along the FUT. On the other hand, box 6.15, which is not a "step" as such, indicates that the user may launch the data processing software independently at any time, even if no acquisition was just completed, to process any previously acquired data file. In step 6.17, the data processor 32 saves the results (e.g. the cumulative PMD curve as a function of z and measurement parameters in a file retrievable via spreadsheet software) and in step 6.18 displays or otherwise outputs the resulting cumulative PMD curve in a tangible form.

The manner in which the data processing step 6.16 processes the stored data will be described in the sections below.

It should note the above steps may obtain rms DGD (i.e. PMD), but it can also obtain DGD as function of wavelength and then rms DGD or mean DGD may be computed as the method described in below sections that may also be included in data processing step 6.16.

It should emphasized that it is preferable that the data be acquired for several or many SOPs and for different midpoint wavelengths.

3.2 Data Processing and Computation: Two-Ended Measurement

3.2.1 Embodiment (1)

Data Processing and Computation for Non-Polarization-Diverse Measurement

The manner in which the data processing step 6.19 processes the stored data will now be described.

3.2.1.1 The Data Structure

Each measured light power from the FUT, obtained with one given setting of the wavelength and of the input and analyzer SOP controllers as described in the Method of Operation for the two-ended PMD measurement, constitutes an elementary data cell, i.e. one datum consists of one power value. The next data unit is one group of four powers (i.e. four data cells), two sets of four powers for the implementations of FIG. 1D and FIG. 1F where two powers are obtained simultaneously from photodetectors 22B and 22C, all obtained with given input and output SOPs as set by I-SOP scrambler 14A and A-SOP scrambler 14B. The two sets of four powers forming group k preferably have been obtained in the following sequence (time flowing from left to right) or other similar means, such as of two repeated powers being measured at the same time but with different detectors (such as simultaneously measuring the same power by two detectors and a coupler), as:

I-SOP$_k^I$, A-SOP$_k^O$ and/or $\lambda_k$:

| $\lambda = \lambda_L^{(k)}$ | | $\lambda = \lambda_L^{(k)}$ | |
|---|---|---|---|
| $Px_L^{(k)}$ | $Px_L''^{(k)}$ | $Px_U^{(k)}$ | $Px_U''^{(k)}$ |
| $Py_L^{(k)}$ | $Py_L''^{(k)}$ | $Py_U^{(k)}$ | $Py_U''^{(k)}$ | where the labels x and y refer to the power obtained simultaneously or at slightly different time from photodetectors 22B and 22C, respectively, $\lambda_U^{(k)}-\lambda_L^{(k)}$ is equal to the step $\delta\lambda$, the midpoint wavelength is defined as $\lambda_k=(\lambda_U^{(k)}+\lambda_L^{(k)})/2$, and the double prime denotes repeated powers.

Finally, the overall data stored in the data file after acquisition is depicted as a matrix in Eq. (3.1) below, to which we will refer in all that follows. The matrix comprises K groups each of four powers of light (two sets of four when two photodetectors are used):

$$\text{Data} = \begin{array}{c|c|c|c|c|} & \lambda = \lambda_L^{(k)} & & \lambda = \lambda_U^{(k)} & \\ \hline SOP_0^I, SOP_0^O \text{ and/or } \lambda_0 \rightarrow & Px_L^{(0)} & Px''_L^{(0)} & Px_U^{(0)} & Px''_U^{(0)} \\ \hline & Py_L^{(0)} & Py''_L^{(0)} & Py_U^{(0)} & Py''_U^{(0)} \\ \hline SOP_1^I, SOP_1^O \text{ and/or } \lambda_1 \rightarrow & Px_L^{(1)} & Px''_L^{(1)} & Px_U^{(1)} & Px''_U^{(1)} \\ \hline & Py_L^{(1)} & Py''_L^{(1)} & Py_U^{(1)} & Py''_U^{(1)} \\ \hline \vdots & \vdots & \vdots & \vdots & \vdots \\ \hline SOP_k^I, SOP_1^O \text{ and/or } \lambda_k \rightarrow & Px_L^{(k)} & Px''_L^{(k)} & Px_U^{(k)} & Px''_U^{(k)} \\ \hline & Py_L^{(k)} & Py''_L^{(k)} & Py_U^{(k)} & Py''_U^{(k)} \\ \hline \vdots & \vdots & \vdots & \vdots & \vdots \\ \hline SOP_{K-1}^I, SOP_{K-1}^O \text{ and/or } \lambda_{K-1} \rightarrow & Px_L^{(K-1)} & Px''_L^{(K-1)} & Px_U^{(K-1)} & Px''_U^{(K-1)} \\ \hline & Py_L^{(K-1)} & Py''_L^{(K-1)} & Py_U^{(K-1)} & Py''_U^{(K-1)} \\ \hline \end{array} \quad (3.1)$$

The input and output SOPs can each be selected randomly ("macroscopic SOP step") from one to another or undergo slow continuous SOP scanning, in both cases in such a way that, over time, each substantially uniformly covers the Poincaré Sphere.

3.2.1.2 Auto Calibration of the Relative Gain

For the PBS-based implementation of FIG. 1F, it is necessary to perform a calibration procedure described hereinafter of the relative gain of the two detectors 22B and 22C before proceeding with any further computation. The same procedure is not performed for the other embodiments, e.g. if there is only one detector.

3.2.1.3 Computation

The powers are processed to obtain the PMD value as will now be described. It should be note that, in all that follows, the symbols refer to the matrix "Data" in equation (17). The labels x and y refer to the backreflected light powers obtained from photodetectors 22B and 22C, respectively.

3.2.1.4 The Normalized Powers

The normalized powers, labelled hereinafter as T, are computed differently according to the implementation of the embodiment.
(i) For the implementation of FIG. 1F (two photodetectors with a PBS), the transmissions (normalized power) are computed as follows either $$T_L^{(k)} = \frac{Px_L^{(k)}}{Px_L^{(k)} + Py_L^{(k)}} \quad T''_L^{(k)} = \frac{Px''_L^{(k)}}{Px''_L^{(k)} + Py''_L^{(k)}} \quad (3.2a)$$

$$T_U^{(k)} = \frac{Px_U^{(k)}}{Px_U^{(k)} + Py_U^{(k)}} \quad T''_U^{(k)} = \frac{Px''_U^{(k)}}{Px''_U^{(k)} + Py''_U^{(k)}}$$

or $$T_L^{(k)} = \frac{1}{2} \cdot \frac{Px_L^{(k)} - Py_L^{(k)}}{Px_L^{(k)} + Py_L^{(k)}} \quad T''_L^{(k)} = \frac{1}{2} \cdot \frac{Px''_L^{(k)} - Py''_L^{(k)}}{Px''_L^{(k)} + Py''_L^{(k)}} \quad (3.2b)$$

$$T_U^{(k)} = \frac{1}{2} \cdot \frac{Px_U^{(k)} - Py_U^{(k)}}{Px_U^{(k)} + Py_U^{(k)}} \quad T''_U^{(k)} = \frac{1}{2} \cdot \frac{Px''_U^{(k)} - Py''_U^{(k)}}{Px''_U^{(k)} + Py''_U^{(k)}}$$

where it should be appreciated that the different Py powers have been pre-multiplied by the measured relative gain, $g_{Forward}$, as indicated in the description of the auto-calibration procedure, before they are used in equations (3.2a) and (3.2b).
(ii) For the implementation of FIG. 1D (two photodetectors with a coupler), the ratio of trace Px over trace Py is first computed as, $$R_L^{(k)} = \frac{Px_L^{(k)}}{Py_L^{(k)}} \quad R''_L^{(k)} = \frac{Px''_L^{(k)}}{Py''_L^{(k)}} \quad (3.2c)$$

$$R_U^{(k)} = \frac{Px_U^{(k)}}{Py_U^{(k)}} \quad R''_U^{(k)} = \frac{Px''_U^{(k)}}{Py''_U^{(k)}}$$

and then the above ratio is normalized with respect to its average over the K groups as, $$T_L^{(k)} = u_o \frac{R_L^{(k)}}{\langle R_L \rangle_{SOP}} \quad T''_L^{(k)} = u_o \frac{R''_L^{(k)}}{\langle R_L \rangle_{SOP}} \quad (3.2d)$$

$$T_U^{(k)} = u_o \frac{R_U^{(k)}}{\langle R_U \rangle_{SOP}} \quad T''_U^{(k)} = u_o \frac{R''_U^{(k)}}{\langle R_U \rangle_{SOP}}$$

where the reference mean-value is $u_o = \frac{1}{2}$ and the average ratio R is defined as, $$\langle R_L \rangle_{SOP} = \frac{1}{2K} \sum_k \left( R_L^{(k)} + R''_L^{(k)} \right) \quad (3.2e)$$

$$\langle R_U \rangle_{SOP} = \frac{1}{2K} \sum_k \left( R_U^{(k)} + R''_U^{(k)} \right)$$

or, when changes of the coupler ratio as a function of wavelength are negligible within a prescribed wavelength range, then $\langle R_L \rangle_{SOP}$ and $\langle R_U \rangle_{SOP}$ can be replaced by:

$$\langle R \rangle_{SOP,v} = \frac{1}{4K} \sum_k \left( R_L^{(k)} + R''_L^{(k)} + R_U^{(k)} + R''_U^{(k)} \right) \quad (3.2f)$$

Here, the auto-calibration procedure is not required, i.e. the above-mentioned pre-multiplication of the powers Py by the measured relative gain may be skipped.

(iii) For the embodiment of FIG. 1B (single photodetector), the only available powers are the Px powers (obtained in this case from photodetector 22A). The normalized power is obtained as in (3.2d) but without computing the ratio of power x over power y first, i.e.

$$T_L^{(k)} = u_o \frac{Px_L^{(k)}}{\langle P_L \rangle_{SOP}} \quad T''_L^{(k)} = u_o \frac{Px''_L^{(k)}}{\langle P_L \rangle_{SOP}} \quad (3.2g)$$

$$T_U^{(k)} = u_o \frac{Px_U^{(k)}}{\langle P_U \rangle_{SOP}} \quad T''_U^{(k)} = u_o \frac{Px''_U^{(k)}}{\langle P_U \rangle_{SOP}}$$

where the average power is defined as, $$\langle P_L \rangle_{SOP} = \frac{1}{2K} \sum_k \left( Px_L^{(k)} + Px''_L^{(k)} \right) \quad (3.2h)$$

$$\langle P_U \rangle_{SOP} = \frac{1}{2K} \sum_k \left( Px_U^{(k)} + Px''_U^{(k)} \right).$$

Here, the detected power is assumed to be roughly constant during the time period for measurement of the initial and repeated powers.

(iv) For the embodiment of FIG. 1C with two photodetectors combined with a coupler after the polarizer 20A (serving as an analyzer), two powers of the Px and Px" powers are obtained from photodetectors 22B and 22C, respectively. The normalized powers are now obtained as, $$T_L^{(k)} = u_o \frac{Px_L^{(k)}}{\langle Px_L \rangle_{SOP}} \quad T''_L^{(k)} = u_o \frac{Px''_L^{(k)}}{\langle Px''_L \rangle_{SOP}} \quad (3.2i)$$

$$T_U^{(k)} = u_o \frac{Px_U^{(k)}}{\langle Px_U \rangle_{SOP}} \quad T''_U^{(k)} = u_o \frac{Px''_U^{(k)}}{\langle Px''_U \rangle_{SOP}}$$

where the average power is defined as, $$\langle Px_L \rangle_{SOP} = \frac{1}{K} \sum_k Px_L^{(k)} \quad \langle Px''_L \rangle_{SOP} = \frac{1}{K} \sum_k Px''_L^{(k)} \quad (3.2j)$$

$$\langle Px_U \rangle_{SOP} = \frac{1}{K} \sum_k Px_U^{(k)} \quad \langle Px''_U \rangle_{SOP} = \frac{1}{K} \sum_k Px''_U^{(k)}$$

Here the auto-calibration procedure is also not required. Note that this embodiment has the advantage of only requiring approximately half the acquisition time of other embodiments.

Note for the normalization procedure described in (iii) and (iv) above, the light power exiting FUT 18 during measurement must be stable. Also, if the power is constant for all wavelengths within a prescribed wavelength range, $\langle \, \rangle_{SOP}$ can be averaged over either SOP or wavelength, or both SOP and wavelength.

Fundamentally all of these relationships are valid in all cases if sufficiently random input and output SOP scrambling is applied, giving the correct value of the DGD at one particular midpoint wavelength, and then it is possible to obtain DGD against midpoint wavelength. Therefore, one can also compute a mean DGD or rms DGD value for a given wavelength range.

It should be appreciated that scanning the midpoint wavelength serves the purpose of averaging DGD over wavelength as per the definition of the statistical PMD value so as to obtain a rms DGD value (not a mean DGD). On the contrary, as discussed earlier, averaging only over wavelength while keeping the input and analyzer SOPs unchanged requires that assumptions about the FUT be met, and also requires a large value of the product PMD·Δν. The same remarks apply for the equations presented hereinafter.

3.2.1.4.1 Noise Variance

The second motivation for sampling repeated traces, which are substantially identical in the absence of noise for each setting of SOP and midpoint wavelength $\lambda_{mid}$, is the ability to obtain an accurate estimate of the variance noise from variations of light polarization and/or laser frequency and/or power (intensity). If this noise variance is known, it may be subtracted. Thanks to the repeated traces, the variance from polarization noise and/or laser frequency and/or power noise and/or any other noises etc. can be estimated independently as follows:

$$\sigma(\nu)_{noise}^2 = \left(\frac{1}{\sigma_{20}}\right)^2 \langle (T_L(\nu) - T''_L(\nu))(T_U(\nu) - T''_U(\nu)) \rangle_{SOP} \quad (3.3a)$$

which is particularly appropriate for determining a DGD estimate at a given wavelength; and $$\sigma_{noise}^2 = \left(\frac{1}{\sigma_{20}}\right)^2 \langle (T_L - T''_L)(T_U - T''_U) \rangle_{SOP;\nu} \quad (3.3b)$$

which is particularly appropriate for determining a PMD estimate, and where, for both cases, $\sigma_{20}^2 = 1/12$.

It should be noted that this "noise variance" could arise from a randomly varied input and output SOP (such as might be induced by a swaying aerial cable, for instance), and/or an instability of laser frequency and intensity, or any other noise sources.

In order to obtain a reliable measurement result, the variance noise, e.g. from polarization variation and similar other effects, such as instability of laser frequency and intensity, should be less than few percent (e.g. of ⟨ 2%) compared to the mean-square difference.

3.2.1.4.2 Relative Variance

The relative variance, for example mainly due to unpolarized ASE light from optical amplifiers in the test link (or any other depolarizing effects), as used in equations (2.8) and (2.9), is computed here as the average of the two available estimates, i.e., $$\sigma'^2_r(\nu) = \left(\frac{1}{\sigma_{20}}\right)^2 \left[\frac{\delta(T_L(\nu)) + \delta(T_U(\nu))}{2}\right] \quad (3.4a)$$

$$\sigma'^2_r = \left(\frac{1}{\sigma_{20}}\right)^2 \left[\frac{\delta(T_L) + \delta(T_U)}{2}\right] \quad (3.4b)$$

where $\sigma_{20}^2 = 1/12$, and the function "δ" is defined as, $$\delta(T_L(\nu)) = \lfloor \langle T_L(\nu) T''_L(\nu) \rangle_{SOP} - \langle T_L(\nu) \rangle_{SOP}^2 \rfloor$$

$$\delta(T_U(\nu)) = \lfloor \langle T_U(\nu) T''_U(\nu) \rangle_{SOP} - \langle T_U(\nu) \rangle_{SOP}^2 \rfloor$$

$$\delta(T_L) = \lfloor \langle T_L T''_L \rangle_{SOP;\nu} - \langle T_L \rangle_{SOP;\nu}^2 \rfloor$$

$$\delta(T_U) = \lfloor \langle T_U T''_U \rangle_{SOP;\nu} - \langle T_U \rangle_{SOP;\nu}^2 \rfloor.$$

Alternatively, the relative variance can also be computed via polarization component $s_p$, for example, $$\sigma_r'^2(v) = \left(\frac{1}{\sigma_{s0}}\right)^2 \left[\frac{\langle s_{PL}(v)s_{PL}''(v)\rangle_{SOP} + \langle s_{PU}(v)s_{PU}''(v)\rangle_{SOP}}{2}\right] \quad (3.4c)$$

$$\sigma_r'^2 = \left(\frac{1}{\sigma_{s0}}\right)^2 \left[\frac{\langle s_{PL}s_{PL}''\rangle_{SOP;v} + \langle s_{PU}s_{PU}''\rangle_{SOP;v}}{2}\right] \quad (3.4d)$$

where $\sigma_{s0}^2 = 1/3$, and $s_p$ as, $$s_{PL} = 2T_L - 1 \quad s_{PL}'' = 2T_L'' - 1$$

$$s_{PU} = 2T_U - 1 \quad s_{PU}'' = 2T_U'' - 1$$

A relative variance computed from equation (3.4b) cannot be applied to any above- or below-mentioned "relative power" related computation for extracting DGD or PMD, i.e. the measured power must be normalized properly.

It should be noted that above equation is valid under the condition of uniformly distributed I-SOPs and A-SOPs on Poincaré Sphere from either or both input and output polarization controllers. It can be only averaged over SOP or averaged over both SOP and wavelength.

The noise variance (equation 3.3) is then subtracted from the first estimation of the relative variance (equation 3.4a) in the computation, and a final relative variance is as follows, $$\sigma_r^2(v) = \sigma_r'^2(v) - \sigma_{noise}^2(v) \quad (3.5a)$$

which is particularly appropriate for determining a DGD estimate at a particular wavelength; and $$\sigma_r^2 = \sigma_r'^2 - \sigma_{noise}^2 \quad (3.5b)$$

which is particularly appropriate for determining a PMD estimate at a particular wavelength.

3.2.1.4.3 Mean-Square Differences

The calculation here differs from the simple mean-square found in equations (2.8) and (2.9) which, for greater clarity, did not take into account the noise. Instead, the product of the repeated differences between normalized power at $\lambda_U$ and $\lambda_L$ is averaged as follows, $$\langle \Delta T^2(v) \rangle_{SOP} = \langle (T_U(v) - T_L(v)) \cdot (T_U''(v) - T_L''(v)) \rangle_{SOP} \quad (3.6a)$$

$$= \frac{1}{K} \sum_k \left(T_U^{(k)}(v) - T_L^{(k)}(v)\right) \cdot \left(T_U''^{(k)}(v) - T_L''^{(k)}(v)\right)$$

$$\langle \Delta T^2(v) \rangle_{SOP;v} = \quad (3.6b)$$

$$\langle (T_U - T_L) \cdot (T_U'' - T_L'') \rangle_{SOP;v} = \frac{1}{K} \sum_k \left(T_U^{(k)} - T_L^{(k)}\right) \cdot \left(T_U''^{(k)} - T_L''^{(k)}\right)$$

In conventional mathematical terms, each of equations (3.6) may be referred to as the second-order joint moment of the repeated differences.

Doing so, the noise averages to zero instead of being "rectified", because the noise superimposed on a given trace is not correlated with the noise superimposed on the corresponding repeated power. That is the first motivation for acquiring repeated data.

Note that $\langle \ \rangle_{SOP}$ in Eq. (3.6a) can refer to averaging over the SOP at a given midpoint frequency ($v_{mid}$) (i.e. midpoint wavelength, $\lambda_{mid}$), i.e., only changing the SOP from one group of powers to other, which is particularly appropriate for determining the DGD at this wavelength, and $\langle \ \rangle_{SOP;v}$ in Eq. (3.6b) indicates averages taken over both the SOP and the midpoint frequencies ($v_{mid}$) (i.e. midpoint wavelength $\lambda_{mid}$). Thus, both SOP and optical frequency are changed from one group of powers to other, which is particularly appropriate for determining the PMD over a particular wavelength range.

3.2.1.4.4 Computation of the DGD or PMD Value

The DGD or rms DGD (i.e. PMD) then is computed according to the arcsine formula as, $$DGD(v) = \frac{1}{\pi\delta v} \arcsin\left(\alpha_{ds}\sqrt{\frac{\langle \Delta T^2(v) \rangle_{SOP}}{\sigma_r^2(v)}}\right) \quad (3.7)$$

where $\langle \ \rangle_{SOP}$ refers to averaging over the SOP only.

$$PMD = \frac{1}{\pi\delta v} \arcsin\left(\alpha_{ds}\sqrt{\frac{\langle \Delta T^2(v) \rangle_{SOP;v}}{\sigma_r^2}}\right) \quad (3.8)$$

where $\langle \ \rangle_{SOP;v}$ refers to averaging over both the SOP and optical frequency (wavelength), and a theoretical constant $$\alpha_{ds} = \sqrt{\frac{9}{2}}.$$

It should be appreciated that the arcsine formula, in equations (3.7) and (3.8), is not the only possible one. The purpose of using this formula is to obtain a result that is unbiased even if using a relatively large step, such that PMD·δv~0.2, without introducing a significant error; this in order to maximize the signal-to-noise ratio and therefore the dynamic range of the instrument. Although applicable to any step size, if one were not concerned with maximizing the dynamic range, one could select a small step, in which case the following simpler differential formula is valid:

$$DGD(v) = \frac{\alpha_{ds}}{\pi\delta v} \cdot \sqrt{\frac{\langle \Delta T^2(v) \rangle_{SOP}}{\sigma_r^2(v)}} \quad (3.7a)$$

$$PMD = \frac{\alpha_{ds}}{\pi\delta v} \cdot \sqrt{\frac{\langle \Delta T^2(v) \rangle_{SOP;v}}{\sigma_r^2}} \quad (3.8a)$$

This is not to infer that these formulas are better or particularly advantageous, but merely that it may conveniently be used if the step is much smaller, i.e., satisfying the condition PMD·δv < 0.01.

It should be noted that in an ideal situation where there is no ASE from optical amplifiers, depolarization effects, or other "noise" related to variations in light polarization, frequency and intensity etc., then $\sigma_r^2=1$, the above equations (3.7) and (3.8) simplify to, $$DGD(v) = \frac{1}{\pi\delta v}\arcsin\left(\alpha_{ds}\sqrt{\langle\Delta T^2(v)\rangle_{SOP}}\right) \quad (3.9)$$

$$PMD = \frac{1}{\pi\delta v}\arcsin\left(\alpha_{ds}\sqrt{\langle\Delta T^2(v)\rangle_{SOP;v}}\right) \quad (3.10)$$

and their corresponding simpler differential formulas are, $$DGD(v) = \frac{\alpha_{ds}}{\pi\delta v} \cdot \sqrt{\langle\Delta T^2(v)\rangle_{SOP}} \quad (3.9a)$$

$$PMD = \frac{\alpha_{ds}}{\pi\delta v} \cdot \sqrt{\langle\Delta T^2(v)\rangle_{SOP;v}} \quad (3.10a)$$

Note that a mean DGD or rms DGD may be computed from averaging DGD(v) from many different midpoint wavelengths over a prescribed wavelength range, such as $$\text{RMS DGD} = \sqrt{\langle DGD^2(v)\rangle_v} \quad (3.11)$$

$$\text{mean DGD} = \langle DGD(v)\rangle_v \quad (3.12)$$

As shown in the equations (3.7) and (3.8), if the DGD(v) and PMD calculation involves the use of the relative variance, $\sigma_r^2(v)$ and $\sigma_r^2$ respectively, of the normalized power (T), then the normalized power need not be necessarily computed to lie between 0 and 1. In other words, some steps of above normalization procedure may be skipped.

For example, for the implementation of FIG. 1D (two photodetectors with a coupler), the relative power ($P_R$) can simply be obtained from the ratio of trace Px over trace Py as, $$P_{RL}^{(k)} = \frac{Px_L^{(k)}}{Py_L^{(k)}} \quad P_{RL}''^{(k)} = \frac{Px_L''^{(k)}}{Py_L''^{(k)}} \quad (3.13)$$

$$P_{RU}^{(k)} = \frac{Px_U^{(k)}}{Py_U^{(k)}} \quad P_{RU}''^{(k)} = \frac{Px_U''^{(k)}}{Py_U''^{(k)}}$$

For the implementation of FIG. 1F (two photodetectors with a PBS) and in FIG. 1D (two photodetectors with a coupler), the relative power ($P_R$) may be obtained without recourse to the aforementioned reference constants and averaging over SOP and/or wavelength in order to obtain a normalized power. Then DGD and PMD may be computed by means of the following arcsine formula as, $$DGD(v) = \frac{1}{\pi\delta v}\arcsin\left(\alpha_{ds}\sqrt{\frac{\langle\Delta P_R^2(v)\rangle_{SOP}}{\sigma_R^2(v)}}\right) \quad (3.14)$$

where $\langle\,\rangle_{SOP}$ refers to averaging over SOP only.

$$PMD = \frac{1}{\pi\delta v}\arcsin\left(\alpha_{ds}\sqrt{\frac{\langle P_R^2(v)\rangle_{SOP;v}}{\sigma_R^2}}\right) \quad (3.15)$$

where $\langle\,\rangle_{SOP;v}$ refers to averaging over both the SOP and wavelength.

Here mean-square $\langle\Delta P_R^2(v)\rangle_{SOP}$ and $\langle\Delta P_R^2(v)\rangle_{SOP;v}$ can be found as follows, $$\langle\Delta P_R^2(v)\rangle_{SOP} = \langle(P_{RU}(v) - P_{RL}(v))\cdot(P_{RU}''(v) - P_{RL}''(v))\rangle_{SOP} \quad (3.16a)$$

$$= \frac{1}{K}\sum_k \left(P_{RU}^{(k)}(v) - P_{RL}^{(k)}(v)\right) \cdot \left(P_{RU}''^{(k)}(v) - P_{RL}''^{(k)}(v)\right)$$

$$\langle\Delta P_R^2(v)\rangle_{SPO;v} = \langle(P_{RU} - P_{RL})\cdot(P_{RU}'' - P_{RL}'')\rangle_{SOP;v} \quad (3.16b)$$

$$= \frac{1}{K}\sum_k \left(P_{RU}^{(k)} - P_{RL}^{(k)}\right) \cdot \left(P_{RU}''^{(k)} - P_{RL}''^{(k)}\right)$$

and the relative variance, $\sigma_R^2$, is computed here as the average of the four available estimates, i.e., $$\sigma_R^2(v) = \left(\frac{1}{\sigma_{20}}\right)^2\left[\frac{\delta(P_{RL}(v)) + \delta(P_{RU}(v))}{2}\right] \quad (3.16c)$$

$$\sigma_R^2 = \left(\frac{1}{\sigma_{20}}\right)^2\left[\frac{\delta(P_{RL}) + \delta(P_{RU})}{2}\right] \quad (3.16d)$$

where $\sigma_{20}^2 = 1/12$, and the function "$\delta$" is defined as, $$\delta(P_{RL}(v)) = \lfloor\langle P_{RL}(v)P_{RL}''(v)\rangle_{SOP} - \langle P_{RL}(v)\rangle_{SOP}^2\rfloor$$

$$\delta(P_{RU}(v)) = \lfloor\langle P_{RU}(v)P_{RU}''(v)\rangle_{SOP} - \langle P_{RU}(v)\rangle_{SOP}^2\rfloor$$

$$\delta(P_{RL}) = \lfloor\langle P_{RL}P_{RL}''\rangle_{SOP;v} - \langle P_{RL}\rangle_{SOP;v}^2\rfloor$$

$$\delta(P_{RU}) = \lfloor\langle P_{RU}P_{RU}''\rangle_{SOP;v} - \langle P_{RU}\rangle_{SOP;v}^2\rfloor$$

Note that $\langle\,\rangle_{SOP;v}$ can refer to averaging over either the SOP, or the optical frequency (wavelength), or over both, i.e., changing both SOP and optical frequency from one group of powers to the next.

If one selected a small step, the arcsine formula, in equations (3.14) and (3.15) may be written as a simpler differential formula:

$$DGD(v) = \frac{\alpha_{ds}}{\pi\delta v} \cdot \sqrt{\frac{\langle\Delta P_R^2(v)\rangle_{SOP}}{\sigma_R^2(v)}} \quad (3.14a)$$

$$PMD = \frac{\alpha_{ds}}{\pi\delta v} \cdot \sqrt{\frac{\langle\Delta P_R^2(v)\rangle_{SOP;v}}{\sigma_R^2}} \quad (3.15a)$$

For the case where the tunable light source has a relatively large linewidth and a high-PMD fiber is under test, a further linewidth "correction factor" may be applied in equations in order to extract a DGD or PMD value of the FUT having a greater accuracy.

It should be appreciated noted that the above-computed forward DGD or PMD for two-ended PMD measurement is in fact the DGD or PMD of FUT.

It should also be noted that repeated powers may be obtained from two or more measurements at different times using the same detectors, or from measurements using different detectors, e.g. after the light power has been split by a coupler (FIG. 1C) and the resulting apportioned powers detected by respective detectors contemporaneously.

3.2.2 Two-Ended DGD and PMD: Data Processing and Computation Using Two Detected Polarization Components with Rapid Wavelength Sweeping

3.2.2.1 The Data Structure

The data structure for the exemplary polarization-diverse detection implementations depicted in FIGS. 1K and 1G, where the wavelength of the detected light is rapidly swept over a prescribed wavelength range, differs somewhat from the other embodiments. Each light power from the FUT 18, obtained with either one given setting of the wavelength from tunable filter A 27B and tunable filter B 27C (FIG. 1K) or from swept tunable laser source 12A (FIG. 1G) and of the SOP couple (I-SOP; A-SOP) for the two-ended PMD measurement provided hereinafter, constitutes an elementary data cell, i.e. one datum consists of one power value. The data unit is one group of N powers, two sets of N powers for the embodiments of FIGS. 1K and 1G where two powers are obtained simultaneously from photodetectors 22B and 22C, all obtained with given approximately same SOP couples as set by I-SOP scrambler 14A and A-SOP scrambler 14B. Preferably, the I-SOP scrambler 14A operates in a slow "continuous scanning" mode, randomly scanning its input SOP, while the A-SOP scrambler 14B sets one analyzer SOP for one group data with N powers.

By "slow" continuous scanning, one means that the I-SOP scrambler 14A scans sufficiently slowly that, in the absence of DGD or PMD from the FUT, the mean-squared equalized transmission (equalized normalized power) difference over a large number of SOPs caused by the input SOP changing is much smaller (e.g. less than few percent) than that (i.e. a mean-squared equalized transmission difference) generated from a given DGD of the FUT for one set optical frequency difference between two closely-spaced frequencies that is used to compute the DGD or PMD of the FUT as used in equations (2.8) and (2.9). The two sets of N powers forming group k preferably have been obtained in the following sequence (time flowing from left to right), for I-SOP$_k^I$, A-SOP$_k^O$ and $v_1$ to $v_N$, as:

| $P_x^{(k)}(v_1)$ | $P_x^{(k)}(v_2)$ | ... | $P_x^{(k)}(v_i)$ | ... | $P_x^{(k)}(v_N)$ |
|---|---|---|---|---|---|
| $P_y^{(k)}(v_1)$ | $P_y^{(k)}(v_2)$ | ... | $P_y^{(k)}(v_i)$ | ... | $P_y^{(k)}(v_N)$ | where the labels x and y refer to the power obtained approximately simultaneously photodetectors 22B and 22C, respectively, $\delta v = v_{i+n} - v_i$ is an optical frequency difference (wavelength step) between two closely-spaced optical frequencies, and its midpoint optical frequency (wavelength) is defined as $$v_{i,mid} = \frac{v_i + v_{i+n}}{2} \left( \lambda_{i,mid} = \frac{2\lambda_i \cdot \lambda_{i+n}}{\lambda_i + \lambda_{i+n}} \right)$$

(where n is an acquired data number difference for the optical frequency difference, $\delta v$, between two closely-spaced optical frequencies (wavelengths)).

Typically an optical frequency being scanned from $v_1$ to $v_N$ is actually incrementally or decrementally stepped in, preferably approximately equal, small optical frequency (wavelength) steps, for example, ~125-1250 MHz (~1-10 pm). The precise value of each step need not be known. Also it should be noted that as long as knowing accurate optical frequency, for example optical frequency being measured by a wavelength meter during data acquisition, a step from one frequency to next may be different. However, it is desirable for equations (6.8) and (6.9), for the sake of convenience, to use approximately equal optical frequency differences to calculate a rms DGD or PMD.

The overall data can be acquired by many scans over wavelength (e.g. 3-10,000 scans) for which the input and analyzer SOPs are different, that can be either achieved by tunable filter means 27 or tunable laser 12A. A desirable tunable filter means (FIG. 1K) may be based on a polarization-diverse two-channel scanning monochromator, such as comprised within a commercial optical spectrum analyzer such as the model FTB-5240, manufactured by EXFO Inc.

The acquired data are stored in the data file as a matrix (3.17), in analogous fashion to matrix (3.1) described hereinabove. The matrix comprises K groups each of 2×N light powers (i.e. two sets of N) are acquired from two photodetectors 22B and 22C (FIGS. 1K and 1G):

| | | | | | | | (3.17) |
|---|---|---|---|---|---|---|---|
| $SOP_0^I, SOP_0^O$ | $P_x^{(0)}(v_1)$ | $P_x^{(0)}(v_2)$ | ... | $P_x^{(0)}(v_i)$ | ... | $P_x^{(0)}(v_N)$ | |
| | $P_y^{(0)}(v_1)$ | $P_y^{(0)}(v_2)$ | ... | $P_y^{(0)}(v_i)$ | ... | $P_y^{(0)}(v_N)$ | |
| $SOP_1^I, SOP_1^O$ | $P_x^{(1)}(v_1)$ | $P_x^{(1)}(v_2)$ | ... | $P_x^{(1)}(v_i)$ | ... | $P_x^{(1)}(v_N)$ | |
| | $P_y^{(1)}(v_1)$ | $P_y^{(1)}(v_2)$ | ... | $P_y^{(1)}(v_i)$ | ... | $P_y^{(1)}(v_N)$ | |
| ⋮ | ⋮ | ⋮ | ⋮ | ⋮ | ⋮ | ⋮ | |
| $SOP_k^I, SOP_k^O$ | $P_x^{(k)}(v_1)$ | $P_x^{(k)}(v_2)$ | ... | $P_x^{(k)}(v_i)$ | ... | $P_x^{(k)}(v_N)$ | |
| | $P_y^{(k)}(v_1)$ | $P_y^{(k)}(v_2)$ | ... | $P_y^{(k)}(v_i)$ | ... | $P_y^{(k)}(v_N)$ | |
| ⋮ | ⋮ | ⋮ | ⋮ | ⋮ | ⋮ | ⋮ | |
| $SOP_{K-1}^I, SOP_{K-1}^O$ | $P_x^{(K-1)}(v_1)$ | $P_x^{(K-1)}(v_2)$ | ... | $P_x^{(K-1)}(v_i)$ | ... | $P_x^{(K-1)}(v_N)$ | |
| | $P_y^{(K-1)}(v_1)$ | $P_y^{(K-1)}(v_2)$ | ... | $P_y^{(K-1)}(v_i)$ | ... | $P_y^{(K-1)}(v_N)$ | |

3.2.2.2 Auto-Calibration of the Relative Gain

For the implementations of FIGS. 1K and 1G, it is necessary to perform a calibration procedure of the relative gain of the two detectors 22B and 22C before proceeding with any further computation, as will now be described. The same procedure is not performed for the other implementations, e.g. if there is only one detector.

The calibration principle is predicated upon the fact that, when input and output SOP scramblers are used to generate a sufficiently large number of SOPs so as to substantially cover the Poincaré Sphere, the average power of the light from the FUT 18 will exit from the two ports of the PBS with a 1:1 ratio (equal). Hence, any observed deviation from this 1:1 ratio for the observed detector powers can be quantified and taken into account, as follows.

After data acquisition is completed, K groups of 2×N light powers obtained from both photodetectors have been stored, i.e., a total number of K·N powers (data) from detector 22B and also K·N powers from detector 22C, as depicted in matrix (7.17). The $i^{th}$ powers at optical frequency $v_i$ (ideally where the optical frequency is selected to correspond to approximately maximum transmitted power or to be in spectral proximity to the central frequency of the test channel or device under test or FUT) from 22B and 22C are referred to below as $P_x(v_i)$ and $P_y(v_i)$, respectively. If the overall losses in the two arms of the PBS were identical and the gains of both photodetectors and associated electronics were also equal, the ratio of the powers $P_x(v_i)$ and $P_y(v_i)$ after averaging over all K, i.e. all input and analyzer SOPs, would be $$\frac{\langle P_x(v_i) \rangle}{\langle P_y(v_i) \rangle} \equiv \frac{\sum_K P_x^k(v_i)}{\sum_K P_y^k(v_i)} = 1 \quad (3.18)$$

In practice, the ratio obtained from the average of the measured powers for $P_x(v_i)$ and $P_y(v_i)$ does not equal 1 because of different losses in the arms of the PBS and different "effective" gains of the photodetectors, which includes the photodiode responsivity as well as the overall gains of the following electronics, amplifiers and sampling circuitry. (Note that it is not necessary to determine the individual gains separately.) Therefore, before proceeding with the rest of the computations, all the K·N powers obtained from photodetector 22C, i.e. all the $P_y^{(k)}(v_i)$ (i=1, 2 ... N; and k=1, 2, ... K), are multiplied as follows:

$$P_y^{(k)}(v_i) \equiv g_{Forward} \cdot P_y^{(k)}(v_i) \quad (3.19)$$

where $$g_{Forward} = \frac{\langle P_x(v_i) \rangle}{\langle P_y(v_i) \rangle} \equiv \frac{\sum_K P_x^k(v_i)}{\sum_K P_y^k(v_i)}$$

It should be noted that above auto-calibration assumes the relative gain to have negligible wavelength (optical frequency) dependence. Indeed it holds for a narrow wavelength range, especially for a narrow DWDM channel under test. However, if a wide optical frequency range is used for the test, e.g. encompassing either the C, L or C+L band, an auto-calibration for the relative gain may be performed at each optical frequency. The calibration process may need only be carried out once per PMD measurement sequence.

3.2.2.3 Computation for Implementations Employing Two Orthogonal Polarization Analyzers with a Polarization Beam Splitter The powers are processed to obtain the DGD(v) and PMD values using detected two "physically" orthogonal (i.e. 180 degrees on the Poincare sphere) polarization components from a polarization beam splitter by rapid wavelength sweeping of either tunable filter means or swept tunable laser, as will now be described. The labels x and y refer to the probed light powers obtained from photodetectors 22B and 22C, respectively.

3.2.2.3.1 the Normalized Powers

The transmissions (normalized powers), labeled as $T_x$ and $T_y$, are computed for the implementations of FIGS. 1K and 1G for two photodetectors with a PBS as follows either $$T_x^{(k)}(v) = \frac{P_x^{(k)}(v)}{\langle P_x^{(k)}(v) + P_y^{(k)}(v) \rangle_{SOP}} \quad T_y^{(k)}(v) = \frac{P_y^{(k)}(v)}{\langle P_x^{(k)}(v) + P_y^{(k)}(v) \rangle_{SOP}} \quad (3.20a)$$

or $$T_x^{(k)}(v) = \frac{P_x^{(k)}(v)}{u_0 \langle P_x^{(k)}(v) \rangle_{SOP}} \quad T_y^{(k)}(v) = \frac{P_y^{(k)}(v)}{u_0 \langle P_y^{(k)}(v) \rangle_{SOP}} \quad (3.20b)$$

where $\langle \; \rangle_{SOP}$ refers to an average over all or many I-SOPs and A-SOPs at a given optical frequency v, and the reference mean-value is $u_o = \frac{1}{2}$. Equations (3.20a) and (3.20b) assume a measured overall total power, i.e. the sum of the two measurements from, respectively, A 22B and detector B 22C, is stable over the entire measurement time.

If a measured overall total power, i.e. sum of the two measurements from, respectively, detector A 22B and detector B 22C, has negligible noise (which typically holds for most commercial instruments, such as a power meter or an optical spectrum analyzer, if the incident light power is not too low), the transmissions (normalized powers) can then be written as:

$$T_x^{(k)}(v) = \frac{P_x^{(k)}(v)}{P_x^{(k)}(v) + P_y^{(k)}(v)} \quad T_y^{(k)}(v) = \frac{P_y^{(k)}(v)}{P_y^{(k)}(v) + P_y^{(k)}(v)} \quad (3.20c)$$

Advantageously, the transmissions (normalized powers) being obtained in the way as described in equation (3.20c) have negligible dependence on the test light source stability, which otherwise might be important for a test being performed in a live DWDM network where there may be many live channels being operated during the data acquisition.

It should be noted that above normalized power is computed at each optical frequency (v), i.e. from one wavelength to another, for the entire optical frequency range. This is because there may be different measured light power levels and light noise (i.e. ASE) levels at different optical frequencies (wavelengths), especially if the measurement is performed in a narrow optical channel, e.g. a DWDM channel, so that their relative variance may be different from one optical frequency to another.

3.2.2.3.2 Relative Variance

The relative variance, for example mainly due to unpolarized ASE light from optical amplifiers in the test network fiber link or any other depolarizing effects, as used in equations (3.22) and (3.23) below, is computed at each optical frequency as $$\sigma_r^2(v) = \left(\frac{1}{\sigma_{20}}\right)^2 \left[-1 \cdot \langle T_x(v)T_y(v)\rangle_{SOP} + \frac{1}{4} \cdot \langle T_x(v) + T_y(v)\rangle_{SOP}^2\right] \quad (3.21a)$$

or $$\sigma_r^2(v) = \left(\frac{1}{\sigma_{20}}\right)^2 [-1 \cdot \langle T_x(v)T_y(v)\rangle_{SOP} + \langle T(v)\rangle_{SOP}^2] \quad (3.21b)$$

where $\sigma_{20}^2 = 1/12$, $\langle\ \rangle_{SOP}$ refers to an average over all or many (I-SOP, A-SOP) couples at each given optical frequency $v$, and $\langle T(v)\rangle_{SOP}$ refers to an average over all or many input and output SOP couples at each given optical frequency, $v$, for these transmissions (normalized powers) measured from two photodetectors.

Advantageously, the above computed relative variance exhibit negligible or minimal dependence on noise in the detected powers. However, under an assumption of negligible noise from the measured powers for each individual detectors of A and B (22B and 22C), a relative variance may be obtained as $$\sigma_r^2(v) = \left(\frac{1}{\sigma_{20}}\right)^2 \left[\frac{\langle T_x^2(v)\rangle_{SOP} + \langle T_y^2(v)\rangle_{SOP} - 2 \cdot \langle T(v)\rangle_{SOP}^2}{2}\right] \quad (3.22a)$$

$$\sigma_{r,x}^2(v) = \left(\frac{1}{\sigma_{20}}\right)^2 [\langle T_x^2(v)\rangle_{SOP} - \langle T_x(v)\rangle_{SOP}^2] \quad (3.22b)$$

$$\sigma_{r,y}^2(v) = \left(\frac{1}{\sigma_{20}}\right)^2 [\langle T_y^2(v)\rangle_{SOP} - \langle T_y(v)\rangle_{SOP}^2] \quad (3.22c)$$

It should be noted that Equation (3.22b) or (3.22c) can be applied to the implementations of FIGS. 1K and 1G where the PBS is replaced by a linear polarizer 20A (as shown in FIGS. 1I and 1B) and only one photodetector 22A is used.

Also note that after averaging over sufficient a large number of input and output SOP couples, relative variances being obtained from equations (3.22a), (3.22b) and (3.22c) are equal, i.e. $\sigma_r^2(v) = \sigma_{r,x}^2(v) = \sigma_{r,y}^2(v)$.

3.2.2.3.3 Equalization of Normalized Powers

The transmissions (or normalized powers) computed above normally do not include equalization, i.e. they may be affected by ASE and any depolarization effects, etc., therefore they may not be equalized between 0 and 1 even with uniformly distributed input and analyzer SOPs. However, to compute the DGD and PMD as defined in equations (6.8) and (6.9) hereinbefore, one must equalize the measured transmissions (or normalized powers) so that they have a uniform distribution between 0 and 1 if the input and analyzer SOPs are uniformly distributed. The purpose of the equalization procedure for the normalized powers is to remove these "depolarization" effects on the polarized test light source, and thereby enable these equalized transmissions (or equalized normalized powers) to be directly used to calculate the mean-square difference for the DGD and PMD computation.

The equalized transmissions (or equalized normalized powers), labelled as $T_{e,x}$ and $T_{e,y}$, are computed for the implementations of FIGS. 1K and 1G for two photodetectors with a PBS as follows $$T_{e,x}^{(k)}(v) = \frac{T_x^{(k)}(v)}{\sigma_r(v)} - \frac{1}{2} \cdot \left(\frac{1}{\sigma_r(v)} - 1\right) \quad (3.23a)$$

$$T_{e,y}^{(k)}(v) = \frac{T_y^{(k)}(v)}{\sigma_r(v)} - \frac{1}{2} \cdot \left(\frac{1}{\sigma_r(v)} - 1\right)$$

where $\sigma_r(v)$ can be obtained from equation (6.7).

Under the assumption of negligible noise from the measured powers for each individual detectors of A and B (22B and 22C) the equalized transmissions (or equalized normalized powers) can also be expressed as $$T_{e,x}^{(k)}(v) = \frac{T_x^{(k)}(v)}{\sigma_{r,x}(v)} - \frac{1}{2} \cdot \left(\frac{1}{\sigma_{r,x}(v)} - 1\right) \quad (3.23b)$$

$$T_{e,y}^{(k)}(v) = \frac{T_y^{(k)}(v)}{\sigma_{r,y}(v)} - \frac{1}{2} \cdot \left(\frac{1}{\sigma_{r,y}(v)} - 1\right)$$

where $\sigma_{r,x}(v)$ and $\sigma_{r,y}(v)$ can be obtained from equation (6.7).

Note that Equation (3.23b) can be applied to the embodiments of FIGS. 1K and 1G in which the PBS is replaced by a linear polarizer 20A (e.g. implementations shown in FIGS. 1I and 1B) and only one photodetector 22A is used.

It should be noted that the equalization for transmissions (or normalized powers) needs to be performed at each optical frequency. This is because a relative variance may be different at different optical frequency (wavelength), especially for a narrow bandwidth channel of the DWDM network system under test with ASE from optical amplifiers. However, if there is no difference for relative variance against optical frequency (wavelength), one or an averaged relative variance may be calculated.

3.2.2.3.4 Mean-Square Differences

The calculation of mean-square differences using equalized transmissions (or equalized normalized powers), $T_{e,x}$ and $T_{e,y}$, from two photodetectors with a PBS for the implementations of FIGS. 1K and 1G, can be found as $$\langle\Delta T_e^2(v)\rangle_{SOP} = \left\{-1 \cdot \left(T_{e,x}^{(k)}\left(v+\frac{1}{2}\delta v\right) - T_{e,x}^{(k)}\left(v-\frac{1}{2}\delta v\right)\right) \cdot \right. \quad (3.24a)$$

$$\left. \left(T_{e,y}^{(k)}\left(v+\frac{1}{2}\delta v\right) - T_{e,y}^{(k)}\left(v-\frac{1}{2}\delta v\right)\right)\right\}_{SOP}$$

$$= -\frac{1}{K}\sum_k \left(T_{e,x}^{(k)}\left(v+\frac{1}{2}\delta v\right) - T_{e,x}^{(k)}\left(v-\frac{1}{2}\delta v\right)\right) \cdot$$

$$\left(T_{e,y}^{(k)}\left(v+\frac{1}{2}\delta v\right) - T_{e,y}^{(k)}\left(v-\frac{1}{2}\delta v\right)\right)$$

$$\langle \Delta T_e^2(v) \rangle_{SOP,v} = \left\langle -1 \cdot \left( T_{e,x}^{(k)}\left(v + \frac{1}{2}\delta v\right) - T_{e,x}^{(k)}\left(v - \frac{1}{2}\delta v\right) \right) \cdot \right. \quad (3.24b)$$

$$\left. \left( T_{e,y}^{(k)}\left(v + \frac{1}{2}\delta v\right) - T_{e,y}^{(k)}\left(v - \frac{1}{2}\delta v\right) \right) \right\rangle_{SOP,v}$$

$$= -\frac{1}{K \cdot N'} \sum_{k,n} \left( T_{e,x}^{(k)}\left(v + \frac{1}{2}\delta v\right) - T_{e,x}^{(k)}\left(v - \frac{1}{2}\delta v\right) \right) \cdot$$

$$\left( T_{e,y}^{(k)}\left(v + \frac{1}{2}\delta v\right) - T_{e,y}^{(k)}\left(v - \frac{1}{2}\delta v\right) \right)$$

where K is the total number of input and output SOP couples and N' is the total number of midpoint optical frequencies.

As shown in equations (3.24a) and (3.24b), by using equalized transmissions (or equalized normalized powers), $T_{e,x}$ and $T_{e,y}$, to compute the mean-square difference for the PBS-based implementations of FIGS. 1K and 1G with two photodetectors, the noise averages to zero instead of being "rectified", because the noise superimposed on a measured power by one detector is not correlated with the noise superimposed on the measured power by a different detector. That is achieved by acquiring data with different detectors A and B (22B and 22C) in the exemplary implementations of FIGS. 1K and 1G.

Equalized transmissions (or equalized normalized powers) obtained from one photodetector connected either after one of two ports of a PBS or after a linear polarizer, for example for implementations in FIGS. 1I and 1B where only one photodetector 22A is used, can also be used to calculate mean-square difference as, $$\langle \Delta T_e^2(v) \rangle_{SOP} = \left\langle \left( T_{e,x}^{(k)}\left(v + \frac{1}{2}\delta v\right) - T_{e,x}^{(k)}\left(v - \frac{1}{2}\delta v\right) \right)^2 \right\rangle_{SOP} \quad (3.25a)$$

$$= \frac{1}{K} \sum_k \left( T_{e,x}^{(k)}\left(v + \frac{1}{2}\delta v\right) - T_{e,x}^{(k)}\left(v - \frac{1}{2}\delta v\right) \right)^2$$

$$\langle \Delta T_e^2(v) \rangle_{SOP} = \left\langle \left( T_{e,y}^{(k)}\left(v + \frac{1}{2}\delta v\right) - T_{e,y}^{(k)}\left(v - \frac{1}{2}\delta v\right) \right)^2 \right\rangle_{SOP} \quad (3.25b)$$

$$= \frac{1}{K} \sum_k \left( T_{e,y}^{(k)}\left(v + \frac{1}{2}\delta v\right) - T_{e,y}^{(k)}\left(v - \frac{1}{2}\delta v\right) \right)^2$$

and $$\langle \Delta T_e^2(v) \rangle_{SOP,v} = \left\langle \left( T_{e,x}^{(k)}\left(v + \frac{1}{2}\delta v\right) - T_{e,x}^{(k)}\left(v - \frac{1}{2}\delta v\right) \right)^2 \right\rangle_{SOP,v} \quad (3.26a)$$

$$= \frac{1}{K \cdot N'} \sum_{k,n} \left( T_{e,x}^{(k)}\left(v + \frac{1}{2}\delta v\right) - T_{e,x}^{(k)}\left(v - \frac{1}{2}\delta v\right) \right)^2$$

$$\langle \Delta T_e^2(v) \rangle_{SOP,v} = \left\langle \left( T_{e,y}^{(k)}\left(v + \frac{1}{2}\delta v\right) - T_{e,y}^{(k)}\left(v - \frac{1}{2}\delta v\right) \right)^2 \right\rangle_{SOP,v} \quad (3.26b)$$

$$= \frac{1}{K \cdot N'} \sum_{k,n} \left( T_{e,y}^{(k)}\left(v + \frac{1}{2}\delta v\right) - T_{e,y}^{(k)}\left(v - \frac{1}{2}\delta v\right) \right)^2$$

where K is total input and analyzer SOP couples and N' is total midpoint optical frequency number. Equations (2.7) and (2.8) assume that there is negligible noise for the measured powers for each individual detectors of A or B (22B and 22C) or photodetector 22A of FIGS. 1I and 1B.

Note that $\langle \ \rangle_{SOP}$ in above equations refers only to an average taken over the SOP at a given midpoint frequency ($v_{i,mid}$) (or midpoint wavelength, $\lambda_{i,mid}$), i.e., only changing the (I-SOP, A-SOP) couples from one group of powers to other, and $\langle \ \rangle_{SOP,v}$ in above equations refers to an average taken over the (I-SOP, A-SOP) couples and midpoint frequencies ($v_{i,mid}$).

3.2.2.3.5 Computation of the DGD and PMD Value Using Mean-Square Differences of Equalized Transmissions The DGD(v) is computed according to the arcsine formula from calculated mean-square differences using equalized transmissions (or equalized normalized powers) in equation (3.25) or (3.26) for the implementations of FIGS. 1K and 1G with PBS and two photodetectors as, $$DGD(v) = \frac{1}{\pi \delta v} \arcsin\left( \alpha_{ds} \sqrt{\langle \Delta T_e^2(v) \rangle_{SOP}} \right) \quad (3.27a)$$

where $\langle \ \rangle_{SOP}$ refers to average over the (I-SOP, A-SOP) couples only.

A rms DGD can be written as $$rmsDGD = \frac{1}{\pi \delta v} \arcsin\left( \alpha_{ds} \sqrt{\langle \Delta T_e^2(v) \rangle_{SOP,v}} \right) \quad (7.28a)$$

where $\langle \ \rangle_{SOP;v}$ refers to averaging over both the (I-SOP, A-SOP) couples and optical frequency (i.e. wavelength), and a theoretical constant $$\alpha_{ds} = \sqrt{\frac{9}{2}},$$

and, $\delta v = v_{i+n} - v_i$, an optical frequency difference between two closely-spaced optical frequencies, $v_i$ and $v_{i+n}$, is used for computing DGD and PMD.

It should be appreciated that the arcsine formula, in above equations, is not the only possible one. The purpose of using this formula is to obtain a result that is unbiased even if using a relatively large step, such that PMD·δv~0.2, without introducing a significant error; thereby to maximize the signal-to-noise ratio and therefore the dynamic range of the instrument. Although applicable to any step size, if one were not concerned with maximizing the dynamic range, one could select a small step and apply the following simpler differential formulae, which represent the limiting cases of Equations (3.27a) and (3.28a) as the small optical-frequency difference approaches zero:

$$DGD(v) = \frac{1}{\pi \delta v} \left( \alpha_{ds} \sqrt{\langle \Delta T_e^2(v) \rangle_{SOP}} \right) \quad (3.27b)$$

$$RMSDGD = \frac{1}{\pi \delta v} \left( \alpha_{ds} \sqrt{\langle \Delta T_e^2(v) \rangle_{SOP,v}} \right) \quad (3.28b)$$

This is not to infer that these formulae are better or particularly advantageous, but merely that it may conveniently be used if the step is much smaller, i.e., satisfying the condition DGD·δν or rms DGD·δν ⟨ 0.01.

For the equations (3.27) and (3.28), an optical frequency difference, δν, is the same or approximately the same for all midpoint optical frequencies.

Note that the relationships in equations (3.27a) and (3.28a) hold for DGD·δν ⟨ 0.5 or PMD·δν ⟨ 0.2 for the two-ended measurement configuration, thus clarifying the meaning of "closely-spaced optical frequencies".

Also note that in equation (3.28b) an averaging optical frequency range can be small, for example as small as of ⟨ 20 GHz, or very wide, for example close to 10 THz.

It should also be noted that above equations can be used for any situation where there is no ASE where the ASE arising from optical amplifiers is significant, for example for which the signal-to-noise ratio may be as low as of ~3 dB, and accompanied by other depolarization effects etc. This is because the equalization for transmissions (or normalized powers) will have already been performed.

A mean DGD or rms DGD may be computed by averaging DGD(ν) (obtained from equation (3.27a) or (3.27b)) from many different midpoint optical frequencies over a prescribed optical frequency range, such as $$\text{RMS DGD} = \sqrt{\langle DGD^2(v) \rangle_v} \quad (3.29a)$$

$$\text{mean DGD} = \langle DGD(v) \rangle_v \quad (3.29b)$$

3.2.2.4 Computation for Implementations Using Two Polarization Analyzers Having an Arbitrary Relative Orientation The powers are processed, for exemplary rapid wavelength-sweeping implementations employing either a tunable filter or a swept laser, to obtain the DGD(ν) and PMD values, for the more general case where the two analyzers have a relative angle of θ (as measured on the Poincare sphere), without restricting θ to be 0 degrees (e.g. from a 50/50 polarization-independent splitter) or 180 degrees (e.g. from a PBS). As will become apparent, the relative angle must not be 90 or 270 degrees (as measured on the Poincare sphere). The labels x and y refer to the measured light powers obtained by two photodetectors followed two polarization analyzers.

3.2.2.4.1 The Normalized Powers

The transmissions (normalized powers) can be written as $$T_x^{(k)}(v) = \frac{P_x^{(k)}(v)}{u_0 \langle P_x^{(k)}(v) \rangle_{SOP}} \quad T_y^{(k)}(v) = \frac{P_y^{(k)}(v)}{u_0 \langle P_y^{(k)}(v) \rangle_{SOP}} \quad (3.30)$$

where $\langle \ \rangle_{SOP}$ refers to an average over all or many (I-SOP, A-SOP) couples at a given optical frequency ν, and the reference mean-value is $u_o = \frac{1}{2}$. Equation (3.30) assumes that the overall total power is stable over entire measurement time.

3.2.2.4.2 Relative Variance

The relative variance, for example mainly due to unpolarized ASE light from optical amplifiers in the test network fiber link or any other depolarizing effects, as used in equation (49) below, is computed at each optical frequency as $$\sigma_r^2(v) = \left(\frac{1}{\sigma_{20}}\right)^2 \left[\frac{\langle T_x(v)T_y(v) \rangle_{SOP} - \frac{1}{4} \cdot \langle T_x(v) + T_y(v) \rangle_{SOP}^2}{\cos \theta}\right] \quad (3.31a)$$

or $$\sigma_r^2(v) = \left(\frac{1}{\sigma_{20}}\right)^2 \left[\frac{\langle T_x(v)T_y(v) \rangle_{SOP} - \langle T(v) \rangle_{SOP}^2}{\cos \theta}\right] \quad (3.31)$$

where θ is an angle between two polarization analyzers (not 90 or 270 degree (in Poincare sphere)), $\sigma_{20}^2 = \frac{1}{12}$, $\langle \ \rangle_{SOP}$ refers to an average over all or many (I-SOP, A-SOP) couples at each given optical frequency ν, and $\langle T(v) \rangle_{SOP}$ refers to an average over all or many (I-SOP, A-SOP) couples at each given optical frequency, ν, for these transmissions (normalized powers) measured from two photodetectors. Advantageously, the above computed relative variance exhibits negligible or very small dependence on noise in the detected powers.

3.2.2.4.3 Equalization of Normalized Powers

The equalized transmissions (or equalized normalized powers), labelled as $T_{e,x}$ and $T_{e,y}$, are computed for two photodetectors from two analyzers in the same way as in equation (40a) as follows $$T_{e,x}^{(k)}(v) = \frac{T_x^{(k)}(v)}{\sigma_r(v)} - \frac{1}{2} \cdot \left(\frac{1}{\sigma_r(v)} - 1\right) \quad (3.32a)$$

$$T_{e,y}^{(k)}(v) = \frac{T_y^{(k)}(v)}{\sigma_r(v)} - \frac{1}{2} \cdot \left(\frac{1}{\sigma_r(v)} - 1\right)$$

where $\sigma_r(v)$ can be obtained from equation (3.31).

3.2.2.4.4 Mean-Square Differences

The calculation of mean-square differences using equalized transmissions (or equalized normalized powers) from two photodetectors with two arbitrary orientated polarization analyzers having an angle, θ, but not 90 or 270 degrees on the Poincare sphere) between them can be found as $$\langle \Delta T_e^2(v) \rangle_{SOP} = \left\langle \left(T_{e,x}^{(k)}\left(v + \frac{1}{2}\delta v\right) - T_{e,x}^{(k)}\left(v - \frac{1}{2}\delta v\right)\right) \cdot \right. \quad (3.33a)$$
$$\left. \left(T_{e,y}^{(k)}\left(v + \frac{1}{2}\delta v\right) - T_{e,y}^{(k)}\left(v - \frac{1}{2}\delta v\right)\right) \right\rangle_{SOP} =$$
$$\frac{1}{K} \sum_k \left(T_{e,x}^{(k)}\left(v + \frac{1}{2}\delta v\right) - T_{e,x}^{(k)}\left(v - \frac{1}{2}\delta v\right)\right) \cdot$$
$$\left(T_{e,y}^{(k)}\left(v + \frac{1}{2}\delta v\right) - T_{e,y}^{(k)}\left(v - \frac{1}{2}\delta v\right)\right)$$

$$\langle \Delta T_e^2(v) \rangle_{SOP,v} = \left\langle \left(T_{e,x}^{(k)}\left(v + \frac{1}{2}\delta v\right) - T_{e,x}^{(k)}\left(v - \frac{1}{2}\delta v\right)\right) \cdot \right. \quad (3.33b)$$
$$\left. \left(T_{e,y}^{(k)}\left(v + \frac{1}{2}\delta v\right) - T_{e,y}^{(k)}\left(v - \frac{1}{2}\delta v\right)\right) \right\rangle_{SOP,v} =$$
$$\frac{1}{K \cdot N'} \sum_{k,n} \left(T_{e,x}^{(k)}\left(v + \frac{1}{2}\delta v\right) - T_{e,x}^{(k)}\left(v - \frac{1}{2}\delta v\right)\right) \cdot$$
$$\left(T_{e,y}^{(k)}\left(v + \frac{1}{2}\delta v\right) - T_{e,y}^{(k)}\left(v - \frac{1}{2}\delta v\right)\right)$$

where K is the total number of (I-SOP, A-SOP) couples and N' is the total number of midpoint optical frequencies.

As shown in equations (3.33a) and (3.33b), by using equalized transmissions (or equalized normalized powers), $T_{e,x}$ and $T_{e,y}$, to compute the mean-square difference from two polarization analyzers followed by two tunable filters and two photodetectors (for the implementation using broadband source) or two photodetectors (for the implementation using tunable laser source), the noise averages to zero instead of being "rectified", because the noise superimposed on a given measured power from one detector is not correlated with the noise superimposed on the another power measured by a different detector.

3.2.2.4.5 Computation of the DGD and PMD Value Using Mean-Square Differences of Equalized Transmissions If the two polarization analyzers have an arbitrary mutual angle θ that is substantially not equal to 90 or 270 degrees on the Poincaré sphere, the DGD(v) may be computed according to the following arcsine formula from calculated mean-square differences using equalized transmissions (or equalized normalized powers) as defined in equation (49) and as measured by two photo detectors:

$$DGD(v) = \frac{1}{\pi \delta v} \arcsin\left( \alpha_{ds} \sqrt{\frac{\langle \Delta T_e^2(v) \rangle_{SOP}}{\cos\theta}} \right) \quad (3.34a)$$

where $\langle \ \rangle_{SOP}$ refers to an average over the (I-SOP, A-SOP) couples only.

A rms DGD can be written as $$rms\,DGD(v) = \frac{1}{\pi \delta v} \arcsin\left( \alpha_{ds} \sqrt{\frac{\langle \Delta T_e^2(v) \rangle_{SOP,v}}{\cos\theta}} \right) \quad (3.35a)$$

where $\langle \ \rangle_{SOP;v}$ refers to an average over both the (I-SOP, A-SOP) couples and optical frequency (i.e. wavelength), and a theoretical constant $$\alpha_{ds} = \sqrt{\frac{9}{2}},$$

and, $\delta v = v_{i+n} - v_i$, an optical-frequency difference between two closely-spaced optical frequencies, $v_i$ and $v_{i+n}$, is used for computing DGD and PMD.

It should be appreciated that the arcsine formula, in above equations, is not the only possible one. For a small step, i.e. satisfying the condition DGD·δv or rms DGD·δv < 0.01, the small-step limit of equations (3.34a) and (3.35a) tend to the following simpler differential formulas:

$$DGD(v) = \frac{1}{\pi \delta v} \left( \alpha_{ds} \sqrt{\frac{\langle \Delta T_e^2(v) \rangle_{SOP}}{\cos\theta}} \right) \quad (3.34b)$$

$$RMS\,DGD(v) = \frac{1}{\pi \delta v} \arcsin\left( \alpha_{ds} \sqrt{\frac{\langle \Delta T_e^2(v) \rangle_{SOP,v}}{\cos\theta}} \right) \quad (3.35b)$$

A mean DGD or rms DGD may be computed by averaging DGD(v) (obtained from equations (6.1) or (6.8)) over many different midpoint optical frequencies across a prescribed optical frequency range, such as $$rms\,DGD = \sqrt{\langle DGD^2(v) \rangle_v} \quad (3.36a)$$

$$mean\,DGD = \langle DGD(v) \rangle_v \quad (3.36b)$$

It should be noted that the two analyzer axes may also be oriented in exactly the same direction or even replaced by only one polarization analyzer followed by a coupler 21 and two detectors A and B (22B and 22C) as shown in the implementation of FIG. 1C.

3.3 Embodiment (2)

Partial DGD Measurement and PMD Estimation Therefrom

3.3.1 Method of Operation

The method of operation for the instrument for DGD measurement and PMD measurement, illustrated schematically in FIG. 2K, will now be described in more detail.

The user first inserts the test module in the platforms, then starts testing software to cause the system to initialize the test module, specifically initializing the analyzing means, the detection and processing sections. Then the analyzer-and-detection module (e.g. FTB-5240BP Optical Spectrum Analyzer sold by EXFO Inc., comprising a polarization controller just "downstream" from its input 10) is connected to a point in the optical link that is usually tapped from a network transmission line (i.e. a monitor port 26 or 27, as shown in FIG. 11) or at the distal end of an optical path (i.e. at a receiver (Rx) side 28) by patch cords with either a PC or an APC connector (such as FC/PC or FC/APC), or direct bulkhead connectors, are used to connect the test module 10. Most instrument parameters will usually be factory set according to customer requirements, but the user may manually select parameters for analyzer in its application interface. Assuming that the user selects manual parameter setting, the program proceeds to the manual parameter setting and prompts the user as follows:
(a) Set a scan wavelength range, e.g. C-band.
(b) Set the number K of OSA scans or states of polarization (A-SOP). For example, K may be set as 3 to 10,000.
(c) Set an overall total acquisition number of $DGD_P$ monitoring and PMD measurement as well as its waiting time between any two monitoring and measurements.
(d) Set a SUT bandwidth, e.g. 1, or 3, or 10, or 20 dB, or 30 dB, for a computation of weighting average of $DGD_P$ value over a SUT bandwidth from measured $DGD_P(\lambda)$ and signal spectrum $S(\lambda)$ (i.e. set a SUT bandwidth for $DGD_P(\lambda)$ and $S(\lambda)$ monitoring and measurement).

If, in decision step, the user selects automatic parameter setting, the program starts the auto parameter setting procedure and carries out the following steps. Auto mode may also be designed to automatically provide the cable or fiber name and/or associated relevant information.

Once the measurement parameters have been entered, whether manually or automatically, the program proceeds and computes wavelength step δλ (or frequency difference δv) if the anticipated $DGD_P$, PMD-induced penalty, and total PMD values have been specified or estimated via the aforementioned auto-setting procedure, and the appropriate sequence of wavelengths λs based on the parameter settings.

For the case of estimating a PMD penalty, user may also need to select or set the dimensionless parameter(s) (e.g. the factor A in Equation (2.27)) according to experiment (reference/calibration) or simulations for the SUTs.)

Finally, all the measurement parameters, whether directly specified or computed as described above, are stored in the header of the data file or instrument.

It should be noted that the spectral resolution bandwidth (RBW) of the tunable optical filters will usually be set, in the factory or by design, and will normally be quite small (e.g. of 20 to 80 pm) in order to ensure the ability to measure a high $DGD_P$ or PMD.

It should be noted that, conveniently, at each SOP and/or center wavelength, the frequency difference $\delta\nu$ (or wavelength step $\delta\lambda$) between the two closely-spaced optical frequencies $\nu_U$ and $\nu_L$ (wavelengths $\lambda_U$ and $\lambda_L$) may remain the same or similar. Each SOP and/or wavelength may only be set in a short time period.

It should be re-emphasized, that in order to obtain a reliable $DGD_P$ measurement for a SUT 60 and PMD measurement of the optical link 24, it is preferable that the acquisition should be undertaken for several or many A-SOPs, and/or different center (i.e. midpoint) wavelengths. Preferably, for PMD measurement of an optical fiber link, the acquisition may also be undertaken over an extended duration (encompassing environmental changes and perturbations) so as to improve the PMD measurement accuracy and it is especially critical if the measurement is undertaken with a very limited number of SUTs, e.g. only one SUT being available.

It should note the above steps may obtain $DGD_P$ at given midpoint wavelength or $DGD_P$ as function of wavelength or as well as to obtain rms $DGD_P$ over a multiplicity of SUTs (and thereby a PMD estimate) that may be computed as the method described in below sections that may also be included in data processing step.

3.3.2 Data Processing and Computation

The powers are processed to obtain the $DGD_P$ of a SUT 60 and PMD value of a lightpath 24 in a DWDM optical network as will now be described. It should be noted that, in all that follows, the symbols refer to the matrix "Data". The labels x and y refer to the light powers obtained from photodetectors $PD_x$ 22B and $PD_y$ 22C, respectively.

3.3.2.1 Using Two Repeated Powers

3.3.2.1.1 Normalized Powers

The normalized powers, labelled hereinafter as T, are computed differently according to the particular embodiment.

(i) For the embodiment of FIG. 2K (two tunable filters $TF_x$ 27B and $TF_y$ 27C and two photodetectors $PD_x$ 22B and $PD_y$ 22C with a PBS 20C), the transmission values (normalized power) are computed as follows either $$T_L^{(k)} = \frac{Px_L^{(k)}}{Px_L^{(k)} + Py_L^{(k)}} \quad T''_L^{(k)} = \frac{Px''_L^{(k)}}{Px''_L^{(k)} + Py''_L^{(k)}} \quad (3.37a)$$

$$T_U^{(k)} = \frac{Px_U^{(k)}}{Px_U^{(k)} + Py_U^{(k)}} \quad T''_U^{(k)} = \frac{Px''_U^{(k)}}{Px''_U^{(k)} + Py''_U^{(k)}}$$

or $$T_L^{(k)} = \frac{1}{2} \cdot \frac{Px_L^{(k)} - Py_L^{(k)}}{Px_L^{(k)} + Py_L^{(k)}} \quad T''_L^{(k)} = \frac{1}{2} \cdot \frac{Px''_L^{(k)} - Py''_L^{(k)}}{Px''_L^{(k)} + Py''_L^{(k)}} \quad (3.37b)$$

$$T_U^{(k)} = \frac{1}{2} \cdot \frac{Px_U^{(k)} - Py_U^{(k)}}{Px_U^{(k)} + Py_U^{(k)}} \quad T''_U^{(k)} = \frac{Px''_U^{(k)} - Py''_U^{(k)}}{Px''_U^{(k)} + Py''_U^{(k)}}$$

where it should be appreciated that the different $P_y$ powers have been pre-multiplied by a factory calibration factor or a measured relative gain using many measured powers for a large number of A-SOPs, before they are used in equations (3.37a) and (3.37b).

(ii) For the embodiment of FIG. 2I (single tunable filter 27 and single photodetector 22 with linear polarizer 20A), the only available powers are the Px powers (obtained here from photodetector 18). The normalized power is obtained as in Eq. (3.37c) but without computing the ratio of power x over power y first, i.e.

$$T_L^{(k)} = u_0 \frac{Px_L^{(k)}}{\langle P_L \rangle_{SOP}} \quad T''_L^{(k)} = u_o \frac{Px''_L^{(k)}}{\langle P_L \rangle_{SOP}} \quad (3.37c)$$

$$T_U^{(k)} = u_0 \frac{Px_U^{(k)}}{\langle Px_U \rangle_{SOP}} \quad T''_U^{(k)} = u_o \frac{Px''_U^{(k)}}{\langle P_U \rangle_{SOP}}$$

where $u_0 = \frac{1}{2}$, and the average power is defined as, $$\langle P_L \rangle_{SOP} = \frac{1}{2K} \sum_k \left( Px_L^{(k)} + Px''_L^{(k)} \right) \quad (3.37d)$$

$$\langle P_U \rangle_{SOP} = \frac{1}{2K} \sum_k \left( Px_U^{(k)} + Px''_U^{(k)} \right)$$

Here, the detected power is assumed to be roughly constant during the time period for measurement of the initial and repeated powers and the same requirement for the above (i) normalization.

Fundamentally all of these relationships are valid if sufficiently random output SOP scrambling is applied, yielding an accurate estimate of $DGD_P$ at one particular midpoint wavelength, and then it is possible to obtain $DGD_P$ against midpoint wavelength within a SUT bandwidth. Therefore, one can also compute a spectral-power-weighted mean $DGD_P$ or rms $DGD_P$ value for SUT 60.

3.3.2.1.2 Signal Power Spectrum

In order to monitor a traffic signal (SUT 60) PMD penalty, one must compute the "signal-only" power as a function of frequency, i.e. $S(\nu)$, and it is computed differently according to the embodiment.

(i) For the embodiment of FIG. 2K (two tunable filters 27B and 27C and two photodetectors 22B and 22C with a PBS 20C), the transmitted signal power as a function of frequency, $\nu$, is computed as follows $$S(\nu) = \langle |Px(\nu) - Py(\nu)| \rangle_{SOP} S(\nu) = \langle |Px''(\nu) - Py''(\nu)| \rangle_{SOP} \quad (3.38a)$$

or $$S(\nu) = \sqrt{\langle |Px(\nu) - Py(\nu)|^2 \rangle_{SOP}} S(\nu) = \sqrt{\langle |Px''(\nu) - Py''(\nu)|^2 \rangle_{SOP}} \quad (3.38b)$$

or, alternatively, a transmitted signal power may be calculated maximum and minimum power measurements for a large number of A-SOPs as $$S(v)=\max[Px(v),Py(v),Px''(v),Py''(v)]-\min[Px(v),Py(v),Px''(v),Py''(v)] \quad (3.38c)$$

If there is a negligible ASE, for example an OSNR 〉 20 dB, the S(v) of the signal power spectrum may be calculated from an average over two measured optical power at each wavelength from two detectors for any A-SOP as:

$$S(v)=Px(v)+Py(v) \quad (3.38d)$$

or averaging a number of A-SOPs as:

$$S(v)=\langle Px(v)+Py(v)\rangle_{SOP} \quad (7.38d')$$

(ii) For the embodiment of FIG. 2I (single tunable filter 27 and single photodetector 22 with linear polarizer 20A), the only available powers are the Px powers (obtained here from photodetector 22). The transmitted signal power as a function of frequency, v, is computed as follows $$S(v)=\langle |Px(v)_{SOP}-Px(v)_{SOP'}|\rangle_{SOP} \quad (3.38e)$$

or $$S(v)=\sqrt{\langle (Px(v)_{SOP}-Px(v)_{SOP'})^2\rangle_{SOP}} \quad (3.38f)$$

where $Px(v)_{SOP}-Px(v)_{SOP'}$ is a power difference value between two measured powers from two power measurements for two different A-SOPs by single photodetector 22.

Alternatively, a transmitted signal power may be calculated maximum and minimum power measurements for a large number of A-SOPs as $$S(v)=\max[Px(v),Px''(v)]-\min[Px(v),Px''(v)] \quad (3.38g)$$

If there is a negligible ASE, for example where OSNR 〉 20 dB (e.g. as defined, by convention, in a bandwidth of 0.1 nm), the S(v) of the signal power spectrum may be calculated from an average over at least one preferably over a large of number of measured optical powers at each wavelength as:

$$S(v)=\langle P(v)\rangle_{SOP} \quad (3.38h)$$

It should be appreciated that the calculated spectral power, S(v), in equations (11a-h) may be multiplied by any factor that is constant for all optical frequencies within an optical-frequency range of interest.

It should be also appreciated that S(v) is a calculated signal-related intensity (spectrum) at each midpoint wavelength or frequency. Or, otherwise, such P(v) must be measured in order to compute an accurate signal power (intensity) spectrum, S(v).

3.3.2.1.3 Relative Variance

The relative variance, for example arising from un-polarized ASE from optical amplifiers and/or nonlinear effect (e.g. XPM) induced signal depolarization in the optical path (or any other depolarizing effects) is computed here as the average of the two available estimates, i.e., $$\sigma_r^2(v) = 12\left[\frac{\delta(T_L(v))+\delta(T_u(v))}{2}\right] \quad (3.39)$$

where $$\delta(T_L(v))=[\langle T_L(v)T_L''(v)\rangle_{SOP}-\langle T_L(v)\rangle^2_{SOP}]$$

$$\delta(T_L(v))=[\langle T_U(v)T_U''(v)\rangle_{SOP}-\langle T_U(v)\rangle^2_{SOP}]$$

These equations are valid when the A-SOPs are approximately uniformly distributed on the Poincaré Sphere.

It should be noted that noise variance may also be calculated by using the above-obtained normalized power and is then subtracted from the above estimation of the relative variance (equation 7.39) to obtain a noise-free relative variance.

3.3.2.1.4 Mean-Square Differences

The calculation here differs from the simple mean-square found in equation (2.2) which, for greater clarity, did not take into account the noise. Instead, the product of the repeated differences between normalized power at $\lambda_U$ and $\lambda_L$ is averaged as follows, $$\langle \Delta T^2(v)\rangle_{SOP} = \langle (T_U(v)-T_L(v))(T_U''(v)-T_L''(v))\rangle_{SOP} = \quad (3.40)$$

$$\frac{1}{K}\sum_k \left((T_U^{(k)}(v)-T_L^{(k)}(v))(T''_U^{(k)}(v)-T''_L^{(k)}(v))\right)$$

In conventional mathematical terms, equations (3.40) may be referred to as the second-order joint moment of the repeated differences.

The formula of Equation (3.40) leads to the noise being averaged to zero instead of being "rectified", since the noise superimposed on a given trace is not correlated with the noise superimposed on the corresponding repeated power. That is the first motivation for acquiring repeated data.

It should be noted that $\langle\ \rangle_{SOP}$ in Eq. (3.40) refers to an average over the A-SOP at a given midpoint frequency ($v_{mid}$) (i.e. midpoint wavelength, $\lambda_{mid}$), i.e., only changing the output SOP from one group of powers to other, which is particularly appropriate for determining the $DGD_P$ at this wavelength.

3.3.2.1.5 Computation of the $DGD_P$ Value of a SUT

The $DGD_P$ as a function optical frequency for a fixed given launched polarization of a SUT can be calculated according to the arcsine formula as, $$\tau_{PB}(v) = \frac{1}{\pi\delta v}\arcsin\left(\sqrt{3\frac{\langle \Delta T^2(v)\rangle_{SOP}}{\sigma_r^2(v)}}\right) \quad (3.41)$$

where $\langle\ \rangle_{SOP}$ refers to an average taken over A-SOP only.

To obtain the $DGD_P$ parameter to estimate a PMD penalty, an average over computed $DGD_P$ in equation (15) over signal (SUT 60) bandwidth with the spectral intensity (density) weighting can be expressed as:

$$\overline{\tau_{PB}}_{SUT} = \frac{\int_v S(v)\tau_{PB}(v)dv}{\int_v S(v)dv} \quad (3.42a)$$

The light power spectral weighting average in equation (3.42a) can be performed over any pre-defined SUT bandwidth, e.g. −3 dB to −10 dB, or as wide as possible, however, in practice, for example, a −20 dB or −10 dB or −3 dB bandwidth may be chosen. It should be noted that in practice it is preferably to use a signal spectral 'mean' averaging shown equation (3.42a).

Alternatively, if S(v) is set to equal to a constant value (e.g. 1) for above equations (3.42a), a mean $DGD_P$ value over a specified wavelength range of a SUT bandwidth is expressed as:

$$\bar{\tau}_{PB_{SUT}} = \langle \tau_{PB}(v) \rangle_v \tag{3.42b}$$

or alternatively an rms $DGD_P$ value as:

$$\bar{\tau}_{PB_{SUT}} = \sqrt{\langle \tau_{PB}^2(v) \rangle_v} \tag{3.42c}$$

where $\langle \ \rangle_v$ is to average over a specified wavelength range, e.g. of a SUT bandwidth.

It should be appreciated that the arcsine formula, in equation (3.41), is not the only possible one. The purpose of using this formula is to obtain a result that is unbiased even if using a relatively large step (e.g. such that $DGD_P \cdot \delta v \sim 0.20$), without introducing a significant error;

this in order to maximize the signal-to-noise ratio and therefore the dynamic range of the instrument. Although applicable to any step size, if one were not concerned with maximizing the dynamic range, one could select a small step, in which case the following simpler differential formula is valid:

$$\tau_{PB}(v) = \frac{1}{\pi \delta v} \sqrt{3 \frac{\langle \Delta T^2(v) \rangle_{SOP}}{\sigma_r^2(v)}} \tag{3.41a}$$

This is not to infer that this formula is better or particularly advantageous, but merely that it may conveniently be used if the step is much smaller, i.e., satisfying the condition $DGD_P \cdot \delta v < 0.01$.

It should be noted that in an ideal situation where there is no depolarization (i.e. no ASE or other depolarizing phenomena) and no effective depolarization due to rapid temporal fluctuations (e.g. due to rapidly moving aerial cable), then $\sigma_r^2 = 1$ can be used in equations (3.41) and (3.41a) above (and, in analogous fashion, in equations (3.44b) and (3.44c) in sub-section 3.3.2.1 below).

For the case where the tunable filter(s) has/have a relatively large bandwidth(s) (i.e. RBW) and a high-$DGD_P$ is being monitored, a further RBW 'correction factor' may be applied in equations in order to extract a $DGD_P$ value of the SUT 60.

It should also be noted that repeated powers may be obtained from two or more measurements at different times using the same detectors, or from measurements using different detectors, e.g. after light power being split by an optical coupler, where the powers detected by the different detectors are measured contemporaneously.

3.3.2.1.6 Computation of the PMD Penalty of a SUT from an Average $DGD_P$ Value Over a Signal Bandwidth Based on above computed average $DGD_P$ value over a specified wavelength range, (typically corresponding to the SUT bandwidth) in equations (3.42a), (3.42b), (3.42c) or (3.42d), a PMD-induced impairment of a SUT due to pulse broadening from a relative time delay of two orthogonally polarization components propagating along the lightpath may be expressed as a PMD-induced power penalty, $\eta$, as:

$$\eta = A \cdot \left(\frac{\bar{\tau}_{PB_{SUT}}}{2B}\right)^2 \tag{3.43}$$

where a PMD power penalty, $\eta$, is expressed in dB, which is assumed small, and B is a bit interval, i.e. bit period, and A may be a predetermined dimensionless parameter that may depend on modulation format, pulse shape, network characteristics (e.g. optical noise, optical filter, etc.), and receiver characteristics (e.g. electric filter, noise, etc.).

It should be appreciated that the above equation (3.43) is not the only possible one, and it may be expressed as any other formula.

3.3.2.1.7 Computation of the PMD Value of a Fiber Link

From above computed DGD at each wavelength as described above section 1.5, a link PMD in a network may also be determined, specifically estimated, by averaging $DGD_P$ over a prescribed wavelength range encompassing the central wavelengths of a multiplicity of SUTs (e.g. DWDM signals) as, $$PMD = \sqrt{\frac{3}{2} \langle \tau_{PB}^2(v) \rangle_v} \tag{3.44a}$$

or $$PMD = \frac{1}{\pi \delta v} \arcsin\left(\sqrt{\frac{9}{2} \left\langle \frac{\Delta T^2(v)}{\sigma_r^2(v)} \right\rangle_{SOP;v}}\right) \tag{3.74b}$$

where equation (3.44a) is averaged measured $DGD_P$ over a large number of SUT bandwidths and equation (3.44b) is a (directly) average from measured normalized power difference over both A-SOP and optical frequency.

It should be appreciated that the arcsine formula, in equation (3.43), is not the only possible one. The purpose of using this formula is to obtain a result that is unbiased, i.e. does not introduce significant error, even if the separation between the above-described closely-spaced optical frequencies is relatively large step, e.g. such that $PMD \cdot \delta v \sim 0.15$. However, if a much smaller step is selected, the following alternative and simpler differential formula is valid and may be applied:

$$PMD = \frac{1}{\pi \delta v} \sqrt{\frac{9}{2} \left\langle \frac{\Delta T^2(v)}{\sigma_r^2(v)} \right\rangle_{SOP;v}} \tag{3.44c}$$

This is not to infer that these formulas are better or particularly advantageous, but merely that it may conveniently be used if the step is much smaller, i.e., satisfying the condition $PMD \cdot \delta v \langle 0.01$.

Alternatively, PMD of the link may be roughly estimated by averaging these measured $DGD_P$ from a single channel signal (SUT) over a time period sufficiently long that environmental fluctuations may be significant. Such fluctuations may lead to variation of SUT polarization at the input or along the length of the lightpath, and/or variation of PSP axis of the lightpath, and/or DGD variations. In such a case, the PMD may be estimated as:

$$PMD = \sqrt{\frac{3}{2} \langle \tau_{PB}^2(v) \rangle_{(t,v)}} \quad (3.44a')$$

where $\langle\ \rangle_{(t,v)}$ indicates an average over time (t), and/or signal light polarization fluctuation, and or wavelength (optical frequency) over the SUT bandwidth.

It should also be noted that a measured PMD accuracy can be further improved if equations (3.44a), (3.44b) and (3.44c) are further averaged over one or more of time and over possible random variations of the launched SOP of the SUT (i.e. φ) and/or possible variations of the SOP along the link caused by cable movement, etc.

3.3.2.2 Employing Two Physically Orthogonal Polarization Analyzers from a Polarization Beam Splitter with Rapid Wavelength Sweeping In practice, an instrument can be designed in accordance with the configuration illustrated in FIG. 2K, employing polarization-diverse detection and rapid wavelength sweeping, where the wavelength of the detected light is swept over a prescribed wavelength range, e.g. by tunable filters. Each light powers from the SUT, obtained with either one given setting of the wavelength from tunable filter 27B and tunable filter 27C (FIG. 2K) and of the A-SOPs by an A-SOP controller 14B, constitutes an elementary data cell, i.e. one datum consists of one power value. The data unit is one group of N powers, two sets of N powers for the embodiment of FIG. 2K where two powers are obtained substantially simultaneously from two photodetectors 22B and 22C, both acquired with given approximately same SOP as set by an A-SOP controller 14B.

The powers are processed to obtain the $DGD_F(v)$ value of the SUT 60 and PMD value of the optical path using detected two physically orthogonal (i.e. antipodal on the Poincaré sphere) polarization components from PBS 20C by rapid wavelength sweeping of tunable filter means comprising tunable filters 27B and 27C (see FIG. 2K), as will now be described. The labels x and y refer to the probed light powers obtained from photodetectors 22B and 22C, respectively.

3.3.2.2.1 Normalized Powers

The transmissions (normalized powers), labelled as $T_x$ and $T_y$, are computed for the embodiment of FIG. 2K for two photodetectors 22B and 22C with a PBS 20C as follows either $$T_x^{(k)}(v) = \frac{P_x^{(k)}(v)}{\langle P_x^{(k)}(v) + P_y^{(k)}(v) \rangle_{SOP}} \quad (3.45a)$$

$$T_y^{(k)}(v) = \frac{P_y^{(k)}(v)}{\langle P_x^{(k)}(v) + P_y^{(k)}(v) \rangle_{SOP}}$$

or $$T_x^{(k)}(v) = \frac{P_x^{(k)}(v)}{u_0 \langle P_x^{(k)}(v) \rangle_{SOP}} \quad T_y^{(k)}(v) = \frac{P_y^{(k)}(v)}{u_0 \langle P_y^{(k)}(v) \rangle_{SOP}} \quad (3.45b)$$

where $\langle\ \rangle_{SOP}$ refers to an average over all or many analyzer SOPs (A-SOPs) at a given optical frequency v, and the reference mean-value is $u_o = \frac{1}{2}$. Equations (3.45a) and (3.45b) assume that the measured overall total power, i.e. the sum of the two detected polarization-diverse powers, corresponding respectively to orthogonal polarization components x and y, is stable throughout the acquisition time.

Alternatively, the transmission values (normalized powers) may be written as:

$$T_x^{(k)}(v) = \frac{P_x^{(k)}(v)}{P_x^{(k)}(v) + P_y^{(k)}(v)} \quad T_y^{(k)}(v) = \frac{P_y^{(k)}(v)}{P_x^{(k)}(v) + P_y^{(k)}(v)} \quad (3.45c)$$

Consequently, the so-obtained transmission values (normalized powers) advantageously exhibit little or negligible dependence on possible instabilities in the transmitter light power over the monitoring/measurement time.

It should be noted that above normalized power is computed at each optical frequency (v), i.e. from one wavelength to others, for the entire optical frequency range. This is because there may be different measured optical-power levels and optical-noise (i.e. ASE) levels at different frequencies (wavelengths), especially if the measurement is performed within a narrow optical channel, e.g. a DWDM channel, so that their relative variance may be different from one optical frequency to another.

3.3.2.2.2 Signal Power Spectrum

In order to monitor a traffic signal (SUT) PMD penalty, one must compute signal-only power as a function of frequency, i.e. S(v), and preferably S(v) is calculated at each midpoint wavelength or frequency. For the embodiment of FIG. 2K, comprising two tunable filters (27B, 27C), two photodetectors (22B, 22C) and PBS 20C, the transmitted signal power as a function of optical frequency, v, is computed as follows $$S(v) = \langle |P_x^{(k)}(v) - P_y^{(k)}(v)| \rangle_{SOP} \quad (3.46a)$$

or $$S(v) = \sqrt{\langle (P_x^{(k)}(v) - P_y^{(k)}(v))^2 \rangle_{SOP}} \quad (3.46b)$$

or, alternatively, a transmitted signal power may be calculated maximum and minimum power measurement method, e.g. polarization nulling, for a large number of A-SOPs as $$S(v) = \max[P_x^k(v), P_y^k(v)]_{SOP} - \min[P_x^k(v), P_y^k(v)]_{SOP} \quad (3.47)$$

If the ASE power is negligible, for example when OSNR 〉 20 dB, the S(v) of the signal power at each wavelength and for any A-SOP, may be calculated by the sum of the powers measured with the two photodetectors $PD_x$ 22B and $PD_y$ 22C as $$S(v) = P_x^{(k)}(v) + P_y^{(k)}(v) \quad (3.48)$$

Alternatively, an average over measured optical powers at each wavelength for at least two A-SOPs may be expressed as $$S(v) = \langle (P_x^{(k)}(v) + P_y^{(k)}(v)) \rangle_{SOP} (22a) S_x(v) =$$
$$\langle P_x^{(k)}(v) \rangle_{SOP} \quad (3.49b)$$

$$S_y(v) = \langle P_y^{(k)}(v) \rangle_{SOP} \quad (3.49c)$$

where equations (3.49b) and (3.49c) can also be applied for the embodiment of FIG. 2I where one tunable filter 27 and one photodetector 22 with a linear polarizer 20A are used.

It should be appreciated that the calculated spectral power, S(v), in equations (3.46), (3.47), (3.48) and (3.49)

may be multiplied by any factor, but this factor should be the same for any optical frequency within the optical-frequency range of interest for further application of a computation of the spectrally-weighted average $DGD_P$ for estimating a PMD penalty of a SUT 60.

As well, the calculated S(v) in above equations (3.46 to 3.49) should be at each midpoint wavelength or frequency that corresponds to a middle-point wavelength of computed $DGD_P$.

3.3.2.2.3 Relative Variance

The relative variance arises principally from (un-polarized) ASE from optical amplifiers, polarization noise, especially for high-density DWDM networks, depolarization induced by nonlinear effects (e.g. XPM). It may be computed at each optical frequency as $$\sigma_r^2(v) = 12\left[-1 \cdot \langle T_x(v)T_y(v)\rangle_{SOP} + \frac{1}{4}\cdot\langle T_x(v)+T_y(v)\rangle_{SOP}^2\right] \quad (3.50a)$$

or $$\sigma_r^2(v) = 12\lfloor -1\cdot(T_x(v)T_y(v))_{SOP} + \langle T(v)\rangle_{SOP}^2 \rfloor \quad (3.50b)$$

where $\langle\ \rangle_{SOP}$ refers to an average over all or many A-SOPs at each given optical frequency v, and $\langle T(v)\rangle_{SOP}$ refers to an average over all or many output SOPs at each given optical frequency, v, for these transmissions (normalized powers) measured from two photodetectors 22B and 22C.

Advantageously, the above computed relative variance exhibit negligible or minimal dependence on noise in the detected powers. However, assuming negligible noise from the measured powers for each of the two polarization-diverse detectors 22B, 22C (corresponding to x and y, respectively), relative variance may be obtained as $$\sigma_r^2(v) = 12\left[\frac{\langle T_x^2(v)\rangle_{SOP} + \langle T_y^2(v)\rangle_{SOP} - 2\cdot\langle T(v)\rangle_{SOP}^2}{2}\right] \quad (3.51a)$$

$$\sigma_{r,x}^2(v) = 12\lfloor \langle T_x^2(v)\rangle_{SOP} - (T_x(v))_{SOP}^2 \rfloor \quad (3.51b)$$

$$\sigma_{r,y}^2(v) = 12\lfloor \langle T_y^2(v)\rangle_{SOP} - \langle T_y(v)\rangle_{SOP}^2 \rfloor \quad (3.51c)$$

It should be noted that Equation (3.51b) or (3.51c) can be applied to the embodiments of FIG. 2I where the PBS 14 is replaced by a linear polarizer 15 and only one photodetector PD 18 is employed.

Also note that after averaging over sufficient large number of output SOPs (A-SOPs), relative variances being obtained from equations (3.51a), (3.51b) and (3.51c) are equal, i.e. $\sigma_r^2(v) = \sigma_{r,x}^2(v) = \sigma_{r,y}^2(v)$.

3.3.2.2.4 Equalization of Normalized Powers

The transmission values (or normalized powers) computed in Section 2.1 have not undergone an "equalization" procedure, i.e. they may be affected by ASE and any signal-depolarizing effects, e.g. depolarization induced by inter-channel XPM, etc., therefore they may not be equalized between 0 and 1. However, to compute the $DGD_P$ of the SUT 60 and therefrom the PMD of the optical link 24 as used in equations (24a) and (24b) below, the measured transmission values (or normalized powers) must be equalized so as to be uniformly distributed between 0 and 1 if the A-SOPs are themselves substantially uniformly distributed on the Poincare sphere. This equalization procedure applied to the normalized powers thus effectively acts to remove any 'depolarization' effects on the polarized signal-under-test (SUT) 60. These equalized transmission values (or equalized normalized powers) are then can be directly used to calculate the mean-square difference for the $DGD_P$ and PMD computations.

The equalized transmissions (or equalized normalized powers), labelled as $T_{e,x}$ and $T_{e,y}$, are computed for the implementation of FIG. 2K for two photodetectors 22B and 22C with a PBS 14 as follows $$T_{e,x}^{(k)}(v) = \frac{T_x^{(k)}(v)}{\sigma_r(v)} - \frac{1}{2}\cdot\left(\frac{1}{\sigma_r(v)} - 1\right) \quad (3.52a)$$

$$T_{e,y}^{(k)}(v) = \frac{T_y^{(k)}(v)}{\sigma_r(v)} - \frac{1}{2}\cdot\left(\frac{1}{\sigma_r(v)} - 1\right)$$

where $\sigma_r(v)$ can be obtained from equations (3.50).

Under the assumption of negligible noise contribution in the power detected by the polarization-diverse detectors, the equalized transmission values (or equalized normalized powers) may also be expressed as $$T_{e,x}^{(k)}(v) = \frac{T_x^{(k)}(v)}{\sigma_{r,x}(v)} - \frac{1}{2}\cdot\left(\frac{1}{\sigma_{r,x}(v)} - 1\right) \quad (3.52b)$$

$$T_{e,y}^{(k)}(v) = \frac{T_y^{(k)}(v)}{\sigma_{r,y}(v)} - \frac{1}{2}\cdot\left(\frac{1}{\sigma_{r,y}(v)} - 1\right)$$

where $\sigma_{r,x}(v)$ and $\sigma_{r,y}(v)$ can be obtained from equations (3.51).

Note that equation (20b) can be applied to the implementation of FIG. 2I in which the PBS 20C is replaced by a linear polarizer 20A and only one photodetector 22 is used.

It should be noted that the equalization of the transmission values (or normalized powers) needs to be performed at each optical frequency, since relative variance is in general not constant for different optical frequencies (wavelengths), especially for example for a narrow SUT bandwidth in the in-service DWDM network with a high ASE from optical amplifiers. However, if there is no difference for relative variance against optical frequency (wavelength), an averaged relative variance may be calculated.

3.3.2.2.5 Mean-Square Differences

The calculation of mean-square differences using equalized transmissions (or equalized normalized powers), $T_{e,x}$ and $T_{e,y}$, from two photodetectors 22B and 22C with a PBS 20C for the embodiments of FIG. 2K, can be expressed as $$\langle \Delta T_e^2(v)\rangle_{SOP} = \left\{-1\cdot\left(T_{e,x}^{(k)}\left(v+\frac{1}{2}\delta v\right) - T_{e,x}^{(k)}\left(v-\frac{1}{2}\delta v\right)\right)\cdot \right. \quad (3.53)$$

$$\left.\left(T_{e,y}^{(k)}\left(v+\frac{1}{2}\delta v\right) - T_{e,y}^{(k)}\left(v-\frac{1}{2}\delta v\right)\right)\right\}_{SOP} =$$

$$-\frac{1}{K}\sum_k\left(\left(T_{e,x}^{(k)}\left(v+\frac{1}{2}\delta v\right) - T_{e,x}^{(k)}\left(v-\frac{1}{2}\delta v\right)\right)\cdot\right.$$

$$\left.\left(T_{e,y}^{(k)}\left(v+\frac{1}{2}\delta v\right) - T_{e,y}^{(k)}\left(v-\frac{1}{2}\delta v\right)\right)\right)$$

where K is total output SOPs (A-SOPs).

As shown in equation (3.53), by using equalized transmissions (or equalized normalized powers), $T_{e,x}$ and $T_{e,y}$, to compute the mean-square difference for the PBS-based implementation of FIG. 2K with two photodetectors, the noise averages to zero instead of being 'rectified', because the noise superimposed on a measured power by one detector is not correlated with the noise superimposed on the measured power by a different detector. That is achieved by acquiring data with different detectors x and y (22B and 22C).

Equalized transmission values (or equalized normalized powers) obtained from one photodetector connected either after one of two ports of a PBS or after a linear polarizer, for example for implementation in FIG. 2I where only one photodetector PD 18 (e.g. that corresponding to x or y in equations (3.54a) or (3.54b), respectively) is employed, can also be used to calculate mean-square difference as, $$\langle \Delta T_e^2(v) \rangle_{SOP} = \left\{ \left( T_{e,x}^{(k)}\left(v+\frac{1}{2}\delta v\right) - T_{e,x}^{(k)}\left(v-\frac{1}{2}\delta v\right) \right)^2 \right\}_{SOP} \quad (3.54a)$$

$$= \frac{1}{K} \sum_k \left( \left( T_{e,x}^{(k)}\left(v+\frac{1}{2}\delta v\right) - T_{e,x}^{(k)}\left(v-\frac{1}{2}\delta v\right) \right)^2 \right)$$

$$\langle \Delta T_e^2(v) \rangle_{SOP} = \left\{ \left( T_{e,y}^{(k)}\left(v+\frac{1}{2}\delta v\right) - T_{e,y}^{(k)}\left(v-\frac{1}{2}\delta v\right) \right)^2 \right\}_{SOP} \quad (3.54b)$$

$$= \frac{1}{K} \sum_k \left( \left( T_{e,y}^{(k)}\left(v+\frac{1}{2}\delta v\right) - T_{e,y}^{(k)}\left(v-\frac{1}{2}\delta v\right) \right)^2 \right)$$

where K is total A-SOPs. Equations (3.54a) and (3.54b) are under an assumption of negligible noise for the measured powers for the photodetector PD (18) of FIG. 2I or each individual detectors of $PD_x$ or $PD_y$ (22B and 22C) in FIG. 2I.

Note that an angle $\phi$ is related to launched polarization of a SUT 60, i.e. a signal polarization dependent parameter, that is usually kept constant during an acquisition time, however, if $\phi$ is varied in an acquisition time period, an averaged value of rms or mean difference (as well of $DGD_P$ and PMD) over varied angle $\phi$ may be obtained.

Note that $\langle \ \rangle_{SOP}$ in above equations refer to only averaging over the SOP at a given midpoint frequency ($v_{i,mid}$) (or midpoint wavelength, $\lambda_{i,mid}$), i.e., only changing the A-SOP from one group of powers to another.

3.3.2.2.6 Computation of the $DGD_P$ Value of SUT Using Mean-Square Differences of Equalized Transmissions The $DGD_P(v)$, $\tau_{PB}(v)$, is computed according to the arcsine formula from calculated mean-square differences using equalized transmissions (or equalized normalized powers) for the embodiments of FIG. 2K with PBS 20C and two photodetectors 22B and 22C as, $$\tau_{PB}(v) = \frac{1}{\pi \delta v} \arcsin\left(\sqrt{3 \cdot \langle \Delta T_e^2(v) \rangle_{SOP}}\right) \quad (3.55a)$$

where $\langle \ \rangle_{SOP}$ refers to average over the A-SOPs only, $\delta v = v_{i+n} - v_i$, an optical frequency difference between two closely-spaced optical frequencies, $v_i$ and $v_{i+n}$, is used for computing $DGD_P$.

It should be appreciated that the arcsine formula, in above equations, is not the only possible one. This formula provides a result that is unbiased even if a relatively large optical-frequency step is used, e.g. such that $DGD_P \cdot \delta v \sim 0.20$, thereby maximizing the signal-to-noise ratio and therefore the dynamic range of the instrument. Although applicable to any step size, if one were not concerned with maximizing the dynamic range, one could select a small step, in which case the following simpler differential formula is valid:

$$\tau_{PB}(v) = \frac{1}{\pi \delta v} \sqrt{3 \cdot \langle \Delta T_e^2(v) \rangle_{SOP}} \quad (3.55b)$$

This is not to infer that this formula is better or particularly advantageous, but merely that it may conveniently be used if the optical-frequency step is much smaller, i.e., satisfying the condition $DGD_P \cdot \delta v \langle 0.01\text{-}0.05$.

It should also be noted that above equations are applicable whether or not the SUT exhibits any significant ASE (typically from optical amplifiers, and leading to signal-to-noise ratio as low as ~3 dB) or any depolarization effects etc. This insensitivity to ASE is a consequence of the equalization of the transmission values (or normalized powers) that has been performed in an earlier step.

In order to estimate the PMD-induced penalty, an average $DGD_P$ value over SUT bandwidth with the spectral power weighting can be expressed as:

$$\bar{\tau}_{PB_{SUT}} = \frac{\int_v S(v) \tau_{PB}(v) dv}{\int_v S(v) dv} \quad (3.56a)$$

where the $DGD_P$ is obtained from equation (3.55a) or (3.55b) and preferably a SUT bandwidth for such average may be defined to fall within the spectral range for which the level of the SUT spectral profile is greater than a specified number (e.g. −3 to −20 dB) with respect to the spectral peak value.

The light power spectral weighting factor, S(v), can be obtained from equations (3.46) to (3.49). Again, the average can be performed over any pre-defined SUT bandwidth, for example, from 3 dB to 10-20 dB bandwidth may be chosen.

Alternatively, if S(v) is set to equal to any constant value (e.g. 1) in equations (3.56a) above, a mean $DGD_P$ value over a specified wavelength range, e.g. of a SUT bandwidth, is obtained as:

$$\bar{\tau}_{PB_{SUT}} = \langle \tau_{PB}(v) \rangle_v \quad (3.56b)$$

or, alternatively, a rms $DGD_P$ value may be used, which is expressed as:

$$\bar{\tau}_{PB_{SUT}} = \sqrt{\langle \tau_{PB}^2(v) \rangle_v} \quad (3.56c)$$

where $\langle \ \rangle_v$ indicates an average performed over a specified wavelength range within the SUT bandwidth, e.g. −3 to −10 dB down with respect to the spectral peak power.

3.3.2.2.7 Computation of the PMD Penalty of a SUT from an Average $DGD_P$ Value Over a Signal Bandwidth Based on the above-computed average $DGD_P$ value over a specified wavelength range, e.g. of a SUT bandwidth, in equation (3.56a), (3.56b) or (3.56c), an PMD-induced impairment of a SUT due to pulse broadening from a relative time delay of two orthogonally-polarized components during transmission passing through an optical path (lightpath) of a DWDM network may be written as a PMD penalty, η, as:

$$\eta = A \cdot \left(\frac{\overline{\tau}_{PB_{SUT}}}{2B}\right)^2 \qquad (7.57)$$

where η, is expressed in dB, which is assumed small, and B is the bit (or symbol interval), and A may be a predetermined parameter, for example, that depends on modulation format, pulse shape, network characteristics (e.g. optical noise, optical filter, etc.), and receiver characteristics (e.g. electrical filter, electrical noise, etc.).

It should be appreciated that the PMD-induced system penalty, η(φ), may be alternatively expressed as:

$$\eta = A_1 \cdot \left(\frac{\overline{\tau}_{PB_{SUT}}}{2B}\right)^2 + A_2 \cdot \left(\frac{\overline{\tau}_{PB_{SUT}}}{2B}\right)^4 \qquad (3.57')$$

where a PMD power penalty, η(φ), is expressed in dB, B is a bit period, and $A_1$ and $A_2$ may be predetermined parameters, for example, that may be extracted from measurements or simulations.

It should be appreciated that the above predetermined parameters A, $A_1$ and $A_2$ in respective equations (3.57) and (3.57') may be extracted from either or both of the measured values (e.g. calibration, reference, etc.) and or simulations.

It should be appreciated that a PMD penalty in equation (3.57') may include higher-order PMD (e.g. second-order, etc.) induced penalty while a PMD penalty expressed in equation (3.57) may mainly include a first-order PMD penalty for the SUT. For example an 'equivalent' $DGD_P$, $\overline{\tau}_{PB,1st+2nd_{SUT}}$, that may replace an average $DGD_P$, $\overline{\tau}_{PB_{SUT}}$, in equation (3.57) or (3.57') may be expressed as:

$$\overline{\tau}_{PB,1st+2nd_{SUT}} = \frac{\int_v S(v)\tau_{PB}(v)dv}{\int_v S(v)dv} + \frac{\chi}{B} \cdot \frac{\int_v S(v)\left|\frac{d\tau_{PB}(v)}{dv}\right|dv}{\int_v S(v)dv} \qquad (3.56a')$$

where χ is a constant.

3.3.2.2.8 Computation of the Lightpath DGD or Link PMD Value from a Single Channel SUT $DGD_P$ Measurement Based on above-computed DGD at each wavelength in equation (3.55a) or (3.55b) and if there may be environmental fluctuations, e.g. causing variation of the SOP of the SUT, variation of the PSP axes of a lightpath of a DWDM network, and/or DGD variation, lightpath PMD in a DWDM network may also be roughly estimated by averaging $DGD_P$ over some or all of these fluctuations, e.g. over time or signal SOP fluctuations, etc., and/or over wavelength of a SUT bandwidth as, $$PMD = \sqrt{\frac{3}{2}\langle\tau_{PB}^2(v)\rangle_{(t,v)}} \qquad (3.58)$$

respectively, where τ(v) is DGD at each wavelength, and $\langle\ \rangle_{(t,v)}$ indicates an average over time (t), and/or signal light polarization fluctuation, and/or optical frequency over the SUT bandwidth.

Thus, PMD of an optical path may be roughly estimated from the $DGD_P$ measured on only a single SUT if the measurement time extends over a sufficiently long period, e.g. many hours to several days, and, in some cases, many months. However, such "single-SUT" PMD estimations generally have greater uncertainty than measurements taken concurrently over multiple, widely-spaced SUTs. A rough guide to the reliability of PMD estimation using multiple measurements with a single-SUT may be gleaned from the degree to which the measured $DGD_P$ values adhere to a Rayleigh distribution [6] over a long time.

3.3.2.2.9 Computation of the PMD Value of a Link from $DGD_P$ Measurements of Multiple SUTs Based on above-computed $DGD_P$ at each wavelength in equation (3.55a) or (3.55b) and if there may be a large number of SUTs, e.g. 2-40, a lightpath PMD in a DWDM network may also be measured or estimated by averaging $DGD_P$ over all (or some) of wavelengths corresponding to the number of SUTs, as:

$$PMD = \sqrt{\frac{3}{2}\langle\tau_{PB}^2(v)\rangle_{(v)}} \qquad (3.59a)$$

or $$PMD = \frac{1}{\pi\delta v}\arcsin\left(\sqrt{\frac{9}{2}\langle\Delta T_e^2(v)\rangle_{SOP,v}}\right) \qquad (3.59b)$$

where the equation (3.59a) is averaged measured $DGD_P$ over these wavelengths for a large number of SUT bandwidths, and equation (3.59b) is an average from measured normalized power differences over both SOP (i.e. A-SOP) and optical frequency (wavelength).

It should be appreciated that the arcsine formula, in equation (3.59), is not the only possible one. This formula permits a substantially unbiased result to be obtained even if using a relatively large step, such that PMD·δv~0.15-0.20. However, for the case where a small step is selected, the following simpler differential formula is valid:

$$PMD = \frac{1}{\pi\delta v}\sqrt{\frac{9}{2}\langle\Delta T_e^2(v)\rangle_{SOP,v}} \qquad (3.59c)$$

This is not to infer that this formula is better or particularly advantageous, but merely that it may conveniently be used if the step is much smaller, i.e., satisfying the condition PMD·δv<0.01-0.05.

It should be noted that measured PMD accuracy can be further improved if an average is performed both over time and over varied SOPs of the launched signals are applied to equations (3.59a), (3.59b) and (3.59c), as described in commonly-owned United States patent publication number US2010/0073637A1 (Cyr et al.) supra, wherein a test source is employed. However, when the launched input light is a data-carrying signal from a network Tx, it is not generally feasible to vary or control its SOP.

For the case where the tunable filters have a relatively large bandwidth (i.e. RBW) and a high-PMD is under test, a further RBW "correction factor" may be applied in equations in order to extract a PMD value of the lightpath. Thus, although optional, data "post-processing" step may correct for any bias on the measured PMD introduced by the instrumental RBW by multiplying an appropriate correction factor with an appropriate formulas or relationships that can be computed either analytically or numerically.

3.3.2.2.10 Computation of an Average of the Second-Order $DGD_P$ for Improving Link PMD Measurement Accuracy Based on above computed $DGD_P$ (i.e. a first-order $DGD_P$, $\tau_{PB}(v)$) at each wavelength in equations (3.55a) or (3.55b), it may also be possible to compute a second-order $DGD_P$ that may be written as:

$$\tau_{PB,\omega}(v) = \frac{1}{2\pi} \cdot \frac{d\tau_{PB}(v)}{dv} \tag{3.60}$$

where $\tau_{PB,\omega}(v)$ is a calculated second-order $DGD_P$.

If there are a multiplicity of SUTs, e.g. 2-40, the link PMD in a DWDM network may also be estimated from an average over some or all of the so-obtained second-order $DGD_P$ values (e.g. $\tau_{PB,\omega}(v)$ in equation (3.60)) according to a predefined function. For example, it may be expressed as:

$$PMD = C_0 \sqrt[4]{\langle \tau_{PB,\omega}^2(v) \rangle} \tag{7.61a}$$

where $C_0$ is a constant that may be obtained theoretically, or from simulation or experiment.

Advantageously, the optical-link PMD may be computed directly from second-order normalized power (i.e. transmission), $\Delta(\Delta T_e(v,\phi))$, for example, for a small frequency step it may be written as following differential formula as:

$$PMD = \frac{C_1}{\delta v} \cdot \sqrt[4]{\langle (\Delta(\Delta T_e(v)))^2 \rangle} \tag{3.61b}$$

where $C_1$ is a constant that may be obtained theoretically, or from simulation or experiment.

It should be appreciated other equations than equation (3.61a) and (3.61b)) may be used for computing PMD from either second-order $DGD_P$ or second-order normalized power difference. For instance, alternative equations may be expressed as any other formula by using second-order $DGD_P$, or second-order normalized power difference, or any other similar second-order parameter, for example, an absolute value of a second-order normalized power (i.e. transmission), $|\Delta(\Delta T_e(v,\phi))|$, may be used with different formula.

It should further be appreciated that any normalized power described in the present invention may be used in the above formula (i.e. equation (3.61b) to compute PMD and, in the case that the SUTs may be depolarized, it may be necessary to compensate for this depolarization by including relative variance, i.e. $\sigma_r^2(v)$, in the computations.

Furthermore, an accurate PMD measurement of an optical link in a network may be estimated from an average of both estimated PMD values from first- and second-order $DGD_P$ measurements or from first- and second-order normalized power difference as a predefined function. In this way, a PMD measurement uncertainty [10] may be reduced or decreased.

It should be noted that for the aforedescribed embodiment in FIG. 2K, for which the A-SOP controller 14B is operable as be a two-state polarization switch such that the successively generated pair of A-SOPs are orthogonal on the Poincare sphere (e.g. 0 degrees linear, 45 degrees linear), then a third normalized power, $T_{3,x}(v)$, related to the third Stokes component may be calculated based on the first two measured normalized powers, $T_{1,x}(v)$, and $T_{2,x}(v)$, related to their Stokes components corresponding to orthogonal analyzer A-SOPs under an assumption of negligible or known depolarized lights as:

$$T_{3,x}(v) = \frac{1}{2}\left(1 \pm \sqrt{1 - (2T_{1,x}(v) - 1)^2 - (2T_{2,x}(v) - 1)^2}\right) \tag{3.62}$$

a. where $T_{1,x}(v) = \frac{P_{1,x}(v)}{P_{1,x}(v) + P_{1,y}(v)}$, $T_{2,x}(v) = \frac{P_{2,x}(v)}{P_{2,x}(v) + P_{2,y}(v)}$, and $P_{1,x}(v)$, $P_{1,y}(v)$, $P_{2,x}(v)$, and $P_{2,y}(v)$ are measured powers after a PBS for two switchable A-SOPs, respectively, by assuming to have negligible depolarized lights or such depolarized lights being subtracted from such measured powers. Therefore, a third normalized power difference between two closely-spaced optical frequencies is ready to be computed for further calculating $DGD_P$, PMD, etc. using above described equations, e.g. Eqs (3.55), (3.58), (3.59), etc.

We point also out here that other methods may also be possible, for example to obtain a third normalized power difference from a predefined function of first two normalized powers and their differences.

3.4 Data Processing and Computation: Single-Ended Overall PMD Measurement

3.4.1 Single-Ended Overall PMD: The Data Structure

Each backreflected light power from the localized reflection (such as a Fresnel reflection) at the distal end of FUT 18, obtained with any given setting of the wavelength and of the (I-SOP, A-SOP) couples constitutes the elementary data cell, i.e. one datum consists of one power value. The next data unit is one group of four powers (i.e. four data cells), two sets of four backreflected powers for the implementations of FIG. 3C and FIG. 3G where two backreflected powers are obtained simultaneously from photodetectors 22B and 22C, all obtained with a given (I-SOP$_k$, A-SOP$_k$) as set by VA-SOP controller 14. The two sets of four powers forming group k preferably are obtained in the following sequence (time flowing from left to right):
(I-SOP$_k$, A-SOP$_k$, and/or $\lambda_k$):

| $\lambda = \lambda_L^{(k)}$ | | $\lambda = \lambda_U^{(k)}$ | |
|---|---|---|---|
| $Px_L^{(0)}$ | $Px_L''^{(0)}$ | $Px_U^{(0)}$ | $Px_U''^{(0)}$ |
| $Py_L^{(0)}$ | $Py_L''^{(0)}$ | $Py_U^{(0)}$ | $Py_U''^{(0)}$ | where the labels x and y refer to the power obtained simultaneously (or at slightly different times from photodetectors 22B and 22C, respectively, $\lambda_U^{(k)} - \lambda_L^{(k)}$ is equal to the step $\delta\lambda$, the midpoint wavelength is defined as $\lambda_k = (\lambda_U^{(k)} + \lambda_L^{(k)})/2$, and the double prime indicates the repeated power measurements.

Finally, the overall data stored in the data file after acquisition is depicted as a matrix in Equation (3.63) below, to which we will refer in all that follows. The matrix comprises K groups each of four powers of backreflected light (two sets of four when two photodetectors are used):

(3.63)

$$\text{Data} = \begin{array}{c|cccc} & \multicolumn{2}{c}{\lambda = \lambda_L^{(k)}} & \multicolumn{2}{c}{\lambda = \lambda_U^{(k)}} \\ \hline SOP_0 \text{ and/or } \lambda_0 \rightarrow & Px_L^{(0)} & Px_L''^{(0)} & Px_U^{(0)} & Px_U''^{(0)} \\ & Py_L^{(0)} & Py_L''^{(0)} & Py_U^{(0)} & Py_U''^{(0)} \\ SOP_1 \text{ and/or } \lambda_1 \rightarrow & Px_L^{(1)} & Px_L''^{(1)} & Px_U^{(1)} & Px_U''^{(1)} \\ & Py_L^{(1)} & Py_L''^{(1)} & Py_U^{(1)} & Py_U''^{(1)} \\ \vdots & \vdots & \vdots & \vdots & \vdots \\ SOP_k \text{ and/or } \lambda_k \rightarrow & Px_L^{(k)} & Px_L''^{(k)} & Px_U^{(k)} & Px_U''^{(k)} \\ & Py_L^{(k)} & Py_L''^{(k)} & Py_U^{(k)} & Py_U''^{(k)} \\ \vdots & \vdots & \vdots & \vdots & \vdots \\ SOP_{K-1} \text{ and/or } \lambda_{K-1} \rightarrow & Px_L^{(K-1)} & Px_L''^{(K-1)} & Px_U^{(K-1)} & Px_U''^{(K-1)} \\ & Py_L^{(K-1)} & Py_L''^{(K-1)} & Py_U^{(K-1)} & Py_U''^{(K-1)} \end{array}$$

3.4.2 Single-Ended Overall PMD: Auto-Calibration of the Relative Gain

For the preferred implementation of FIG. 3 using a polarization beam splitter (PBS), as shown in FIG. 3F, it is necessary to perform the below-described calibration procedure of the relative gain of the two detectors 22B and 22C before proceeding with any further computation. (A very similar procedure is also performed for an implementation of Embodiment (4), the "single-ended cumulative PMD" measurement embodiment described in a subsequent section hereinbelow.)

The calibration principle is predicated upon the fact that, when an VA-SOP scrambler 14 is used to generate a sufficiently large number of SOPs so as to substantially cover the Poincaré Sphere, the average power of the backreflected light from the distal end (or other positions) of the FUT 18 will exit from the two ports of the PBS with a 2:1 ratio, the higher power corresponding to the port to which detector 22B is connected and the lower power corresponding to the port to which detector 22C is connected. Hence, any observed deviation from this 2:1 ratio for the observed detector powers can be quantified and taken into account, as follows.

After data acquisition is completed, K groups of four backreflected light powers obtained from both photodetectors have been stored, i.e., a total number of J=4·K powers (data) from detector 22B and also J=4·K traces from detector 22C, as depicted in matrix (53). The $j^{th}$ powers (j=0, 1 . . . (J−1)) from 22B and 22C are referred to below as $Px_j$ and $Py_j$, respectively. If the overall losses in the two arms of the PBS were identical and the gains of both photodetectors and associated electronics were also equal, the ratio of the powers Py and Px after averaging both populations over all J occurrences would be $$\frac{\langle Px \rangle}{\langle Py \rangle} \equiv \frac{\sum_j Px_j}{\sum_j Py_j} = 2$$

In practice, the ratio obtained from the average of the measured powers does not equal 2 because of different losses in the arms of the PBS and different "effective" gains of the photodetectors, which includes the photodiode responsivity as well as the overall gains of the following electronics, amplifiers and sampling circuitry. (Note that it is not necessary to determine the individual gains separately.) Therefore, before proceeding with the rest of the computations, all the J powers obtained from photodetector 22C, i.e. all the $Py_j$, are multiplied as follows:

$$Py_j = g_{RoundTrip} \cdot Py_j$$

where $$g_{RoundTrip} = \frac{1}{2} \frac{\langle Px \rangle}{\langle Py \rangle} = \frac{\sum_j Px_j}{\sum_j Py_j}$$

In practice, for center wavelengths that are relatively closely-spaced (e.g. ⟨ 20 nm), the relative wavelength dependence of the optical components, detectors, etc. may be neglected and this calibration process need only be carried out once per single-ended PMD measurement sequence. Otherwise, this calibration may need to be carried out at every center wavelength, thereby increasing the overall measurement time of the measurement sequence.

As a result of the calibration, i.e. after all Py powers (data) have been multiplied by the measured relative gain as described above, the data processor 34 can compute the normalized backreflected light powers. More precisely, the normalized powers in the case of the implementation of FIG. 3F (or FIG. 3G) using a PBS are obtained by dividing the sampled and averaged signal Px from detector 22B, or the signal Py from detector 22C, or (and preferably) the difference (Px−Py)/2 or (Py−Px)/2, or any weighted difference $(1+w)^{-1}(Px-w \cdot Py)$, where w is a weighting factor, by the sum (Px+Py) of the sampled and averaged signals from both of the detectors 22B and 22C, which sum represents the total power impinging on the PBS, i.e., without selection of a particular polarization component.

It should be noted that other calibration methods may be envisaged. For example, a potential alternative calibration technique is to use an internal reference with fiber couplers (splitters) or internal reflector to send a predefined amount (percentage) of light power from launched OTDR light to two different detectors.

The preferred computational approach for determining the normalized powers of the preferred embodiments will now be described in detail.

3.4.3 Single-Ended Overall PMD: Computation

The powers are processed to obtain the DGD or PMD values, as will now be described. It should be note that, in all that follows, the symbols refer to the matrix "Data" in Equation (3.63). The labels x and y refer to the backreflected light powers obtained from photodetectors 22B and 22C, respectively.

3.4.3.1 the Normalized Powers

The normalized powers (i.e. transmissions), labelled hereinafter as T, are computed differently according to the implementation.
(i) For the implementation of FIG. 3F (two photodetectors with a PBS), the normalized power is computed in the same manner as a normalization procedure for the previously-described "two-ended" implementation of FIG. 1F (two photodetectors with a PBS). Note that the different Py powers are presumed to have been already pre-multiplied by the measured relative gain, $g_{RoundTrip}$, from single-ended measurement, as indicated in the description of the auto-calibration procedure, before they are used in this normalization procedure.
(ii) For the implementation of FIG. 3D (two photodetectors with a coupler), the normalized power is computed in the same manner as the normalization procedure for the implementation of FIG. 1D (two photodetectors with a coupler) for the two-ended PMD measurement previously described hereinabove, except that a different reference mean-value $u_o = 2/3$ is used for the single-ended measurement case. Here, the auto-calibration procedure is not required, i.e. the above-mentioned pre-multiplication of the powers Py by the measured relative gain may be skipped.
(iii) For the implementation of FIG. 3B (single photodetector), again the normalized power is computed in the same manner as a normalization procedure for the implementation of FIG. 1B (single photodetector) for the two-ended PMD measurement as already described in the previous related section and a reference mean value of $u_o = 2/3$ for single-ended measurement must also be used in this normalization procedure.

Here we assume that light powers being launched into FUT at $\lambda_U^{(k)}$ and $\lambda_L^{(k)}$ are nearly the same.

It should be noted that, in the equations above, $\langle \rangle_{SOP;v}$ can refer to averaging over either the I-SOPs, the A-SOPs, or the midpoint optical frequency (wavelength), ideally over all three, i.e., changing both the (I-SOP, A-SOP) couple and wavelength from one group of powers to the next. All of these relationships are fundamentally valid in all cases even if only polarization scrambling is applied, giving the correct value of the DGD at one particular midpoint wavelength. Then, scanning the midpoint wavelength only serves the purpose of averaging DGD over wavelength as per the definition of the statistical PMD value. On the contrary, as discussed earlier, averaging only over wavelength while keeping the (I-SOP, A-SOP) couple unchanged requires that assumptions about the FUT be met, and also requires a large value of the product PMD·Δv. The same remarks apply for the equations presented hereinafter.

3.4.3.2 Mean-Square Differences

The calculation here differs from the simple mean-square found in Eqs. (2.1), (2.2) (2.3) and (2.4), which, for greater clarity, did not take into account the noise. Instead, the product of the repeated differences between normalized traces at $\lambda_U$ and $\lambda_L$ is averaged as follows, $$\langle \Delta T^2(v) \rangle_{SOP;v} = \qquad (3.53')$$

$$\langle (T_U - T_L) \cdot (T_U'' - T_L'') \rangle_{SOP;v} = \frac{1}{K} \sum_k \left( T_U^{(k)} - T_L^{(k)} \right) \cdot \left( T_U''^{(k)} - T_L''^{(k)} \right)$$

Note the equation (3.53') is the same as equation (3.53). In conventional mathematical terms, equation (3.53') may be referred to as the second-order joint moment of the repeated differences. Doing so, the noise averages to zero instead of being "rectified", because the noise superimposed on a given trace is not correlated with the noise superimposed on the corresponding repeated trace. That is the first motivation for sampling repeated traces.

3.4.3.3 Computation of the PMD Value

The PMD then is directly computed according to the arcsine formula as, $$PMD = \alpha_{rt} \frac{1}{\pi \delta v} \arcsin \left( \alpha_{ds} \sqrt{\langle \Delta T^2(v) \rangle_{SOP;v}} \right) \qquad (3.64)$$

where a roundtrip factor $$\alpha_{rt} = \sqrt{\frac{3}{8}}.$$

A theoretical constant $$\alpha_{ds} = \sqrt{\frac{15}{4}}$$

is valid for the cases where a common (same) state of polarization controller (scrambler) is used to control both input and output light SOPs, such as for FIGS. 2, 2C-G.

It should be appreciated that the arcsine formula, in Eq. (3.64), is not the only possible one. The purpose of using this formula is to obtain a result that is unbiased even if using a relatively large step, such that PMD·δv~0.15, without introducing a significant error; this in order to maximize the signal-to-noise ratio and therefore the dynamic range of the instrument. If one were not concerned with maximizing the dynamic range, or keeping the overall measurement time reasonable, one might select a much smaller step, and use the simpler differential formula that follows, $$PMD = \alpha_{rt} \cdot \frac{\alpha_{ds}}{\pi \delta v} \cdot \sqrt{\langle \Delta T^2(v) \rangle_{SOP,v}} \quad (3.64a)$$

This is not to infer that this formula is better or particularly advantageous, but merely that it may conveniently be used if the step is much smaller, i.e., satisfying the condition $PMD \cdot \delta v < 0.01$.

It should be noted that a forward PMD calculated from equations (3.64) and (3.64a) is a PMD or rms DGD of FUT.

It should also be noted that roundtrip rms DGD or roundtrip mean DGD can also obtained from a root-mean-square for $DGD_{RoundTrip}(v)$ or mean for $DGD_{RoundTrip}(v)$ at many different wavelengths for a given wavelength range and $DGD_{RoundTrip}(v)$ at each given wavelength can be computed the arcsine formula as either, $$DGD_{RoundTrip}(v) = \frac{1}{\pi \delta v} \arcsin\left(\alpha_{ds}\sqrt{\langle \Delta T^2(v) \rangle_{SOP}}\right). \quad (3.65)$$

or use the simpler differential formula that follows, $$DGD_{RoundTrip}(v) = \frac{\alpha_{ds}}{\pi \delta v} \cdot \sqrt{\langle \Delta T^2(v) \rangle_{SOP}}. \quad (3.65a)$$

where normalized power (T) is obtained from each give wavelength.

A rms DGD and mean DGD (forward) can also be obtained by simply multiplying a roundtrip factor of $\sqrt{3/8}$ and $2/\pi$ on rms $DGD_{RoundTrip}$ and mean $DGD_{RoundTrip}$, respectively, where a rms $DGD_{RoundTrip}$ or mean $DGD_{RoundTrip}$ can be obtained from measured $DGD_{RoundTrip}(v)$ for many different midpoint wavelengths by root-mean square or mean $DGD_{RoundTrip}(v)$ from equations (3.65) or (3.65a) over a prescribed wavelength range, e.g. rms $DGD_{RoundTrip} = \sqrt{\langle DGD_{RoundTrip}^2(v) \rangle_v}$ and mean $DGD_{RoundTrip} = \langle DGD_{RoundTrip}(v) \rangle_v$.

It should also noted that above computation equations for extracting DGD and PMD using normalized power (usually a normalized power is ranged between 0 to 1) may be replaced by other methods. For example, only a relative power may be computed from the measured powers, then a "normalization factor" may be employed in the equations (3.64) and (3.65) to cancel this factor that is multiplied on mean-square difference, so as to obtain correct a DGD or PMD value.

It should be noted that the above equations for calculating the DGD or PMD include a factor representing a theoretical constant $$\alpha_{ds} = \sqrt{\frac{15}{4}}.$$

This theoretical constant value is valid for the cases where the same common state of polarization controller (scrambler) is used for controlling both input and output SOPs, such as for FIGS. 3B-3G. However, when two separate independent input- and analyzer-SOP controllers (scramblers) are used in conjunction with a polarizer or PBS located just before the detector, for example as shown in FIG. 3, a different theoretical constant, i.e.

$$\alpha_{ds} = \sqrt{\frac{9}{2}},$$

must be used. (Note that this theoretical constant is the same as that employed with the two-ended PMD measurement equations described in the corresponding section hereinbefore).

For the case where the tunable pulsed light source has a relatively big linewidth and a high PMD fiber is under test, a linewidth "correction factor" may need to be applied in Eq. (3.64, 7.64a) in order to extract an accurate PMD value from the FUT.

It should also be noted that repeated powers may be obtained from two or more measurements at different times using the same detectors, or from measurements using different detectors, e.g. where the light power is split by a coupler, and the power is detected by the different detectors contemporaneously.

3.5 Data Processing and Computation: Single-Ended Cumulative PMD Measurement

3.5.1 Single-Ended Cumulative PMD: The Data Structure

Each OTDR trace, obtained with one given setting of the wavelength and of the (I-SOP, A-SOP) couple, as described in the Method of Operation for the single-ended cumulative PMD measurement (also called as single-ended POTDR-based cumulative PMD measurement), constitutes the elementary data cell. One trace consists of N power values corresponding to N values $z_n$ of the distance z, with $n = 0 \ldots (N-1)$.

The next larger data unit is one group of four traces, two sets of four traces for the implementations of FIG. 4 and FIG. 4B where two traces are obtained simultaneously from photodetectors 22B and 22C (or sequentially in the case where an optical switch is used with one detector), all obtained with a given (I-SOP, A-SOP) couple as set by I/O-SOP controller 14. The two sets of four traces forming group k preferably have been obtained in the following sequence (time flowing from left to right), where the labels x and y refer to the traces obtained simultaneously from photodetectors 22B and 22C, respectively, $\lambda_U^{(k)} - \lambda_L^{(k)}$ is equal to the step $\delta\lambda$, the midpoint wavelength is defined as $\lambda_k = (\lambda_U^{(k)} + \lambda_L^{(k)})/2$, and the double prime indicates the repeated traces:

| | $\lambda = \lambda_L^{(k)}$ | | $\lambda = \lambda_U^{(k)}$ | |
|---|---|---|---|---|
| (I-SOP$_k$, A-SOP$_k$, $\lambda_k$) | $Px_L^{(k)}$ | $Px_L''^{(k)}$ | $Px_U^{(k)}$ | $Px_U''^{(k)}$ |
| | $Py_L^{(k)}$ | $Py_L''^{(k)}$ | $Py_U^{(k)}$ | $Py_U''^{(k)}$ |

Finally, the overall data stored in the data file after acquisition is depicted as a matrix in Eq. (3.66) below, to which we will refer in all that follows. The matrix comprises K groups each of four OTDR traces (two sets of four when two photodetectors are used), each trace consisting of N points corresponding to N values of distance $z_n$, where $n = 0 \ldots (N-1)$:

$$Data = \begin{array}{c|c|c|c|c|} & \lambda = \lambda_L^{(k)} & & \lambda = \lambda_U^{(k)} & \\ \hline SOP_0 \text{ and/or } \lambda_0 \rightarrow & Px_L^{(0)} & Px_L''^{(0)} & Px_U^{(0)} & Px_U''^{(0)} \\ \hline & Py_L^{(0)} & Py_L''^{(0)} & Py_U^{(0)} & Py_U''^{(0)} \\ \hline SOP_1 \text{ and/or } \lambda_1 \rightarrow & Px_L^{(1)} & Px_L''^{(1)} & Px_U^{(1)} & Px_U''^{(1)} \\ \hline & Py_L^{(1)} & Py_L''^{(1)} & Py_U^{(1)} & Py_U''^{(1)} \\ \hline \vdots & \vdots & \vdots & \vdots & \vdots \\ \hline SOP_k \text{ and/or } \lambda_k \rightarrow & Px_L^{(k)} & Px_L''^{(k)} & Px_U^{(k)} & Px_U''^{(k)} \\ \hline & Py_L^{(k)} & Py_L''^{(k)} & Py_U^{(k)} & Py_U''^{(k)} \\ \hline \vdots & \vdots & \vdots & \vdots & \vdots \\ \hline SOP_{K-1} \text{ and/or } \lambda_{K-1} \rightarrow & Px_L^{(K-1)} & Px_L''^{(K-1)} & Px_U^{(K-1)} & Px_U''^{(K-1)} \\ \hline & Py_L^{(K-1)} & Py_L''^{(K-1)} & Py_U^{(K-1)} & Py_U''^{(K-1)} \\ \hline \end{array}$$

(3.66)

The data structure of equation (3.66) is similar to that of equation (3.63), but data in equation (3.66) correspond to OTDR traces as function of distance z instead of powers reflected from the distal end of FUT.

3.5.2 Single-Ended Cumulative PMD: Auto Calibration of the Relative Gain

For the preferred implementation of FIG. 4, it is necessary to perform a calibration procedure very similar to that described hereinabove in the context of Embodiment (3): "single-ended overall PMD" measurement. The calibration principle is predicated upon the fact that, when an VA-SOP scrambler 14 is used to generate a sufficiently large number of SOPs so as to substantially cover the Poincaré Sphere, the average power of the backreflected light originating from any position along the FUT 18 will exit from the two ports of the PBS with a 2:1 ratio, the higher power corresponding to the port to which detector 22B is connected and the lower power corresponding to the port to which detector 22C is connected. Hence, any observed deviation from this 2:1 ratio for the observed detector powers can be quantified and taken into account, as follows.

After data acquisition is completed, K groups of four OTDR traces obtained from both photodetectors have been stored, i.e., a total number of J=4·K traces from detector 26A and also J=4·K traces from detector 22B, as depicted in matrix (56). The $j^{th}$ traces (j=0, 1, . . . , (J−1)) from 22C and 22B are referred to below as $Px(z)_j$ and $Py(z)_j$, respectively. If the overall losses in the two arms of the PBS were identical and the gains of both photodetectors and associated electronics were also equal, the ratio of the traces Py and Px after averaging both populations over all J occurrences and over all the N values of z would be $$\frac{\langle Px \rangle}{\langle Py \rangle} \equiv \frac{\sum_j \sum_n Px(z_n)_j}{\sum_j \sum_n Py(z_n)_j} = 2$$

In practice, the ratio obtained from the average of the measured traces does not equal 2 because of different losses in the arms of the PBS and different "effective" gains of the photodetectors, which includes the photodiode responsivity as well as the overall gains of the following electronics, amplifiers and sampling circuitry. (Note that it is not necessary to determine the individual gains separately.) Therefore, before proceeding with the rest of the computations, all the J traces obtained from photodetector 22C, i.e. all the $Py(z)_j$, are multiplied as follows:

$$Py(z)_j = g_{RoundTripC} \cdot P_y(z_n)_j$$

where $$g_{RoundTripC} = \frac{1}{2} \frac{\langle Px \rangle}{\langle Py \rangle} = \frac{\sum_j \sum_n Px(z_n)_j}{\sum_j \sum_n Py(z_n)_j}$$

In practice, for midpoint wavelengths that are relatively closely-spaced (e.g. ⟨20 nm), the relative wavelength dependence of the components, detectors, etc. is usually negligible and this calibration process need only be carried out once per POTDR measurement sequence. Otherwise, this calibration may need to be carried out at every midpoint wavelength, thereby increasing the overall measurement time.

As a result of the calibration, i.e. after all Py traces have been multiplied by the measured relative gain as described above, the data processor 34 can compute the normalized OTDR traces. More precisely, the normalized traces in the case of the implementation of FIG. 1 are obtained by dividing either the sampled signal Px from detector 22B, or signal Py from detector 22C, preferably the difference between the sampled signals from detectors 22B and 22C, (Px−Py)/2 or (Py−Px)/2, or any weighted difference $(1+w)^{-1}Px−w·Py$), by the sum (Px+Py) of the sampled signals from both of the detectors 22B and 22C which represents the total backreflected power impinging on the PBS, i.e., without selection of a particular polarization component.

The preferred computations giving the normalized OTDR traces for all preferred implementations will now be described in detail.

3.5.3 Single-Ended Cumulative PMD: The Point-by-Point Computation

The OTDR traces are processed to obtain the cumulative PMD as will now be described. It should be noted that the computation of $PMD_n$ at each point $z_n$ along the FUT 18 is performed independently of any other point n. Each is deduced from averages over at least one of I-SOP, A-SOP and wavelength, preferably over all. Thus, in the computations described below it is inappropriate to use the index n; it must simply be understood that the calculation is repeated in the same way for each point n, or, in other words, effectively at each distance $z_n$. In all that follows, the symbols refer to the matrix "Data" in Eq. (56). It should also be emphasized that the labels x and y refer to the traces obtained from photodetectors 22B and 22C, respectively.

3.5.3.1 The Normalized Traces

The normalized traces, labelled hereinafter as T(z), are computed differently according to the implementation.
(i) For the implementation of FIG. 4 (two photodetectors with a PBS), the normalized OTDR trace is computed as follows, either $$T_L^{(k)} = \frac{Px_L^{(k)}}{Px_L^{(k)} + Py_L^{(k)}} \quad T_L^{''(k)} = \frac{Px_L^{''(k)}}{Px_L^{''(k)} + Py_L^{''(k)}} \quad (3.67a)$$

$$T_U^{(k)} = \frac{Px_U^{(k)}}{Px_U^{(k)} + Py_U^{(k)}} \quad T_U^{''(k)} = \frac{Px_U^{''(k)}}{Px_U^{''(k)} + Py_U^{''(k)}}$$

or $$T_L^{(k)} = \frac{1}{2} \cdot \frac{Px_L^{(k)} - Py_L^{(k)}}{Px_L^{(k)} + Py_L^{(k)}} \quad T_L^{''(k)} = \frac{1}{2} \cdot \frac{Px_L^{''(k)} - Py_L^{''(k)}}{Px_L^{''(k)} + Py_L^{''(k)}}$$

$$T_U^{(k)} = \frac{1}{2} \cdot \frac{Px_U^{(k)} - Py_U^{(k)}}{Px_U^{(k)} + Py_U^{(k)}} \quad T_U^{''(k)} = \frac{1}{2} \cdot \frac{Px_U^{''(k)} - Py_U^{''(k)}}{Px_U^{''(k)} + Py_U^{''(k)}}$$

where it should be appreciated that the different Py traces have been pre-multiplied by the measured relative gain, $g_{RoundTripC}$, as indicated in the description of the auto calibration procedure, before they are used in Eq. (3.67a).
(ii) For the implementation of FIG. 4B (two photodetectors with a coupler), the ratio of trace Px over trace Py is first computed as, $$R_L^{(k)} = \frac{Px_L^{(k)}}{Py_L^{(k)}} \quad R_L^{''(k)} = \frac{Px_L^{''(k)}}{Py_L^{''(k)}} \quad R_U^{(k)} = \frac{Px_U^{(k)}}{Py_U^{(k)}} \quad R_U^{''(k)} = \frac{Px_U^{''(k)}}{Py_U^{''(k)}} \quad (3.67b)$$

and then the above ratio is normalized with respect to its average over the K groups as, $$T_L^{(k)} = u_o \frac{R_L^{(k)}}{\langle R \rangle_{SOP;v}} \quad T_L^{''(k)} = u_o \frac{R_L^{''(k)}}{\langle R \rangle_{SOP;v}} \quad (3.67c)$$

$$T_U^{(k)} = u_o \frac{R_U^{(k)}}{\langle R \rangle_{SOP;v}} \quad T_U^{''(k)} = u_o \frac{R_U^{''(k)}}{\langle R \rangle_{SOP;v}}$$

where the reference mean-value is $u_o = 2/3$ by assuming measured power for an input SOP aligned with an analyzer axis, and the average ratio R is defined as, $$\langle R \rangle_{SOP;v} = \frac{1}{4K} \sum_k \left( R_L^{(k)} + R_L^{''(k)} + R_U^{(k)} + R_U^{''(k)} \right), \quad (3.67d)$$

Here, the auto-calibration procedure is not required, i.e. the above-mentioned pre-multiplication of the traces Py by the measured relative gain may be skipped.

(iii) For the implementation of FIG. 4A (single photodetector), the only available traces are the Px traces (obtained here from photodetector 22). The normalized trace is obtained as in (3.67c) but without computing the ratio of trace x over trace y first, i.e.

$$T_L^{(k)} = u_o \frac{Px_L^{(k)}}{\langle P \rangle_{SOP;v}} \quad T_L^{''(k)} = u_o \frac{Px_L^{''(k)}}{\langle P \rangle_{SOP;v}} \quad (3.67e)$$

$$T_U^{(k)} = u_o \frac{Px_U^{(k)}}{\langle P \rangle_{SOP;v}} \quad T_U^{''(k)} = u_o \frac{Px_U^{''(k)}}{\langle P \rangle_{SOP;v}}$$

where the average trace is defined as, $$\langle P \rangle_{SOP;v} = \frac{1}{4K} \sum_k \left( Px_L^{(k)} + Px_L^{''(k)} + Px_U^{(k)} + Px_U^{''(k)} \right) \quad (3.67f)$$

All of these relationships are fundamentally valid in all cases even if only I/A-SOP scrambling is applied, giving an estimation of the DGD at one particular midpoint wavelength. If these measurements are then repeated for a multiplicity of wavelengths across a prescribed wavelength range, the average DGD value so obtained then represents definition of the PMD. On the other hand, as discussed earlier, averaging only over wavelength while keeping the I/A-SOP unchanged requires that assumptions about the FUT be met, and also requires a large value of the product PMD·Δ·ν. The same remarks apply for the equations presented hereinafter.

It should be also noted that Equations (3.67d) and (3.67f) assume that there is negligible wavelength dependence on coupling ratio and detected powers, respectively.

3.5.3.2 Relative Variance

The relative variance, as in equation (3.67b), is computed here as the average of the four available estimates, i.e., $$\sigma_r'^2 = \left(\frac{1}{\sigma_{10}}\right)^2 \left[\frac{\text{var}(T_L) + \text{var}(T_U)}{2}\right] \quad (3.68)$$

where the reference variance is $\sigma_{10}^2 = 4/45$, and the function "var" is defined as, $$\text{var}(T_L) = [\langle T_L T_L'' \rangle_{SOP;v} - \langle T_L \rangle_{SOP;v}^2]$$

$$\text{var}(T_U) = [\langle T_U T_U'' \rangle_{SOP;v} - \langle T_U \rangle_{SOP;v}^2].$$

3.5.3.3 Mean-Square Differences

The calculation here differs from the simple mean-square found in Eq. (2.2) which, for greater clarity, did not take into account the noise. Instead, the product of the repeated differences between normalized traces at $\lambda_U$ and $\lambda_L$ is averaged as follows, $$\langle \Delta T^2(v) \rangle_{SOP;v} = \quad (3.69)$$

$$\langle (T_U - T_L) \cdot (T_U'' - T_L'') \rangle_{SOP;v} = \frac{1}{K} \sum_k \left( T_U^{(k)} - T_L^{(k)} \right) \cdot \left( T_U^{''(k)} - T_L^{''(k)} \right)$$

In conventional mathematical terms, Eq. (3.69) may be referred to as the second-order joint moment of the repeated differences. Doing so, the noise averages to zero instead of being "rectified", because the noise superimposed on a given trace is not correlated with the noise superimposed on the corresponding repeated trace. That is the first motivation for sampling repeated traces.

3.5.3.4 Noise Variance

The second motivation for sampling repeated traces, which are substantially identical in the absence of noise, for each setting of center wavelength λ and SOP, is the ability to obtain an accurate estimate of the noise variance. That is because the relative variance, as computed in Eq. (3.68), includes both the variance of the hypothetical noiseless trace and the variance of the noise. However, if the noise variance is known, it can be subtracted since the variance of the sum of two independent random variables is equal to the sum of the variances. But thanks to the repeated traces, the noise variance can be estimated independently as follows:

$$\sigma_{noise}^2 = \left(\frac{1}{\sigma_{10}}\right)^2 \langle (T_L - T_L'')(T_U - T_U'') \rangle_{SOP;v} \quad (3.70)$$

The noise variance (Eq. 3.70) is then subtracted from the first estimate of the relative variance (Eq. 3.68) in the computation of the final relative variance as follows, $$\sigma_r^2 = \sigma_r'^2 - \sigma_{noise}^2 \quad (3.71)$$

3.5.3.5 Computation of the Cumulative PMD

The cumulative PMD then is computed according to the arcsine formula as, $$PMD(z) = \alpha_{rt} \frac{1}{\pi \delta v} \arcsin\left(\alpha_{ds} \sqrt{\frac{\langle \Delta T^2(v, z) \rangle_{SOP;v}}{\sigma_r^2(z)}}\right) \quad (3.72)$$

where a roundtrip factor $$\alpha_{rt} = \sqrt{\frac{3}{8}}.$$

A theoretical constant $$\alpha_{ds} = \sqrt{\frac{15}{4}}$$

is valid for the cases where a common state of polarization controller (scrambler) is used to control the SOP of both light input to and output from the FUT, such as depicted in FIGS. 4, 4A and 4B.

It should be appreciated that the arcsine formula, (3.72), is not the only possible one. The purpose of using this formula is to obtain a result that is unbiased even if using a relatively large step, such that PMD·δv~0.15, without introducing a significant error; this in order to maximize the signal-to-noise ratio and therefore the dynamic range of the instrument. If one were not concerned with maximizing the dynamic range, or keeping the overall measurement time reasonable, one might select a much smaller step, and use the simpler differential formula that follows, $$PMD(z) = \alpha_{rt} \alpha_{ds} \frac{1}{\pi \delta v} \cdot \sqrt{\frac{\langle \Delta T^2(v, z) \rangle_{SOP;v}}{\sigma_r^2(z)}} \quad (3.73)$$

This is not to infer that this formula is better or particularly advantageous, but merely that it may conveniently be used if the step is much smaller, i.e., satisfying the condition PMD·δv<0.01. The cumulative PMD curve as a function of z is obtained by repeating the computation above, from equations (3.67) to equation (3.72), at each point n corresponding to distance $z_n$.

It should be noted that the above equations employ the theoretical constant $$\alpha_{ds} = \sqrt{\frac{15}{4}}$$

(see Equation 2.11 a), which applies when a common (I/A-SOP) polarization controller for the light launched into and the backreflected light received from the FUT, such as for the implementations shown in FIGS. 4, 4A, and 4B. However, when separate I-SOP and A-SOP polarization controllers (scramblers) are used with a polarizer or if the PBS is located just before the detector, for example as shown in FIG. 4C, then the theoretical constant corresponding to "uncorrelated" polarization scrambling must be used, i.e.

$$\alpha_{ds} = \sqrt{\frac{9}{2}}$$

(see Equation 2.11b).

It should also be noted that the above computation equations (3.72) and (3.73) for extracting cumulative PMD using a normalized OTDR trace may be replaced by using a relative OTDR trace that is proportional to a normalized OTDR trace.

It should be noted that a forward PMD calculated from equations (3.72) and (3.73) is PMD (according to the rms DGD definition) of FUT.

It should further be emphasized that the cumulative PMD may also be obtained by averaging over either rms or mean roundtrip DGDs at different optical frequencies:

$$rms\ DGD_{RoundTrip}(z) = \sqrt{\langle DGD_{RoundTrip}^2(z,v) \rangle_v} \quad (3.74a)$$

$$mean\ DGD_{RoundTrip}(z) = \langle DGD_{RoundTrip}(z,v) \rangle_v \quad (3.74b)$$

where rms $DGD_{RoundTrip}(z)$ or mean $DGD_{RoundTrip}(z)$ can be obtained from measured $DGD_{RoundTrip}(z,v)$ for many different midpoint wavelengths by root-mean square or mean $DGD_{RoundTrip}(z,v)$ over a prescribed wavelength range. The measured and calculated roundtrip DGDs at different optical frequencies is $$DGD_{RoundTrip}(z, v) = \frac{\alpha_{ds}}{\pi \delta v} \sqrt{\frac{\Delta T^2(z, v)}{\sigma_r^2(z, v)}} \quad (3.75)$$

where $$\sigma_r^2(z, v) = \left(\frac{1}{\sigma_{10}}\right)^2 [\langle T(z, v) \cdot T''(z, v) \rangle_{SOP,v} - \langle T(z, v) \rangle_{SOP,v}^2]. \quad (3.76)$$

The rms DGD(z) and mean (forward) DGD(z) can also be obtained by simply multiplying rms DGD$_{RoundTrip}$(z) and mean DGD$_{RoundTrip}$(z), by a roundtrip factor of $\sqrt{3/8}$ and $2/\pi$, respectively.

As shown in the equations (3.75) and (3.76), if the PMD calculation involves the use of the relative variance, $\sigma_r^2$(z, v), of the normalized power (T), then it is not necessary that the power be normalized to lie between 0 and 1. In other words, some steps of above normalization procedure for obtaining normalized powers may be skipped. The relative power $P_R$(z,v) and relative variance $\sigma_R^2$(z,v) computed from relative suffice to compute the cumulative PMD with equations similar to equations (3.75) and (3.76).

It should also be noted that repeated powers may be obtained from two or more measurements at different times using the same detectors, or from measurements using different detectors, e.g., where the light power is split by a coupler and the power detected contemporaneously using two detectors.

3.5.4 Optional Application of a Linewidth Correction Factor

If the effective spectral linewidth of the pulsed laser source is large, it may be desirable to perform an additional, although optional, data "post-processing" step to take into account the dependence of the measured cumulative PMD on the linewidth of the laser. Thus, one may multiply the N above-measured cumulative PMD values at $z_n$, PMD$_n$, by an appropriate linewidth-dependent correction factor. One expression of such a correction factor, suitable when the laser lineshape is approximately Gaussian, is:

$$\alpha_{LW_n} = \frac{1}{\sqrt{1 - \left(\frac{PMD_n}{PMD_{sat}}\right)^2}} \quad (3.77)$$

where PMD$_{sat}$ is the saturation cumulative PMD value, i.e., the limiting value towards which the measured cumulative PMD tends as the actual cumulative PMD grows toward infinity, if no linewidth correction factor is applied. It is given by:

$$PMD_{sat} = \frac{1}{4\pi} \cdot \frac{1}{\sigma_{vL}} \quad (3.78)$$

where $\sigma_{vL}$ is the rms-width of the laser spectrum. (Note: for a Gaussian lineshape, the full-width at half-maximum is related to the rms-width by $\Delta v_L = \sqrt{8 \cdot \ln(2)} \sigma_{vL}$.)

The last, optional, step comprises the computation of the N values of the correction factor according to Equation (3.78), and then the obtaining of the corrected PMD values, PMD'$_n$, via multiplication of the PMD values measured before correction by the correction factor, i.e.

$$PMD'_n = \alpha_{LW_n} \cdot PMD_n \quad (3.79)$$

For example, if no correction factor is applied, Eqs. (3.77) and (3.78) indicate that the maximum cumulative PMD value corresponding to a bias of, say, −10%, is PMD$_{max}$=0.0817$\Delta v_L^{-1}$. For this example, a full-width at half-maximum $\Delta v_L$=2 GHz gives PMD$_{sat}$~94 ps and PMD$_{max}$~41 ps. If the measured value happens to be equal to this pre-determined maximum value of 41 ps then the actual PMD is in fact approximately 45 ps, i.e., the measured value suffers a bias of −10%, as stated. Such a residual bias level may be acceptable in many field applications.

However, under these same physical circumstances, if the correction factor $\alpha_{LW}$=1.11 is applied according to Eq. (3.79), one obtains the actual cumulative PMD' of 45 ps. In practice, the uncertainty on the correction factor itself will grow if the correction factor becomes very large, i.e., when the directly measured (i.e., uncorrected) cumulative PMD is too close to PMD$_{sat}$, since any small error in the directly-measured PMD value or in the laser linewidth (or uncertainties as to the effective laser lineshape) can make the correction factor very unreliable, as can be appreciated from Equation (3.77). However, the uncertainty remains small if the maximum allowable value of the correction factor is limited to a predetermined value, which then determines the maximum PMD that can be measured when the correction factor is applied. Doing so, not only is PMD$_{max}$ larger than it would be without the correction, but more importantly, in contrast with the case where no correction is applied, there is no systematic bias when the actual PMD is equal to PMD$_{max}$, but rather only a small additional, zero-mean uncertainty. Using the previous example, and setting the correction factor to a reasonable maximum value of 1.25, i.e., still close to unity, the maximum value of the actual PMD that can be measured, without bias, is PMD$_{max}$~70 ps, compared to 41 ps with a bias of −10% if no linewidth correction factor is used.

Obviously, whenever the product PMD·$\Delta v_L$ is much smaller than unity, the application of such a correction factor is superfluous.

It should be appreciated that Equation (3.78) applies for the case of a nearly Gaussian-shaped laser spectrum, and is given by way of example. Other formulas or relationships can be computed either analytically or numerically for any particular laser lineshape that deviates substantially from a Gaussian lineshape. The Gaussian lineshape is a special, though practically relevant, case for which the correction factor can be expressed as a simple analytical formula, whereas such simple analytical formulas cannot be found for arbitrary laser lineshapes.

4. OPTICAL SOURCE MEANS APPROPRIATE FOR IMPLEMENTATIONS OF EMBODIMENTS OF THIS INVENTION

4.1 Tunable Laser Source Suitable for Two-Ended PMD Measurement

Examples of tunable laser sources capable of successively and repetitively generating coherent light at two or more closely spaced wavelengths are detailed in commonly-owned United States patent publication number application US2010/0073667 (Cyr et al), supra. FIG. 7A therein shows schematically such a tunable modulated light source (suitable for use in 12A in FIGS. 1(B-H)), designed to emit three closely-spaced wavelength, in rapid sequence, where an optical chopper (reference number 130 therein) enables switches between the closely-spaced wavelengths. Tuning of the "midpoint" wavelength may be carried out by means of a rotatable diffraction grating, for instance.

Other kinds of tunable modulatable light source could be used. For example, it is envisaged that an external phase modulator could be used to generate optical sidebands on the output of an external cavity laser (ECL), distributed Bragg reflector laser (DBR), or distributed feedback laser (DFB).

A person skilled in this art will be aware of other alternatives for this tunable modulatable coherent source.

The spectral linewidth of suitable tunable modulated coherent sources in the various above-described implementations might range from less than 1 GHz to about 4 GHz. It may be advantageous for this linewidth to be known, at least approximately, in order to facilitate application of the linewidth correction factor as described hereinbefore.

Figure 1L:
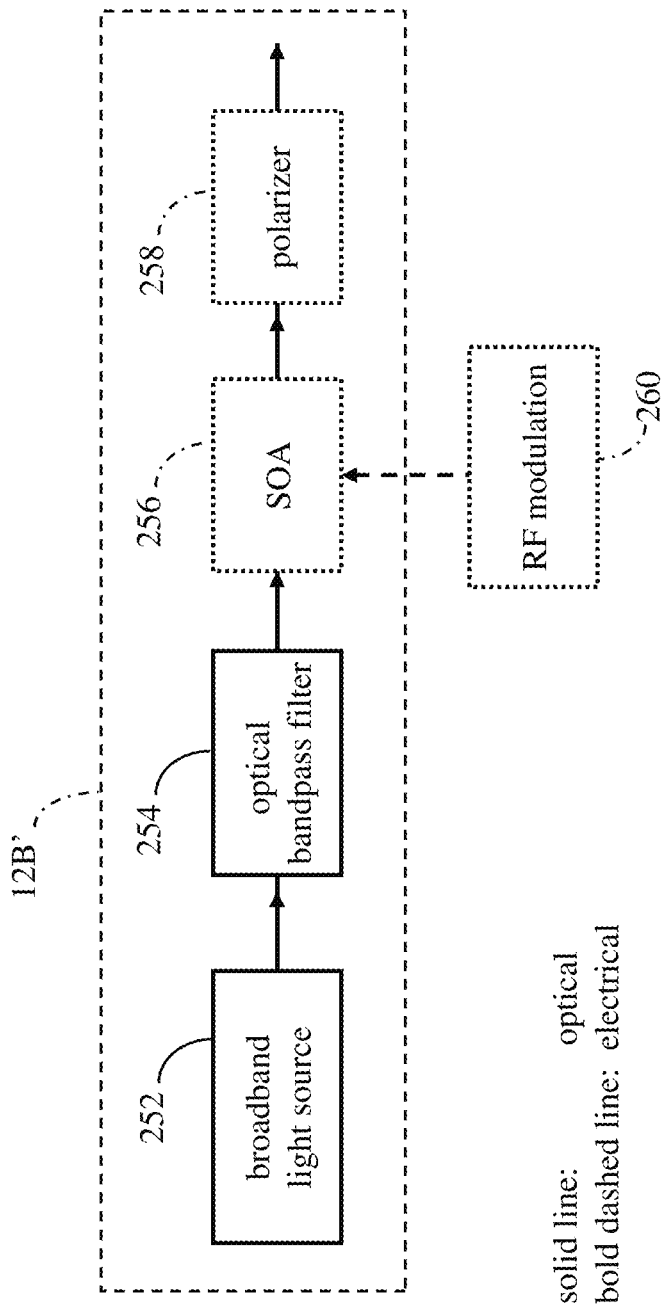
FIG. 1L illustrates schematically an alternative broadband source for the measurement instrumentation of FIGS. 1I, 1J and 1K that is particularly well-suited for in-channel measurement of DGD and shows, in broken lines, an optional optical amplifier, preferably a semiconductor optical amplifier (SOA), and, for use where chromatic dispersion is to be measured, a source of RF modulation and, if appropriate, a polarizer.

4.2 Tunable Moderately Broadband Optical Source for Two-Ended PMD Measurement A type of broadband source 12B, a tunable moderately broadband light source 12B', that is well suited for many implementations of Embodiment (1) of this invention is depicted schematically in FIG. 1L. This source could be advantageously used in the exemplary implementations of FIGS. 1I, 1J, and 1K, for two-ended measurement of the DGD within one or more narrow DWDM channels lying within a prescribed spectral range (e.g. such as the telecom C and/or L bands).

The tunable moderately broadband light source 12B' comprises a broadband light source 252, which could be an a substantially un-polarized light source such as an amplified spontaneous emission (ASE) source, or a partially or substantially polarized source such as a superluminescent diode (SLED) or light emitting diode (LED).

The broadband light source 252 is filtered by an optical bandpass filter 254 to provide moderately broadband CW light, e.g. sufficient to encompass most or all of the bandwidth corresponding to a DWDM channel, for instance. For example, appropriate bandwidth (FWHM) values of the optical bandpass filter 254 may be from 0.5-2.0 nm, but should not be considered to be limited to this range. The optical bandpass filter 254 is preferably a tunable optical bandpass filter, whose center bandpass wavelength can be tuned or adjusted over a much wider wavelength range than the spectral extent of the filter bandpass. It is often desirable to amplify the filtered light, for instance to a power level of about 0 dBm that would make it compatible with power levels expected in active optical networks, especially if the broadband light source 252 is a low-power (and hence low-cost) SLED or LED, for instance. To this end, the filtered moderately broadband light, e.g. usually a CW light source, then passes through an optional semiconductor optical amplifier (SOA) 256 where it is amplified. If the resulting light exiting the SOA 256 is not highly or sufficiently polarized, it may be transformed into a nearly 100% degree of polarization (DOP) using an optional polarizer 258 (possibly using a polarization controller—not shown—disposed between the SOA 256 and polarizer 258 to maximize the exiting output power. However, if the output light from the SOA is well polarized, the polarizer 258 may not be required.

It is envisaged that this tunable moderately tunable light source 12B' could be easily modified to render it appropriate as a source for in-channel relative group delay (i.e. chromatic dispersion) measurements, using a variant of the well known "phase shift" method, as described in commonly-owned patent Babin et al, U.S. Pat. No. 6,429,929. To this end, the gain of the SOA 256 could be modulated by a sinusoidal RF modulation 260. A typical modulation frequency may be in the range from 100 MHz to 2 GHz. (It should be emphasized that such an rf modulation is not required for the two-ended PMD or DGD measurement embodiments specified herein.)

If the light emitted by the broadband light source 252 such as a SLED exhibits a high DOP (e.g. 〉90%), and the optical bandpass filter 254 and SOA 256 are also polarization-dependent components, then it is preferable to employ PMF (polarization maintaining fiber) to interconnect these components. (Alternatively, as already described hereinabove, factory-adjustable polarization controllers may be placed between each component to ensure optimal polarization alignment.)

It should be noted for the two-ended chromatic dispersion measurement, the light exiting the tunable moderately-broadband light source 12B' needs to have a DOP close to 0%. This may be achieved by using I-SOP controller 14A to "temporally scramble" the polarized light at a very rapid rate (i.e. much faster than the electronic bandwidth of the sampling circuitry in the processing means 40). However, such temporal scrambling would not be necessary for chromatic dispersion measurement if the light emitted by SOA 256 is un-polarized, for example if a polarization-insensitive SOA were "seeded" with moderately-broadband-filtered light (via optical bandpass filter 254). It should be also noted that the different design for the broadband source 12B/12B' for the two-ended PMD and DGD measurement is also possible, for example a (wavelength tunable or fixed) filtered moderately broadband optical light source may be amplified by an erbium doped optical amplifier (EDFA) rather than a SOA. However, advantageously if a SOA is used it can not only amplify the input light power but it can also act as a fast optical light modulator because of its fast response time so that this filtered moderately broadband optical light source can be used for both the PMD and DGD measurement and the chromatic dispersion measurement in which a phase-shift dispersion measurement method may be used.

4.3 Tunable OTDR for Single-Ended PMD Measurements

As mentioned hereinbefore, it is desirable to use many midpoint wavelengths $\lambda_{mid}$ as well as many I-SOPs and A-SOPs. Consequently, it is desirable for the tunable OTDR to be tunable over a large range of wavelengths. Suitable tunable OTDRs, that are tunable over a range of several hundred nanometers, are known to those skilled in this art and so are not described in detail herein.

A tunable pulsed laser source 12 that is particularly well suited for the single-ended PMD measurements embodiments is disclosed in commonly-owned United States patent H. Chen et al, U.S. Pat. No. 7,957,436, filed Jul. 18, 2007, the contents of which are incorporated herein by reference.

It should be appreciated that other kinds of tunable pulsed light source could be used instead of that described hereinbefore. For example, FIG. 8B of an earlier published application, US2010/0073667 A1 to H. Chen et al. (from which the present application is a Continuation-in-Part), schematically depicts an alternative tunable pulse laser design to that described in aforementioned U.S. Pat. No. 7,957,436. This alternative low-cost design employs no delay line. and can effectively generate a long pulse from 275 ns to 20 µs. However, it may not suitable to produce an OTDR pulse of less than 275 ns.

A further example of a suitable tunable pulsed light source, where an acousto-optic modulator is used to pulse the light from a continuous-wave tunable laser, is disclosed by Rossaro et al. (J. Select. Topics Quantum Electronics, Vol. 7, pp 475-483 (2001)), specifically in FIG. 3 thereof.

Other suitable tunable sources that may emit pulsed light are also described in United States patent publication US2010/0073667 A1 supra. It should also be noted that the semiconductor-optical-amplifier-based light sources described in United States patent publication US2010/0073667 A1 do not yield a very narrow linewidth laser. The laser linewidth strongly depends on the TBF bandpass width. Typically, laser linewidth is about 4 to 15 GHz (for TBF bandwidth of 30-80 pm). However, a wide laser linewidth (bandwidth) is advantageous for any OTDR application (including POTDR), as it reduces coherence noise on the OTDR traces.

The spectral linewidth of the tunable pulsed laser sources in the various above-described embodiments may range from less than 1 GHz to more than 15 GHz. It may be advantageous for this linewidth to be known, at least approximately, in order to facilitate application of the linewidth correction factor as described hereinbefore. It may also be very advantageous for the laser linewidth to be adjustable in a known controlled manner, at least over some range, so as to circumvent or significantly mitigate the above mentioned limitation regarding maximum measurable PMD. If such an ability to adjust the laser linewidth is available, one may select a larger linewidth where a small PMD value is to be measured, and select a smaller linewidth where a large PMD value is to be measured. Optimally, the laser linewidth would always be set as equal to approximately one half of the selected step δν.

A person skilled in this art will be aware of other alternatives to these tunable light sources.

Scrambling

The term "pseudo-random-scrambling" as used herein is to emphasize that no deterministic relationship between one SOP and the next is needed or assumed by the computation. That is not to say, however, that the physical SOP controller 14 must be truly random as such. It may also follow, for example, that the SOPs define a uniform grid of points on the Poincaré Sphere, with equal angles between the Stokes vectors.

Uniformly-Distributed

A "pseudo-random" SOP means that each of the three components (s1, s2, s3) of the Stokes vector that represents that SOP on the Poincaré Sphere is a random variable uniformly distributed between −1 and 1, and that any one of the three components is uncorrelated with the two others (average of the product=0). Nonetheless, whether the SOPs are on a grid or form a random set, the points on the Sphere must be uniformly-distributed.

However, if a grid is used instead of a random set, the calculation or processing must not assume a deterministic relationship between one SOP and the next. Otherwise, if the FUT 16 moves, as may occur in real telecommunications links, such deterministic relationships between traces obtained with a deterministic grid will be lost.

5. ADVANTAGES OF EMBODIMENTS OF THE PRESENT INVENTION

(1) Two-Ended PMD Measurement

The FUT 18 stability requirements are relaxed with the pseudo-random-scrambling approach in comparison with most other prior art techniques because no deterministic relationships have to be assumed between powers obtained with different SOPs and/or wavelengths. Consequently, the measurement may be tolerant to FUT-induced SOP changes on timescales as small as 10 ms or even smaller, depending upon the particular embodiment;

The measurement result is reliable for any optical-fiber type;

Certain embodiments readily permit the measurement of DGD at one given wavelength, and, when repeated at different wavelengths, permit the determination of DGD as function of wavelength and, hence, to further obtain mean DGD or rms DGD;

Permit the measurement of very high DGD or overall PMD values (e.g. 50 to 100 ps) of the FUT if light of relatively high coherence (e.g. linewidth of less than 1-2 GHz) is detected, while the use of random scrambling also enables measurement of small PMD values (e.g. less than 0.1 ps) to good accuracy;

The dynamic range of this approach can be very high (typically 30 dB to over 60 dB for overall acquisition times ranging from approximately 30 minutes to a few minutes);

Permit measurement of a FUT comprising in-line optical amplifiers, for example erbium doped fiber amplifiers (EDFAs) or Raman fiber amplifiers, since reliable measurements can be taken even in the presence of significant ASE light arising from these optical amplifiers; and Most embodiments require minimal two-way communications between the two ends of the FUT.

(3) Single-Ended Overall PMD Measurement

FUT 18 stability requirement via the pseudo-random-scrambling approach is relaxed with respect to most other prior-art techniques because no deterministic relationships have to be assumed between powers obtained with different SOPs and/or wavelengths. The method thereby can relax the FUT stability requirement even for instabilities occurring over a very short time period, for example 0.2 to 0.4 seconds, depending upon the particular implementation and the choice of light source and/or tunable filter means;

The measurement result is reliable for any optical-fiber type;

They permit all measurement equipment to be located at only one end of the FUT,

They permit the use of very long pulses, e.g. about 1 to 20 μs or more, provided that the OTDR can distinguish the localized refection at the distal end from other reflections, leading to a significantly high dynamic range, an overall short acquisition time, and a reduction of interference or coherence noise. For example, the total acquisition time may range from less than 2 minutes to over 5 minutes for a dynamic range exceeding 25 dB;

Permit the measurement of very high overall PMD values (e.g. 50 ps or more) from the FUT if the tunable pulsed laser has an appropriately narrow linewidth (e.g. of 1-2 GHz or less), while maintaining the capability to satisfactorily measure a small PMD (e.g. less than 0.1 ps);

The single-ended overall PMD measurement method uses an OTDR-based technique that can distinguish the Rayleigh backscattering from the localized reflection at the distal end of fiber, so that one does not need to take into account the Rayleigh backscattering or other reflections, such as from connectors between fiber sections, thereby improving the reliability of the PMD measurement;

Embodiments of this single-ended PMD measurement method disclosed here further may measure PMD from a test instrument to any strong localized reflection along the fiber, well separated from other localized reflections, for example from any connector or splice of along FUT, if its backreflected light power is high enough to be adequately detected.

(4) Single-Ended Cumulative PMD Measurement

Relaxes the FUT 18 stability requirement via the pseudo-random-scrambling approach because no deterministic relationships have to be assumed between traces obtained with different SOPs and/or wavelengths. Moreover, this advantageous relaxing of the FUT 18 stability requirement is obtained whether it is actually performed via I/A-SOP scrambling (the preferred method), or, in the case of an "ideal" FUT (as defined previously), by relying only on the "natural" scrambling of the input PSPs of the optical link that occur randomly and uniformly as a function of wavelength and fiber length;

Permit the use of optical pulses having a spatial extent greater than the beat length of the FUT, leading to:
(i) significantly increased dynamic range, for example from 10 dB to over 20 dB for overall acquisition times ranging from less than 10 minutes to over 30 minutes for a typical pulse length of 100 or 200 ns;
(ii) reduction of OTDR coherence noise that may be superimposed on the traces;
(iii) increased maximum measurable PMD for a given laser spectral linewidth;

Cumulative PMD is measured directly, in contrast to previously-known POTDRs of the first type discussed herein, so no assumed specific birefringence model is needed, in particular, they are especially suitable for measuring cumulative PMD of spun fibers, They produce quantitative results; and The measurement result from this invention is a consequence of the random scrambling approach which leads notably to a simple relationship, Equation (2.4), that is valid for any FUT 18 and any pulse length according to theory, and of the associated signal processing. Embodiments of the invention can measure PMD over a range extending from a few hundredths of picoseconds to over 50 picoseconds and can be used to locate high PMD fiber sections with excellent spatial resolution.

For two-ended measurement, the said polarization-and-analyzer means may be connected to the optical path at or adjacent the distal end of the optical path.

In embodiments for measurement of DGD at a specified wavelength, for example, for narrow DWDM channel measurement, each said group may comprise wavelength pairs having substantially the same said prescribed midpoint wavelength, and the said at least one polarization-related optical path characteristic is the differential group delay (DGD) at the said midpoint wavelength.

The said measured power parameter may be the computed normalized power T(v), and said predetermined function can be expressed, for small optical-frequency differences (δv), according to the following differential formula:

$$DGD(v) = \frac{\alpha_{ds}}{\pi \delta v} \cdot \sqrt{\langle \Delta T^2(v) \rangle_{SOP}}$$

where the constant $$\alpha_{ds} = \sqrt{\frac{9}{2}},$$

and ν is the optical frequency corresponding to the said midpoint wavelength and ΔT(ν) is normalized power difference obtained for a particular I-SOP and A-SOP couple.

INDUSTRIAL APPLICABILITY

Although embodiments of the invention have been described and illustrated in detail, it is to be clearly understood that the same are by way of illustration and example only and not to be taken by way of the limitation, the scope of the present invention being limited only by the appended claims.

Polarization mode dispersion is a major cause of impairment in modern fiber-optic networks, and hence measurements enabling its characterization, in all of its manifestations (e.g. fiber PMD, channel or lightpath DGD, and partial-DGD) are of great important to telecom network operators. Armed with such information, remedial action might be undertaken, for instance to replace particular problematic sections of an optical link, or identify the cause of otherwise unexplained intermittent error bursts in a DWDM channel. In addition, such information might be used by the operator to indicate that the particular already field-deployed optical link is not suitable to be "upgraded" to carry higher-bandwidth optical signals.

Preferred embodiments of this invention are directed towards practical implementations of such measurements and diagnostics in the field, and include:

Non-intrusive PMD measurement of an "in-service" optical fiber link of an optical network using a test source launched into "dark" DWDM channels;

Non-intrusive PMD measurement of an "in-service" optical fiber link of an optical network using the polarized light from multiple data-carrying DWDM signals propagating therein;

Measurement of DGD of a DWDM channel in order to ensure that it is capable of carrying high-bandwidth traffic;

Measurement of the partial-DGD, and hence the degree of pulse spreading (or equivalently, "PMD penalty") of a real data-carrying signal in a DWDM channel;

Rapid characterization, from a single-end, of overall PMD over long distances of an optical fiber via a cost-effective variant of field-portable OTDR-based instrumentation;

Detailed characterization of cumulative PMD along an optical fiber, normally already having been identified as having excessive PMD, in order to identify the or those segments of the long fiber responsible for most of the overall PMD, and thereby enable a link to be markedly improved for a cost much less than replacing the entire length of fiber.

REFERENCES

[1] C. D. Poole, D. L. Favin, 'Polarization-mode dispersion measurements based on transmission spectra through a polarizer', Journal of Lightwave Technology, Vol. 12 (6), pp. 917-929 (1994).

[2] 'Method and apparatus for measuring polarization mode dispersion', U.S. Pat. No. 7,227,645 B2, Jun. 5, 2007.

[3] N. Cyr, 'Polarization-mode dispersion measurement: generalization of the interferometric method to any coupling regime', Journal of Lightwave Technology, Vol. 22(3), pp. 794-805 (2004).

[4] 'Fiber optical dispersion method and apparatus', U.S. Pat. No. 4,750,833, Jun. 14, 1988.

[5] P. A. Williams, A. J. Barlow, C. Mackechnie, J. B. Schlager, Narrowband measurements of polarization-mode dispersion using the modulation phase shift technique', Proceedings SOFM, Boulder Colo., 1998, pp. 23-26.

[6] R. Noe, et al, 'Polarization mode dispersion detected by arrival time measurement of polarization-scrambled light', Journal of Lightwave Technology, Vol. 20(2), pp. 229-235 (2002).

[7] 'Monitoring Mechanisms for Optical Systems', United States Patent Applications Publication US 2005/0201751 A1, Sep. 15, 2005.

[8] S. X. Wang, A. M. Weiner, S. H. Foo, D. Bownass, M. Moyer, M. O'Sullivan, M. Birk, M. Boroditsky, 'PMD Tolerance Testing of a Commercial Communication System Using a Spectral Polarimeter', Journal of Lightwave Technology, Vol. 24 (11), pp. 4120-4126 (2006).

[9] 'Method and apparatus for polarization mode dispersion monitoring in a multiple wavelength optical system', U.S. Pat. No. 7,203,428, Apr. 10, 2007.

[10] S. Wielandy, M. Fishteyn, B. Zhu, 'Optical performance monitoring using nonlinear detection', Journal of Lightwave Technology, Vol. 22(3), pp. 784-793 (2004).

[11] N. Kikuchi, 'Analysis of signal degree of polarization degradation used as control signal for optical polarization mode dispersion compensation', Journal of Lightwave Technology, Vol. 19(4), pp. 480-486 (2001).

[12] F. Corsi, A. Galtarossa, L. Palmieri, M. Schiano, T. Tambosso, "Continuous-Wave Backreflection Measurement of Polarization Mode Dispersion Characterization", IEEE Photonics Technology Letters, Vol. 11 No. 4, April 1999, pp. 451-453.

[13] A. Galtarossa, L. Palmieri, M. Schiano, T. Tambosso, "Single-End Polarization Mode Dispersion Measurement Using Backreflected Spectra Through a Linear Polarizer", IEEE/OSA J. Lightwave Technology, Vol. 17 No. 10, October 1999, pp. 1835-1842.

[14] H. Sunnerud, B.-E. Olsson, M. Karlsson, P. A. Andrekson, J. Brentel "Polarization-Mode Dispersion Measurements Along Installed Optical Fibers Using Gated Backscattered Light and a Polarimeter", IEEE/OSA J. Lightwave Technology, Vol. 18 No. 7, July 2000, pp. 897-904.

[15] H. Sunnerud, B.-E. Olsson, M. Karlsson, P. A. Andrekson, "Measurement of Polarization Mode Dispersion Accumulation Along Installed Optical Fibers", IEEE Photonics Technology Letters, Vol. 11 No. 7, July 1999, pp. 860-862.

[16] U.S. Pat. No. 6,229,599 (A. Galtarossa).

[17] H. Dong, P. Shum, J. G. Zhou, Y. D. Gong, "Single-end Spectral Resolved Measurement of Polarization Mode Dispersion in Optical Fibers", Paper JThA20, Optical Fiber Communications Conference, Mar. 25-29, 2007, Anaheim, Calif., USA.

[18] U.S. Pat. No. 6,724,469 (M. Leblanc).

[19] F. Corsi, A. Galtarossa, L. Palmieri, "Beat Length Characterization Based on Backscattering Analysis in Randomly Perturbed Single-Mode Fibers," Journal of Lightwave Technology, Vol. 17, No. 7, July 1999.

[20] A. Galtarossa, L. Palmieri, A. Pizzinat, M. Schiano, T. Tambosso, "Measurement of Local Beat Length and Differential Group Delay in Installed Single-Mode Fibers", Journal of Lightwave Technology, Vol. 18, No. 10, October 2000.

[21] A. Galtarossa, L. Palmieri, M. Schiano, T. Tambosso, "Measurement of Beat Length and Perturbation Length in Long Single-Mode Fibers," Optics Letters, Vol. 25, No. 6, Mar. 15, 2000.

[22] B. Huttner, B. Gisin, N. Gisin, "Distributed PMD measurement with a polarization-OTDR in optical fibers", Journal of Lightwave Technology, Vol. 17, pp. 1843-1948, October 1999.

[23] U.S. Pat. No. 6,946,646 (X. Chen et al.)

[24] US published patent application number 2004/0046955, Fayolle et al.

The invention claimed is:

1. A method of measuring a polarization-related characteristic of an optical path (18) wherein light comprising polarized light is propagated, the method comprising the steps of using:

polarization-controller-and-analyzer means (14,20A; 14A, 14B,20; 14A, 14B,20A; 14,20; 14,20C; 14A,45) connected to the optical path at or adjacent either a proximal end thereof or a distal end thereof or both the proximal end and the distal end to control at least one of state of polarization (I-SOP) of light launched in the optical path and state of polarization (A-SOP) used to analyze light leaving the optical path, detecting means (22; 22A,22B; 22D) to detect the analyzed light and provide corresponding detection signals, and processing means (40) to process the detection signals to derive said polarization-related characteristic, wherein said light leaving the optical path is analyzed to provide transmitted coherent optical power at each wavelength of light in each of at least two groups of wavelengths, and wherein the lowermost ($\lambda_L$) and uppermost ($\lambda_U$) said wavelengths in each said group of wavelengths are separated by a first small optical frequency difference; and wherein each of the said at least two groups comprises a wavelength pair, said pair in each group defining a midpoint wavelength therebetween, and being mutually spaced by a second small optical-frequency difference, the second small optical-frequency difference being equal to or less than the first optical-frequency difference, said second small optical-frequency difference ($\delta v$) being the same for corresponding wavelength pairs in different groups, and wherein the I-SOP and A-SOP are substantially constant for each coherent optical power at each said wavelength in each said group, and wherein at least one of the midpoint wavelength, I-SOP and A-SOP is different between the respective said groups, the step of using processing means (40) to process the detection signals including the steps of:

(i) computing at least one difference between a pair of measured power parameters each corresponding to a respective one of the wavelengths in said wavelength pair for each of the said at least two groups, each said measured power parameter being proportional to transmitted coherent optical power of the said analyzed and subsequently detected light, thereby defining for said at least two groups a set of at least two measured power parameter differences;

(ii) computing a mean-square value of said set of at least two measured power parameter differences; and (iii) calculating the polarization-related optical path characteristic as a predetermined function of said mean-square value, said predetermined function being dependent upon the said second small optical-frequency difference between the wavelengths corresponding to the said each of at least said two pairs of wavelengths.

2. A method according to claim 1, further comprising using light source means connected to the optical path at or adjacent the proximal end thereof to launch light comprising polarized light into the optical path, and wherein the said polarization-controller-and-analyzer means comprises input controller means connected to the optical path at or adjacent the proximal end thereof and analyzer means connected to the optical path at or adjacent the distal end thereof.

3. A method according to claim 2, wherein:
(a) corresponding wavelength pairs in different groups have substantially the same midpoint wavelength,
(b) the second small optical frequency difference ($\delta v$) multiplied by differential group delay (DGD) is less than 0.5, and
(c) the said polarization-related optical path characteristic comprises a differential group delay (DGD) at the said midpoint wavelength.

4. A method according to claim 3, wherein the said measured power parameter is normalized power T(v), and the limit of said predetermined function as said second small optical-frequency difference ($\delta v$) tends to zero is expressed according to the following differential formula:

$$DGD(v) = \frac{\alpha_{ds}}{\pi \delta v} \cdot \sqrt{\langle T^2(v) \rangle_{SOP}}$$

where the constant $$\alpha_{ds} = \sqrt{\frac{9}{2}},$$

v is the optical frequency corresponding to the said midpoint wavelength, and $\Delta T(v)$ is the difference in the normalized power obtained for a particular I-SOP and A-SOP couple.

5. A method according to claim 3, wherein the said measured power parameter is normalized power T(v), and the mean-square value computing step (ii) further comprises computation of relative variance ($\sigma_r^2(v)$) of normalized powers T(v) according to the expression:

$$\sigma_r^2(v) = \left(\frac{1}{\sigma_{20}}\right)^2 [\langle T^2(v) \rangle_{SOP} - \langle T(v) \rangle_{SOP}^2]$$

where a reference variance $\sigma_{20}^2 = 1/12$, $\Delta T(v)$ is the difference in the normalized power obtained for a particular I-SOP and A-SOP couple, and the limit of said predetermined function as the second small optical-frequency difference $\delta v$ tends to zero may be expressed according to the following differential formula:

$$DGD(v) = \frac{\alpha_{ds}}{\pi \delta v} \cdot \sqrt{\frac{\langle \Delta T^2(v) \rangle_{SOP}}{\sigma_r^2(v)}}$$

where the constant $$\alpha_{ds} = \sqrt{\frac{9}{2}},$$

and v is the optical frequency corresponding to the said midpoint wavelength.

6. A method according to claim 3, wherein
a) the said polarized light is launched using light source means connected to the optical path at or adjacent the proximal end thereof, said light source means comprising broadband light having a spectral width encompassing the said second small optical-frequency difference;
b) the said polarization-controller-and-analyzer means comprises spectral filter means having a filter width sufficiently less than the said second small optical-frequency difference as to allow each wavelength in said wavelength pair to be spectrally resolved, thereby rendering coherent the light selected from the light source means; and
c) the said spectral filter means is operable to select for detection each of the wavelengths corresponding to the said groups comprising the said wavelength pair.

7. A method according to claim 2, wherein:
a) corresponding wavelength pairs in at least two different groups have midpoint wavelengths that are different, and a maximum difference between corresponding midpoint wavelengths defines a prescribed wavelength range;
b) said second small optical-frequency difference ($\delta v$) multiplied by rms DGD is approximately equal to or less than 0.2; and
c) the said at least one polarization-related optical path characteristic is rms DGD of the optical path measured over said prescribed wavelength range.

8. A method according to claim 2, wherein:
for said light leaving the optical path being analyzed, at least one quasi-continuum of transmitted coherent optical powers as a function of optical frequency are detected and stored for further analysis in said step (i), said optical frequency spanning a prescribed wavelength range,
a) said measured power parameters are computed from said transmitted coherent optical powers;
b) the degree of any variation of I-SOP and A-SOP with respect to the optical frequency is low, such that both of I-SOP and A-SOP, respectively, are substantially the same for the coherent optical powers at each of the wavelengths composing each of said wavelength pairs.

9. A method according to claim 8, wherein the step of detecting and storing at least one quasi-continuum detects and stores first and second quasi-continua, wherein either or both of the I-SOP and A-SOP corresponding to at least some of the coherent optical powers at wavelengths in said first quasi-continuum are substantially different than the either or both of the I-SOP and A-SOP, respectively, for the corresponding said coherent optical powers in said second quasi-continuum, said polarization-related optical-path characteristic comprising at least one of
a) rms DGD value over a prescribed wavelength range; and
b) when the said at least some of stored measured power parameters correspond to a particular midpoint wavelength, DGD at said particular midpoint wavelength.

10. A method according to claim 8, wherein
a) the polarized light launched by said light source means comprises broadband light encompassing the prescribed wavelength range;
b) the said polarization-controller-and-analyzer means includes spectral filter means having a filter width sufficiently less than the said second small optical-frequency difference as to allow each wavelength in said wavelength pair to be spectrally resolved, such that the light selected from the broadband light is coherent; and c) the said spectral filter means is operable to sweep substantially continuously to sequentially select for detection each of the wavelengths corresponding to the said groups comprising the said wavelength pairs, said sweep enabling said detection and storage of a quasi-continuum of transmitted coherent optical powers as a function of optical frequency.

11. A method according to claim 10, wherein d) said spectral filter means comprises a polarization-diverse dual-channel scanning monochromator; and e) said measured power parameters comprise pairs of orthogonally-analyzed power parameters measured with said polarization-diverse dual-channel scanning monochromator.

12. A method according to claim 1, wherein the said polarization-controller-and-analyzer means is connected to the optical path at or adjacent the proximal end of the optical path and there is provided a localized reflection at or adjacent the distal end of the optical path.

13. A method according to claim 12, wherein:

a) corresponding wavelength pairs in at least two different groups have midpoint wavelengths that are different, and a maximum difference between corresponding midpoint wavelengths defines a prescribed wavelength range, b) said second small optical-frequency difference ($\delta v$) multiplied by rms DGD is approximately equal to or less than 0.15 and c) the said at least one polarization-related optical path characteristic is the rms DGD over a prescribed wavelength range.

14. A method according to claim 13, wherein the said measured power parameter is normalized transmitted coherent power T($v$), and the limit of said predetermined function as said second small optical-frequency difference $\delta v$ tends to zero is expressed according to the following differential formula:

$$\mathrm{rms}DGD = \frac{\alpha_{rt} \cdot \alpha_{ds}}{\pi \delta v} \cdot \sqrt{\langle \Delta T^2(v) \rangle_{SOP,v}}$$

where the roundtrip factor $$\alpha_{rt} = \sqrt{\frac{3}{8}},$$

and the constant $\alpha_{ds}=\sqrt{9/2}$ if changes in I-SOP and A-SOP are not correlated, and $\alpha_{ds}=\sqrt{15/4}$ if said changes are correlated.

15. A method according to claim 13, wherein the said measured power parameter is normalized transmitted coherent optical power T($v$), and the mean square value computing step (ii) compensates for the possible presence of unpolarized noise in the detected power parameters, by the steps of:

a) computing relative variance ($\sigma_r^2$) of the normalized transmitted optical powers at wavelengths corresponding to respective ones of a wavelength pair centered about said midpoint wavelength; and b) computing the ratio of the mean-square difference over said relative variance, said rms DGD computed as a predetermined function of said ratio, and the limit of said predetermined function as said second small optical-frequency difference $\delta v$ tends to zero may be expressed according to the following differential formula:

$$\mathrm{rms}DGD = \frac{\alpha_{rt} \cdot \alpha_{ds}}{\pi \delta v} \cdot \sqrt{\frac{\langle \Delta T^2(v) \rangle_{SOP,v}}{\sigma_r^2}}$$

where the roundtrip factor $$\alpha_{rt} = \sqrt{\frac{3}{8}},$$

the relative variance of the normalized powers is defined as, $$\sigma_r^2 = \left(\frac{1}{\sigma_{10}}\right)^2 [\langle T^2(v) \rangle_{SOP,v} - \langle T(v) \rangle_{SOP,v}^2]$$

where the constant $$\sigma_{10}^2 = \frac{4}{45},$$

the roundtrip factor $$\alpha_{rt} = \sqrt{\frac{3}{8}},$$

and the constant $\alpha_{ds}=\sqrt{9/2}$ if changes in I-SOP and A-SOP are not correlated, and $\alpha_{ds}=\sqrt{15/4}$ if said changes are correlated.

16. A method according to claim 1, wherein:

a) the said polarization-controller-and-analyzer means is connected to the optical path at or adjacent the proximal end and used to analyze said light leaving the optical path at the proximal end;

b) each group comprises at least one wavelength pair of series of light pulses, each pair of series having both a common I-SOP of the launched light and a common A-SOP used to analyze the light leaving the optical path;

c) the light pulses in each of the two series composing the pair have substantially the same wavelengths;

d) corresponding wavelength pairs in at least two different groups have midpoint wavelengths that are different, and a maximum difference between corresponding midpoint wavelengths defines a prescribed wavelength range;

e) said second small optical-frequency difference ($\delta v$) multiplied by rms DGD is approximately equal to or less than 0.15;

f) the analyzed light comprises resulting backreflected light caused by either or both of Rayleigh scattering and discrete reflections along the optical path;

g) the said measured power parameter is backreflected power of the analyzed backreflected light as a function of distance along the optical path, and the said polarization-related characteristic of the optical path is cumulative PMD value over the prescribed wavelength range corresponding to a distance z along the optical path, this said cumulative PMD value being estimated from cumulative rms round-trip DGD for the same said prescribed wavelength range;

wherein said measured power parameter is determined by:
- I) for each of at least some of the light pulses in each series of light pulses in each said group, analyzing and subsequently detecting the resulting backreflected light to provide a corresponding impulse-response, said state of polarization (A-SOP) used to analyze the backreflected light being the same for each of the said series in said group, and converting each of the impulse-responses into a corresponding electrical impulse-response signal;
- II) for each said series of light pulses in each said group, sampling and averaging the electrical impulse-response signals of said at least some of the light pulses to provide an OTDR trace as a function of time delay; and
- III) converting said OTDR trace as a function of time delay to an OTDR trace representing backreflected power as a function of distance.

17. A method according to claim 16, wherein detected coherent light is substantially fully polarized, the said measured power parameter is the computed normalized power $T(v,z)$ as a function of distance z along the optical path (18), and the limit of said predetermined function as the small second optical-frequency difference $\delta v$ tends to zero is expressed according to the differential formula:

$$PMD(z) = \frac{\alpha_{rt} \cdot \alpha_{ds}}{\pi \delta v} \cdot \sqrt{\langle \Delta T^2(v, z) \rangle_{SOP;v}}$$

where the roundtrip factor $$\alpha_{rt} = \sqrt{\frac{3}{8}},$$

and where the constant $\alpha_{ds} = \sqrt{9/2}$, if changes in I-SOP and A-SOP are not correlated, and $\alpha_{ds} = \sqrt{15/4}$ if said changes are correlated.

18. A method according to claim 16, wherein the said measured power parameter is the computed relative power $P_R(v,z)$ and the mean square value computing step (ii) comprises the steps of:
- a) computing relative variance ($\sigma_R^2(z)$) of said set of at least two measured power parameter differences; and
- b) computing the ratio of the mean-square difference of said set of at least two measured power parameter differences over said relative variance, said rms DGD being computed as said predetermined function of said ratio, and the limit of said predetermined function as the small second optical-frequency difference $\delta v$ tends to zero is expressed according to the differential formula:

$$PMD(z) = \frac{\alpha_{rt} \cdot \alpha_{ds}}{\pi \delta v} \cdot \sqrt{\frac{\langle \Delta P_R^2(v, z) \rangle_{SOP;v}}{\sigma_R^2(z)}}$$

where the roundtrip factor $$\alpha_{rt} = \sqrt{\frac{3}{8}},$$

the relative variance of the normalized powers is defined as, $$\sigma_r^2(z) = \left(\frac{1}{\sigma_{10}}\right)^2 [\langle P_R(z, v) \cdot P_R''(z, v) \rangle_{SOP;v} - \langle T_R(z, v) \rangle_{SOP;v}^2]$$

where the constant $$\sigma_{10}^2 = \frac{4}{45},$$

and the constant $\alpha_{ds} = \sqrt{9/2}$ if changes in changes in I-SOP and A-SOP are not correlated, and $\alpha_{ds} = \sqrt{15/4}$ if said changes are correlated.

19. A method according to claim 1, wherein each said group of wavelengths comprises at least one repeated said wavelength pair, corresponding to an initial first wavelength pair, wherein the I-SOP and A-SOP for each of these repeated wavelength pairs are substantially the same within each said group, the computation of the at least one said polarization-related optical path characteristic including the measured power parameters at wavelengths corresponding to these repeated wavelength pairs.

20. A method according to claim 1, wherein the measured power parameter of step (i) is a normalized power T proportional to the transmitted coherent optical power, determined by one of the following steps:
- a) a power corresponding to one polarization component composing the transmitted coherent optical power is measured using one detector, and then the normalized power (T) is obtained by dividing said measured power corresponding to one polarization component by the average of at least some of said measured powers corresponding to one polarization component at the same corresponding wavelength in the different groups;
- b) two powers corresponding to respective orthogonal polarization components composing the transmitted coherent optical power are measured simultaneously and each of the normalized powers (T) is obtained by either
  - (I) dividing at least one of the measured said two powers by the sum of the measured said two powers; or
  - (II) dividing a weighted difference of the measured said two powers by the sum of the measured said two powers;
- c) a first optical power corresponding to one polarization component of the transmitted coherent optical power and a second optical power directly proportional to the output of light from the optical path are measured, using respective first and second detectors, and the normalized power (T) is obtained by dividing said first optical power by said second optical power to obtain the relative power of said first power at said wavelength, and then dividing said relative power by the average of at least some of the relative powers at the same wavelength in the different groups;

d) using one detector and one optical switch, two powers corresponding to respective orthogonal polarization components composing the transmitted coherent optical power are detected at different times by the same detector where the optical switch is used to route said two powers to the same detector, and then the normalized power T for each wavelength of said powers is obtained by either
  (I) dividing at least one of said two powers by the sum of said two powers; or
  (II) dividing a weighted difference of said two powers by the sum of said two powers;

e) using one detector and one optical switch, a first optical power corresponding to one polarization component of the transmitted coherent optical power and a second optical power directly proportional to the output of light from the optical path are measured at different times by the same detector, the optical switch being operable to route successively the first optical power and the second optical power to the same detector, and the normalized power (T) is obtained by first dividing said first power by said second power to obtain a ratio representing the relative power of said first power, and dividing said relative power by the average of at least some of the relative powers at the same wavelength in the different groups.

21. A method according to claim 1, wherein the measured power parameter of step (i) is a relative power $P_R$ proportional to the detected transmitted coherent optical power, determined by one of the following steps:

a) a power corresponding to one polarization component composing the transmitted coherent optical power is measured using one detector, and then the relative power ($P_R$) is obtained for each wavelength by dividing said power corresponding to one polarization component by the average of at least some of respective said powers in the different groups;

b) two powers corresponding to respective orthogonal polarization components composing the transmitted coherent optical power are detected simultaneously, and the relative power ($P_R$) is obtained by either
  (I) dividing at least one of said two powers by the sum of said two powers; or
  (II) dividing a weighted difference of said two powers by the sum of said two powers;

c) a first optical power corresponding to one polarization component composing the transmitted coherent optical power and a second optical power directly proportional to the output light from the optical path are measured using respective first and second detectors and the relative power ($P_R$) corresponding to each wavelength of coherent light is obtained by dividing said first optical power by said second optical power;

d) using one detector and one optical switch, two powers corresponding to respective orthogonal polarization components of the light are measured at different times by the same detector, the optical switch being operable to route successively said two powers to said same detector, and the relative power ($P_R$) for said powers is obtained by either
  (I) dividing at least one of said two powers corresponding to the two detected different polarization components for that coherent light by the sum of said two powers; or
  (II) dividing a weighted difference of said two powers by the sum of said two powers;

e) using one detector and one optical switch, a first optical power corresponding to one polarization component composing the transmitted coherent optical power and a second optical power directly proportional to the output light from the optical path are measured at different times by said one detector, the optical switch being operable to route successively said first and second optical powers to said one detector, and the relative power ($P_R$) is obtained by dividing said first power by said second power.

22. A method according to claim 1, wherein:
(a) said polarization-controller-and-analyzer means comprises at least two polarization discriminators for analyzing light leaving the optical path, said at least two polarization discriminators having mutually linearly-independent state-of-polarization conditions (A-SOPs); and
(b) respective transmitted coherent optical powers from said polarization discriminators are detected substantially simultaneously by corresponding detectors in the said detecting means.

23. A method according to claim 22, wherein said polarization-controller-and-analyzer means comprises a polarimetric head, said polarimetric head comprising at least three said polarization discriminators having mutually linearly-independent state-of-polarization conditions (A-SOPs).

24. A method according to claim 1, wherein said polarization-controller-and-analyzer means combines said light leaving the optical path with a polarized coherent local oscillator beam having a respective local-oscillator state of polarization ($SOP_{LO}$), thereby producing a corresponding heterodyne signal at the detecting means, which is indicative of the transmitted coherent optical power of said analyzed light according to a state of polarization (A-SOP) corresponding to said $SOP_{LO}$.

25. A method according to claim 1, wherein said light propagating in said optical path comprises light from at least one data-carrying Signal-Under-Test (SUT) connected to the optical path at or adjacent the proximal end thereof, and launching light comprising polarized light into the optical path, and wherein the said polarization-controller-and-analyzer means connected to the optical path at or adjacent a distal end thereof.

26. A method according to claim 25, wherein said polarization-related characteristic comprises a partial DGD imparted upon said at least one SUT.

27. A method according to claim 25, wherein
said at least one data-carrying SUT comprises at least two data-carrying SUTs;
at least one partial DGD value is measured for each of said data-carrying SUTs; and
said polarization-related characteristic comprises polarization mode dispersion (PMD) of said optical path and is calculated from the measured partial DGD values.

28. A method according to claim 26, wherein the said measured power parameter is a normalized power T(v), and the limit of said predetermined function as said second small optical-frequency difference ($\delta v$) tends to zero is expressed according to the following differential formula:

$$DGD_P(v) = \frac{\alpha_{ds}}{\pi \delta v} \sqrt{\langle \Delta T^2(v) \rangle_{SOP}}$$

where the constant $\alpha_{ds}=\sqrt{3}$, $v$ is the optical frequency corresponding to the said midpoint wavelength, and $\Delta T(v)$ is the difference in the normalized power obtained for a particular analyzer state-of-polarization (A-SOP).

29. A method according to claim 26, wherein the said measured power parameter is a normalized power $T(v)$, and the mean-square value computing step (ii) further comprises computation of relative variance ($\sigma_r^2(v)$) of normalized powers $T(v)$ according to the expression:

$$\sigma_r^2(v) = \left(\frac{1}{\sigma_{20}}\right)^2 [\langle t^2(V) \rangle_{SOP} - \langle T(v) \rangle_{SOP}^2]$$

where a reference variance $\sigma_{20}^2=1/12$, $\Delta T(v)$ is the difference in the normalized power obtained for a particular analyzer state-of-polarization (A-SOP), and the limit of said predetermined function as the second small optical-frequency difference $\delta v$ tends to zero is expressed according to the following differential formula:

$$DGD_P(v) = \frac{\alpha_{ds}}{\pi \delta v} \cdot \sqrt{\frac{\langle T^2(v) \rangle_{SOP}}{\sigma_r^2(v)}}$$

where the constant $\alpha_{ds}=\sqrt{3}$, and $v$ is the optical frequency corresponding to the said midpoint wavelength.

30. A method according to claim 26, wherein said polarization-controller-and-analyzer means comprises spectral filter means having a filter width sufficiently less than the said second small optical-frequency difference as to allow each wavelength in said wavelength pair to be spectrally resolved.

31. A method according to claim 25, wherein said polarization-controller-and-analyzer means comprises a polarimetric head.

32. A method according to claim 25, wherein said distal end of said optical path corresponds to a monitoring port tapped from an optical fiber link and from which a portion of said signal under test is extracted from the optical fiber link.

33. A method according to claim 1, wherein the distal end of the optical path is terminated reflectively and the polarization-controller-and-analyzer means comprises polarization control means (14) connected to the proximal end of the optical path and used both to control state of polarization (I-SOP) of the launched light and state of polarization (A-SOP) used to analyze the light leaving the proximal end of the optical path.

34. A method according to claim 16, wherein the said measured power parameter is normalized transmitted coherent optical power $T(v,z)$ as a function of distance $z$ along the optical path (18), and the mean-square value computing step (ii) compensates for the possible contribution of unpolarized light to the detected power parameters, by the steps of:
  a) computing relative variance ($\sigma_r^2(z)$) of the normalized transmitted optical powers corresponding to respective ones of a wavelength pair centered about said midpoint wavelength as a function of distance $z$ along the optical path (18); and
  b) computing the ratio of the mean-square difference over said relative variance, said rms DGD computed as a function of said ratio as said predetermined function being determined for small optical-frequency differences $\delta v$ as a function of distance $z$ along the optical path (18), according to the following differential formula:

$$PMD(z) = \frac{\alpha_{rt} \cdot \alpha_{ds}}{\pi \delta v} \cdot \sqrt{\frac{\langle \Delta T^2(v, z) \rangle_{SOP,v}}{\sigma_r^2(z)}}$$

where the roundtrip factor $$\alpha_{rt} = \sqrt{\frac{3}{8}},$$

the relative variance of the normalized powers is defined as, $$\sigma_r^2(z) = \left(\frac{1}{\sigma_{10}}\right)^2 [\langle T(z, v) \cdot T''(z, v) \rangle_{SOP,v} - \langle T(z, v) \rangle_{SOP,v}^2]$$

where the constant $$\sigma_{10}^2 = \frac{4}{45},$$

and the constant $\alpha_{ds}=\sqrt{9/2}$ if changes in I-SOP and A-SOP are not correlated, and $\alpha_{ds}=\sqrt{15/4}$ if said changes are correlated.

35. A method according to claim 5, wherein said mean-square value is computed in accordance with one of:
  $\langle \Delta T^2(v) \rangle_{SOP} = \langle \Delta T(v) \Delta T(v) \rangle_{SOP}$, where $\Delta T(v)$ is the difference in the normalized transmitted coherent optical powers measured for a particular I-SOP and A-SOP couple;
  $\langle \Delta T^2(v) \rangle_{SOP} = \langle \Delta T(v) \Delta T''(v) \rangle_{SOP}$, where $\Delta T''(v)$ is a normalized power difference calculated from repeated measurements of transmitted coherent optical powers measured under the same I-SOP and A-SOP conditions as those of $\Delta T(v)$; and
  $\langle \Delta T^2(v) \rangle_{SOP} = \langle \Delta T(v) \Delta T''(v) \rangle_{SOP}$, where $\Delta T''(v)$ is a normalized power difference calculated from transmitted coherent optical powers for which A-SOP for $\Delta T(v)$ is orthogonal to A-SOP for $\Delta T''(v)$.

36. A method according to claim 15, wherein said mean-square value is computed in accordance with one of:
  $\langle \Delta T^2(v) \rangle_{SOP} = \langle \Delta T(v) \Delta T(v) \rangle_{SOP}$, where $\Delta T(v)$ is the difference in the normalized transmitted coherent optical power obtained for a particular I-SOP and A-SOP couple;
  $\langle \Delta T^2(v) \rangle_{SOP} = \langle \Delta T(v) \Delta T''(v) \rangle_{SOP}$ where $\Delta T(v)$ is the difference in the normalized transmitted coherent optical power obtained for a particular I-SOP and A-SOP couple, and $\Delta T''(v)$ is a normalized transmitted coherent optical power difference calculated from repeated measurements of transmitted coherent optical powers measured under the same I-SOP and A-SOP conditions as those of $\Delta T(v)$; and
  $\langle \Delta T^2(v) \rangle_{SOP} = \langle \Delta T(v) \Delta T''(v) \rangle_{SOP}$, where $\Delta T(v)$ is the difference in the normalized transmitted coherent optical power obtained for a particular I-SOP and A-SOP couple, where $\Delta T''(v)$ is a normalized transmitted coherent optical power difference calculated from transmitted coherent optical powers for which A-SOP for $\Delta T(v)$ is orthogonal to A-SOP for $\Delta T''(v)$.

37. A method according to claim 18, wherein said mean-square value is computed in accordance with one of:

$\langle \Delta P_R^2(v) \rangle_{SOP} \langle \Delta P_R(v) \Delta P_R(v) \rangle_{SOP}$, where $\Delta P_R(v)$ is the difference in the relative powers obtained for a particular I-SOP and A-SOP couple;

$\langle \Delta P_R^2(v) \rangle_{SOP} = \langle \Delta P_R(v) \Delta P_R''(v) \rangle_{SOP}$, where $\Delta P_R(v)$ is the difference in the relative power obtained for a particular I-SOP and A-SOP couple, and where is a relative power difference calculated from repeated measurements of transmitted coherent optical powers under the same I-SOP and A-SOP conditions as those of $\Delta P(v)$; and $\langle \Delta P_R^2(v) \rangle_{SOP} = \langle \Delta P_R(v) \Delta P_R''(v)_{SOP}$, where $\Delta P_R(v)$ is the difference in the relative power obtained for a particular I-SOP and A-SOP couple, where $\Delta P_R''(v)$ is a power difference calculated from transmitted coherent optical powers for which A-SOP for $\Delta P_R(v)$ is orthogonal to A-SOP for $\Delta P_R''(v)$.

38. A method according to claim 29, wherein said mean-square value is computed in accordance with one of:

$\langle \Delta T^2(v) \rangle_{SOP} = \langle \Delta T(v) \Delta T(v) \rangle_{SOP}$;

$\langle \Delta T^2(v) \rangle_{SOP} = \langle \Delta T(v) \Delta T''(v) \rangle_{SOP}$, where $\Delta T''(v)$ is a normalized power difference calculated from repeated measurements of transmitted coherent optical powers under the same I-SOP and A-SOP conditions as those of $\Delta T(v)$; and $\langle \Delta T^2(v) \rangle_{SOP} = \langle \Delta T(v) \Delta T''(v) \rangle_{SOP}$, where $\Delta T''(v)$ is a normalized power difference calculated from transmitted coherent optical powers for which A-SOP for $\Delta T(v)$ is orthogonal to A-SOP for $\Delta T''(v)$.

39. Measurement instrumentation for measuring a polarization-related characteristic of an optical path (18) wherein light comprising polarized light is propagated, the measurement instrumentation comprising:

polarization-controller-and-analyzer means (14,20A; 14A,14B,20; 14A,14B,20A; 14,20; 14,20C; 14A,45) for connection to the optical path at or adjacent either a proximal end thereof or a distal end thereof or both the proximal end and the distal end and operable to control at least one of a state of polarization (I-SOP) of light launched in the optical path and a state of polarization (A-SOP) used to analyze light leaving the optical path, detecting means (22; 22A,22B; 22D) for detecting the analyzed light corresponding to at least one analyzer SOP (A-SOP) and providing corresponding detection signals, and processing means (40) for processing the detection signals to derive said polarization-related characteristic, wherein said light leaving the optical path is analyzed to provide transmitted coherent optical power at each wavelength of light in each of at least two groups of wavelengths, and wherein the lowermost ($\lambda_L$) and uppermost ($\lambda_U$) said wavelengths in each said group of wavelengths are separated by a first small optical frequency difference;

and wherein each of the said at least two groups comprises a wavelength pair, said pair in each group defining a midpoint wavelength therebetween, and being mutually spaced by a second small optical-frequency difference, the second small optical-frequency difference being equal to or less than the first small optical-frequency difference, and defining a midpoint wavelength therebetween, said second small optical-frequency difference ($\delta v$) being the same for corresponding wavelength pairs in different groups, and wherein the I-SOP and A-SOP are substantially constant for each said wavelength in each said group, and wherein at least one of the midpoint wavelength, I-SOP and A-SOP is different between the respective said groups, the measurement instrumentation being operable to:

i) compute at least one difference between a pair of measured power parameters each corresponding to either or an average of the measured optical power parameters at wavelengths corresponding to respective ones of a wavelength pair centered about said midpoint wavelength, said wavelength pair comprised within each of the said at least two groups, each said measured power parameter being proportional to transmitted coherent optical power of the said analyzed and subsequently detected light, thereby defining for said at least two groups a set of at least two measured power parameter differences;

ii) compute a mean-square value of said set of at least two measured power parameter differences; and iii) calculate the polarization-related optical path characteristic as a predetermined function of said mean-square value, said predetermined function being dependent upon the said second small optical-frequency difference between the wavelengths corresponding to the said each of at least said two pairs of wavelengths.

40. A method of measuring a polarization-related characteristic of an optical path wherein light comprising polarized light is propagated, the method comprising:

polarization analyzing light having propagated in the optical path according to at least two different analyzer states of polarization (A-SOP);

for each said at least two different analyzer states of polarization:
  detecting transmitted coherent optical power of the analyzed light at each wavelength of light in a group of wavelengths, wherein said group comprises at least one wavelength pair, said pair defining a midpoint wavelength therebetween and being mutually spaced by a small optical-frequency difference, and
  computing a difference between a pair of measured power parameters each corresponding to a respective one of the wavelengths in said wavelength pair, each said measured power parameter being proportional to transmitted coherent optical power of the said analyzed and subsequently detected light, thereby defining a set of corresponding at least two measured power parameter differences;

computing a mean-square value of said set of measured power parameter differences; and calculating the polarization-related optical path characteristic as a predetermined function of said mean-square value.

* * * * *